United States Patent [19]
Salvati et al.

[11] Patent Number: 6,022,307
[45] Date of Patent: Feb. 8, 2000

[54] SUBSTITUTED DIBENZOTHIOPHENES HAVING ANTIANGIOGENIC ACTIVITY

[75] Inventors: Mark E. Salvati, Lawrenceville, N.J.; Nancy H. Eudy, Cornwall, N.Y.; William A. Hallett, New City, N.Y.; Dennis William Powell, Cortland Manor, N.Y.

[73] Assignee: American Cyanamid Company, Madison, N.J.

[21] Appl. No.: 09/340,353

[22] Filed: Jun. 28, 1999

Related U.S. Application Data

[60] Provisional application No. 60/112,024, Jul. 14, 1998, abandoned.

[51] Int. Cl.$^7$ .......................... A61K 31/38; A61K 31/41; A61K 31/44; C07D 333/00; C07D 333/74
[52] U.S. Cl. .......................... 519/443; 444/437; 444/359; 444/406; 444/414; 444/337; 549/6; 549/26; 549/43; 549/46; 548/255; 548/360.5; 548/364.4; 548/454; 546/22; 546/281.1
[58] Field of Search ................... 549/6, 26, 43, 549/46; 514/443, 444, 437, 359, 406, 414, 337; 548/255, 360.5, 364.4, 454; 546/22, 281.1

[56] References Cited

U.S. PATENT DOCUMENTS

| | | |
|---|---|---|
| 2,563,498 | 8/1951 | Scalera et al. . |
| 2,573,652 | 10/1951 | Scalera et al. . |
| 2,590,632 | 3/1952 | Long et al. . |
| 2,620,343 | 12/1952 | Tsang . |
| 2,911,415 | 11/1959 | Freyermuth et al. . |
| 2,937,089 | 5/1960 | Jones et al. . |
| 2,961,318 | 11/1960 | Jones et al. . |
| 3,226,247 | 12/1965 | Forster . |
| 3,257,324 | 6/1966 | Wearn et al. . |
| 3,346,502 | 10/1967 | Wixon . |
| 3,649,288 | 3/1972 | Shiba et al. . |
| 3,682,640 | 8/1972 | Shiba et al. . |
| 3,705,036 | 12/1972 | Amano et al. . |
| 3,728,125 | 4/1973 | Shiba et al. . |
| 3,897,453 | 7/1975 | Gante et al. .......................... 514/443 |
| 3,952,014 | 4/1976 | Albrecht et al. .......................... 514/443 |
| 3,953,601 | 4/1976 | Bondesson et al. .......................... 514/443 |
| 4,334,078 | 6/1982 | Berger et al. .......................... 549/43 |
| 5,017,600 | 5/1991 | Bair .......................... 514/443 |
| 5,929,246 | 7/1999 | Yuan et al. .......................... 546/281.1 |

FOREIGN PATENT DOCUMENTS

| | | |
|---|---|---|
| 560574 | 7/1958 | Canada . |
| 1045977 | 7/1963 | United Kingdom . |

OTHER PUBLICATIONS

Jackson et al., 1997, FASEBJ, 457–465.
Colville–Nash et al., 1997, Mol. Med. Today, 14–23.
Seed, 1996, Exp. Opin. Invest. Drugs, 1617–1637.
Toi et al., 1995, Breast Cancer Res. & Treatment, 193–204.
Holmgren et al., 1995, Nature Medicine, 149–153.
Folkman, 1995, Nature Medicine, 27–31.
Yaun et al., 1996, 14765–14770, Proc. Natl. Acad. Sci.
Borgstrom et al., Cancer Res., 1996, 4032–4039.
Kim et al., Nature, 1995, 841–844.
Tilton et al., 1997, J. Clin. Invest., 2192–2202.
Aiello et al., 1995, Proc. Natl. Acad. Sci., 10457–10461.
Larock, Comprehensive Organic Transformations, VCH Publishers, 411–415, 1989.
Tamargo et al., Cancer Res. 53:329–333, 1993.
Campaigne & Ashby, J. Het. Chem., Aug. 1969, 517–522.
Landauer and Rydon, J. Chem. Soc., 1953, 2224, 2233.
Hashmell et al., J. Am. Chem. Soc., 103, pp. 289–295, 1981.
R.B. DuVernet et al., J. Am. Chem. Soc., 100, 2457–2464 (1978).
Hugh Ryan et al., Chem. Abstracts, vol. 12, No. 23, Dec. 1918, pp. 2541–2542.
Hugh Ryan et al., Proc. Roy. Irish Acad., 34B, 85–96 (1918).
Robert K. Brown et al., J. Am. Chem. Soc., 70, 1748–49 (1948).
Schlesinger, J. Am. Chem. Soc., vol. 73, 2614–2616 (1951).
Robert K. Brown et al., J. Am. Chem. Soc., 74, 1165–1167 (1952).
Henry Gilman and Donald L. Esmay, J. Amer. Chem. Soc., 76, 5786–5787 (1954).

*Primary Examiner*—Deborah C. Lambkin
*Attorney, Agent, or Firm*—Daniel B. Moran

[57] ABSTRACT

The invention provides novel substituted dibenzothiophenes of Formulae (I), (II), (III) and (IV) which have antiangiogenic activity and further provides a method using substituted dibenzothiophenes of Formula (V) as antiangiogenic agents.

173 Claims, No Drawings

SUBSTITUTED DIBENZOTHIOPHENES HAVING ANTIANGIOGENIC ACTIVITY

CROSS REFERENCE TO RELATED APPLICATIONS

This application claims the benefit of U.S. Provisional Application Ser. No. 60/112,024, which was converted from U.S. patent application Ser. No. 09/115,390, filed Jul. 14, 1998, pursuant to a petition filed under 37 C.F.R. 1.53(c)(2) filed Nov. 2, 1998.

FIELD OF THE INVENTION

This invention relates to novel substituted dibenzothiophenes of Formulae (I), (II), (III) and (IV) which have antiangiogenic activity for treating or inhibiting abnormal angiogenic growth, pharmaceutical compositions containing them, novel processes for preparing them, and novel intermediates.

This invention further relates to methods and pharmaceutical compositions for treating or inhibiting abnormal angiogenic growth using tricyclic substituted dibenzothiophenes of Formula (V).

BACKGROUND OF THE INVENTION

Normal angiogenesis is required in many physiological conditions such as wound healing, female reproduction, and fetal development. Abnormal or pathological angiogenesis has been implicated in neoplastic diseases including solid tumor growth, metastasis, and Kaposi's sarcoma; various eye diseases including diabetic retinopathy, and macular degeneration; inflammatory conditions including rheumatoid arthritis, and osteoarthritis; skin diseases including psoriasis, eczema, and scleroderma; as well as ulcerative colitis and childhood haemangiomas (Toi et. al., 1995, Breast Cancer Res. and Treat., 192–204; Holmgren et. al., 1995, Nature Medicine, 149–153; Folkman, 1995, Nature Medicine, 27–31; Jackson et. al., 1997, FASEB J., 457–465). Several growth factors have been implicated in the angiogenesis process including basic and acidic fibroblast growth factor (bFGF and aFGF), transforming growth factor (TGF), and vascular endothelial growth factor (VEGF)(Seed, 1996, Exp. Opin. Invest. Drugs, 1617–1637; Colville-Nash et. al., 1997, Mol. Med. Today, 14–23).

VEGF receptors are localized to endothelial cells in contrast to the other growth factors described above. In addition, VEGF has the unique ability to induce vascular permeability (VEGF was first described as vascular permeability factor) as well as serve as a survival factor for newly developed blood vessels (Yaun et. al., 1996, 14765–14770, Proc. Nat. Acad. Sci). These properties, in addition to its mitogenic effects, makes VEGF a critical target in pathological diseases that require neovascularization. Inhibition of VEGF function has been shown to inhibit disease progression in tumors (Borgstrom et. al., Cancer Res., 1996, 4032–4039; Kim, et. al., 1993, Nature, 841–844) and retinal neovascularization (Aiello et. al., 1995, Proc. Nat. Acad. Sci., 10457–10461) as well as vascular dysfunction mediated by glucose in models of diabetes (Tilton et. al., 1997, J. Clin. Invest., 2192–2202).

VEGF is produced in cells in a number of isoforms including, VEGF205, VEGF189, VEGF165, and VEGF121, of which VEGF165 and VEGF121 are normally seen in the serum. The receptors for VEGF (e.g., KDR and Flt-1 are expressed on endothelial cells and interaction of the ligand, VEGF, and the receptors is responsible for the effects described above. Interruption of VEGF binding to its receptors, via antibodies or small molecules, would be an effective therapy for the treatment of diseases mediated by aberrant angiogenesis.

SUMMARY OF THE INVENTION

This invention relates to new substituted dibenzothiophene compounds selected from those of the general Formulae (I), (II), (III) and (IV), which have antiangiogenic activity, with pharmaceutical formulations and methods of treating or inhibiting abnormal or pathological angiogenic maladies specifically exemplified, which include, but are not limited to ocular neovascular disease, neovascular glaucoma, diabetic retinopathy, fibroplasia, hemangioma, angiofibroma, psoriasis, rheumatoid arthritis and solid tumor growth in warm blooded animals employing these new compounds, with pharmaceutical preparations containing these new compounds, processes for preparing these new compounds and with novel intermediate compounds.

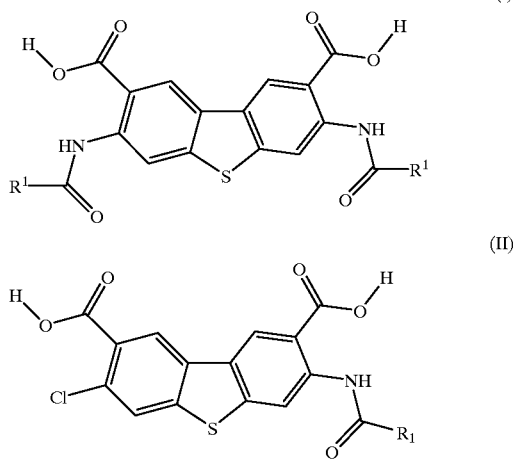

In general Formulae (I), and (II);

wherein:

$R^1$ is a moiety selected from the group:

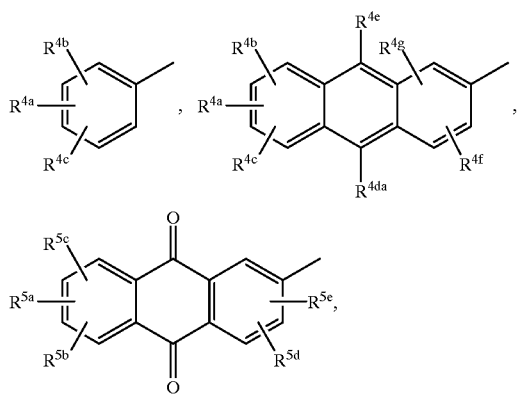

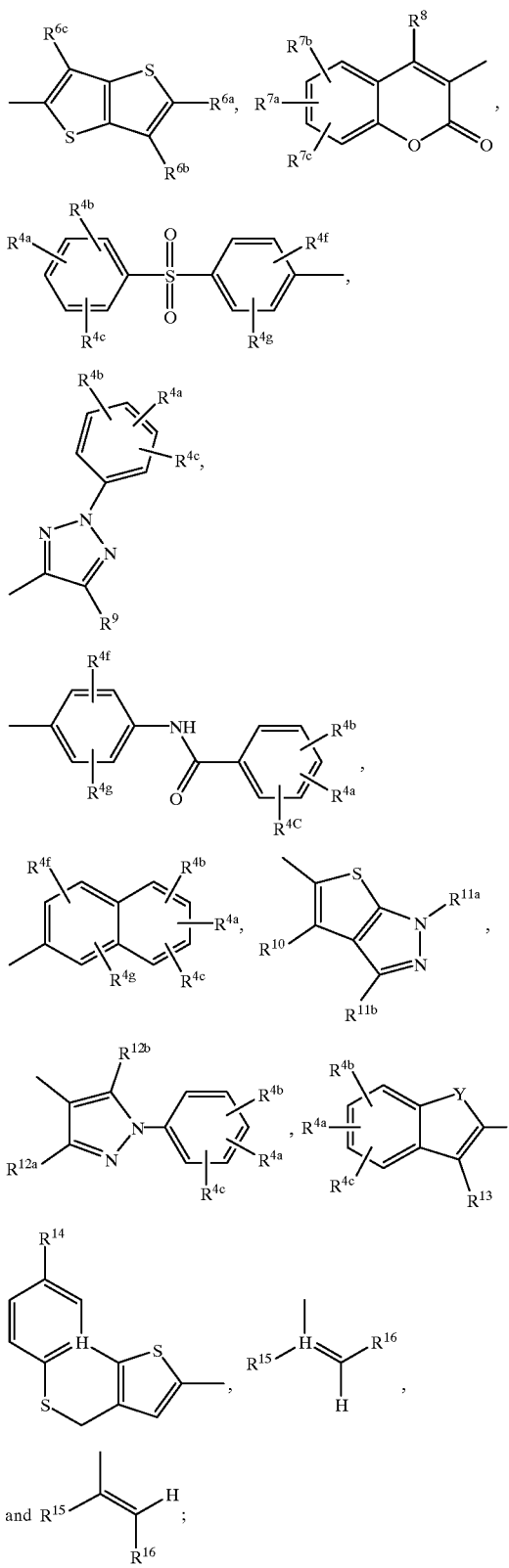

Y is sulfur, oxygen, nitrogen or carbon;

$R^{4a}$, $R^{4b}$, $R^{4c}$, $R^{4d}$, $R^{4e}$, $R^{4f}$ and $R^{4g}$ are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, trifluoromethyl, cyano, nitro, carboxy, alkoxycarbonyl of 1 to 6 carbon atoms, alkoxy of 1 to 6 carbon atoms, alkylcarbonyl of 1 to 6 carbon atoms, alkylcarbonylamino of 1 to 6 carbon atoms, thiol, alkylthio of 1 to 6 carbon atoms, alkylamino of 1 to 6 carbon atoms; —N($R^{4h}$)($R^{4i}$), phenyl, phenylamino, and carboxaldehyde;

$R^{4h}$ and $R^{4i}$, independent from each other, are straight chain alkyl of 1 to 6 carbon atoms;

$R^{5a}$, $R^{5b}$, $R^{5c}$, $R^{5d}$, and $R^{5e}$ are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, cyano, nitro, alkylamino of 1 to 6 carbon atoms, and —N($R^{4h}$)($R^{4i}$);

$R^{6a}$ and $R^{6b}$ are independently selected from hydrogen, halogen, straight chain alkyl of 1 to 6 carbon atoms, branched chain alkyl of 3 to 7 carbon atoms, alkenyl of 2 to 6 carbon atoms, and alkynyl of 2 to 6 carbon atoms;

$R^{6c}$ is hydrogen, methyl, cyano, or halogen;

$R^{7a}$, $R^{7b}$ and $R^{7c}$ are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, alkoxy of 1 to 6 carbon atoms, cyano, nitro, alkoxycarbonyl of 1 to 6 carbon atoms, alkylcarbonyl of 1 to 6 carbon atoms, alkylamino of 1 to 6 carbon atoms, and —N($R^{4h}$)($R^{4i}$);

$R^8$ is hydrogen, hydroxy, amino, straight chain alkyl of 1 to 6 carbon atoms or branched chain alkyl of 3 to 7 carbon atoms;

$R^9$, $R^{10}$, $R^{11a}$, and $R^{11b}$ are independently hydrogen or alkyl of 1 or 2 carbon atoms;

$R^{12a}$ and $R^{12b}$ are independently hydrogen, straight chain alkyl of 1 to 6 carbon atoms, alkenyl of 2 to 6 carbon atoms, alkynyl of 2 to 4 carbon atoms, hydroxyalkyl of 2 to 4 carbons, carboxy, alkoxycarbonyl of 1 to 6 carbon atoms, alkoxy of 1 to 6 carbon atoms, thiol, alkylthio of 1 to 4 carbon atoms, alkylamino of 1 to 4 carbon atoms, —N($R^{12c}$)($R^{12d}$) or trifluoromethyl;

$R^{12c}$ and $R^{12d}$, independent from each other, are straight chain alkyl of 1 to 4 carbon atoms;

$R^{13}$ independently hydrogen, alkyl of 1 or 2 carbon atoms, hydroxy, amino, halogen, hydroxymethyl, or aminomethyl;

$R^{14}$ is hydrogen, alkyl of 1 or 2 carbon atoms, or halogen;

$R^{15}$ is hydrogen or cyano;

$R^{16}$ is a moiety selected from the group:

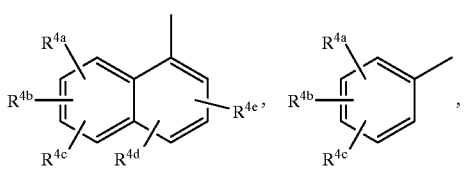

-continued

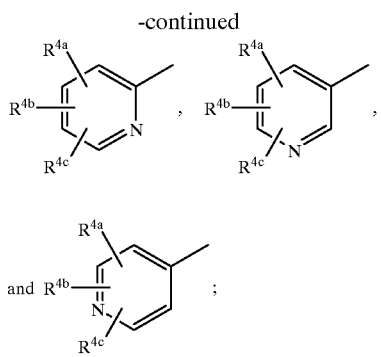

or a pharmaceutically acceptable salt thereof.

It is understood in references to alkoxycarbonyl of 1 to 6 carbon atoms, alkylcarbonyl of 1 to 6 carbon atoms, alkyl carbonylamino of 1 to 6 carbon atoms described herein in Formulae (I), (II), (III), (IV) and (V) that reference to 1 to 6 carbon atoms describes the length of the alkyl or alkoxy as bonded to the carbonyl carbon.

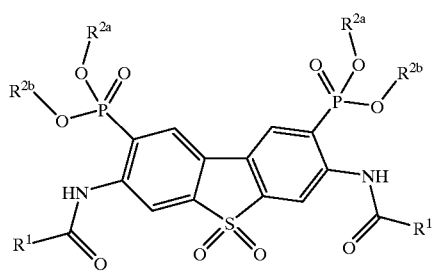
(III)

In general formula (III):
wherein:

$R^{2a}$, and $R^{2b}$ are independently hydrogen, straight chain alkyl of 1 to 6 carbon atoms optionally substituted with trifluoromethyl, branched chain alkyl of 3 to 8 carbon atoms or benzyl with the proviso that each independent $R^{2a}$ and $R^{2b}$ may not simultaneously be hydrogen or a pharmaceutically acceptable salt;

$R^1$, $R^{4a}$, $R^{4b}$, $R^{4c}$, $R^{4d}$, $R^{4e}$, $R^{4f}$, $R^{4g}$, $R^{4h}$, $R^{4i}$, $R^{5a}$ $R^{5b}$, $R^{5c}$, $R^{5d}$, $R^{5e}$, $R^{6a}$, $R^{6b}$, $R^{6c}$, $R^{7a}$, $R^{7b}$, $R^{7c}$, $R^8$, $R^9$, $R^{10}$, $R^{11a}$, $R^{11b}$, $R^{12a}$, $R^{12b}$, $R^{12c}$, $R^{12d}$, $R^{13}$, $R^{14}$, $R^{15}$, $R^{16}$ and Y are as defined for general Formulae (I) and (II);

or a pharmaceutically acceptable salt thereof.

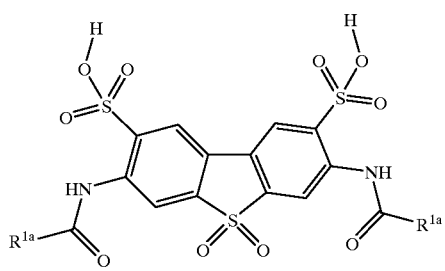
(IV)

In general formula (IV):
wherein:

$R^{1a}$ is a moiety selected from the group:

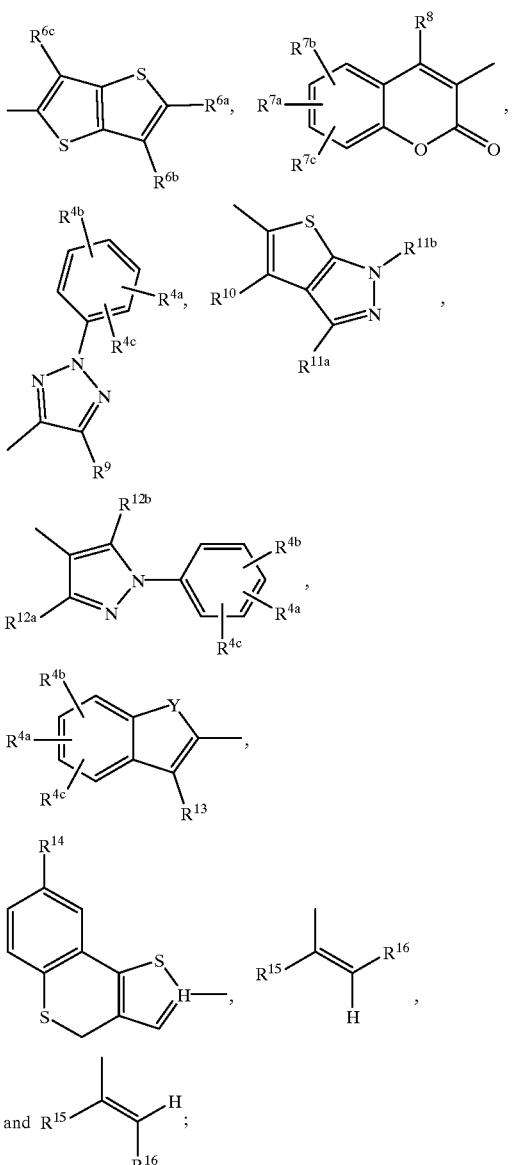

$R^{4a}$, $R^{4b}$, $R^{4c}$, $R^{4h}$, $R^{4i}$, $R^{6a}$, $R^{6b}$, $R^{6c}$, $R^{7a}$, $R^{7b}$, $R^{7c}$, $R^8$, $R^9$, $R^{10}$, $R^{11a}$, $R^{11b}$, $R^{12}$, $R^{12b}$, $R^{12c}$, $R^{12d}$, $R^{13}$, $R^{14}$, $R^{15}$, $R^{16}$ and Y are as defined for general Formulae (I), (II) and (III); with the proviso that $R^{15}$ is not H when $R^{16}$ is phenyl;

or a pharmaceutically acceptable salt thereof.

In particular, this invention also provides a method of treating or inhibiting abnormal or pathological angiogenesis. Among the abnormal or pathological angiogenic maladies specifically exemplified, which include but are not limited to ocular neovascular disease, neovascular glaucoma, diabetic retinopathy, fibroplasia, hemangioma, angiofibroma, psoriasis, rheumatoid arthritis and solid tumor growth in warm blooded animals in need thereof, which comprises administering to said warm blooded animals preferably mammals, most preferably humans an effective amount of a compound of general Formula (V) or a pharmaceutically acceptable salt thereof.

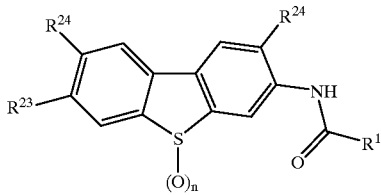
(V)

In general Formula (V);
wherein:
n is an integer of 0 or 2;
$R^1$ is a moiety selected from the group:

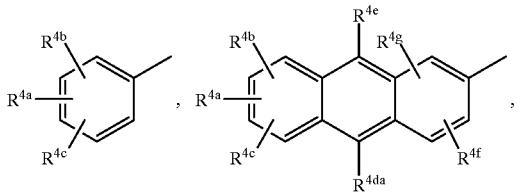

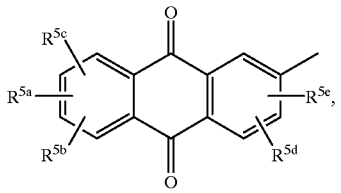

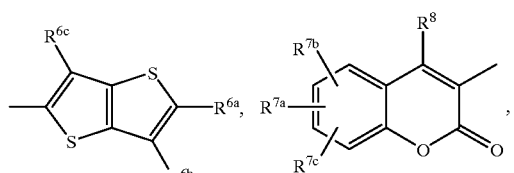

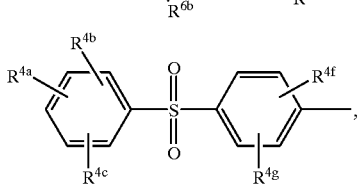

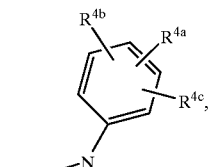

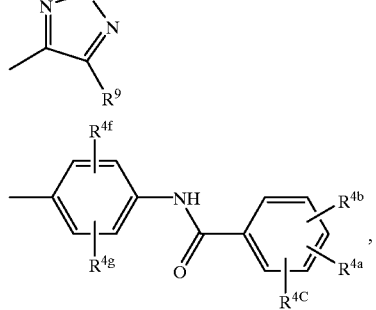

-continued

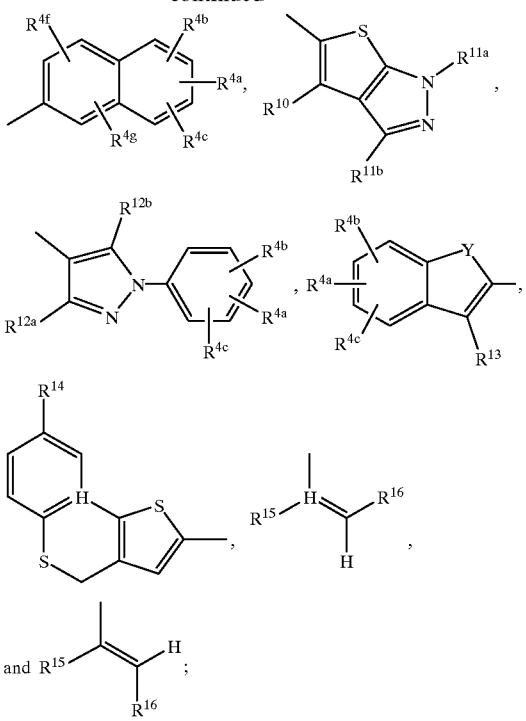

Y is sulfur, oxygen, nitrogen or carbon;
$R^{4a}$, $R^{4b}$, $R^{4c}$, $R^{4d}$, $R^{4e}$, $R^{4f}$, and $R^{4g}$, are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, trifluoromethyl, cyano, nitro, carboxy, alkoxycarbonyl of 1 to 6 carbon atoms, alkoxy of 1 to 6 carbon atoms, alkylcarbonyl of 1 to 6 carbon atoms, alkylcarbonylamino of 1 to 6 carbon atoms, thiol, alkylthio of 1 to 6 carbon atoms, alkylamino of 1 to 6 carbon atoms, —N($R^{4h}$)($R^{4i}$), phenyl, phenylamino, and carboxaldehyde;
$R^{4h}$ and $R^{4i}$, independent from each other, are straight chain alkyl of 1 to 6 carbon atoms;
$R^{5a}$, $R^{5b}$, $R^{5c}$, $R^{5d}$, and $R^{5e}$ are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, cyano, nitro, alkylamino of 1 to 6 carbon atoms, and —N($R^{4h}$)($R^{4i}$);
$R^{6a}$ and $R^{6b}$ are independently selected from hydrogen, halogen, straight chain alkyl of 1 to 6 carbon atoms, branched chain alkyl of 3 to 7 carbon atoms, alkenyl of 2 to 6 carbon atoms, and alkynyl of 2 to 6 carbon atoms;
$R^{6c}$ is hydrogen, methyl, cyano, or halogen;
$R^{7a}$, $R^{7b}$ and $R^{7c}$ are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, alkoxy of 1 to 6 carbon atoms, cyano, nitro, alkoxycarbonyl of 1 to 6 carbon atoms, alkylcarbonyl of 1 to 6 carbon atoms, alkylamino of 1 to 6 carbon atoms, and —N($R^{4h}$)($R^{4i}$)

R⁸ is hydrogen, hydroxy, amino, straight chain alkyl of 1 to 6 carbon atoms or branched chain alkyl of 3 to 7 carbon atoms;

R⁹, R¹⁰, R¹¹ and R¹¹ᵇ are independently hydrogen or alkyl of 1 or 2 carbon atoms;

R¹²ᵃ and R¹²ᵇ are independently hydrogen, straight chain alkyl of 1 to 6 carbon atoms, alkenyl of 2 to 6 carbon atoms, alkynyl of 2 to 4 carbon atoms, hydroxyalkyl of 2 to 4 carbon atoms, carboxy, alkoxy-carbonyl of 1 to 6 carbon atoms, alkoxy of 1 to 6 carbon atoms, thiol, alkylthio of 1 to 4 carbon atoms, alkylamino of 1 to 4 carbon atoms, —N(R¹²ᶜ)(R¹²ᵈ) or trifluoromethyl;

R¹²ᶜ and R¹²ᵈ, independent from each other, are straight chain alkyl of 1 to 4 carbon atoms;

R¹³ is independently hydrogen, alkyl of 1 or 2 carbon atoms, hydroxy, amino, halogen, hydroxymethyl, or aminomethyl;

R¹⁴ is hydrogen, alkyl of 1 or 2 carbon atoms, or halogen;

R¹⁵ is hydrogen or cyano;

R¹⁶ is a moiety selected from the group:

[chemical structures]

R²³ is —NH—C(O)—R¹ and Cl;

R²⁴ is a moiety selected from the group:

[chemical structures]

R²ᵃ and R²ᵇ are independently hydrogen, straight chain alkyl of 1 to 6 carbon atoms optionally substituted with trifluoromethyl, branched chain alkyl of 3 to 8 carbon atoms or benzyl, with the proviso that each independent R²ᵃ and R²ᵇ may not simultaneously be hydrogen or a pharmaceutically acceptable salt;

or a pharmaceutically acceptable salt thereof.

Among the more preferred pharmaceutically acceptable salts of compounds of Formulae (I), (II), (III), (IV) and (V) included in this invention are sodium, potassium, calcium, magnesium or ammonium salts.

Among the preferred groups of compounds of Formula (I) of this invention including pharmaceutically acceptable salts thereof are those in the subgroups below, wherein the other variables of Formula I in the subgroups are as defined above wherein:

a)

R¹ is a moiety selected from the group:

[chemical structures]

b)

R¹ is a moiety selected from the group:

[chemical structures]

-continued

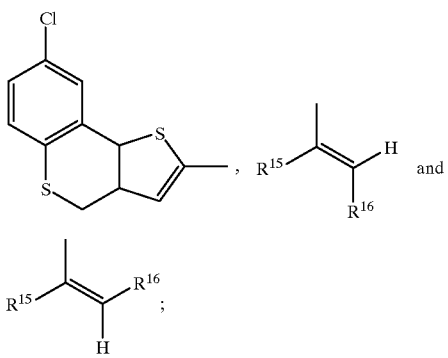
and

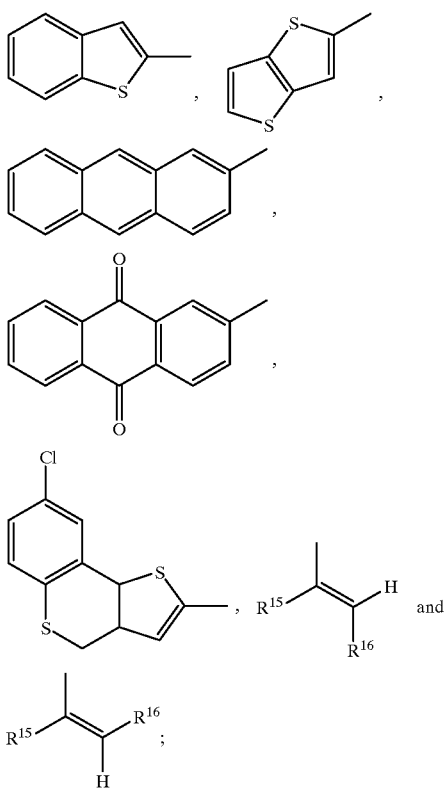

c)

R$^1$ is a moiety selected from the group:

R$^{15}$ is hydrogen;
R$^{16}$ is a moiety selected from the group:

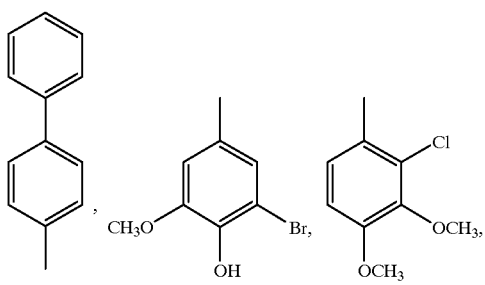

-continued

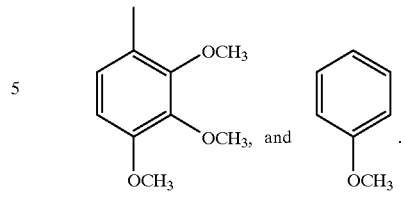

Also among the most preferred groups of compounds of Formula (I) of this invention including pharmaceutically acceptable salts thereof are those in the subgroups below, wherein the other variables of Formula (I) in the subgroups are as defined above wherein:

a)

R$^1$ is a moiety selected from the group:

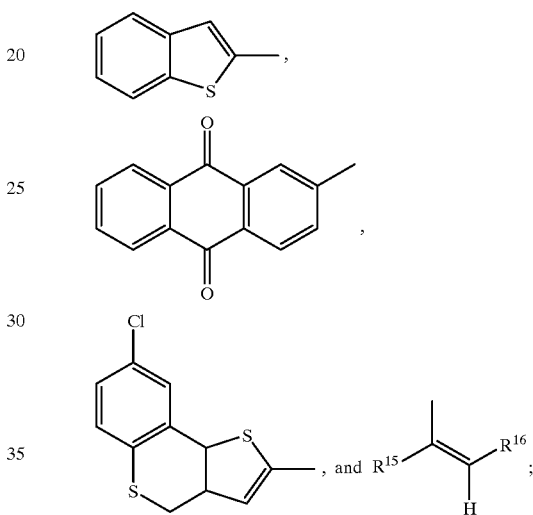

R$^{15}$ is hydrogen;
R$^{16}$ is a moiety selected from the group:

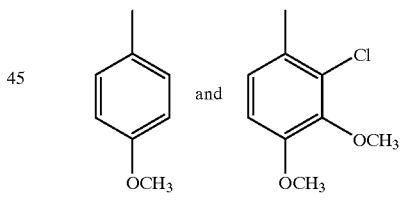

Also among the most particularly preferred compounds of this invention according to general Formula (I) are the following compounds or a pharmaceutically acceptable salt thereof, particularly including the disodium salt form thereof:

3,7-bis-[(benzo[b]thiophene-2-carbonyl)amino] dibenzothiophene-2,8-dicarboxylic acid, 3,7-bis[(2-anthracenylcarbonyl)amino]-2,8-dibenzothiophene-2,8-dicarboxylic acid, 3,7-bis{[(9,10-dihydro-9,10-dioxo-2-anthracenyl) carbonyl]amino}-dibenzothiophene-2,8-dicarboxylic acid, 3,7-bis[(thieno[3,2-b]thien-2-ylcarbonyl) amino] dibenzothiophene-2,8-dicarboxylic, 3,7-bis-[(8-chloro-4H-thieno[3,2-c][1]benzothiopyran-2-carbonyl)amino]dibenzothiophene-2,8-dicarboxylic acid, 3,7-bis-[3-(2-chloro-3,4-dimethoxyphenyl)
   acryloylamino]dibenzothiophene-2,8-dicarboxylic
   acid,
3,7-bis-(3-biphenyl-4-ylacryloylamino)
   dibenzothiophene-2,8-dicarboxylic acid,
3,7-bis-[3-(3-bromo-4-hydroxy-5-methoxyphenyl)
   acryloylamino]dibenzothiophene-2,8-dicarboxylic
   acid,
3,7-bis-[3-(2,3,4-trimethoxyphenyl)acryloylamino]
   dibenzothiophene-2,8-dicarboxylic acid,
3,7-bis{[3-(4-methoxyphenyl)acryloylamino]-
   dibenzothiophene-2,8-dicarboxylic acid.

Among the preferred groups of compounds of Formula (II) of this invention including pharmaceutically acceptable salts thereof are those in the subgroups below, wherein the other variables of Formula (II) in the subgroups are as defined above wherein:

a)
   $R^1$ is a moiety selected from the group:

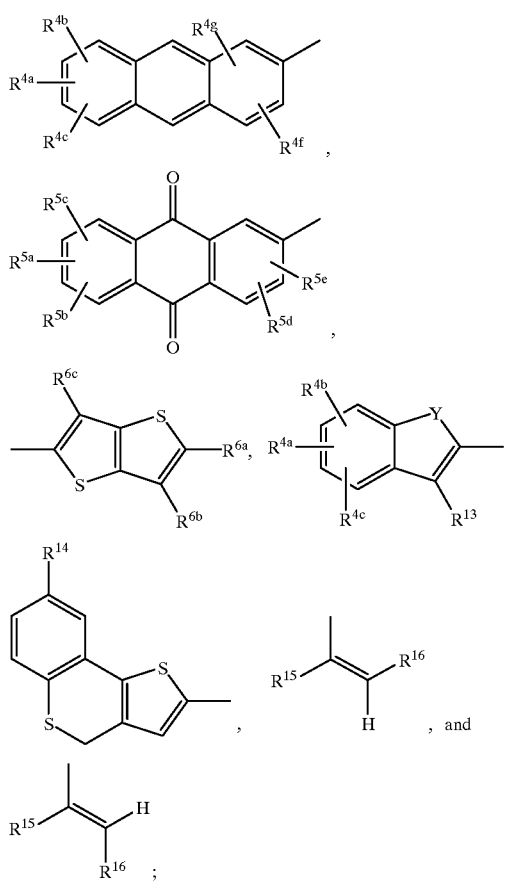

b)
   $R^1$ is a moiety selected from the group:

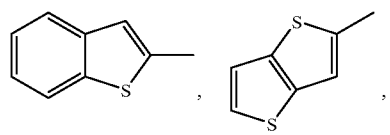

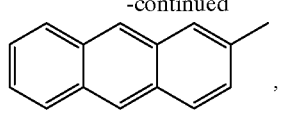

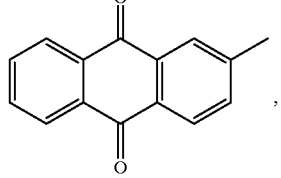

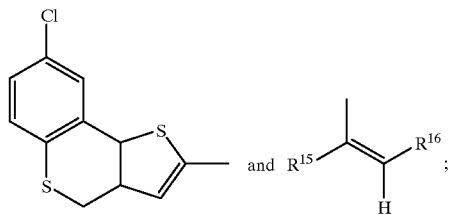

c)
   $R^1$ is a moiety selected from the group:

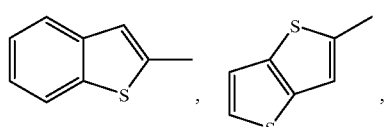

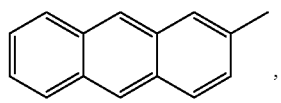

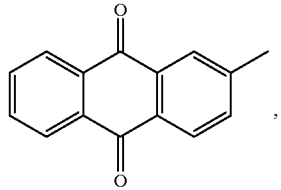

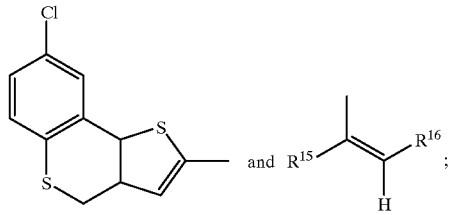

$R^{15}$ is hydrogen;
$R^{16}$ a moiety selected from the group:

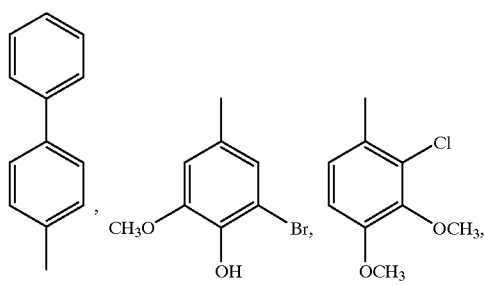

-continued

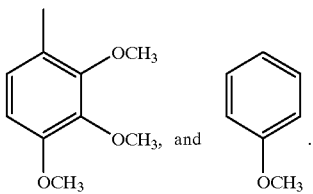

Also among the most preferred groups of compounds of this invention according to general Formula (II) including pharmaceutically acceptable salts thereof are those in the subgroups below wherein the other variables of Formula (II) in the subgroups are as defined above wherein:

a)

$R^1$ is a moiety selected from the group:

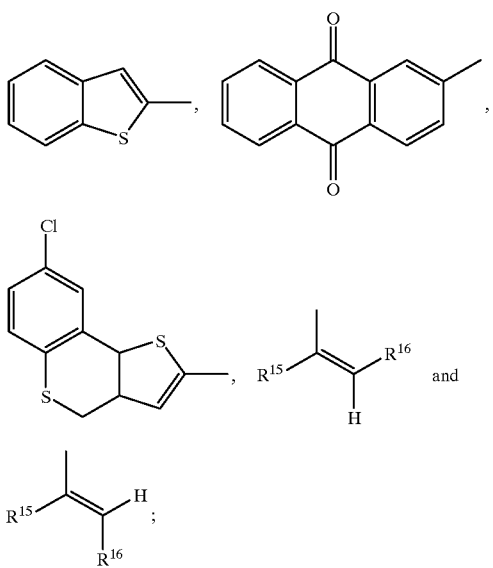

$R^{15}$ is hydrogen;

$R^{16}$ a moiety selected from the group:

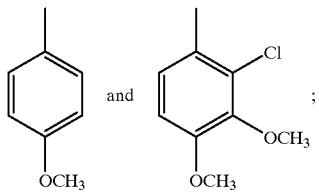

b)

$R^1$ is selected from

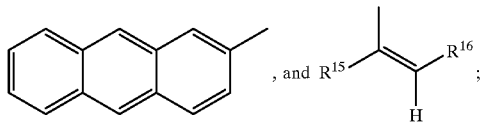

$R^{15}$ is hydrogen;

$R^{16}$ a moiety selected from the group:

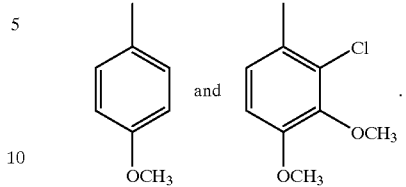

Also among the most particularly preferred compounds of this invention according to general Formula (II) are the following compounds or a pharmaceutically acceptable salt thereof, particularly including the disodium salt form thereof:

3-[(2-anthracenylcarbonyl)amino]-7-chlorodibenzothiophene-2,8-dicarboxylic acid, 3-chloro-7-[2-(2-chloro-3,4-di-methoxyphenyl)acryloylamino]dibenzothiophene-2,8-dicarboxylic acid.

Among the preferred groups of compounds of Formula (III) including pharmaceutically acceptable salts thereof of this invention are those in the subgroups below wherein the other variables of Formula (III) in the subgroups are as defined above wherein:

a)

$R^1$ is a moiety selected from the group:

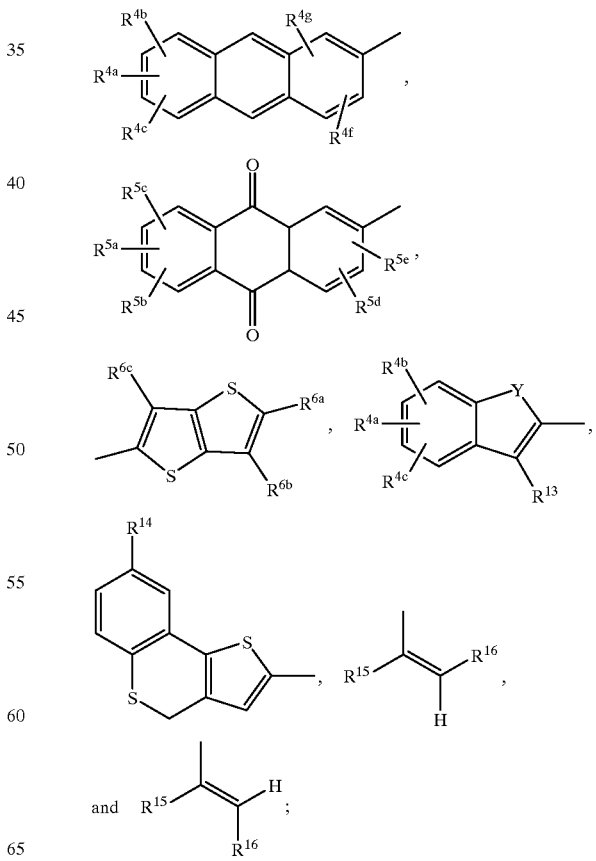

b)
R[1] is a moiety selected from the group:

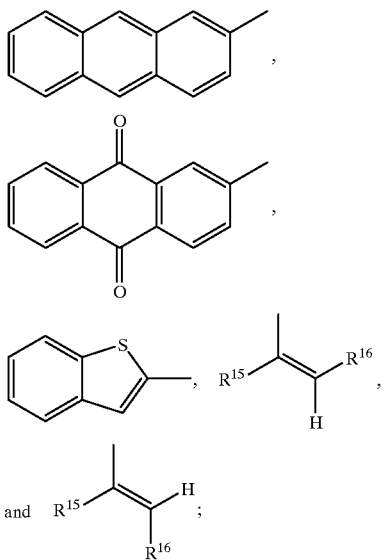

R[2a] and R[2b] are independently hydrogen or ethyl with the proviso that each independent R[2a] and R[2b] may not simultaneously be hydrogen or a pharmaceutically acceptable salt;
R[15] is hydrogen;
R[16] is a moiety selected from the group:

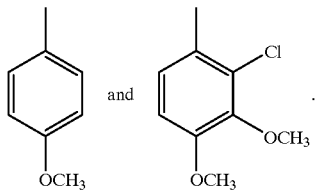

Among the most preferred groups of compounds of this invention according to general Formula (III) including pharmaceutically acceptable salts thereof are those in the subgroups below, wherein the other variables of Formula (III) in the subgroups are as defined above wherein:
a)
R[1] is a moiety selected from the group:

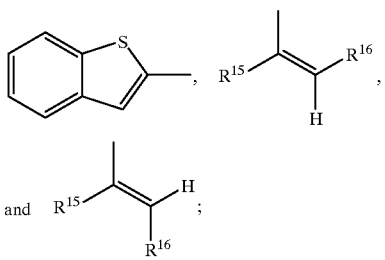

R[2a] and R[2b] are independently hydrogen or ethyl with the proviso that each independent R[2a] and R[2b] may not simultaneously be hydrogen or a pharmaceutically acceptable salt;

R[15] is hydrogen;
R[16] is

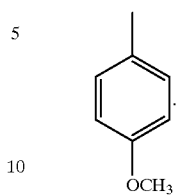

Also among the most particularly preferred compounds of this invention according to general Formula (III) are the following compounds or a pharmaceutically acceptable salt thereof, particularly including the disodium salt form thereof:

[3,7-bis-[(benzo[b]thiophene-2-carbonyl)amino]-8-(ethoxyhydroxyphosphoryl)-5,5-dioxo-5H-5λ[6]-dibenzothiophen-2-yl]phosphonic acid monoethyl ester,

[3,7-bis-[(9,10-dioxo-9,10-dihydroanthracene-2-carbonyl)amino]-8-(ethoxyhydroxyphosphoryl)-5,5-dioxo-5H-5λ[6]-dibenzothiophen-2-yl]phosphonic acid monoethyl ester,

[3,7-bis-[(anthracene-2-carbonyl)amino]-8-(ethoxyhydroxyphosphoryl)-5,5-dioxo-5H-5λ[6]-dibenzothiophen-2-yl]phosphonic acid monoethyl ester,

[3,7-bis-[3-(2-chloro-3,4-dimethoxyphenyl)acryloylamino]-8-(ethoxyhydroxyphosphoryl)-5,5-dioxo-5H-5λ[6]-dibenzothiophen-2-yl]-phosphonic acid monoethyl ester,

[3,7-bis-[4-methoxyphenyl]-acryloylamino]-8-(ethoxyhydroxyphosphoryl)-5,5-dioxo-5H-5λ[6]-dibenzothiophen-2-yl]phosphonic acid monoethyl ester.

Also among the most particularly preferred compounds of this invention according to general Formula (III) is the following compound or a pharmaceutically acceptable salt thereof, particularly including the monosodium salt form thereof:

[3,7-bis-[(benzo[b]thiophene-2-carbonyl) amino]-8-(ethoxyhydroxyphosphoryl)-5,5-dioxo-5H-5λ[6]-dibenzothiophen-2-yl]phosphonic acid monoethyl ester.

Among the preferred groups of compounds of Formula (IV) including pharmaceutically acceptable salts thereof of this invention are those in the subgroups below, wherein the other variables of Formula (IV) in the subgroups are as defined above wherein:
a)
R[1a] is a moiety selected from the group:

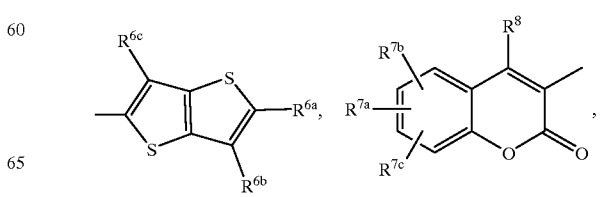

19
-continued
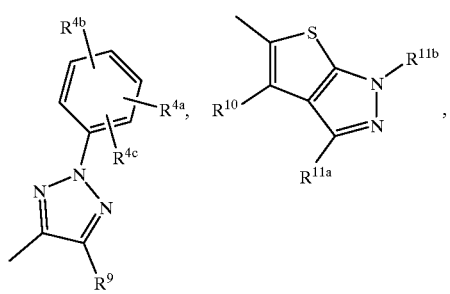
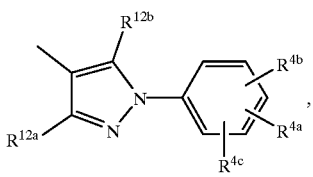
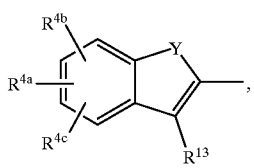
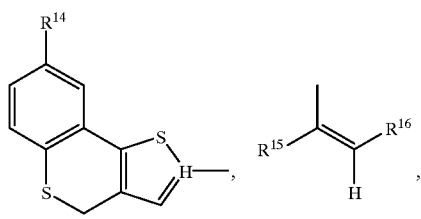
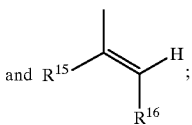
b)
$R^{1a}$ is a moiety selected from the group:
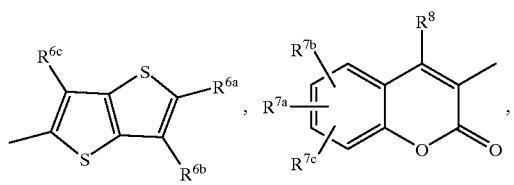
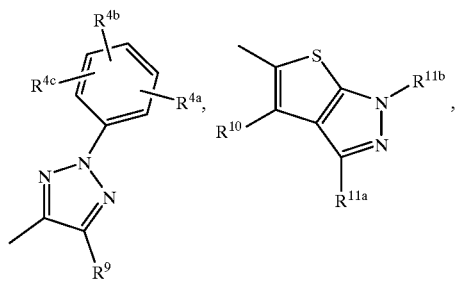
20
-continued
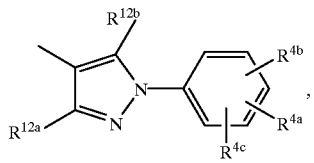
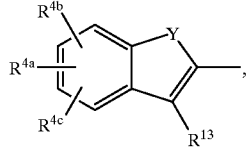
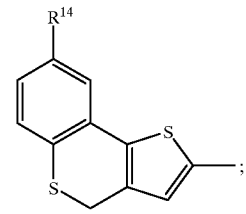
and
c)
$R^{1a}$ is a moiety selected from the group:
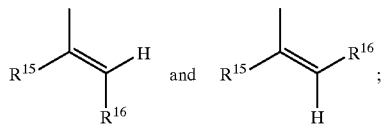
d)
$R^{1a}$ is a moiety selected from the group:
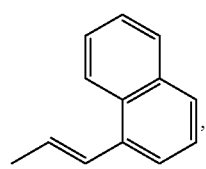
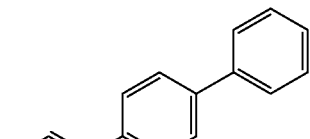
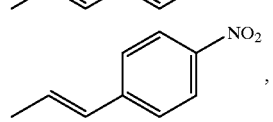
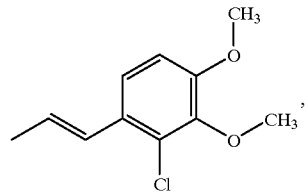
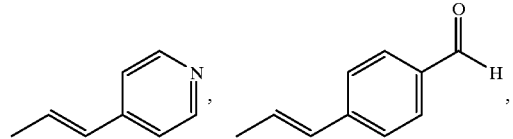

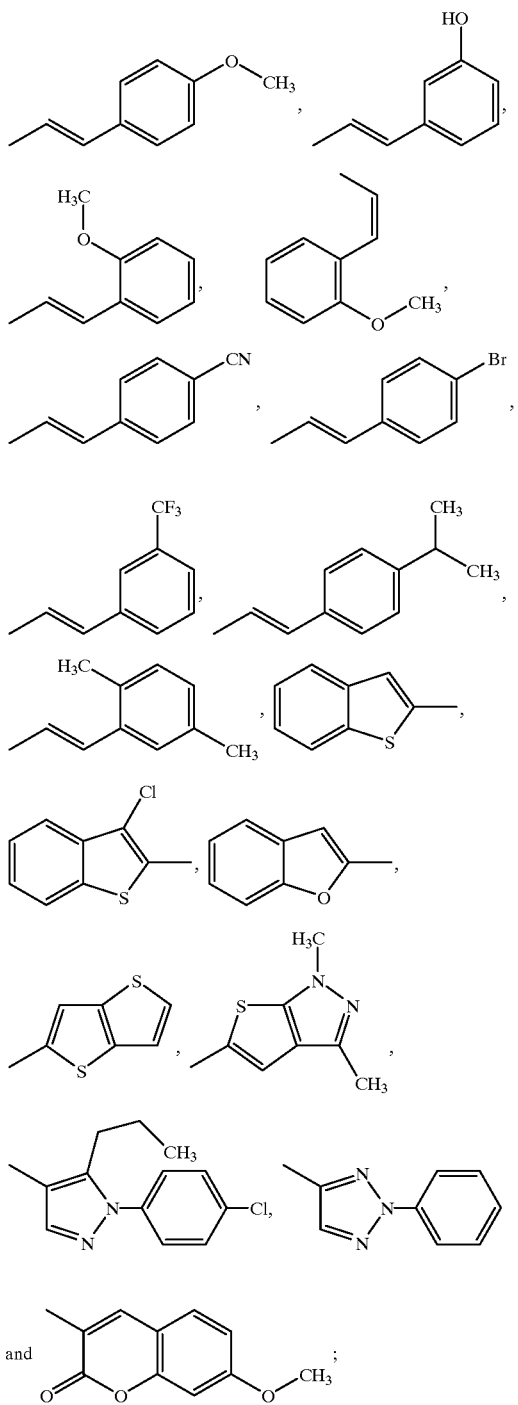
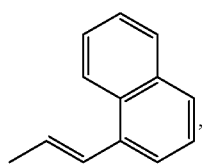
e)
R[1a] is a moiety selected from the group:
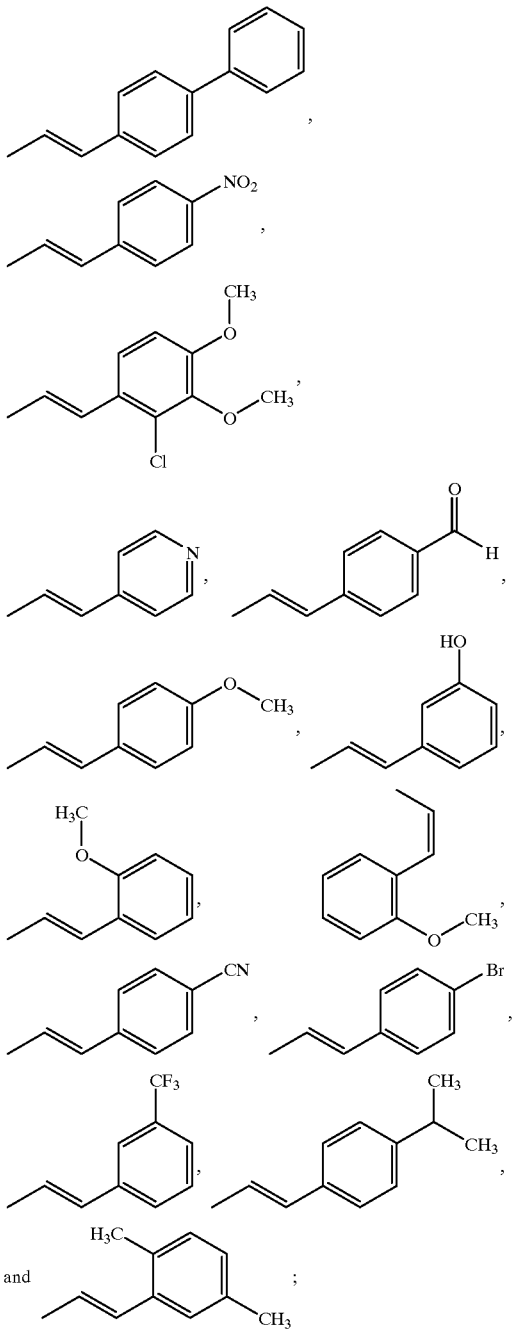
f)
R[1a] is a moiety selected from the group:
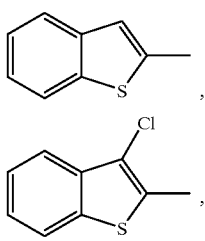

23

-continued

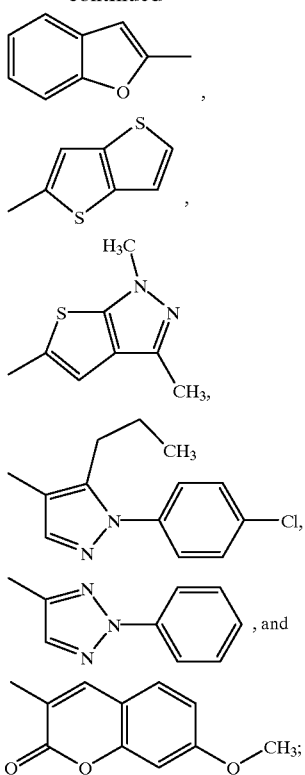

g) $R^{1a}$ is a moiety selected from the group:

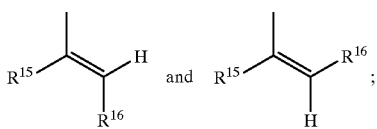

$R^{16}$ is a moiety selected from the group:

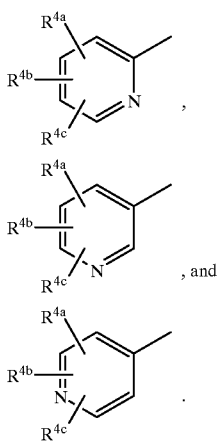

Among the most preferred groups of compounds of Formula (IV) including pharmaceutically acceptable salts thereof of this invention are those in the subgroups below including the pharmaceutically acceptable salts thereof wherein the other variables of Formula (IV) in the subgroups are as defined above wherein:

24 a) $R^{1a}$ is a moiety selected from the group:

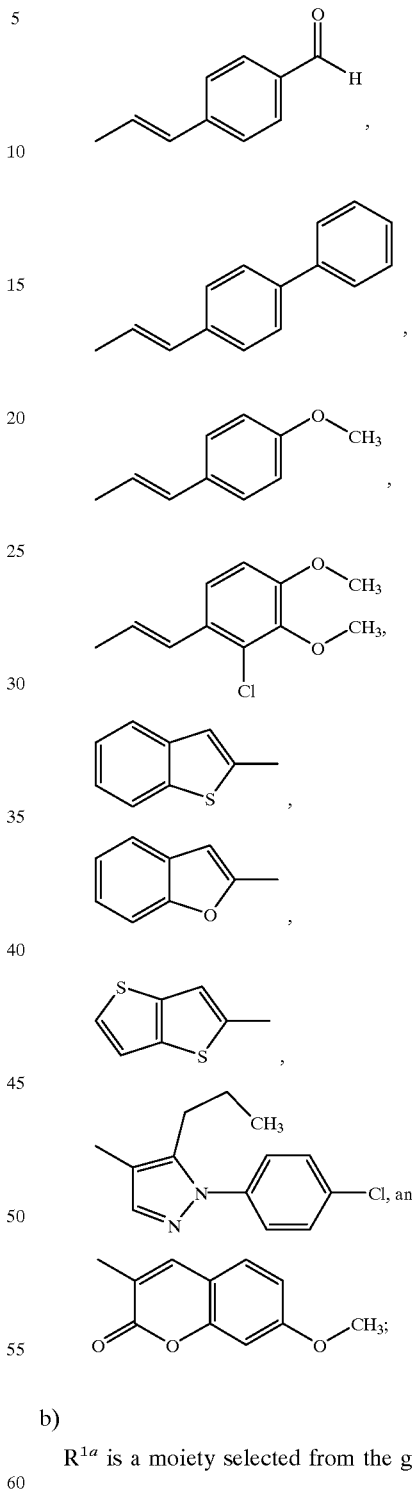

b) $R^{1a}$ is a moiety selected from the group:

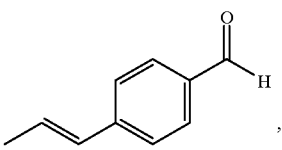

-continued

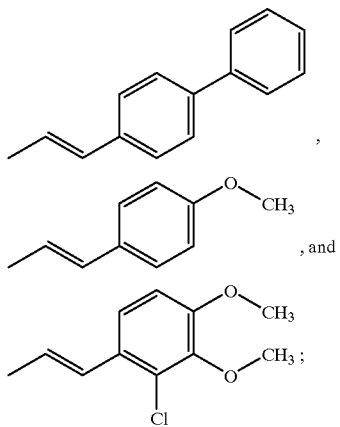, and

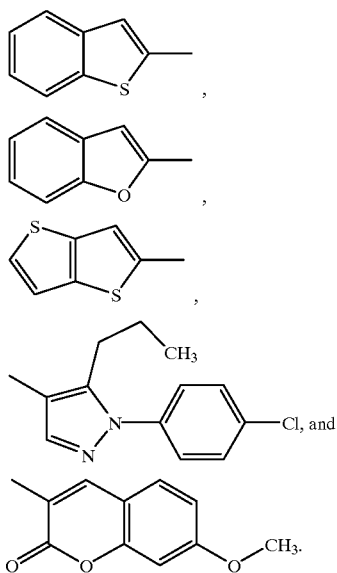

c) $R^{1a}$ is a moiety selected from the group:

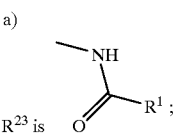,

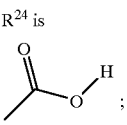,

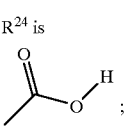,

Also among the most particularly preferred compounds of this invention according to general Formula (IV) are the following compounds or a pharmaceutically acceptable salt thereof, particularly including the disodium salt form thereof:

3,7-bis-[3-(4-nitrophenyl)acryloylamino]-5,5-dioxo-5H-5$\lambda^6$-dibenzothiophene-2,8-disulfonic acid, 3,7-bis-(3-naphthalen-1-ylacryloylamino)-5,5-dioxo-5H-5$\lambda^6$-dibenzothiophene-2,8-disulfonic acid, 3,7-bis-[3-(4-phenylphenyl)acryloylamino]-5,5-dioxo-5H-5$\lambda^6$-dibenzothiophene-2,8-disulfonic acid, 3,7-bis-[3-(2-chloro-3,4-di-methoxyphenyl)acryloylamino]-5,5-dioxo-5H-5$\lambda^6$-dibenzothiophene-2,8-disulfonic acid, 5,5-dioxo-3,7-bis-(3-pyridin-4-ylacryloylamino)-5H-5$\lambda^6$-dibenzothiophene-2,8-disulfonic acid, 3,7-bis-[3-(4-formylphenyl)acryloylamino]-5,5-dioxo-5H-5$\lambda^6$-dibenzothiophene-2,8-disulfonic acid, 3,7-bis-[3-(4-methoxyphenyl)acryloylamino]-5,5-dioxo-5H-5$\lambda^6$-dibenzothiophene-2,8-disulfonic acid, 3,7-bis-[(E)-3-(3-hydroxyphenyl)acryloyl amino]-5,5-dioxo-5H-5$\lambda^6$-dibenzothiophene-2,8-disulfonic acid, 3,7-bis-[3-(4-cyanophenyl)acryloyiamino]-5,5-dioxo-5H-5$\lambda^6$-dibenzothiophene-2,8-disulfonic acid, 3,7-bis-[3-(4-bromophenyl)acryloylamino]-5,5-dioxo-5H-5$\lambda^6$-dibenzothiophene-2,8-disulfonic acid, 3,7-bis-[3-(2-methoxyphenyl)acryloylamino]-5,5-dioxo-5H-5$\lambda^6$-dibenzothiophene-2,8-disulfonic acid, 3,7-bis-[3-(2,5-dimethylphenyl)acryloylamino]-5,5-dioxo-5H-5$\lambda^6$-dibenzothiophene-2,8-disulfonic acid, 3,7-bis-[3-(4-isopropylphenyl)acryloylamino]-5,5-dioxo-5H-5$\lambda^6$-dibenzothiophene-2,8-disulfonic acid, 3,7-bis-[3-(2-methoxyphenyl)acryloylamino]-5,5-dioxo-5H-5$\lambda^6$-dibenzothiophene-2,8-disulfonic acid, 3,7-bis-[3-(3-trifluoromethylphenyl)acryloylamino]-5,5-dioxo-5H-5$\lambda^6$-dibenzothiophene-2,8-disulfonic acid, 3,7-bis-[(benzo[b]thiophene-2-carbonyl)amino]-5,5-dioxo-5H-5$\lambda^6$-dibenzothiophene-2,8-disulfonic acid, 3,7-bis-[(benzo[b]thiophene-2-carbonyl-3-chloro)amino]-5,5-dioxo-5H-5$\lambda^6$-dibenzothiophene-2,8-disulfonic acid, 3,7-bis-[(benzo[b]furan-2-carbonyl)amino]-5,5-dioxo-5H-5$\lambda^6$-dibenzothiophene-2,8-disulfonic acid, 5,5-dioxo-3,7-bis-[(thieno[3,2-b]thiophene-2-carbonyl)amino]-5H-5$\lambda^6$-dibenzothiophene-2,8-disulfonic acid, 3,7-bis-[(1,3-dimethyl-1H-thieno [2,3-c]pyrazole-5-carbonyl)amino]-5,5-dioxo-5H-5$\lambda^6$-dibenzothiophene-2,8-disulfonic acid, 3,7-bis-{[1-(4-chlorophenyl)-5-propyl-1H-pyrazole-4-carbonyl]amino}-5,5-dioxo-5H-5$\lambda^6$-dibenzothiophene-2,8-disulfonic acid, 5,5-dioxo-3,7-bis-[(2-phenyl-2H-[1,2,3]triazole-4-carbonyl)amino]-5H-5$\lambda^6$-dibenzothiophene-2,8-disulfonic acid, 3,7-bis-[(7-methoxy-2-oxo-benzopyran-3-yl)carbonylamino]-5,5-dioxo-5H-5$\lambda^6$-dibenzothiophene-2,8-disulfonic acid.

Among the preferred groups of compounds of Formula (V) including pharmaceutically acceptable salts thereof of this invention having antiangiogenic activity for the method of treating or inhibiting abnormal angiogenic growth are those in which $R^{23}$ and $R^{24}$ are as shown in the subgroups below, wherein the other variables of Formula (V) in the subgroups are as defined above wherein:

a)

$R^{23}$ is 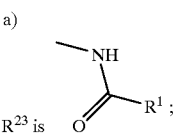;

$R^{24}$ is 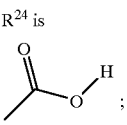;

b)

$R^{23}$ is Cl;

$R^{24}$ is

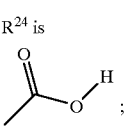;

-continued c)

$R^{23}$ is 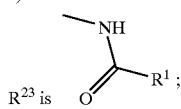;

$R^{24}$ is

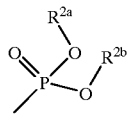

d)

$R^{23}$ is 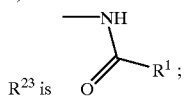;

$R^{24}$ is

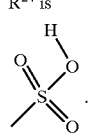

Among the most preferred groups of compounds of Formula (V) including pharmaceutically acceptable salts thereof of this invention having antiangiogenic activity for the method of treating or inhibiting abnormal angiogenic growth are those in which $R^{23}$ and $R^{24}$ are as shown in the subgroups below, wherein the other variables of Formula (V) in the subgroups are as defined above wherein:

a)

$R^1$ is a moiety selected from the group:

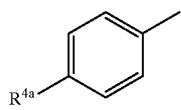,

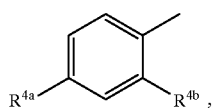,

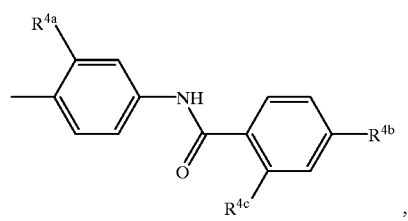,

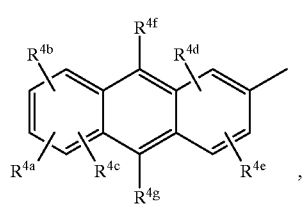,

-continued

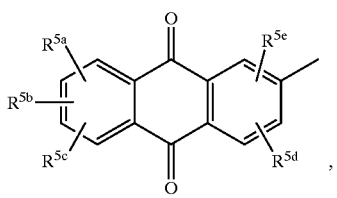,

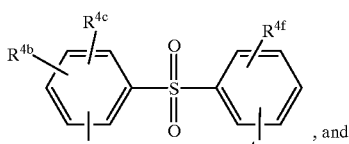, and

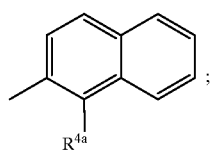;

b)

$R^1$ is a moiety selected from the group:

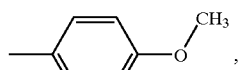,

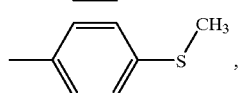,

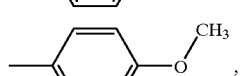,

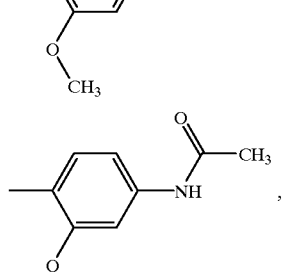,

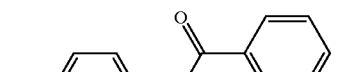,

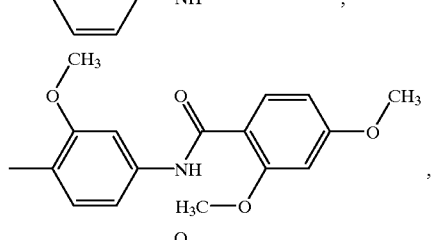,

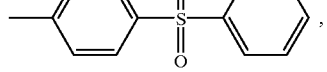,

-continued

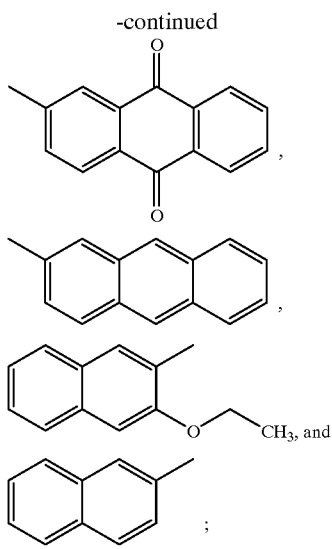

c)
R$^1$ is a moiety selected from the group:

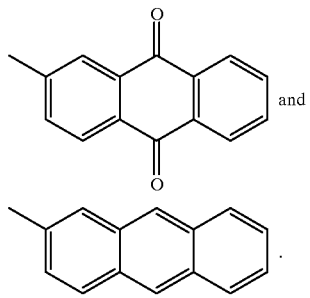

Among the most particularly preferred compounds of Formula (V) or a pharmaceutically acceptable salt thereof, particularly including the disodium salt form thereof of this invention having antiangiogenic activity for the method of treating or inhibiting abnormal angiogenic growth are:

3,7-bis-[(benzo[b]thiophene-2-carbonyl)amino] dibenzothiophene-2,8-dicarboxylic acid, 3,7-bis[(2-anthracenylcarbonyl)amino]-2,8-dibenzothiophene-2,8-dicarboxylic acid, 3,7-bist[(9,10-dihydro-9,10-dioxo-2-anthracenyl) carbonyl]amino}-dibenzothiophene-2,8-dicarboxylic acid, 3,7-bis[(thieno[3,2-b]thien-2-ylcarbonyl) amino] dibenzothiophene-2,8-dicarboxylic acid, 3,7-bis-[(8-chloro-4H-thieno[3,2-c][1]benzothiopyran-2-carbonyl)amino]dibenzothiophene-2,8-dicarboxylic acid, 3,7-bis-[3-(2-chloro-3,4-dimethoxyphenyl) acryloylamino]dibenzothiophene-2,8-dicarboxylic acid, 3,7-bis-(3-biphenyl-4-ylacryloylamino) dibenzothiophene-2,8-dicarboxylic acid, 3,7-bis-[3-(3-bromo-4-hydroxy-5-methoxyphenyl) acryloylamino]dibenzothiophene-2,8-dicarboxylic acid, 3,7-bis-[3-(2,3,4-trimethoxyphenyl)acryloylamino] dibenzothiophene-2,8-dicarboxylic acid, 3,7-bist[3-(4-methoxyphenyl)acryloylamino]-dibenzothiophene-2,8-dicarboxylic acid, 3-[(2-anthracenylcarbonyl)amino]-7-chlorodibenzothiophene-2,8-dicarboxylic acid, 3-chloro-7-[2-(2-chloro-3,4-dimethoxyphenyl) acryloylamino]dibenzothiophene-2,8-dicarboxylic acid,

[3,7-bis-[(benzo[b]thiophene-2-carbonyl)amino]-8-(ethoxyhydroxyphosphoryl)-5,5-dioxo-5H-5λ$^6$-dibenzothiophen-2-yl]phosphonic acid monoethyl ester,

[3,7-bis-[(9,10-dioxo-9,10-dihydroanthracene-2-carbonyl)amino]-8-(ethoxyhydroxyphosphoryl)-5,5-dioxo-5H-5λ$^6$-dibenzothiophen-2-yl]phosphonic acid monoethyl ester,

[3,7-bis-[(anthracene-2-carbonyl)amino]-8-(ethoxyhydroxyphosphoryl)-5,5-dioxo-5H-5λ$^6$-dibenzothiophen-2-yl]phosphonic acid monoethyl ester,

[3,7-bis-[3-(2-chloro-3,4-dimethoxyphenyl) acryloylamino]-8-(ethoxyhydroxyphosphoryl)-5,5-dioxo-5H-5λ$^6$-dibenzothiophen-2-yl]-phosphonic acid monoethyl ester,

[3,7-bis-[4-methoxyphenyl]-acryloylamino]-8-(ethoxyhydroxyphosphoryl)-5,5-dioxo-5H-5λ$^6$-dibenzothiophen-2-yl]phosphonic acid monoethyl ester, 3,7-bis-[3-(4-nitrophenyl)acryloylamino]-5,5-dioxo-5H-5λ$^6$-dibenzothiophene-2,8-disulfonic acid, 3,7-bis-(3-naphthalen-1-ylacryloylamino)-5,5-dioxo-5H-5λ$^6$-dibenzothiophene-2,8-disulfonic acid, 3,7-bis-[3-(4-phenylphenyl)acryloylamino]-5,5-dioxo-5H-5λ$^6$-dibenzothiophene-2,8-disulfonic acid, 3,7-bis-[3-(2-chloro-3,4-dimethoxyphenyl) acryloylamino]-5,5-dioxo-5H-5λ$^6$-dibenzothiophene-2,8-disulfonic acid, 5,5-dioxo-3,7-bis-(3-pyridin-4-ylacryloylamino)-5H-5λ$^6$-dibenzothiophene-2,8-disulfonic acid, 3,7-bis-[3-(4-formylphenyl)acryloylamino]-5,5-dioxo-5H-5λ$^6$-dibenzothiophene-2,8-disulfonic acid, 3,7-bis-[3-(4-methoxyphenyl)acryloylamino]-5,5-dioxo-5H-5λ$^6$-dibenzothiophene-2,8-disulfonic acid, 3,7-bis-[(E)-3-(3-hydroxyphenyl)acryloylamino]-5,5-dioxo-5H-5,6-dibenzothiophene-2,8-disulfonic acid, 3,7-bis-[3-(4-cyanophenyl)acryloylamino]-5,5-dioxo-5H-5λ$^6$-dibenzothiophene-2,8-disulfonic acid, 3,7-bis-[3-(4-bromophenyl)acryloylamino]-5,5-dioxo-5H-5λ$^6$-dibenzothiophene-2,8-disulfonic acid, 3,7-bis-[3-(2-methoxyphenyl)acryloylamino]-5,5-dioxo-5H-5λ$^6$-dibenzothiophene-2,8-disulfonic acid, 3,7-bis-[3-(2,5-dimethylphenyl)acryloylamino]-5,5-dioxo-5H-5λ$^6$-dibenzothiophene-2,8-disulfonic acid, 3,7-bis-[3-(4-isopropylphenyl)acryloylamino]-5,5-dioxo-5H-5λ$^6$-dibenzothiophene-2,8-disulfonic acid, 3,7-bis-[3-(2-methoxyphenyl)acryloylamino]-5,5-dioxo-5H-5λ$^6$-dibenzothiophene-2,8-disulfonic acid, 3,7-bis-[3-(3-trifluoromethylphenyl)acryloylamino]-5,5-dioxo-5H-5λ$^6$-dibenzothiophene-2,8-disulfonic acid, 3,7-bis-[(benzo[b]thiophene-2-carbonyl)amino]-5,5-dioxo-5H-5λ⁶-dibenzothiophene-2,8-disulfonic acid, 3,7-bis-[(benzo[b]thiophene-2-carbonyl-3-chloro)amino]-5,5-dioxo-5H-5λ⁶-dibenzothiophene-2,8-disulfonic acid, 3,7-bis-[(benzo[b]furan-2-carbonyl)amino]-5,5-dioxo-5H-5λ⁶-dibenzothiophene-2,8-disulfonic acid, 5,5-dioxo-3,7-bis-[(thieno[3,2-b]thiophene-2-carbonyl)amino]-5H-5λ⁶-dibenzothiophene-2,8-disulfonic acid, 3,7-bis-[(1,3-dimethyl-1H-thieno [2,3-c]pyrazole-5-carbonyl)amino]-5,5-dioxo-5H-5λ⁶-dibenzothiophene-2,8-disulfonic acid, 3,7-bis-{[1-(4-chlorophenyl)-5-propyl-1H-pyrazole-4-carbonyl]amino}-5,5-dioxo-5H-5λ⁶-dibenzothiophene-2,8-disulfonic acid, 5,5-dioxo-3,7-bis-[(2-phenyl-2H-[1,2,3]triazole-4-carbonyl)amino]-5H-5λ⁶-dibenzothiophene-2,8-disulfonic acid, 3,7-bis-[(7-methoxy-2-oxo-benzopyran-3-yl)carbonylamino]-5,5-dioxo-5H-5λ⁶-dibenzothiophene-2,8-disulfonic acid.

Among the most particularly preferred compounds of this invention according to general Formula (V) is the following compound or a pharmaceutically acceptable salt thereof, particularly including the monosodium salt form thereof:

[3,7-bis-[(benzo[b]thiophene-2-carbonyl)amino]-8-(ethoxyhydroxyphosphoryl)-5,5-dioxo-5H-5λ⁶-dibenzothiophen-2-yl]-phosphonic acid monoethyl ester.

Also among the most particularly preferred compounds of this invention according to general Formula (V) are the following compounds or a pharmaceutically acceptable salt thereof, particularly including the disodium salt form thereof:

3,7-bis-(4-methoxybenzoylamino)-5,5-dioxo-5H-5λ⁶-dibenzothiophene-2,8-disulfonic acid, 3,7-bis-(2,4-dimethoxybenzoylamino)-5,5-dioxo-5H-5λ⁶-dibenzothiophene-2,8-disulfonic acid, 5,5-dioxo-3,7-bis-(4-phenylsulfonylbenzoylamino)-5H-5λ⁶-dibenzothiophene-2,8-disulfonic acid, 3,7-bis-(3-ethoxynaphthalen-2-ylcarbonylamino)-5,5-dioxo-5H-5λ⁶-dibenzothiophene-2,8-disulfonic acid, 3,7-bis-(anthracen-2-ylcarbonylamino)-5,5-dioxo-5H-5λ⁶-dibenzothiophene-2,8-disulfonic acid, 3,7-bis-[(9,10-dihydro-9,10-dioxoanthracen-2-yl)carbonyl-amino]-5,5-dioxo-5H-5λ⁶-dibenzothiophene-2,8-disulfonic acid, 3,7-bis-(4-ethylthiobenzoylamino)-5,5-dioxo-5H-5λ⁶-dibenzothiophene-2,8-disulfonic acid, 3,7-bis-[(naphthalen-2-yl)carbonylamino]-5,5-dioxo-5H-5λ⁶-dibenzothiophene-2,8-disulfonic acid, 3,7-bis-({4-[(2,4-dimethoxyphenyl)carbonylamino]-2-methoxyphenyl}carbonylamino)-5,5-dioxo-5H-5λ⁶-dibenzothiophene-2,8-disulfonic acid, 3,7-bis-[(4-acetylamino-2-methoxyphenyl)carbonylamino]-5,5-dioxo-5H-5λ⁶-dibenzothiophene-2,8-disulfonic acid, 3,7-bis-4(benzoylaminobenzoylamino)-5,5-dioxo-5H-5λ⁶-dibenzothiophene-2,8-disulfonic acid.

Also included in the present invention are compounds useful as intermediates for producing the above compounds of general Formulae (I), (II), (III), (IV) and (V.) Such intermediates include those having the Formula (VI) and (VII):

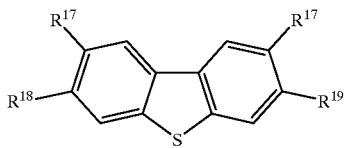

(VI)

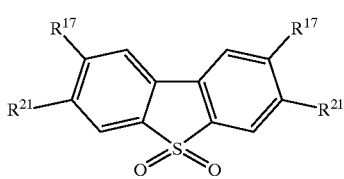

(VII)

wherein:

$R^1$ is a moiety selected from the group:

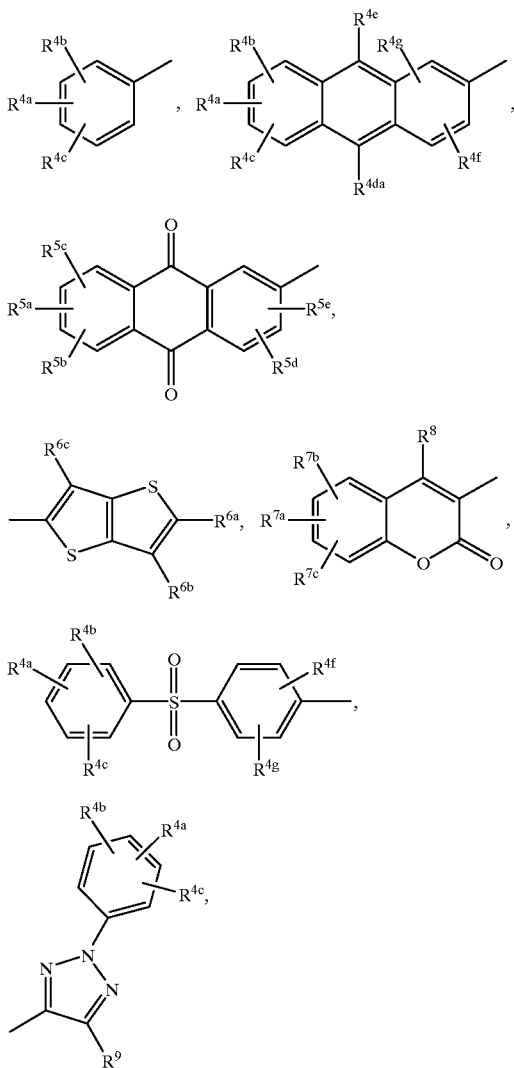

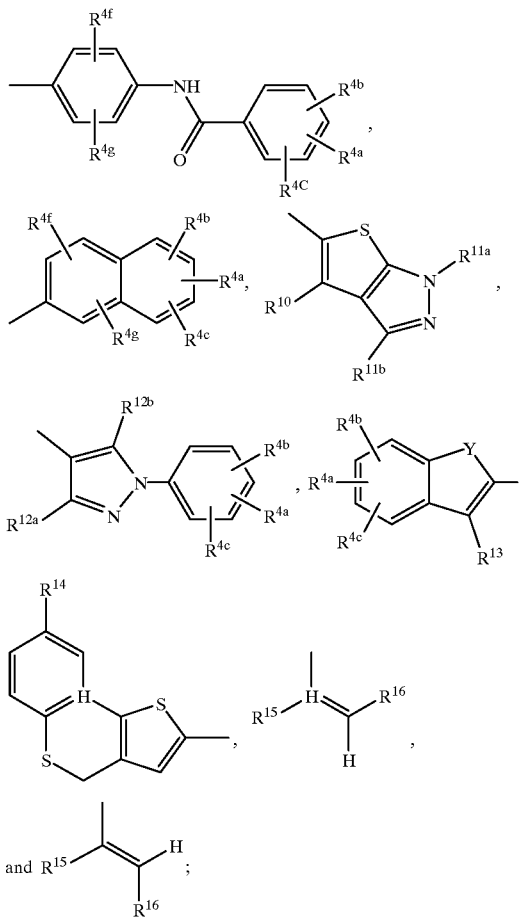

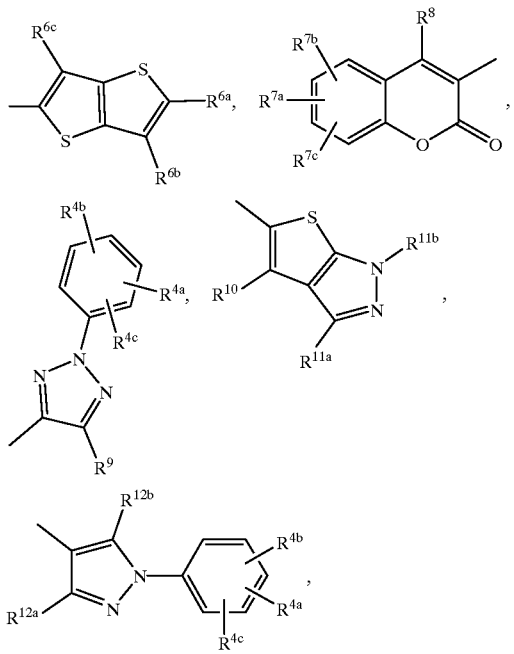

Y is sulfur, oxygen, nitrogen or carbon;

$R^{1a}$ is a moiety selected from the group:

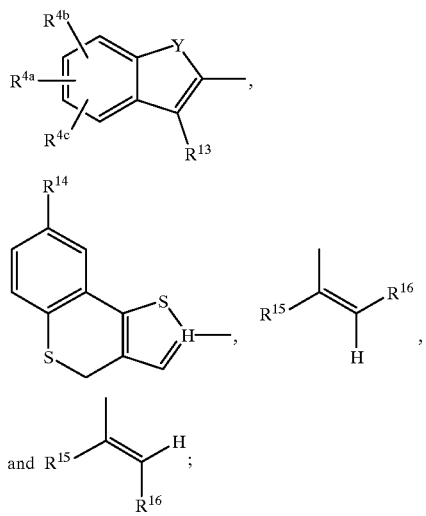

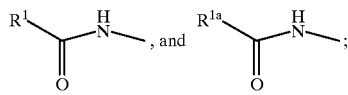

$R^{17}$ is —CN or a moiety —COOR$^3$;

$R^3$ is hydrogen, straight chain alkyl of 1 to 5 carbon atoms, branched chain alkyl of 3 to 5 carbon atoms or benzyl;

$R^{18}$ is nitro, chloro or amino;

$R^{19}$ is nitro or amino;

$R^{21}$ is nitro, amino or a moiety selected from the group:

$R^{4a}$, $R^{4b}$, $R^{4c}$, $R^{4d}$, $R^{4e}$, $R^{4f}$ and $R^{4g}$ are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, trifluoromethyl, cyano, nitro, carboxy, alkoxycarbonyl of 1 to 6 carbon atoms, alkoxy of 1 to 6 carbon atoms, alkylcarbonyl of 1 to 6 carbon atoms, alkylcarbonylamino of 1 to 6 carbon atoms, thiol, alkylthio of 1 to 6 carbon atoms, alkylamino of 1 to 6 carbon atoms, —N($R^{4h}$)($R^{4i}$), phenyl, phenylamino, and carboxaldehyde;

$R^{4h}$ and $R^{4i}$, independent from each other, are straight chain alkyl of 1 to 6 carbon atoms;

$R^{5a}$, $R^{5b}$, $R^{5c}$, $R^{5d}$, and $R^{5e}$ are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, cyano, nitro, alkylamino of 1 to 6 carbon atoms, and —N($R^{4h}$)($R^{4i}$);

$R^{6a}$ and $R^{6b}$ are independently selected from hydrogen, halogen, straight chain alkyl of 1 to 6 carbon atoms, branched chain alkyl of 3 to 7 carbon atoms, alkenyl of 2 to 6 carbon atoms, and alkynyl of 2 to 6 carbon atoms;

$R^{6c}$ is hydrogen, methyl, cyano, or halogen;

$R^{7a}$, $R^{7b}$ and $R^{7c}$ are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, alkoxy of 1 to 6 carbon atoms, cyano, nitro, alkoxycarbonyl of 1 to 6 carbon atoms, alkylcarbonyl of 1 to 6 carbon atoms, alkylamino of 1 to 6 carbon atoms, and —N($R^{4h}$)($R^{4i}$);

$R^8$ is hydrogen, hydroxy, amino, straight chain alkyl of 1 to 6 carbon atoms or branched chain alkyl of 3 to 7 carbon atoms;

$R^9$, $R^{10}$ and $R^{11b}$ are independently, hydrogen or alkyl of 1 or 2 carbon atoms;

$R^{12a}$ and $R^{12b}$ are independently hydrogen, straight chain alkyl of 1 to 6 carbon atoms, alkenyl of 2 to 6 carbon atoms, alkynyl of 2 to 4 carbon atoms, hydroxyalkyl of 2 to 4 carbon atoms, carboxy, alkoxycarbonyl of 1 to 6 carbon atoms, alkoxy of 1 to 6 carbon atoms, thiol, alkylthio of 1 to 4 carbon atoms, alkylamino of 1 to 4 carbon atoms, —N($R^{12c}$)($R^{12d}$); or trifluoromethyl;

$R^{12c}$ and $R^{12d}$, independent from each other, are straight chain alkyl of 1 to 4 carbon atoms;

$R^{13}$ is independently hydrogen, alkyl of 1 or 2 carbon atoms, hydroxy, amino, halogen, hydroxymethyl, or aminomethyl;

$R^{14}$ is hydrogen, alkyl of 1 or 2 carbon atoms, or halogen;

$R^{15}$ is hydrogen or cyano;

$R^{16}$ is a moiety selected from the group:

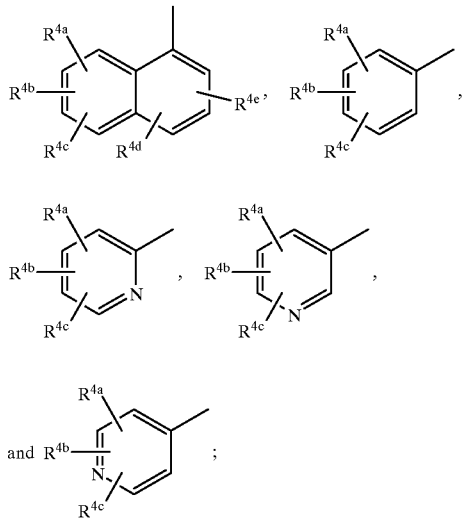

or a pharmaceutically acceptable salt thereof.

It is understood in references to alkoxycarbonyl of 1 to 6 carbon atoms, alkylcarbonyl of 1 to 6 carbon atoms, alkylcarbonylamino of 1 to 6 carbon atoms described herein in Formulae (VI) and (VII) that reference to 1 to 6 carbon atoms describes the length of the alkyl or alkoxy as bonded to the carbonyl carbon.

For the compounds defined above and referred to herein, unless otherwise noted, the following terms are defined.

The term halogen may be selected from fluorine, chlorine, bromine and iodine, unless otherwise specified.

The term alkyl means a branched or unbranched, saturated aliphatic hydrocarbon radical. Examples of alkyl radicals include methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylphentyl, 2,2-dimethylbutyl, n-heptyl, 2-methylhexyl, and the like unless otherwise specified.

The term alkenyl means a branched or unbranched hydrocarbon radical containing at least one carbon-carbon double bond, each double bond being independently cis, trans or a nongeometric isomer.

The term alkynyl means a branched or unbranched hydrocarbon radical containing at least one carbon-carbon triple bond.

The term alkoxy means a branched or unbranched hydrocarbon radical attached through an oxygen bridge and including for example methoxy, ethoxy, n-propoxy, isopropoxy, n-butoxy, t-butoxy and the like. Phenyl as used herein refers to a 6-membered aromatic ring.

The above compounds of Formulae (I) to (V) may be obtained as inorganic or organic salts using methods known to those skilled in the art (Richard C. Larock, Comprehensive Organic Transformations, VCH publishers, 411–415, 1989). It is well known to one skilled in the art that an appropriate salt form is chosen based on physical and chemical stability, flowability, hydroscopicity and solubility. The inorganic salts may be calcium, potassium, magnesium, sodium or equivalent thereof. The organic salts may come from a suitable alkylamine base such as triethylamine, N,N-diethylmethylamine, N,N-diethylaniline, N,N-diethylethylenediamine, N,N-diisopropylethylamine, pyridine or equivalent thereof.

The present invention accordingly provides a pharmaceutical composition which comprises a compound of this invention in combination or association with a pharmaceutically acceptable carrier. In particular, the present invention provides a pharmaceutical composition which comprises an effective amount of a compound of this invention and a pharmaceutically acceptable carrier.

DESCRIPTION OF THE INVENTION

The novel compounds of the present invention may be readily prepared in accordance with one or more of the following reaction schemes.

Scheme I

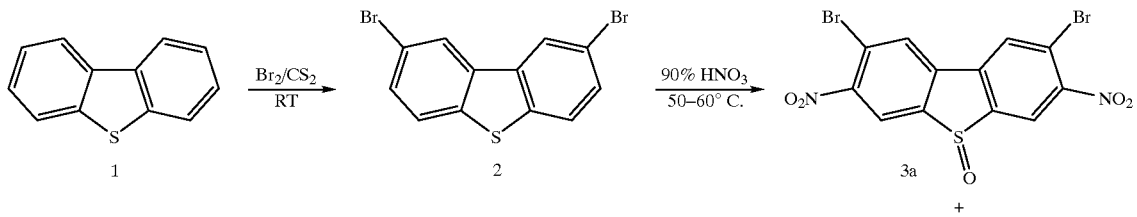

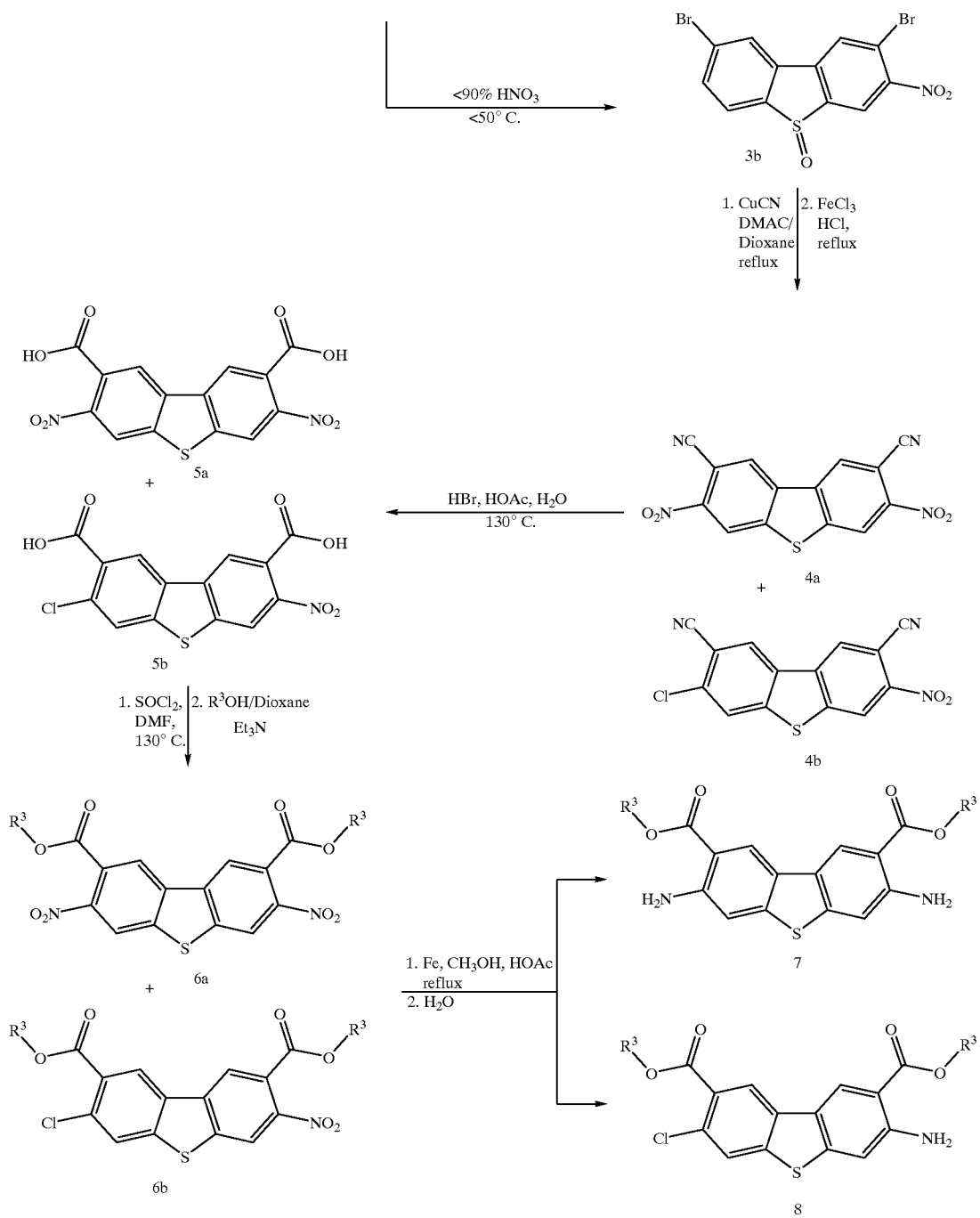

Referring to the process of Scheme I, 3,7-diaminodibenzothiophene-2,8-dicarboxylic acid diester 7 where $R^3$ is a straight chain alkyl of 1 to 5 carbon atoms, branched chain alkyl of 3 to 5 carbon atoms or benzyl is formed as the primary product and 3-amino-7-chloro-dibenzothiophene-2,8-dicarboxylic acid diester 8 where $R^3$ is hereinbefore defined is formed as a minor product when starting with 2,8-dibromodibenzothiophene 2.

Again, referring to Scheme I, modifying a procedure as described (E. Campaigne and John Ashby, J. Het. Chem. 517–521, August 1969 on page 521) dibenzothiophene 1 was treated with bromine in carbon disulfide to afford 2,8-dibromo-dibenzothiophene 2. Reaction of 2,8-dibromo-dibenzothiophene 2 with >90% nitric acid at 50–60° C. gave as the major product 2,8-dibromo-3,7-dinitrodibenzothiophene-5-oxide 3a. A mixture of 2,8-dibromo-3,7-dinitrodibenzothiophene-5-oxide 3a in 1:1 dimethylacetamide (DMAC)/dioxane was treated with copper (I) cyanide (Cu(I)CN) for about 10 hours at 50–150° C. followed by further treatment with ferric chloride/concentrated hydrochloric acid to yield as the major product 3,7-dinitrodibenzothiophene-2,8-dicarbonitrile 4a. Further treatment of 3,7-dinitrodibenzothiophene-2,8-dicarbonitrile 4a with glacial acetic acid, hydrobromic acid and water at 50–100° C. followed by treatment with sodium hydroxide at 50–100° C. for 0.5 to 3 hours followed by acidification to a pH of 1 to 5 affords as the major product 3,7-dinitrodibenzothiophen-2,8-dicarboxylic acid 5a. Reaction of 3,7-dinitrodibenzothiophene-2,8-dicarboxylic acid 5a with an excess of halogenating agent which include but are not limited to thionyl chloride, thionyl chloride in the presence of N,N-dimethylformamide (DMF), oxalyl chloride, selenium tetrafluoride, phosphorus trichloride, phosphorus tribromide or pentabromide and the like at reflux under anhydrous conditions in the presence of an anhydrous polar organic solvent which include but are not limited to p-dioxane, tetrahydrofuran, methyl alcohol, chloroform followed by further treatment with 1–100 equivalents of an alkylamine base, which include but are not limited to triethylamine, N,N-diethylmethylamine, N,N-diethylaniline, N,N-diethylethylenediamine, N,N-diisopropylethylamine, or pyridine and the like in an alcohol, $R^3OH$, where $R^3$ is straight chain alkyl of 1 to 5 carbon atoms, branched chain alkyl of 3 to 5 carbon atoms or benzyl which include but are not limited to methyl, ethyl, propyl, isopropyl, butyl or benzyl alcohol, stirred at a temperature range from 0–75° C. for about 1 to 100 hours to give as the major product 3,7-dinitrodibenzothiophene-2,8-dicarboxylic acid diester 6a where $R^3$ is hereinbefore defined. A heterogeneous mixture containing major product 3,7-dinitrodibenzothiophene-2,8-dicarboxylic acid diester 6a was treated with a reducing agent which include but are not limited to powdered iron, tin(II) chloride, zinc metal or palladium on charcoal with hydrogen in alcoholic solvents which include but are not limited to methyl alcohol, ethyl alcohol, propyl alcohol or 2-methoxyethanol and the like and an organic acid which include but are not limited to acetic acid at a temperature range from 50–120° C. for about 2 hours or until completion as indicated by thin-layer chromatography (TLC). Chromatographic purification on silica gel affords 3,7-diaminodibenzothiophene-2,8-dicarboxylic acid diester 7 where $R^3$ is hereinbefore defined and 3-amino-7-chlorodibenzothiophene-2,8-dicarboxylic acid diester 8 where $R^3$ is hereinbefore defined.

While not wishing to be bound by theory and once again referring to Scheme I, it is contemplated that 3-amino-7-chlorodibenzothiophene-2,8-dicarboxylic acid diester 8 where $R^3$ is hereinbefore defined is also formed during the process of Scheme I through the sequence of steps starting with reaction of 2,8-dibromodibenzothiophene 2 with >90% nitric acid at 50–60° C. which gave 2,8-dibromo-3,7-dinitrodibenzothiophene-5-oxide 3a as the primary product and which also contains a minor product 2,8-dibromo-3-nitrodibenzothiophene-5-oxide 3b. A mixture of 2,8-dibromo-3,7-dinitrodibenzothiophen-5-oxide 3a containing minor product 2,8-dibromo-3-nitrodibenzothiophene-5-oxide 3b in 1:1 DMAC/dioxane was treated with copper (I) cyanide (Cu(I)CN) for about 10 hours at 50–150° C. followed by further treatment with ferric chloride/concentrated hydrochloric acid to yield 3,7-dinitrodibenzothiophene-2,8-dicarbonitrile 4a as the primary product containing a minor product 3-chloro-7-nitrodibenzothiophene-2,8-dicarbonitrile 4b. Further treatment of 3,7-dinitrodibenzothiophene-2,8-dicarbonitrile 4a containing minor product 3-chloro-7-nitrodibenzothiophene-2,8-dicarbonitrile 4b with glacial acetic acid, hydrobromic acid and water at 50–100° C. followed by treatment with sodium hydroxide at 50–100° C. for 0.5 to 3 hours followed by acidification to a pH of 1 to 5 affords 3,7-dinitrodibenzothiophene-2,8-dicarboxylic acid 5a as the primary product containing minor product 3-chloro-7-nitrodibenzothiophene-2,8-dicarboxylic acid 5b. Reaction of 3,7-dinitrodibenzothiophene-2,8-dicarboxylic acid 5a containing minor product 3-chloro-7-nitrodibenzothiophen-2,8-dicarboxylic acid 5b with an excess of an acid chloride producing agent which include but are not limited to thionyl chloride, oxalyl chloride, selenium tetrafluoride, phosphorus trichloride, phosphorus tribromide or pentabromide and the like; at reflux temperature of the reaction mixture, under anhydrous conditions, in the presence of an anhydrous polar organic solvent which include but are not limited to p-dioxane, tetrahydrofuran, methyl alcohol, chloroform and the like; followed by further treatment with 1–100 equivalents of an alkylamine base which include but are not limited to triethylamine, N,N-diethylmethylamine, N,N-diethylaniline, N,N-diethylethylenediamine, N,N-diisopropylethylamine, or pyridine and the like; in an alcohol, $R^3OH$, where $R^3$ is a straight chain alkyl of 1 to carbon atoms, branched chain alkyl of 3 to 5 carbon atoms or benzyl which include but are not limited to methyl, ethyl, propyl, isopropyl, butyl or benzyl alcohol; stirred at a temperature range from 0–75° C. for about 1 to 100 hours to give the major product 3,7-dinitrodibenzothiophene-2,8-dicarboxylic acid diester 6a and a minor product 3-chloro-7-nitrodibenzothiophene-2,8-dicarboxylic acid diester 6b where $R^3$ is hereinbefore defined. A heterogeneous mixture of 3,7-dinitrodibenzothiophen-2,8-dicarboxylic acid diester 6a containing minor product 3-chloro-7-nitrodibenzothiophene-2,8-dicarboxylic acid diester 6b was treated with a reducing agent which include but are not limited to powdered iron, tin(II) chloride, zinc metal or palladium on charcoal with hydrogen in alcoholic solvents which include but are not limited to methyl alcohol, ethyl alcohol, propyl alcohol or 2-methoxy-ethanol and the like; and an organic acid which include but are not limited to acetic acid; at a temperature range from 50–120° C. for about 2 hours or until completion as indicated by TLC. Chromatographic purification of the reaction mixture on silica gel affords 3,7-diaminodibenzothiophene-2,8-dicarboxylic acid diester 7 as the major product where $R^3$ is hereinbefore defined and 3-amino-7-chlorodibenzothiophene-2,8-dicarboxylic acid diester 8 as the minor product where $R^3$ is hereinbefore defined.

Referring to Scheme I, it is also suggested that 2,8-dibromo-3-nitrodibenzothiophene-5-oxide 3b may be prepared by nitration of 2,8-dibromodibenzothiophene 2 by using nitric acid at <90% concentration and temperatures <50° C.

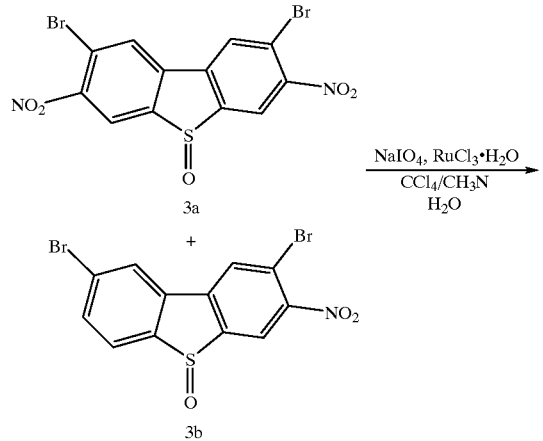

-continued

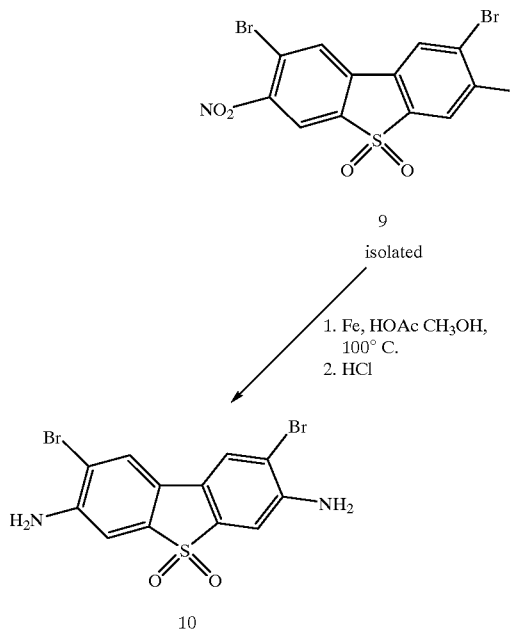

9
isolated

1. Fe, HOAc CH₃OH, 100° C.
2. HCl

10

Referring to Scheme II, a mixture of 2,8-dibromo-3,7-dinitrodibenzothiophene-5-oxide 3a and 2,8-dibromo-3-nitrodibenzothiophene-5-oxide 3b was treated in a heterogeneous solvent mixture which include but not limited to acetonitrile, carbon tetrachloride and water, p-dioxane and water, acetonitrile, tetrahydrofuran and water; with an oxidizing agent which include but not limited to sodium periodate and ruthenium(III) chloride; stirred at a temperature range from 15–75° C. until completion as indicated by TLC to yield 2,8-dibromo-3,7-dinitrodibenzothiophene-5,5-dioxide 9 as the isolated product. Treating 2,8-dibromo-3,7-dinitrodibenzothiophen-5,5-dioxide 9 with a reducing agent which include but are not limited to powdered iron, tin (II) chloride, zinc metal or palladium on charcoal with hydrogen in alcoholic solvents which include but are not limited to methyl alcohol, ethyl alcohol, propyl alcohol or 2-methoxy-ethanol and the like; and an organic acid which includes but is not limited to acetic acid; at a temperature range from 50–120° C. for about 2 hours or until completion to give 2,8-dibromo-5,5-dioxo-5H-5$\lambda^6$-dibenzothiophene-3,7-diamine 10.

Compounds of Formula (I) of this invention may be prepared as shown in Scheme III. To 3,7-diaminodibenzothiophene-2,8-dicarboxylic acid diester 7 in a polar-aprotic solvent which include but are not limited to 1,3-dimethyl-3,4,5,6-tetrahydro-2(1H)pyrimidone, (DMPU), hexamethylphosphoramide (HMPA) or dimethylacetamide (DMAC) and the like; and an alkylamine base which include but are not limited to triethylamine, N,N-diethylmethylamine, N,N-diethylaniline, N,N-diethylethylenediamine, N,N-diisopropylethylamine, or pyridine and the like; was added acid chloride 11 where $R^1$ is as defined above, followed by reaction at room temperature to the reflux temperature of the reaction mixture; for from 0.25 to 24 hours to give 3,7-bis-($R^1$-carbonylamino)dibenzothiophene-2,8-dicarboxylic acid alkyl ester 12. Acid chloride 11 where $R^1$ is as defined above was prepared from the corresponding carboxylic acid by reaction with thionyl chloride, oxalyl chloride and the like, neat or optionally in a halogenated hydrocarbon solvent which include but are not limited to methylene chloride or a co-solvent which include but are not limited to p-dioxane.

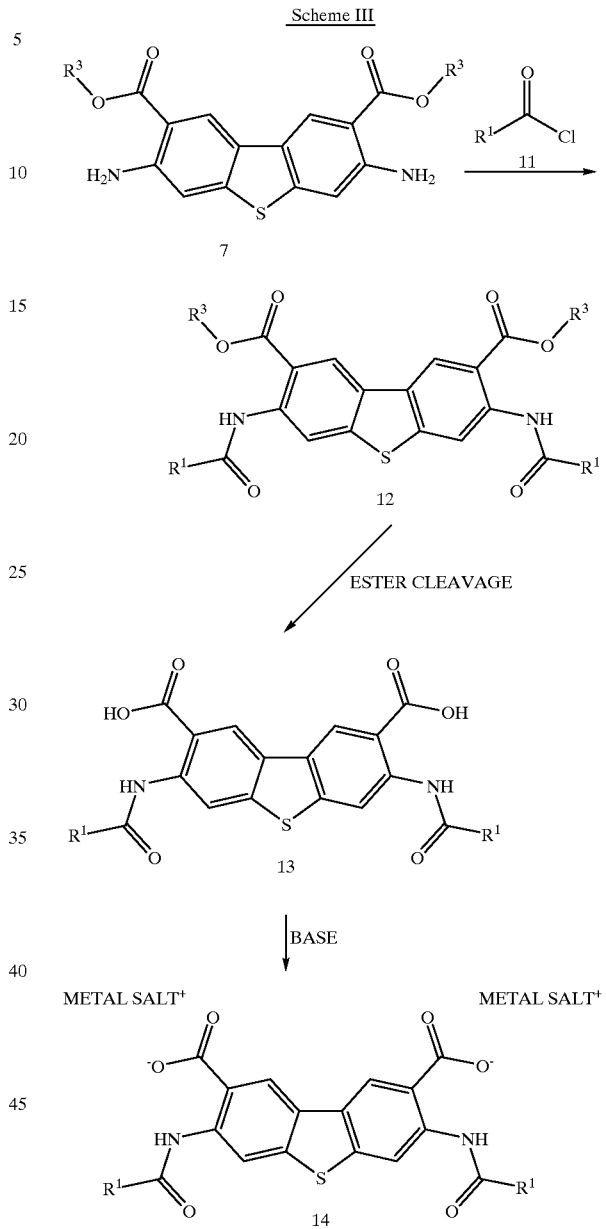

The 3,7-bis-($R^1$-carbonylamino)dibenzothiophen-2,8-dicarboxylic acid alkyl ester 12 dissolved in a polar solvent which include but are not limited to dimethyl sulfoxide, N,N-dimethylformamide or 2-methoxyethanol and the like; was treated with agents capable of cleaving organic esters including but not limited to sodium cyanide, hydrogen and palladium, lithium and ammonia, lithium hydroxide and hydronium ion, potassium hydroxide with aluminum oxide/hydronium ion, barium hydroxide and hydronium ion, potassium tert-butoxide or potassium thiocyanate; at a temperature range from room temperature to 155° C. for from 0.10 to 24 hours; to form the corresponding 3,7-bis-($R^1$-carbonylamino)dibenzothiophen-2,8-dicarboxylic acid 13 of Formula (I). Further treatment of 3,7-bis-($R^1$-carbonylamino)dibenzothiophen-2,8-dicarboxylic acid 13 of Formula (I) with an alkaline metal or alkaline earth metal base which include but are not limited to sodium methoxide, sodium hydroxide and sodium carbonate; affords 3,7-bis-($R^1$-carbonylamino)dibenzothiophene-2,8-dicarboxylic acid dimetal salt 14 of Formula (I) as a pharmaceutically acceptable salt.

Compounds of Formula (I) of this invention where $R^1$ is hereinbefore defined are described in Scheme III with the exception as shown in Scheme IV where $R^1$ is a moiety selected from

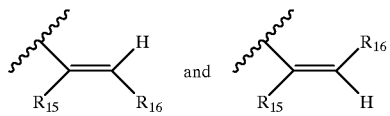

and where $R^{15}$ and $R^{16}$ are hereinbefore defined. The required substituted cinnamoyl chloride 15 prepared from the corresponding carboxylic acid by reaction with thionyl chloride, oxalyl chloride and the like; neat or optionally in a halogenated hydrocarbon solvent which includes but is not limited to methylene chloride or a co-solvent which includes but is not limited to p-dioxane.

The exception may be prepared by reaction of a mixture of 3,7-diaminodibenzothiophene-2,8-dicarboxylic acid diester 7 in a polar-aprotic solvent which include but is not limited DMPU, HMPA or DMAC and the like; and a alkylamine base which include but are not limited to triethylamine, N,N-diethylmethylamine, N,N-diethylaniline, N,N-diethylethylenediamine, N,N-diisopropylethylamine, or pyridine and the like; followed by the addition of a substituted cinnamoyl chloride 15, where $R^1$ is the exception as discussed and shown in Scheme IV and where $R^{15}$ and $R^{16}$ are hereinbefore defined, followed by reaction at room temperature to the reflux temperature of the reaction mixture; for from 0.25 to 24 hours to give diester 16 where $R^1$ is the exception as discussed and shown in Scheme IV and where $R^{15}$ and $R^{16}$ are hereinbefore defined. Diester 16 was treated under the most particularly preferred ester cleavage conditions of contact with a freshly made solution of potassium-t-butoxide (0.5–3M) in dimethylsulfoxide at 5–75° C. followed by acidification to afford 3,7-bis-($R^1$-carbonylamino)dibenzothiophene-2,8-dicarboxylic acid 17 of Formula (I) where $R^1$ is the exception as discussed and shown in Scheme IV and where $R^{15}$ and $R^{16}$ are hereinbefore defined. 3,7-Bis-($R^1$-carbonylamino)dibenzothiophene-2,8-dicarboxylic acid 17 was treated in a mixture of chloroform-methyl alcohol-water with an alkali metal or alkaline earth metal base which include but are not limited to sodium methoxide, sodium hydroxide and sodium carbonate; to afford 3,7-bis-($R^1$-carbonylamino) dibenzothiophene-2,8-dicarboxylic acid dimetal salt 18 of Formula (I) as a pharmaceutically acceptable salt where $R^1$ is the exception as discussed and shown in Scheme IV and where $R^{15}$ and $R^{16}$ are hereinbefore defined.

Scheme IV

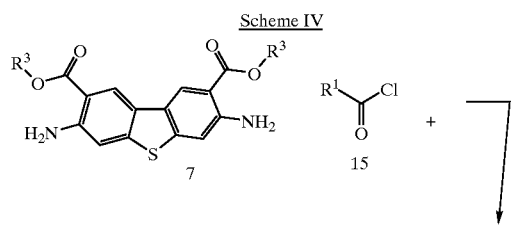

-continued

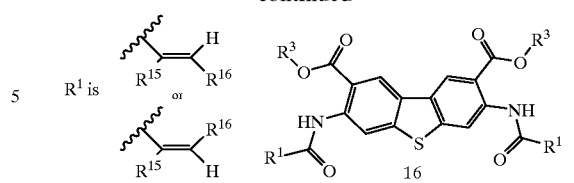

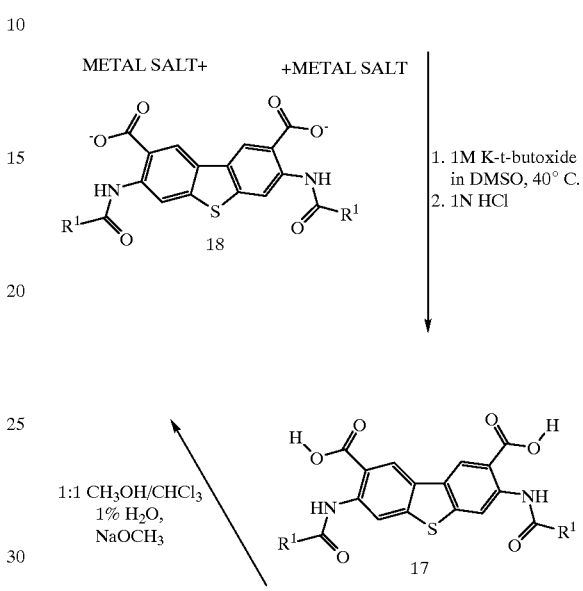

Compounds of Formula (II) of this invention may be prepared as shown in Scheme V by reaction of 3-amino-7-chlorodibenzothiophene-2,8-dicarboxylic acid diester 8 where $R^3$ is hereinbefore defined, mixed with a polar aprotic solvent which include but are not limited to DMPU, HMPA or DMAC and the like; and an alkylamine base which include but are not limited to triethylamine, N,N-diethylmethylamine, N,N-diethylaniline, N,N-diethylethylenediamine, N,N-diisopropylethylamine, or pyridine and the like; followed by the addition of acid chloride 11 where $R^1$ is hereinbefore defined followed by reaction at room temperature to up to 150° C. for from 0.25 to 24 hours to give 3-($R^1$-carbonylamino)-7-chlorodibenzothiophene-2,8-dicarboxylic acid diester 19 where $R^1$ and $R^3$ are hereinbefore defined. The 3-($R^1$-carbonylamino)-7-chlorodibenzothiophene-2,8-dicarboxylic acid diester 19 dissolved in a polar solvent which include but are not limited to dimethyl sulfoxide, N,N-dimethylformamide or 2-methoxyethanol and the like; was treated with agents capable of cleaving organic esters including but not limited to sodium cyanide, hydrogen and palladium, lithium and ammonia, lithium hydroxide and hydronium ion, potassium hydroxide with aluminum oxide/hydronium ion, barium hydroxide and hydronium ion, potassium tert-butoxide or potassium thiocyanate; at a temperature range from room temperature to 155° C. for from 0.10 to 24 hours; to form the corresponding 3-($R^1$-carbonylamino)-7-chloro-dibenzothiophene-2,8-dicarboxylic acid 21 where $R^1$ is hereinbefore defined. Treating 3-($R^1$-carbonylamino)-7-chlorodibenzothiophene-2,8-dicarboxylic acid 21 in alcohol/chloroform/water with an alkali metal or alkaline earth metal base which include but are not limited to sodium methoxide, sodium hydroxide or sodium carbonate and the like; affords the 3-($R^1$-carbonylamino)-7-chlorodibenzothiophene-2,8-dicarboxylic acid dimetal salt 23 as a pharmaceutically acceptable salt where $R^1$ is hereinbefore defined.

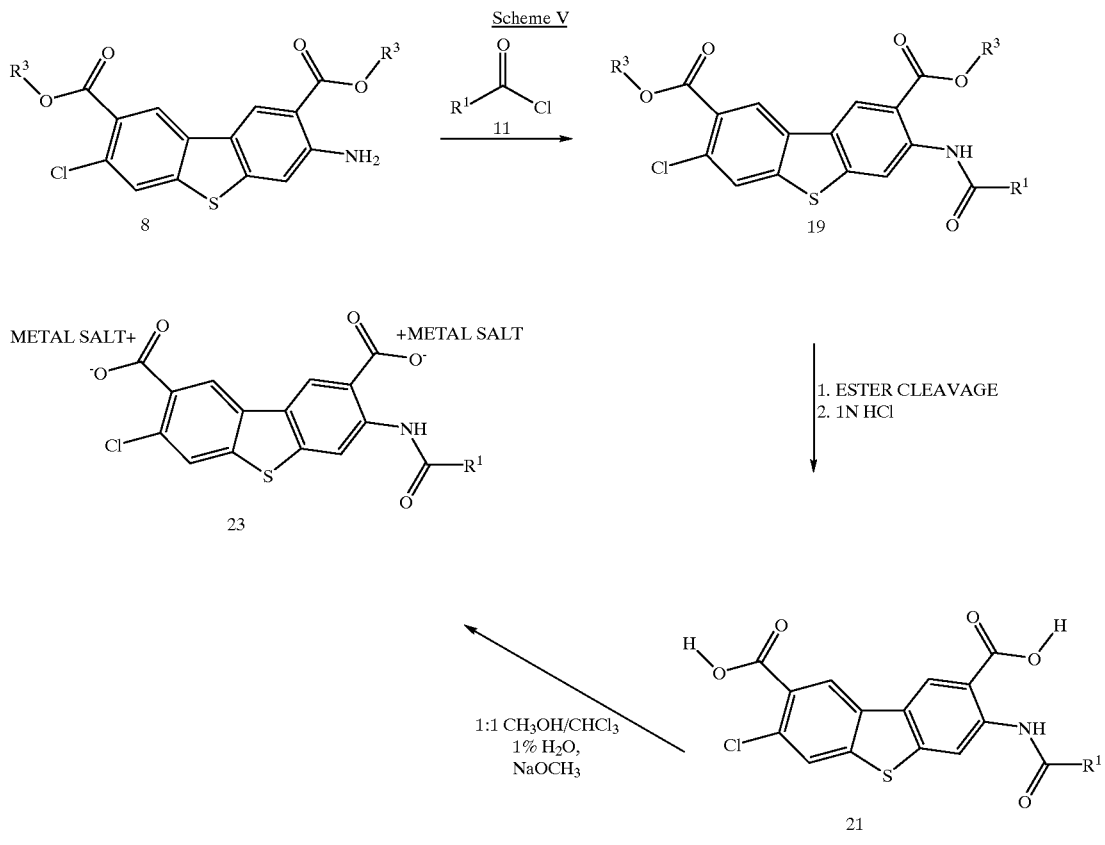

Compounds of Formula (II) of this invention where $R^1$ is hereinbefore defined are described in Scheme V with the exception as shown in Scheme VI where $R^2$ is a moiety selected from

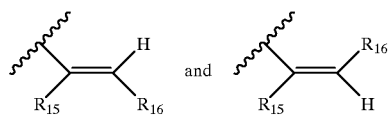

and where $R^{15}$ and $R^{16}$ are hereinbefore defined, the exception which may be prepared by reaction of 3-amino-7-chlorodibenzothiophene-2,8-dicarboxylic acid diester 8 where $R^3$ is hereinbefore defined, mixed with a polar aprotic solvent which include but are not limited to DMPU, HMPA or DMA and the like; and a alkylamine base which include but are not limited to triethylamine, N,N-diethylmethylamine, N,N-diethylaniline, N,N-diethylethylenediamine, N,N-diisopropylethylamine, or pyridine and the like; followed by the addition of substituted cinnamoyl chloride 15, followed by reaction at room temperature to up to 150° C.; for from 0.25 to 24 hours to give 3-($R^1$-carbonylamino)-7-chlorodibenzo-thiophene-2,8-dicarboxylic acid diester 20. The 3-($R^1$-carbonylamino)-7-chlorodibenzothiophene-2,8-dicarboxylic acid diester dissolved in a polar solvent which include but are not limited to dimethyl sulfoxide, N,N-dimethylformamide, or 2-methoxyethanol, and the like; was treated under the most particularly preferred ester cleavage conditions of a freshly made solution of potassium-t-butoxide (0.5–3M) in dimethylsulfoxide at 5–75° C. followed by acidification to give 3-($R^1$-carbonyl-amino)-7-chlorodibenzothiophene-2,8-dicarboxylic acid 22 of Formula (II). Treating 3-($R^1$-carbonylamino)-7-chlorodibenzothiophene-2,8-dicarboxylic acid 22 in alcohol/chloroform/water with an alkali metal or alkaline earth metal base which include but are not limited to sodium methoxide, sodium hydroxide or sodium carbonate and the like; affords the 3-($R^1$-carbonylamino)-7-chlorodibenzothiophene-2,8-dicarboxylic acid dimetal salt 24 as a pharmaceutically acceptable salt where $R^1$ is the exception as discussed and shown in Scheme VI and where $R^{15}$ and $R^{16}$ are hereinbefore defined.

47 48
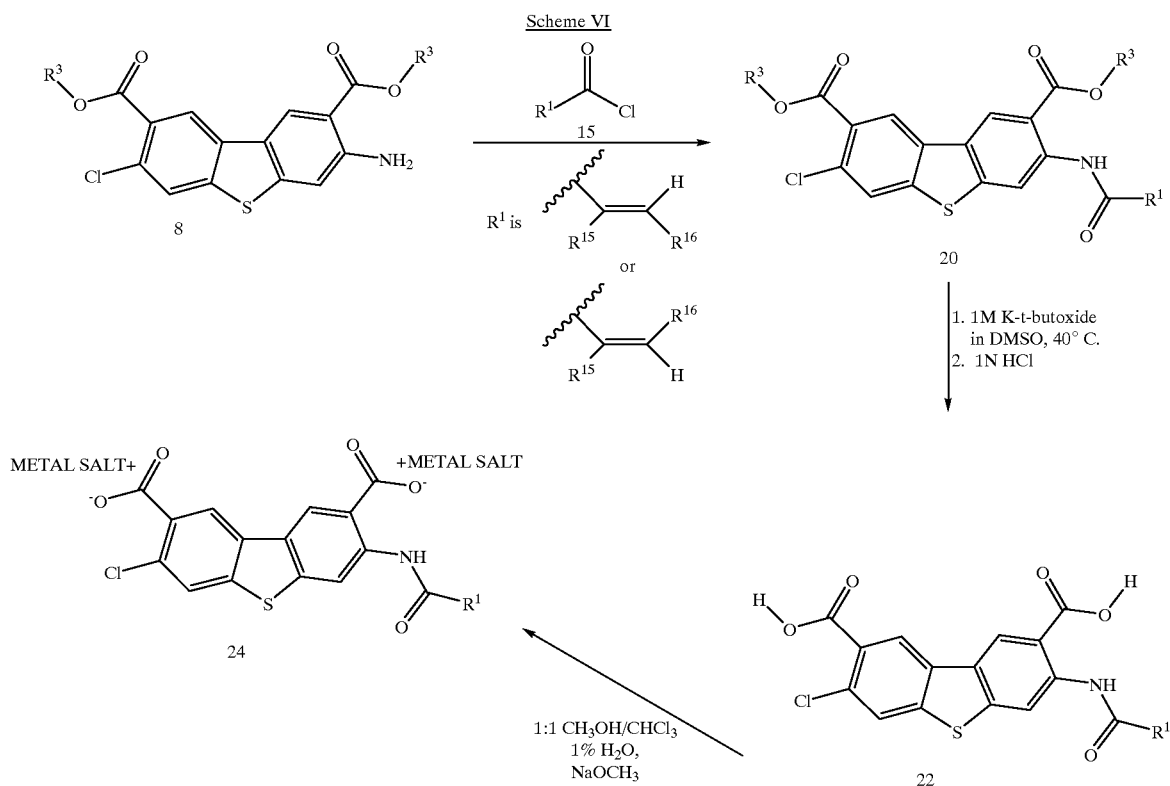
Scheme VI
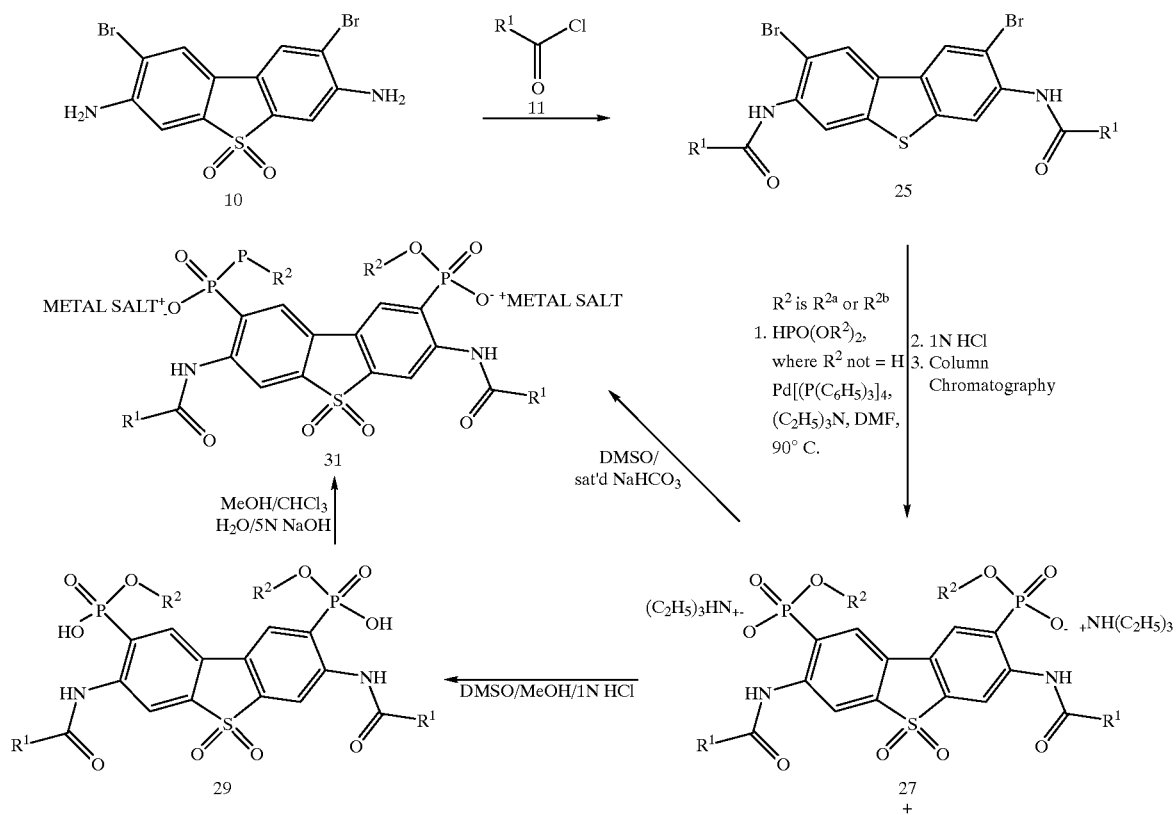
Scheme VII

-continued

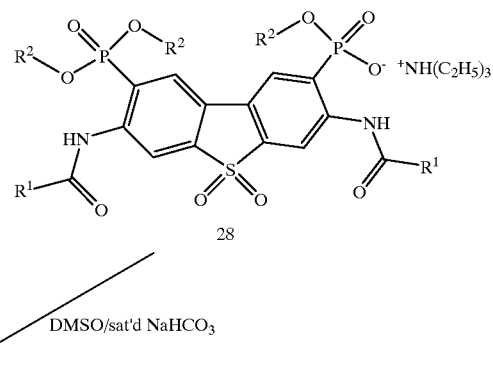

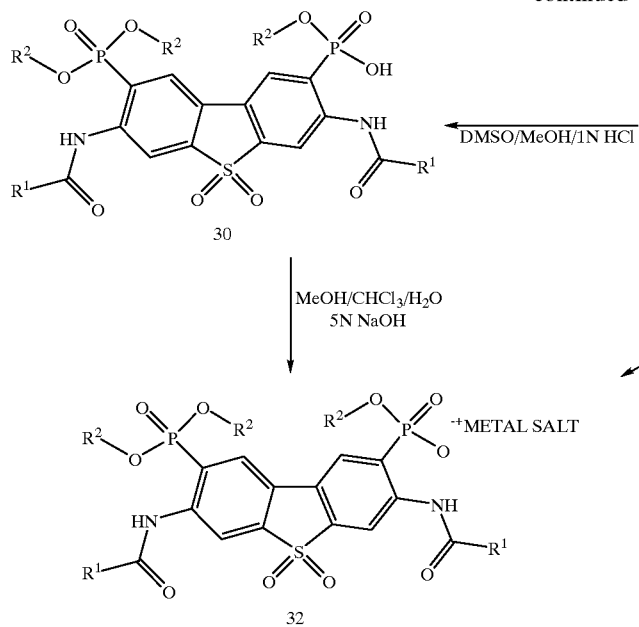

Compounds of Formula (III) of this invention may be prepared in accordance with Scheme VII, where 2,8-dibromo-5,5-dioxo-5H-5$\lambda^6$-dibenzothiophene-3,7-diamine 10 was mixed with a polar-aprotic solvent which include but are not limited to DMPU, HMPA, DMAC and the like; and an alkylamine base which include but are not limited to triethylamine, N,N-diethylmethylamine, N,N-diethylaniline, N,N-diethylethylenediamine, N,N-diisopropylethylamine, or pyridine and the like; heated to 120° C., followed by the addition of acid chloride 11 where $R^1$ is hereinbefore defined, followed by reaction at room temperature to the reflux temperature of the reaction mixture; for from 0.25 to 24 hours to give 2,8-dibromo-3,7-($R^1$-carbonylamino)-5,5-dioxo-5H-5$\lambda^6$-dibenzothiophene 25 which was mixed with a polar aprotic solvent which include but are not limited to DMPU, HMPA or DMAC and the like; and a trisubstituted alkyl amine which include triethylamine or N,N-diisopropylethylamine and the like; followed by the addition of a disubstituted phosphite of the formula, HPO $(R^2)_2$ where $R^2$ is $R^{2a}$ or $R^{2b}$ and are hereinbefore defined, with the proviso that $R^2$ is not H, but not limited to diethylphosphite, dibenzyl phosphite, bis(2-ethylhexyl) phosphite, dimethylphosphite, bis(2,2,2-trifluoroethyl) phosphite, dibutyl phosphite or di-N-hexylphosphite and the like; at from room temperature to up to 150° C. Further hydrolysis of ester products formed where $R^2$ is not H will afford products where $R^2$ is hereinbefore defined including H. To the reaction mixture was rapidly added Pd(O) which include but are not limited to tetrakis (triphenylphosphine) palladium(0) and the like and heating was continued for from about 1.5 to 100 hours until reaction completion followed by acid treatment. Isolation using column chromatography gave [3,7-bis-($R^1$-carbonylamino)-8-[($R^2$-oxy) hydroxyphos-phoryl]-5,5-dioxo-5H-5$\lambda^6$-dibenzothiophene-2-yl]phosphonic acid mono-$R^2$ ester di(trisubstituted alkylamine) salt 27 and [3,7-bis-($R^1$-carbonylamino)-8-[(di-$R^2$-oxy)phos-phoryl)-5,5-dioxo-5H-5$\lambda^6$-dibenzothiophene-2-yl]phosphonic acid mono-$R^2$ ester mono(trisubstituted alkylamine) salt 28. Individually [3,7-bis-($R^1$-carbonylamino)-8-[($R^2$-oxy)hydroxyphosphoryl]-5,5-dioxo-5H-5$\lambda^6$-dibenzothiophene-2-yl]phosphonic acid mono-$R^2$ ester di(trisubstituted alkylamine) salt 27 and [3,7-bis-($R^1$-carbonylamino)-8-[(di-$R^2$-oxy)phosphoryl]-5,5-dioxo-5H-5$\lambda^6$-dibenzothiophen-2-yl]phosphonic acid mono-$R^2$ ester mono(trisubstituted alkylamine) salt 28 were treated with a mixture of DMSO/MeOH/1N HCl to give [3,7-bis-($R^1$-carbonylamino)-8-[($R^2$-oxy) hydroxyphosphoryl]-5,5-dioxo-5H-5$\lambda^6$-dibenzothiophene-2-yl]phosphonic acid mono-$R^2$ ester 29 and [3,7-bis-($R^1$-carbonylamino)-8-[(di-$R^2$-oxy)phosphoryl]-5,5-dioxo-5H-5$\lambda^6$-dibenzothiophene-2-yl]phosphonic acid mono-$R^2$ ester 30(the free acids). [3,7-bis-($R^1$-carbonylamino)-8-[($R^2$-oxy) hydroxyphosphoryl]-5,5-dioxo-5H-5/$^6$-dibenzothiophene-2-yl]phosphonic acid mono-$R^2$ ester 29 and [3,7-bis-($R^1$-carbonylamino)-8-[(di-$R^2$-oxy)phosphoryl)-5,5-dioxo-5H-5$\lambda^6$-dibenzothiophene-2-yl]phosphonic acid mono-$R^2$ ester dissolved in a hot polar solvent mixture which include but are not limited to 1:1 methyl alcohol/chloroform, 1:12-methoxyethanol/water, 1:1 ethylene glycol/water or 1:1 p-dioxane/water and the like; were treated with an alkaline metal or alkaline earth metal base which include but are not limited to 1N to 5N sodium hydroxide, excess sodium methoxide or 1N to 5N sodium carbonate and the like; gave [3,7-bis-($R^1$-carbonylamino)-8-[($R^2$-oxy) hydroxyphosphoryl]-5,5-dioxo-5H-5$\lambda^6$-dibenzothiophene-2-yl]phosphonic acid mono-$R^2$ ester dimetal salt 31 and [3,7-bis-($R^1$-carbonylamino)-8-[(di-$R^2$-oxy)phosphoryl]-5,5-dioxo-5H-5$\lambda^6$-dibenzothiophene- 2-yl]phosphonic acid mono-$R^2$ ester monometal salt 32. Alternatively, [3,7-bis-($R^1$-carbonylamino)-8-[($R^2$-oxy)hydroxyphosphoryl]-5,5-dioxo-5H-5$\lambda^6$-dibenzothiophene-2-yl]phosphonic acid mono-$R^2$ ester di(trisubstituted alkylamine) salt 27 and [3,7-bis-($R^1$-carbonylamino)-8-[(di-$R^2$-oxy)phosphoryl)-5,5-dioxo-5H-5$\lambda^6$-dibenzothiophene-2-yl]phosphonic acid mono-$R^2$ ester mono(trisubstituted alkylamine) salt 28 were independently treated with DMSO/NaHCO$_3$ to give [3,7-bis-($R^1$-carbonylamino)-8-[($R^2$-oxy)hydroxyphosphoryl]-5,5-dioxo-5H-5$\lambda^6$-dibenzothiophene-2-yl]phosphonic acid mono-$R^2$ ester dimetal salt 31 and [3,7-bis-($R^1$-carbonylamino)-8-[(di-$R^2$-oxy)phosphoryl]-5,5-dioxo-5H-5$\lambda^6$-dibenzothiophen-2-yl]phosphonic acid mono-$R^2$ ester monometal salt 32.

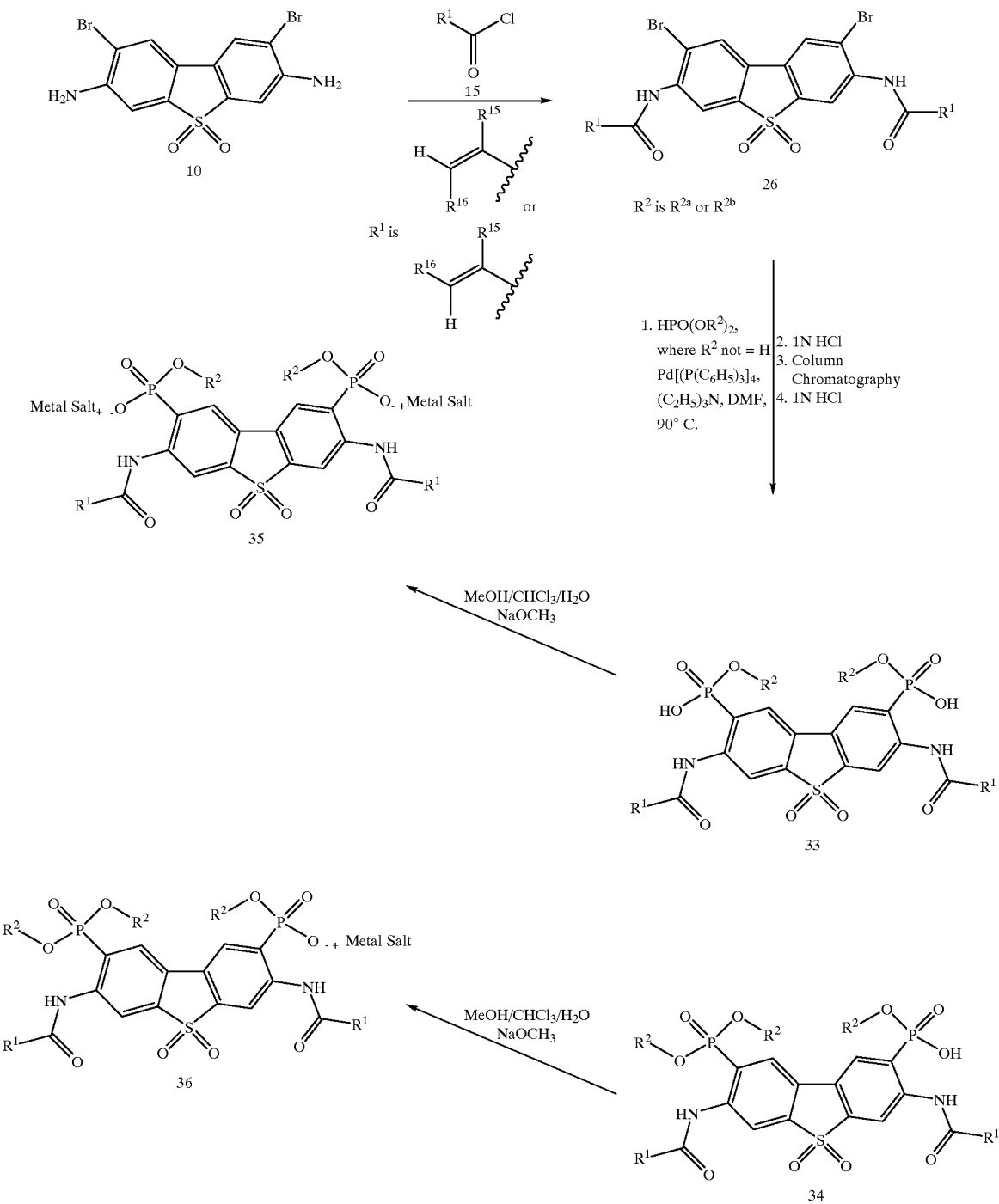

Scheme VIII

Compounds of Formula (III) of this invention where $R^1$ is hereinbefore defined are described in Scheme VII with the exception as shown in Scheme VIII where $R^1$ is a moiety selected from

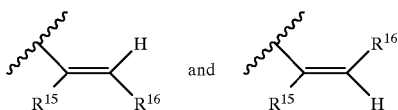

and where $R^5$ and $R^{16}$ are hereinbefore defined, the exception which may be prepared by reaction of 2,8-dibromo-5,5-dioxo-5H-5$\lambda^6$-dibenzothiophene-3,7-diamine 10, mixed with a polar-aprotic solvent which include but are not limited to DMPU, HMPA, DMAC and the like; and an alkylamine base which include but are not limited to triethylamine, N,N-diethylmethylamine, N,N-diethylaniline, N,N-diethylethylenediamine, N,N-diisopropylethylamine, or pyridine and the like; with acid chloride 15 where $R^1$ is the exception as discussed and shown in Scheme VIII and where $R^{15}$ and $R^{16}$ are hereinbefore defined, followed by reaction at room temperature to up to 150° C.; for from 0.25 to 24 hours; to give 2,8-dibromo-3,7-bis-($R^1$-carbonylamino)-5,5-dioxo-5H-5$\lambda^6$-dibenzothiophene 26 which was mixed with a polar aprotic solvent which include but are not limited to DMPU, HMPA or DMAC and the like; and an alkylamine base which include but are not limited to triethylamine, N,N-diethylmethylamine, N,N-diethylaniline, N,N-diethylethylenediamine, N,N-diisopropylethylamine, or pyridine and the like; followed by the addition of HPO(OR$^2$)$_2$ where $R^2$ is hereinbefore defined, with the proviso that $R^2$ is not H, but not limited to diethylphosphite, dibenzyl phosphite, bis(2-ethylhexyl)phosphite, dimethylphosphite, bis(2,2,2-trifluoroethyl)phosphite, dibutyl phosphite or di-N-hexylphosphite and the like; at from room temperature to up to 150° C. To the reaction mixture was added tetrakis(triphenylphosphine) palladium(0) and heating continued for from about 1.5 to 8 hours until reaction completion followed by acid treatment, isolation using column chromatography and an additional treatment with acid gave [3,7-bis-($R^1$-carbonylamino)-8-[($R^2$-oxy)hydroxyphosphoryl]-5,5-dioxo-5H-5$\lambda^6$-dibenzothiophene-2-yl]phosphonic acid mono-$R^2$ ester 33 and [3,7-bis-($R^1$-carbonylamino)-8-[(di-$R^2$-oxy)phosphoryl]-5,5-dioxo-5H-5$\lambda^6$-dibenzothiophene-2-yl]phosphonic acid mono-$R^2$ ester 34. Further hydrolysis of ester products formed where $R^2$ is not H will afford products where $R^2$ is hereinbefore defined including H. Individually [3,7-bis-($R^1$-carbonylamino)-8-[($R^2$-oxy)hydroxyphosphoryl]-5,5-dioxo-5H-5$\lambda^6$-dibenzothiophene-2-yl]phosphonic acid mono-$R^2$ ester 33 and [3,7-bis-($R^1$-carbonylamino)-8-[(di-$R^2$-oxy)phosphoryl]-5,5-dioxo-5H-5$\lambda^6$-dibenzothiophene-2-yl]phosphonic acid mono-$R^2$ ester 34 were dissolved in a hot polar solvent mixture which include but are not limited to 1:1 methyl alcohol/chloroform, 1:12-methoxyethanol/water, 1:1 ethylene glycol/water or 1:1 p-dioxane/water and the like; were treated with a base which include but are not limited to 1N to 5N sodium hydroxide, excess sodium methoxide or 1N to 5N sodium carbonate and the like; to afford [3,7-bis-($R^1$-carbonylamino)-8-[($R^2$-oxy)hydroxyphosphoryl]-5,5-dioxo-5H-5$\lambda^6$-dibenzothiophene-2-yl]phosphonic acid mono-$R^2$ ester dimetal salt 35 and [3,7-bis-($R^1$-carbonylamino)-8-[(di-$R^2$-oxy)phosphoryl]-5,5-dioxo-5H-5$\lambda^6$-dibenzothiophene-2-yl]phosphonic acid mono-$R^2$ ester monometal salt 36.

Compounds of Formula (IV) may be prepared in accordance with Schemes IX and X.

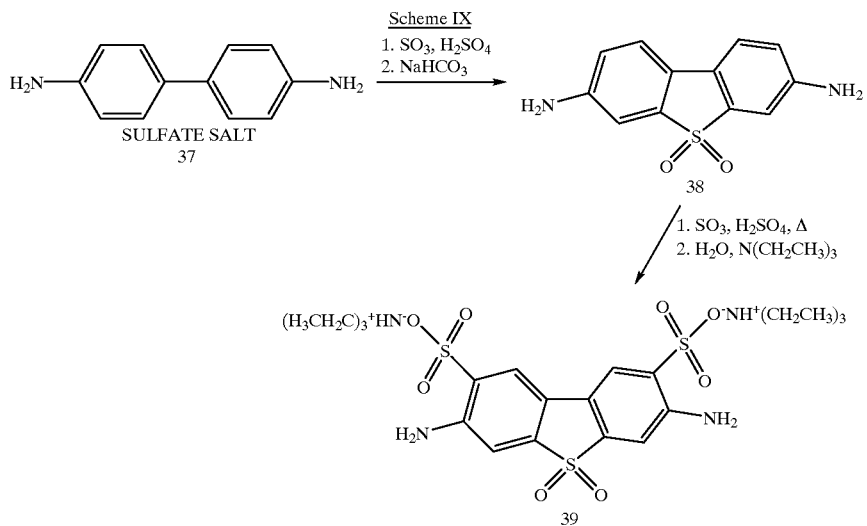

In accordance with Scheme IX, benzidine sulfate 37 as described in U.S. Pat. Nos. 2,590,632 and 2,620,343 was added in portions at 10° C. to fuming sulfuric acid and the reaction maintained at 70° C. for 18 hours, cooled and poured into ice. The resulting solid was collected and washed with water and saturated sodium bicarbonate and dried to give 3,7-diamino dibenzothiophene-5,5-dioxide 38, which was further treated with 20% oleum at 25–200° C. for 0.5–3 hours, followed by cooling to room temperature. The solution was made basic to pH from 8 to 12 with excess base which include but are not limited to triethylamine, N,N-diethylmethylamine, N,N-diethylaniline, N,N-diethylethylenediamine, N,N-diisopropylethylamine or pyridine and the like; and the resulting solution was evaporated to a thick syrup. The syrup was treated with absolute ethyl alcohol and the formed precipitate was collected to give 3,7-diamino-5,5-dioxo-5$\lambda^6$-dibenzothiophene-2,8-disulfonic acid di-triethylamine salt 39.

As outlined in Scheme X, 3,7-diamino-5,5-dioxo-5H,5$\lambda^6$-dibenzothiophene-2,8-disulfonic acid ditriethylamine salt 39 in a minimum amount of dimethylacetamide and the like containing N,N-diisopropylethylamine and the like; was heated in a 90° C. oil bath and acid chloride 40 where $R^{1a}$ is as defined hereinabove, in a minimum amount of DMAC and the like; was added and heating was continued forming 3,7-bis-($R^1$-carbonylamino)-5,5-dioxo-5H,5$\lambda^6$-dibenzothiophene-2,8-disulfonic acid 41. To the warm solution was added excess cold saturated sodium bicarbonate and the resulting solid was isolated, washed with excess water and dried in vacuo. If spectroscopic analysis(NMR) revealed the need, the compound was further purified by dissolving in excess methyl alcohol (boiling) followed by the addition of excess saturated sodium bicarbonate. The solution was boiled to remove the methyl alcohol and allowed to cool. The resulting solid was isolated by filtration, washed with excess water and dried in vacuo to give 3,7-bis-($R^{1a}$-carbonylamino)-5,5-dioxo-5H,5$\lambda^6$-dibenzothiophene-2,8-disulfonic acid dimetal salt 42 of Formula (IV) where $R^{1a}$ is hereinbefore defined.

of the compounds whether free from other stereoisomers or admixed with other stereoisomers in any proportion and thus includes, for instance, raicemic mixture of enantiomers as well as the diastereomeric mixture of isomers. The absolute configuration of any compound may be determined by conventional X-ray crystallography.

According to a further aspect of the present invention there is provided a series of compounds of Formulae (I), (II), (III), (IV) and (V) or the pharmaceutically acceptable salts thereof as defined hereinbefore for use in a method of treatment of human or animal disease.

Compounds of the present invention inhibit the binding of VEGF-165 to the receptor tyrosine kinase KDR and Flt-1 and are therefore of interest for their antiangiogenic effects and/or their ability to reduce vascular permeability.

Thus according to this aspect of this invention there is provided the use of compounds of the Formulae (I), (II), (III), (IV) and (V), or the pharmaceutically acceptable salts thereof in the manufacturing of a medicament for use in the Scheme X

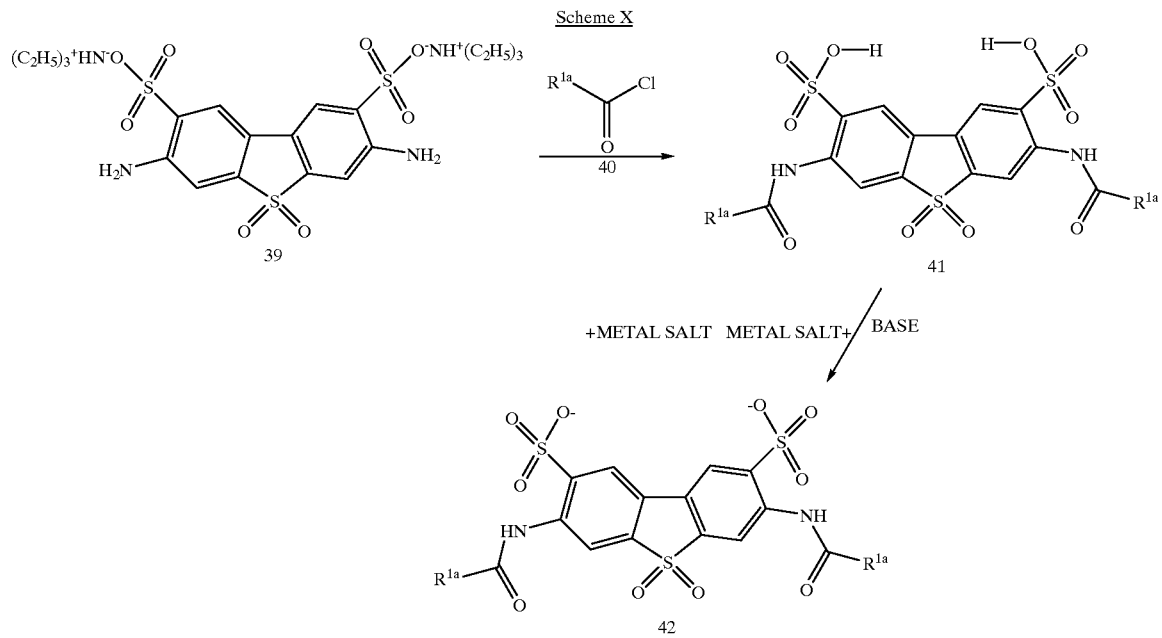

The preparation of the compounds of this invention described by Formula (V) are described in U.S. Pat. Nos. 2,573,652, 2,580,234, 2,911,415, 2,937,089, 2,961,318, 3,226,247, and 3,257,324 which are incorporated herein by reference.

Reactions are performed in a solvent appropriate to the reagents and materials employed and suitable for the transformation being effected. It is understood by those skilled in the art of organic synthesis that the various functionalities present on the molecule must be consistent with the chemical transformations proposed. This may necessitate judgement as to the order of synthetic steps, protecting groups, if required, and deprotection conditions. Substituents on the starting materials may be incompatible with some of the reaction conditions. Such restrictions to the substituents which are compatible with the reaction conditions will be apparent to one skilled in the art.

Some of the compounds of the hereinbefore described schemes have centers of asymmetry. The compounds may, therefore, exist in at least two and often more stereoisomeric forms. The present invention encompasses all stereoisomers production of an antiangiogenic and/or vascular permeability reducing effect in a warm-blooded animal such as a human.

The compounds of this invention may be formulated neat or may be combined with one or more pharmaceutically acceptable carriers for ED administration. For example, solvents, diluents and the like; and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 1000 mg/kg of animal body weight, optionally given in divided doses two to four times a day, or in sustained release form. For most large mammals the total daily dosage is from about 1 to 1000 mg, preferably from about 2 to 500 mg. Dosage forms suitable for internal use comprise from about 0.5 to 1000 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

The compounds of this invention may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The antiangiogenic and/or vascular permeability reducing treatment defined hereinbefore may be applied as a sole therapy or may involve, in addition to a compound of the invention, one or more other substances and/or treatments. Such conjoint treatments may be achieved by way of the simultaneous, sequential or separate administration of the individual components of treatment. In the field of medical oncology it is normal practice to use a combination of therapies to treat a cancer patient. In medicinal oncology the other component(s) of such conjoint treatment defined hereinbefore may be: surgery, radiotherapy or chemotherapy. Such chemotherapy may cover three main categories of therapeutic agents:

(I) other anti-angiogenic agents of different mechanisms of action from those defined hereinbefore (for example linomide, inhibitors of integrin $\alpha v \beta 3$ function, inhibitors of MMP-9, inhibitors of methionine peptidase −1 function, angiostatin, endostatin, razoxin, thalidomide);

(II) cytostatic agents such as antiestrogens (tamoxifen, toremifene, raloxifene, droloxifene, iodoxyfene), progestogens (for example megestrol acetate), aromatase inhibitors (for example anastrozole, letrazole, vorazole, exemestance), antiprogestrogens, antiandrogens (for example flutamide, nilutamide, bicalutamine, cyproterone acetate), LHRH agonists and antagonists (for example goserelin acetate, luprolide), inhibitors of testosterone 5α-dihydroreductase (for example finasteride), anti-invation agents (for example metalloproteinase inhibitors like marimastat and inhibitors of urokinase plasminogen activator receptor function) and inhibitors of growth factor function, (such growth factors include for example EGF, FGFs, platelet derived growth factor and hepatocyte growth factor such inhibitors include growth factor antibodies, growth factor receptor antibodies, tyrosine kinase inhibitors and serine/theonine kinase inhibitors); and (III) antiproliferative/antineoplastic drugs and combinations thereof, as used in medical oncology, such as antimetabolites (for example antifolates like methotrexate, fluoropyrimidines like 5-fluorouracil, purine and adenosine analogs, cytosine arabinoside); antitumor antibiotics (for example anthracyclines like doxorubicin, daunorubicin, epirubicin and idarubicin, mitomycin C, dactinomycin, mithramycin, mitoxantrone); platinum derivatives (for example cisplatin, carboplatin); alkylating agents (for example nitrogen mustard, melphalan, chlorambucil, busulphan, cyclophosphamide, ifosfamide, nitro-soureas, and thiotepa); antimitotic agents (for example vinca alkaloids like vincristine and taxoids like taxol, taxotere); topoisomerase inhibitors (for example epipodophyllotoxins like etoposide and teniposide, amsacrine, and topotecan).

As stated above the compounds of the present invention are of interest for their antiangiogenic and/or vascular permeability reducing effects. Such compounds of the invention are expected to be useful in a wide range of disease states including fibroplasia, hemangiomas, angiofibromas, psoriasis, rheumatoid arthritis, diabetes, Karposi's sarcoma, acute and chronic nephropathies, atheroma, arterial restenosis, autoimmune diseases, acute inflammation and inhibiting and/or reversing ocular neovascularization of the eye in ophthalmic conditions such as corneal transplant rejection, proliferative diabetic retinopathy, neovascular glaucoma, various infectious conditions (for example Herpes and CMV) and neovascularization associated with age-related macular degeneration disease. In particular such compounds of the invention are expected to slow advantageously the growth of primary and recurrent solid tumors of, for example, the colon, breast, prostate, lungs and skin. More particularly such compounds of the invention are expected to inhibit the growth of those primary and recurrent solid tumors which are associated with VEGF, especially those tumors which are significantly dependent on VEGF for their growth and spread, including for example, certain tumors of the colon, breast, prostate, lung, vulva and skin.

In addition to their use in therapeutic medicine, the compounds of the Formulae (I), (II), (III), (IV) and (V) and their pharmaceutically acceptable salts are also useful as pharmacological tools in the development and standardization of test systems for the evaluation of the effects of inhibitors of VEGF binding to its receptors in laboratory animals such as cats, dogs, rabbits, monkeys, rats and mice as part of the search of new therapeutic agents.

The compounds of this invention and their preparation are illustrated by the following non-limiting examples.

REFERENCE EXAMPLE 1

2,8-Dibromo-dibenzothiophene

The product, 2,8-dibromo-dibenzothiophene was prepared by a modification of the procedure described in E. Campaigne and John Ashby, J. Het. Chem., 517, 1969.

To a stirred mixture of 52.24 g dibenzothiophene dissolve in 88 ml of carbon disulfide was added, dropwise over an hour with occasional cooling, 58 ml of bromine. After the addition, the mixture was stirred at room temperature for 1½ hours. The reaction was monitored by TLC, until completion. The resulting slurry was collected, washed with carbon disulfide, 3× with ethyl alcohol, 2× with diethyl ether, and dried in vacuo to give 61.7 g (63%) of the desired product. m.p. 216–218° C.

REFERENCE EXAMPLE 2A 2,8-Dibromo-3,7-dinitrodibenzothiophene-5-oxide
and

REFERENCE EXAMPLE 2B 2,8-Dibromo-3-nitrodibenzothionhene-5-oxide

A mixture of 30 g of the product of Reference Example 1 and 350 ml of >90% nitric acid was heated gradually to 50–60° C. and then maintained at 55° C. for 1 hour. The solution was poured into 1800 ml of cracked ice with vigorous stirring. The mixture was stirred for 2 hours at room temperature, the solid collected, washed with water followed by diethyl ether, dried in a vacuum oven at 60° C. to give 35.9 g (91%) of crude solid. The crude solid was recrystallized from 3.5 L of glacial acetic acid, boiled down to a final volume of 1800 ml and allowed to cool to room temperature. The resulting solid was collected to give 25.444 g (65%) of a mixture of products, Reference Example 2A and Reference Example 2B, m.p. gas released at 317–320° C.

$^1$H NMR(300 MHz, DMSO-d$_6$):δ 9.05(s, 4H). $^{13}$C NMR (300 MHz, DMSO-D$_6$)δ 150.4, 146.8, 138.6, 130.3, 124.7, 118.7. MS(ES): m/z 446.9 (M–H)$^-$, 492.9 (M+CHOOH–H)$^-$, 938.3 (2M+CHOOH–H)$^-$.

REFERENCE EXAMPLE 3A 3,7-Dinitrodibenzothiophene-2,8-dicarbonitrile and

REFERENCE EXAMPLE 3B

3-Nitro-7-chlorodibenzothiophene-2,8-dicarbonitrile

A mixture of 12.0 g of products Reference Example 2A and 2B, in 100 ml of DMAC/p-dioxane (1:1) and 9.6 g of copper(I)cyanide was heated at reflux temperature for 10 hours at which time the TLC showed the disappearance of the starting material. The reaction mixture was cooled in an ice bath and a cooled solution of 26.1 g of ferric chloride in 120 ml of concentrated hydrochloric acid was added in a slow stream. The reaction was heated at reflux temperature for 10 hours and monitored by TLC for the disappearance of the starting complex. The solution was poured into 1,000 ml of ice with vigorous stirring. The mixture was stirred at room temperature for 3 hours and the precipitate was collected, washed with 1% hydrochloric acid and water, then dried to give 8.27 g (95%) of crude solid. The crude solid was boiled in 1,500 ml of acetone, filtered and the volume reduced to 500 ml to allow crystallization. A total of 5.65 g (65%) of solid was obtained, m.p. (dec) 317–320° C. LC/MS Analysis of the solid using a Hewlett-Packard LC/MS system consisting of a 1090 HPLC, a 5989B MS engine and a Waters Symmetry C$_{18}$ (2.0×50 mm) column and a mobile phase as a linear gradient of water-acetonitrile revealed a peak at 5.9 minutes with a molecular ion m/z of 324 which is Reference Example 3A and a peak at 7.4 minutes with a molecular ion m/z of 313 which is Reference Example 3B. Reference Example 3A accounted for 80.7% of the sample and Reference Example 3B accounted for 6.7% of the sample. APCI mass spectral analysis was done in the negative mode.

$^1$H NMR(300 MHz, DMSO-d$_6$):δ 9.49(s, 4H). $^{13}$C NMR (300 MHz, DMSO-d$_6$):δ 146.5, 146.3, 136.2, 131.4, 122.3, 115.7, 104.0. MS(LRCI): m/z 325.1 (M+H)$^+$. I.R. (KBr): 794.89, 1337.15, 1461.33, 1523.99, 1559.08, 2233.87, 3102.65 cm$^{-1}$

REFERENCE EXAMPLE 4A 3,7-Dinitrodibenzothiophene-2,8-dicarboxylic Acid
and

REFERENCE EXAMPLE 4B

3-Nitro-7-chlorodibenzothiophene-2,8-dicarboxylic Acid

A mixture of 2.4 g of the products Reference Example 3A and 3B, 80 ml of glacial acetic acid, 40 ml of hydrobromic acid, and 20 ml of water was heated at reflux temperature for 72 hours. During this time the reaction progress was monitored by TLC (30% acetone/hexane). After 24 hours, an additional 10 ml of hydrobromic acid was added and heating continued. At 48 hours, 20 ml of hydrobromic acid and 50 ml of glacial acetic acid was added and heating continued to completion. The reaction mixture was diluted with 500 ml of water and filtered. To the collected solid was added approximately 100 ml of 0.1N sodium hydroxide and the resulting mixture was heated at 55–60° C. for 1 hour. The solution was cooled in ice, made acidic with concentrated hydrochloric acid, and stirred for ½ hour. The precipitate was collected, washed with excess 1% hydrochloric acid followed by a small volume of acetone, and dried to give 2.0 g (76%) of solid as a mixture of Reference Example 4A and Reference Example 4B, m.p.(dec) 325° C.

$^1$H NMR(300 MHz, DMSO-d$_6$):δ 14.04(sb, 2H), 9.1 (s, 2H), 8.98(s, 2H). $^{13}$C NMR(300 MHz, DMSO-d$_6$):δ 165.7, 147.3, 143.6, 136.0, 125.2, 124.8, 119.8. MS(ES): m/z 360.8 (M–H)$^-$, 407,0 (M+HCOOH–H)$^-$.

REFERENCE EXAMPLE 5A 3,7-Dinitrodibenzothiophene-2,8-dicarboxylic acid dimethyl ester and

REFERENCE EXAMPLE 5B

3-Nitro-7-chlorodibenzothiophene-2,8-dicarboxylic acid dimethyl ester

A mixture of 5.77 g of the products Reference Example 4A and Reference Example 4B and 300 ml of thionyl chloride was heated at reflux temperature for 3 hours. The excess thionyl chloride was removed by distillation under vacuum at 100° C. To the resulting solid was added, under nitrogen, 50 ml of anhydrous p-dioxane followed by 35 ml of a 5% triethylamine/95% methanol solution which had been dried over 4A activated molecular sieves. After 20 minutes a yellow precipitate formed. The reaction mixture was stirred at room temperature for 72 hours and the resulting solid was collected, washed with methanol and ethyl acetate, and dried to give 4.01 g (95%) of a mixture of products Reference Example 5A and Reference Example 5B, m.p. (dec)303° C.

$^1$H NMR (300 MHz, Acetone-d,):δ 9.09(s, 2H), 8.92(s, 2H), 3.98(s, 6H). MS (LREI): m/z 390.1 (M$^+$).

REFERENCE EXAMPLE 6A 3,7-Diaminodibenzothiophene-2,8-dicarboxylic acid dimethyl ester and

REFERENCE EXAMPLE 6B

3-Amino-7-chlorodibenzothiophene-2,8-dicarboxylic acid dimethyl ester

A heterogeneous mixture of 4.92 g of a mixture of Reference Example 5A and 5B, 10.6 g of powdered iron, 170 ml of methanol and 525 ml of glacial acetic acid was heated at reflux temperature for 3 hours. The reaction was monitored by TLC (30% acetone/hexane). The warm reaction was filtered to remove the iron and the iron residue was washed with methanol. The filtrate was poured into 1000 ml of cracked ice and then diluted with 800 ml of water. The resulting solid was collected, washed with water and dried to give 5.65 g of product. The solid was boiled with 1000 ml of ethyl acetate/acetone (1:1) for 30 minutes and filtered. The filtrate was evaporated to 400 ml, the precipitate collected and the filtrate purified by chromatography (Silica gel: 20% acetone/hexane with gradient to 50% acetone/hexane) to give 2.62 g of pure Reference Example 6A and 0.440 g of Reference Example 6B.

REFERENCE EXAMPLE 6A $^1$H NMR(300 MHz, Acetone-d$_6$):δ 8.44(s, 2H), 7.18(s, 2H) 6.54(bs, 4H), 8.44(s, 6H). $^{13}$C NMR(300 MHz, Acetone-d,):δ 206.3, 168.5, 150.7, 145.6, 126.4, 123.2, 109.2, 51.92. MS(ES): m/z 331.0 (M+H)$^+$, 661.4 2(M+H)$^+$. m.p. 255–257° C.

REFERENCE EXAMPLE 6B $^1$H NMR(300 MHz, Acetone-d$_6$):δ 3.74(s, 1H), 8.52(s, 1H), 8.01(s, 1H), 7.3 (s, 1H), 6.76(bs, 2H), 3.95(s, 3H), 3.93(s, 3H) MS(ES): m/z 350.0 (M+H)$^+$, 699.3 2(M+H)$^+$. Anal. Calcd for $C_{16}H_{12}NO_4SCl.H_2O$ Calcd: C=53.56; H=3.65; N=4.0. Found: C=53.51; H=3.62; N=3.80. m.p. 155–158° C.

REFERENCE EXAMPLE 7

2,8-Dibromo-3,7-dinitrodibenzothiophene-5,5-dioxide

To a mixture of 1.0 g of a mixture of Reference Example 2A and 2B in 20 ml of acetonitrile, 20 ml carbon tetrachloride and 40 ml of water was added 1.4 g (6.6 mmol) of sodium periodate and 0.023 g of ruthenium (III) chloride. The white suspension was stirred at room temperature for 24 hours, the precipitate collected, washed with excess sodium bicarbonate solution and dried to give 0.94 g (92%) of the crude desired product. The solid was recrystallized from glacial acetic acid to give 0.802 g (79%) of pure product, m.p.334–336° C.

$^1$H NMR(300 MHz, DMSO-d$_6$):δ 9.07(s, 2H), 8.97(s, 2H) $^{13}$C NMR(300 MHz, DMSO-d$_6$):δ 151.2, 137.4, 132.3, 130.8, 120.5, 119.7. MS(LRCI): m/z 464.8 (M+H)$^+$.

REFERENCE EXAMPLE 8

2,8-Dibromo-5,5-dioxo-5H-5$\lambda^6$-dibenzothiophene-3,7-diamine

A heterogeneous mixture of 0.636 g of the product of Reference Example 7, 32 ml of methanol, 100 ml of glacial acetic acid and 1.15 g iron powder was heated at 100° C. for 3 hours. The mixture was cooled to room temperature and the resulting precipitate was collected, digested in 150 ml of concentrated hydrochloric acid and the solution was stirred at room temperature for 90 minutes. The solid was collected, washed with water, ½ saturated sodium bicarbonate, water, acetone and dried to give 0.370 g (67%) of the desired product. m.p. >355° C.

$^1$H NMR(300 MHz, DMSO-d$_6$):δ 7.86(s, 2H), 6.87(s, 2H), 5.78(bs, 4H). $^{13}$C NMR(300 MHz, DMSO-d$_6$):δ 146.4, 136.7, 125.4, 119.3, 112.4, 106.5. MS(LRCI): m/z 405.0 (M+H)$^+$.

REFERENCE EXAMPLE 9

3,7-Diaminodibenzothiophene-5,5-dioxide

The title compound was prepared as described in U.S. Pat. Nos. 2,590,632 and 2,620,343. At 10° C., 30 g of benzidine sulfate was added, in portions, to 100 ml of fuming sulfuric acid. After the addition, the reaction was maintained at 70° C. for 18 hours, cooled and poured into 250 g of cracked ice. The beige solid was collected, washed with water and saturated sodium bicarbonate yielding a yellow solid. The yellow solid was stirred with bicarbonate solution 2×, collected, washed with large volumes of water, and dried in vacuo to give 22.66 g (87%) of the desired product.

REFERENCE EXAMPLE 10

3,7-Diamino-5,5-dioxo-5$\lambda^6$-dibenzothiophene -2,8-disulfonic acid, ditriethylamine salt Reference Example 10 was prepared as described in U.S. Pat. Nos. 2,590,632 and 2,620,343.

The product of Reference Example 9, 25.0 g, was treated with 100 ml of 20% oleum (fuming sulfuric acid) at 160° C. for 1 hour, followed by cooling to room temperature. The cooled reaction was poured into 2.5 L of ice/water with stirring. The mixture was made basic to pH 10 with the addition of excess triethylamine. The resulting solution was concentrated in vacuo to a thick syrup which was treated with 2 volumes of absolute ethyl alcohol, cooled and the formed precipitate was collected, washed with ethyl alcohol and dried to give 23.3 g (41%) of the desired product as the ditriethylamine salt.

MS(HR): m/z Calculated: 404.9520 Found: 404.9530.

EXAMPLE 1

3,7-Bis-[(benzo[b]thiophene-2-carbonyl)amino] dibenzothiophene-2.8-dicarboxylic acid dimethyl ester To 100 mg of the product of Reference Example 6A was added 5 ml of DMAC and 130μl of N,N- diisopropylethylamine and the mixture was heated in a 90° C. oil bath to afford a solution. To the hot solution was quickly added 238 mg of benzo[b]thiophene-2-carbonyl chloride. The reaction mixture was maintained at 90° C. until TLC indicated the disappearance of the starting diamine. The resulting precipitate was collected while hot, rinsed with warm DMAC, methanol, acetone, and dried in vacuo to give 110 mg of 3,7-bis-[(benzo[b]thiophene-2-carbonyl)-amino]dibenzothiophene-2,8-dicarboxylic acid dimethyl ester as a yellow solid.

Following the method described for Example 1 the following compounds are prepared:

3,7-Bis[(2-anthracenylcarbonyl)amino]-2,8-dibenzothiophene-2,8-dicarboxylic acid dimethyl ester, 3,7-Bis{[(9,10-dihydro-9,10-dioxo-2-anthracenyl)carbonyl]amino}dibenzothiophene-2,8-dicarboxylic acid dimethyl ester, 3,7-Bis[(thieno[3,2-b]thien-2-ylcarbonyl) amino] dibenzothiophene-2,8-dicarboxylic acid dimethyl ester, and 3,7-Bis-[(8-chloro-4H-thieno[3,2-c][1]benzothiopyran-2-carbonyl)-amino]dibenzothiophene-2,8-dicarboxylic acid dimethyl ester.

EXAMPLE 2

3,7-Bis-r(benzo[b]thiophene-2-carbonyl)amino] dibenzothiophene-2,8-dicarboxylic acid, disodium salt A mixture of 40 mg of the product of Example 1 in 5 ml of DMSO, was heated in an oil bath at 155° C. for minutes. To this suspension was added 15 mg of sodium cyanide and the heating was continued for an additional 15 minutes. The reaction mixture was diluted with 50 ml of ½ saturated sodium bicarbonate. The resulting precipitate was collected, washed with ½ saturated sodium bicarbonate, water, and dried in vacuo at 80° C. to give 39 mg of the desired product (white solid) as the disodium salt, m.p.>350° C.

$^1$H NMR(300 MHz, DMSO-d$_6$):δ 13.11(s, 2H), 9.18(s, 2H), 8.95(s, 2H), 8.11(s, 2H), 8.06(m, 4H), 8.50(m, 4H). MS(ES): m/z 621.6 (M−H)$^−$, 623.5 (M+H)$^+$.

Representative compounds of Formula (I) made by the method of Example 1 and Example 2 are shown in Table 1 as the disodium salts.

TABLE 1

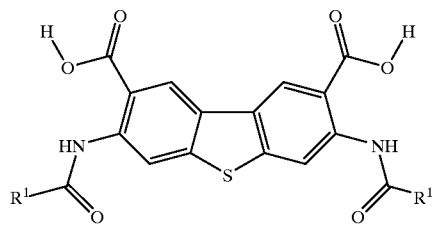

Formula I

| Example No. | Name | R$^1$ = | MP° C. | MS(ES)m/z: | $^1$H NMR (DMSO-d$_6$): δ |
|---|---|---|---|---|---|
| 3 | 3,7-Bis[(2-anthracenylcarbonyl)amino]-2,8-dibenzothiophene-2,8-dicarboxylic acid, disodium salt | anthracenyl | >300 | 709.1 (M−H)$^−$ | 16.27(s, 2H), 9.34(s, 2H), 8.89(m, 6H), 8.69(bs, 2H), 8.22(m, 8H), 7.61(bs, 4H). |
| 4 | 3,7-Bis{[(9,10-dihydro-9,10-dioxo-2-anthracenyl)carbonyl]-amino}dibenzothiophene-2,8-dicarboxylic acid, disodium salt | 9,10-dioxo-anthracenyl | >300 | 769.1 (M−H)$^−$, 384.2 (M−2H)$^−$/2 | 9.35(m, 2H), 8.95(m, 2H), 8.64(m, 2H), 8.35(m, 6H), 8.02(m, 6H). |
| 5 | 3,7-Bis[(thieno[3,2-b] thien-2-ylcarbonyl)amino]dibenzothiophene-2,8-dicarboxylic acid, disodium salt | thieno[3,2-b]thienyl | >300 | 633.0 (M−H)$^−$ | 16.21(s, 2H), 9.06(s, 2H), 8.87(s, 2H), 8.11(s, 2H), 7.88(d, J=3.60Hz, 2H), 7.53(d, J=3.60Hz, 2H). |

TABLE 1-continued

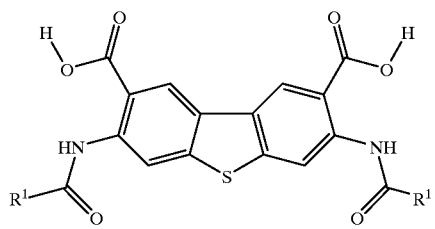

Formula I

| Example No. | Name | R¹ = | MP° C. | MS(ES)m/z: | ¹H NMR (DMSO-d₆): δ |
|---|---|---|---|---|---|
| 6 | 3,7-Bis[(8-chloro-4H-thieno[3,2-c][1]benzo-thiopyran-2-carbonyl)-amino]dibenzothio-phene-2,8-dicarboxylic acid, disodium salt | (structure with Cl) | >400 | 828.9 (M-H)⁻ | 9.04(bs, 2H), 8.80(bs, 2H), 7.70(bs, 2H), 7.62(bs, 2H), 7.45(bm, 2H), 7.32(bm, 2H), 4.17(bs, 4H). |

Following the method described for Example 2 the following salts can be prepared using the appropriate starting metal base.

| STARTING CARBOXYLIC ACID | STARTING BASE | SALT PRODUCT |
|---|---|---|
| 3,7-Bis[(2-anthra-cenylcarbonyl)amino]-2,8-dibenzothiophene-2,8-dicarboxylic acid | potassium hydroxide | potassium |
| 3,7-Bis{[(9,10-dihydro-9,10-dioxo-2-anthra-cenyl)carbonyl]amino}-dibenzothiophene-2,8-dicarboxylic acid | calcium hydroxide | calcium |
| 3,7-Bis[(thieno[3,2-b]thien-2-ylcarbonyl)amino]dibenzothiophene-2,8-dicarboxylic acid | magnesium hydroxide | magnesium |
| 3,7-Bis-[(8-chloro-4H-thieno[3,2-c][1]benzo-thiopyran-2-carbonyl)-amino]dibenzothiophene-2,8-dicarboxylic acid | ammonium hydroxide | ammonium |

EXAMPLE 7

3,7-Bis-[3-(2-chloro-3,4-dimethoxyphenyl) acryloylamino]dibenzothiophene-2,8-dicarboxylic acid dimethyl ester To 100 mg of the product of Reference Example 6A was added 3 ml of DMAC and 263 μl N,N-diisopropylethylamine, and the mixture was heated in a 90° C. oil bath to afford a solution. To the hot solution 626 mg of 3-(2-chloro-3,4-dimethoxyphenyl)-acryloyl chloride was quickly added. The reaction was heated for five minutes and an additional 4 ml of DMAC was added. The reaction was maintained at 90° C. until TLC indicated the disappearance of the starting diamine. The resulting precipitate was collected while hot, rinsed with warm DMAC, methanol, acetone, and dried in vacuo at 80° C. to give 203 mg of 3,7-bis-[3-(2-chloro-3,4-dimethoxyphenyl)acryloylamino] dibenzothiophene-2,8-dicarboxylic acid dimethyl ester as a yellow solid.

Following the method described for Example 7 the following compounds are prepared:

3,7-Bis-(3-biphenyl-4-ylacryloylamino) dibenzothiophene-2,8-dicarboxylic acid dimethyl ester, 3,7-Bis-[3-(3-bromo-4-hydroxy-5-methoxyphenyl) acryloylamino]dibenzothiophene-2,8-dicarboxylic acid dimethyl ester, 3,7-Bis-[3-(2,3,4-trimethoxyphenyl)acryloylamino] dibenzothiophene-2,8-dicarboxylic acid dimethyl ester, and 3,7-Bis{[3-(4-methoxyphenyl)acryloylamino]-dibenzothiophene-2,8-dicarboxylic acid dimethyl ester.

EXAMPLE 8

3,7-Bis-[3-(2-chloro-3,4-dimethoxyphenyl) acryloylamino]dibenzothiophene-2,8-dicarboxylic acid, disodium salt To 746 mg of the product of Example 7 was added 15 ml of freshly made 1M potassium t-butoxide in DMSO. The reaction was heated in a 40° C. oil bath and monitored by Mass Spectra for the appearance of product ion. The mixture was poured into 25 ml of cold 1N hydrochloric acid and stirred cold for 1 hour. The resulting precipitate was collected, washed with 1N hydrochloric acid and a little water, and dried in vacuo to give the desired product 3,7-bis-[3-(2-chloro-3,4-dimethoxyphenyl)acryloylamino] dibenzothiophene-2,8-dicarboxylic acid as the free acid.

The free acid was dissolved in 1 L of hot 1:1 methyl alcohol/chloroform containing 2% water. To this was added 2.5 equivalents of sodium methoxide and the solution reduced in volume until cloudy. Eight to 10 volumes of diethyl ether was added, the precipitate collected, washed with water and diethyl ether and dried in vacuo at 80° C. to give 675 mg of the desired product (yellow solid) as the disodium salt.

¹H NMR(300 MHz, DMSO-d₆):δ 9.16(s, 2H), 8.81(s, 2H) 7.91(d, J=15.60 Hz, 2H), 7.75(d, J=9.00 Hz, 2H), 7.20(d, J=9.00 Hz, 2H), 6.70(d, J=15.60 Hz, 2H), 3.94(s, 3H), 3.84(s, 3H). MS(ES): m/z 749.1 (M–H)⁻. m.p. (dec)350° C.

Following the deblocking method for the conversion of esters to carboxylic acids described in Example 8 the following compounds are prepared:

3,7-Bis-(3-bi phenyl-4-ylacryloylamino) dibenzothiophene-2,8-dicarboxylic acid, 3,7-Bis-[3-(3-bromo-4-hydroxy-5-methoxyphenyl) acryloylamino]dibenzothiophene-2,8-dicarboxylic acid, 3,7-Bis-v[3-(2,3,4-trimethoxyphenyl)acryloylamino] dibenzothiophene-2,8-dicarboxylic acid, and 3,7-wish [3-(4-methoxyphenyl)acryloylamino]- dibenzothiophene-2,8-dicarboxylic acid.

Representative compounds of Formula (I) made by the method of Example 7 and Example 8 are shown in Table 2 as the disodium salts.

TABLE 2

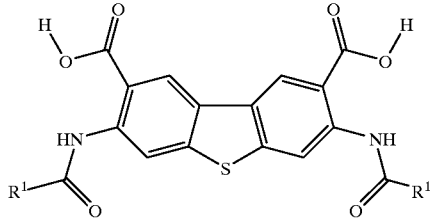

Formula I

| Example No. | Name | R¹ = | MP° C. | MS(ES)m/z: | ¹H NMR (DMSO-d₆): δ |
|---|---|---|---|---|---|
| 9 | 3,7-Bis-(3-biphenyl-4-ylacryloylamino)di-benzothiophene-2,8-dicarboxylic Acid, disodium salt | biphenyl-vinyl group | >400 | 713.1 (M-H)⁻ | 9.10(bs, 2H), 8.82(bs, 2H), 7.73(bm, 14H), 7.45(m, 4H), 7.38(d, J=5.40Hz, 2H), 6.72(d, J=11.70Hz, 2H). |
| 10 | 3,7-Bis-[3-(3-bromo-4-hydroxy-5-methoxy-phenyl)acryloylamino]-dibenzothiophene-2,8-dicarboxylic Acid, disodium salt | 3-bromo-4-hydroxy-5-methoxyphenyl-vinyl group | >350 | 810.8 (M-H)⁻ | 9.12(s, 2H), 8.51(s, 2H), 6.95(s, 2H), 7.89(d, J=8.70Hz, 2H), 6.71(s, 2H), 5.87(d, J=8.70Hz, 2H), 3.66(m, 6H). |
| 11 | 3,7-Bis-[3-(2,3,4-tri-methoxyphenyl)acryloyl-amino]dibenzothiophene-2,8-dicarboxylic Acid, disodium salt | 2,3,4-trimethoxyphenyl-vinyl group | >350 | 741.2 (M-H)⁻ | 9.16(s, 2H), 8.79(s, 2H), 7.75(d, J=15.91Hz, 2H), 7.52(d, J=8.70Hz, 2H), 6.91(d, J=8.70Hz, 2H), 6.65(d, J=15.91Hz, 2H), 3.85(s, 12H), 3.78(s, 6H). |

TABLE 2-continued

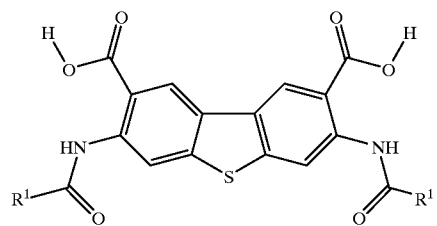

Formula I

| Example No. | Name | R¹ = | MP° C. | MS(ES)m/z: | ¹H NMR (DMSO-d₆): δ |
|---|---|---|---|---|---|
| 12 | 3,7-Bis{[3-(4-methoxy phenyl)acryloylamino]-dibenzothiophene-2,8-dicarboxylic Acid, disodium salt | (structure: CH=CH-C₆H₄-OCH₃) | >300 | 621.1 (M-H)⁻ | 8.92(s, 2H), 8.5(s, 2H), 7.44(d, J=8.70Hz, 4H), 7.38(d, J=15.60Hz, 2H), 6.78(d, J=8.70Hz, 4H), 6.35(d, J=15.60Hz, 2H), 3.60(s, 6H). |

Following the method described for Example 8 the following salts can be prepared using the appropriate starting metal base.

| Starting carboxylic acid | starting base | salt product |
|---|---|---|
| 3,7-Bis-(3-biphenyl-4-ylacryloylamino)di-benzothiophene-2,8-dicarboxylic Acid | potassium hydroxide | potassium |
| 3,7-Bis-[3-(3-bromo-4-hydroxy-5-methoxy-phenyl)acryloylamino]-dibenzothiophene-2,8-dicarboxylic Acid | calcium hydroxide | calcium |
| 3,7-Bis-[3-(2,3,4-tri-methoxyphenyl)acryloyl-amino]dibenzothiophene-2,8-dicarboxylic Acid | magnesium hydroxide | magnesium |
| 3,7-Bis{[3-(4-methoxy phenyl)acryloylamino]-dibenzothiophene-2,8-dicarboxylic Acid | ammonium hydroxide | ammonium |

EXAMPLE 13

3-Chloro-7-[2-(2-chloro-3,4-dimethoxyphenyl) acryloylamino]dibenzothiophene-2,8-dicarboxylic acid dimethyl ester To 250 mg of the product of Reference Example 6B was added 5 ml of DMAC and 373[ti of N,N-diisopropylethylamine. The mixture was heated in a 90° C. oil bath to afford a solution. To the hot solution was quickly added 750 mg of 3-(2-chloro-3,4-dimethoxyphenyl) acryloyl chloride. The reaction was maintained at 90° C. until TLC indicated the disappearance of the starting diamine. The resulting precipitate was collected while hot, rinsed with warm DMAC, methanol, acetone, and dried in vacuo to give 281 mg of the desired product (yellow solid).

Following the method described for Example 13 the following compound was prepared:
  3-[(2-Anthracenylcarbonyl)amino]-7-chlorodibenzothiophene-2,8-dicarboxylic acid dimethyl ester.

EXAMPLE 14

3-Chloro-7-[2-(2-chloro-3,4-dimethoxyphenyl) acryloylamino]dibenzothiophene-2,8-dicarboxylic acid, disodium salt To 275 mg of the product of Example 13 was added 4 ml of freshly made 1M potassium t-butoxide in DMSO. The reaction was heated in a 40° C. oil bath and monitored by Mass Spectra for the appearance of product ion. The mixture was poured into 200 ml of cold 1N hydrochloric acid and stirred in the cold for 1 hour. The resulting precipitate was collected, washed with 1N hydrochloric acid and a little water, and dried in vacuo to give the desired product, 3-chloro-7-[2-(2-chloro-3,4-dimethoxyphenyl)-acryloylamino]dibenzothiophene-2,8-dicarboxylic acid.

To 1 L of hot 1:1 methyl alcohol/chloroform containing 2% water was added 275 mg of the above free acid. To this was added 100 μl of 5N sodium hydroxide and the solution was reduced in volume until cloudy. Once the solution had cooled to room temperature, a 500 ml volume of diethyl ether was added, the precipitate collected, washed with diethyl ether and dried in vacuo to give 127 mg of the desired product (yellow solid) as the disodium salt, m.p. (dec) at 350° C.

¹H NMR(300 MHz, DMSO-d₆):δ 9.16(s, 2H), 8.81(s, 2H), 7.91(d, J=15.60 Hz, 2H), 7.75(d, J=9.00 Hz, 2H), 7.20(d, J=9.00 Hz, 2H), 6.70(d, J=15.60 Hz, 2H), 3.94(s, 3H), 3.84(s, 3H). MS(ES): m/z 749.1 (M–H)⁻. Following the deblocking method for the conversion of esters to carboxylic acids described in Example 14 the following compound was prepared:
  3-[(2-Anthracenylcarbonyl)amino]-7-chlorodibenzothiophene-2,8-dicarboxylic acid.

A representative compound of Formula (II) made by the method of Example 13 and Example 14 is shown in Table 3 as the disodium salts.

TABLE 3

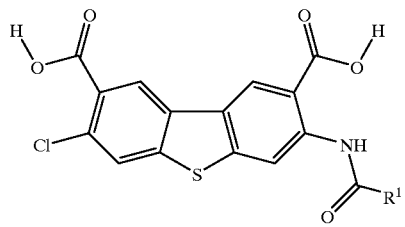

Formula II

| Example No. | Name | R¹ = | MP° C. | MS(ES)m/z: | ¹H NMR (DMSO-d₆): δ |
|---|---|---|---|---|---|
| 15 | 3-[(2-Anthracenyl carbonyl)amino]-7-chlorodibenzothiophene-2,8-dicarboxylic acid, disodium salt | | >300 | 524.1 (M-H)⁻ | 9.31(s, 1H), 8.87(s, 1H), 8.82(s, 1H), 8.69(s, 1H), 8.25(m, 1H), 8.15(m, 5H), 7.94(s, 1H), 7.60(m, 2H). |

Following the method described for Example 14 the following salts can be prepared using the appropriate starting metal base.

| Starting carboxylic acid | starting base | salt product |
|---|---|---|
| 3-Chloro-7-[2-(2-chloro-3,4-dimethoxyphenyl)-acryloylamino]dibenzo-thiophene-2,8-dicarboxylic acid | potassium hydroxide | potassium |
| 3-Chloro-7-[2-(2-chloro-3,4-dimethoxyphenyl)-acryloylamino]dibenzo-thiophene-2,8-dicarboxylic acid | calcium hydroxide | calcium |
| 3-Chloro-7-[2-(2-chloro-3,4-dimethoxyphenyl)-acryloylamino]dibenzo-thiophene-2,8-dicarboxylic acid | magnesium hydroxide | magnesium |
| 3-Chloro-7-[2-(2-chloro-3,4-dimethoxyphenyl)-acryloylamino]dibenzo-thiophene-2,8-dicarboxylic acid | ammonium hydroxide | ammonium |

EXAMPLE 16

3-(2-Chloro-3,4-dimethoxyphenyl)-N-[2,8-dibromo-7-[3-(2-chloro-3,4-dimethoxyphenyl)acryloylamino]-5,5-dioxo-5H-5λ⁶-dibenzothiophen-3-yl}acrylamide To 1.5 g of product of Reference Example 8 was added 25 ml of DMAC and 3.37 ml of N,N-diisopropylethylamine, and the mixture was heated in a 90° C. oil bath to afford a solution. To the hot solution was quickly added 4.96 g of 3-(2-chloro-3,4-dimethoxyphenyl)acryloyl chloride. The reaction was maintained at 90° C. until TLC indicated the disappearance of the starting diamine. The resulting precipitate was collected while hot, rinsed with warm DMAC, methanol, acetone, and dried in vacuo at 80° C. to give 928 mg of the desired product as a white solid.

Following the method described for Example 16 the following compound was prepared:

[4-Methoxyphenyl]-N-{2,8-dibromo-7-[4-methoxyphenyl)acryloylamino]-5,5-dioxo-5H-5λ⁶-dibenzothiophen-3-yl}acrylamide.

EXAMPLE 17

N,N'-(2,8-Dibromo-5,5-dioxo-5H-5λ⁶-dibenzothiophene-3,7-diyl)bis[benzo[b]thiophene-2-carboxamide]

To 1.0 g of the the product from Reference Example 8 was added 35 ml of DMAC and 1.9 ml of N,N-diisopropylethylamine, and the mixture was heated in a 120° C. oil bath to afford solution. To the hot solution was quickly added 3.4 g of benzo[b]thiophene-2-carbonyl chloride. The reaction was maintained at 120° C. until TLC indicated the disappearance of the starting amine. The resulting precipitate was collected while hot, rinsed with warm DMAC, methanol, acetone and dried in vacuo at 40° C. to give 1.37 g of the desired product as a yellow solid.

Following the method described for Example 17 the following compounds were prepared:

N,N'-(2,8-Dibromo-5,5-dioxo-5H-5λ⁶-dibenzothiophene-3,7-diyl)bis[9,10-dioxo-9,10-dihydroanthracene-2-carboxamide], and N,N'-(2,8-Dibromo-5,5-dioxo-5H-5λ⁶-dibenzothiophene-3,7-diyl)bis[anthracene-2-carboxamide]

EXAMPLE 18

[3,7-Bis-[3-(2-chloro-3,4-dimethoxyphenyl)acryloylamino]-8-(ethoxyhydroxyphosphoryl)-5,5-dioxo-5H-5λ⁶-dibenzothiophen-2-yl]phosphonic acid monoethyl ester To a nitrogen flushed flask containing 2.45 g of the product of Example 16 was added, via syringe, 1.04 ml of diethylphosphite, 1.12 ml of triethylamine and 15 ml of N,N-dimethylformamide(DMF). The resulting stirred mixture was heated to 90° C. and 1.66 g of tetrakistriphenylphosphine palladium(0) was added, rapidly. The reaction was cooled, and the product precipitated by the addition of excess (200 ml) of 1N hydrochloric acid. The solid was collected, washed and lip dried in vacuo. The collected solid was dissolved in acetone; dry Silica Gel was added and the solvent was removed in vacuo. The Silica Gel/compound support was applied to a Silica Gel column which was eluted with 20% acetone, 79% hexane, 1% glacial acetic acid gradient to 50% acetone, 49% hexane, 1% glacial acetic acid). The product containing fractions were combined and concentrated in vacuo to give [3,7-bis-[3-(2-chloro-3,4-dimethoxyphenyl)acryloylamino]-8-(ethoxyhydroxyphosphoryl)-5,5-dioxo-5H-5λ⁶-dibenzothiophen-2-yl]-phosphonic acid monoethyl ester. Following the method described for Example 18 the following compound was prepared:

[3,7-Bis-[3-(4-methoxyphenyl)acryloylamino]-8-(ethoxyhydroxyphosphoryl)-5,5-dioxo-5H-5λ⁶-dibenzothiophen-2-yl]phosphonic acid monoethyl ester.

EXAMPLE 19

[3,7-Bis-[3-(2-chloro-3,4-dimethoxyphenyl)acryloylamino]-8-(ethoxyhydroxyphosphoryl)-5,5-dioxo-5H-5λ⁶-dibenzothiophen-2-yl]phosphonic acid monoethyl ester, disodium salt To a mixture of 400 ml of 50/50 methyl alcohol/chloroform containing 2 ml of water and 2 equivalents of sodium methoxide was added the solid product of Example 18. The solution was taken to dryness and the solid dissolved in 50 ml of acetone and heated at the boiling point of the solvent for ½ hour with stirring. Excess hexane was added and the resulting solid collected, washed with hexane and dried to give 0.732 g of the desired product, [3,7-bis-[3-(2-chloro-3,4-dimethoxyphenyl)acryloylamino]-8-(ethoxyhydroxyphosphoryl)-5,5-dioxo-5H-5λ⁶-dibenzothiophen-2-yl]phosphonic acid monoethyl ester disodium salt, m.p.=>355° C.

$^1$H NMR(300 MHz, DMSO-d$_6$):δ 8.99(s, 2H), 8.52(s, 2H), 8.12(d, J=12.30 Hz, 2H), 7.93(d, J=15.60 Hz, 2H), 7.20(d, J=9.00 Hz, 2H), 7.15(d, J 9.00 Hz, 2H), 6.57(d, J=15.60 Hz, 2H), 3.91(s, 6H), 3.78(s, 6H), 3.67(q, J=7.20 Hz, J=21.30 Hz, 4H), 1.05(t, J=6.90 Hz, J=13.80 Hz, 6H). MS(ES): m/z 909.1 (M−H)⁻, 454.0 (M−2H)⁻/2.

Representative compounds of Formula (III), may be made by the methods of Example 16, Example 17, Example 18 and Example 19 and are shown in Table 4 as the monoethyl ester disodium salts.

TABLE 4

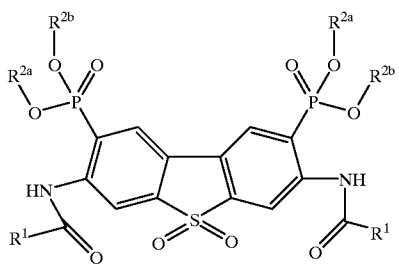

Formula III

| Example No. | Name | R¹ = | MP° C. | MS(ES)m/z: | $^1$H NMR (DMSO-d$_6$): δ |
|---|---|---|---|---|---|
| 20 | [3,7-Bis-[4-methoxyphenyl]-acryloylamino]-8-(ethoxyhydroxy-phosphoryl)-5,5-dioxo-5H-5λ⁶-dibenzothiophen-2-yl]-phosphonic acid monoethyl ester, disodium salt | | >360 | 781.8 (M−H)⁻, 390.4 (M−2H)⁻/2 | 13.15(s, 2H), 8.99(t, J=1.50Hz, J=9.90Hz, 2H), 8.10(d, J=9.00Hz, 2H), 7.66(d, J=6.60Hz, 4H), 7.62(d, J=11.40Hz, 2H), 7.00(d, J=6.60Hz, 4H), 7.62(d, J=11.70Hz, 2H), 3.81(s, 6H), 3.68(m, 4H), 1.05(t, J=5.40Hz, J=20.10Hz, 6H). |

TABLE 4-continued

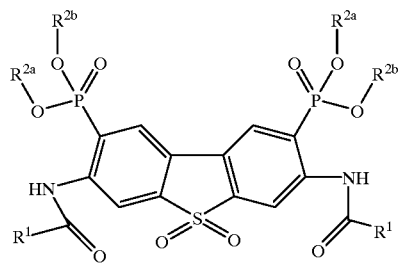

Formula III

| Example No. | Name | R¹ = | MP° C. | MS(ES)m/z: | ¹H NMR (DMSO-d₆): δ |
|---|---|---|---|---|---|
| 21 | [3,7-Bis-[9,10-dioxo-9,10-dihydroanthracene-2-carbonyl)amino]-8-(ethoxyhydroxy-phosphoryl)-5,5-dioxo-5H-5λ⁶-dibenzothiophen-2-yl]phosphonic acid monoethyl ester, disodium salt | (9,10-dioxoanthracen-2-yl) | >360 | 929.2 (M-H)⁻, 464.0 (M-2H)⁻/2 | 9.12(s, 2H), 8.90(s, 2H), 8.60(d, J=7.80Hz, 2H), 8.36(d,J=8.70Hz, 2H), 8.24(m, 6H), 7.97(m, 4H), 3.71(m, 4H), 1.05(t, J=6.90Hz, J=14.10Hz, 6H). |
| 22 | [3,7-Bis-[(anthracene-2-carbonyl)amino]-8-(ethoxyhydroxy-phosphoryl)-5,5-dioxo-5H-5λ⁶-dibenzothiophen-2-yl]-phosphonic acid mono-ethyl ester, disodium salt | (anthracen-2-yl) | >360 | 781.8 (M-H)⁻, 390.4 (M-2H)⁻/2 | 9.20(s, 2H), 8.95(s, 2H), 8.80(s, 2H), 8.68(s, 2H), 8.80(m, 10H),8.68(m, 4H), 3.77(m, 4H), 1.07(t, J=5.40Hz, J=20.10Hz, 6H). |

Following the method described for Example 19 the following salts can be prepared using the appropriate starting base material:

| Starting carboxylic acid | starting base | salt product |
|---|---|---|
| [3,7-Bis-[3-(2-chloro-3,4-dimethoxyphenyl)acryloyl amino]-8-(ethoxyhydroxy-phosphoryl)-5,5-dioxo-5H-5λ⁶-dibenzothiophen-2-yl]phosphonic acid monoethyl ester | potassium hydroxide | potassium |
| [3,7-Bis-[4-methoxyphenyl]-acryloylamino]-8-(ethoxyhydroxy-phosphoryl)-5,5-dioxo-5H-5λ⁶-dibenzothiophen-2-yl]-phosphonic acid monoethyl ester | calcium hydroxide | calcium |
| [3,7-Bis-[(9,10-dioxo-9,10-dihydroanthracene-2-carbonyl)amino]-8-(ethoxyhydroxy-phosphoryl)-5,5-dioxo-5H- 5λ⁶-dibenzothiophen-2-yl]phosphonic acid monoethyl ester | magnesium hydroxide | magnesium |
| [3,7-Bis-[(anthracene-2-carbonyl)amino]-8-(ethoxyhydroxy-phosphoryl)-5,5-dioxo-5H-5λ⁶-dibenzothiophen-2-yl]-phosphonic acid monoethyl ester | ammonium hydroxide | ammonium |

EXAMPLE 23a

[3,7-Bis[(benzo[b]thiophene-2-carbonyl)amino-8-(ethoxyhydroxyphosphoryl)-5,5-dioxo-5H-5λ⁶-dibenzothiophen-2-yl]phosphonic acid monoethyl ester, disodium salt

EXAMPLE 23b

[3,7-Bis[(benzo[b]thiophene-2-carbonyl)amino-8-(diethoxyphosphoryl)-5,5-dioxo-5H-5λ⁶-dibenzothiophen-2-yl]phosphonic acid monoethyl ester, monosodium salt To a nitrogen flushed flask containing 0.20 g of N,N'-(2,8-dibromo-5,5-dioxo-5H-5λ⁶-dibenzothiophene-3,7-diyl)bis[benzo[b]thiophene-2-carboxamide, the product of Example 17, was added, via syringe, 103 [1 of diethylphosphite, 112 μl of triethylamine and 2 ml of DMF. The resulting stirred mixture was heated to 90° C. and 0.166 g of tetrakistriphenylphosphine palladium(0) was added, rapidly. The reaction was heated at 900 for 4 days. The reaction was cooled and the product precipitated by the addition of 50 ml portions of 1N hydrochloric acid. The solid was collected, washed and dried in vacuo. The above solid reaction product was dissolved in acetone; dry Silica Gel was added and the solvent removed in vacuo. The Silica Gel/compound support was applied to a Silica Gel column and eluted with 20% acetone, 1% triethylamine, 79% hexane gradient to 50% acetone, 49% hexane, 1% triethylamine. The product fractions were combined and concentrated in vacuo to give the desired pure products, [3,7-bis[(benzo-[b]thiophene-2-carbonyl)amino-8-(ethoxyhydroxyphosphoryl)-5,5-dioxo-5H-5$\lambda^6$ -dibenzothiophen-2-yl]phosphonic acid monoethyl ester triethylamine salt and [3,7-bis[(benzo[b]thiophene-2-carbonyl)amino-8-(diethoxyphosphoryl)-5,5-dioxo-5H-5$\lambda^6$-dibenzothiophen-2-yl]phosphonic acid monoethyl ester bis-(triethylamine) salt. Each of the triethylamine salts from above were individually dissolved in a minimum amount of DMSO and diluted with excess saturated sodium bicarbonate. The resulting precipitates were collected, washed with a minimum amount of water and dried in vacuo to give:

EXAMPLE 23a

[3,7-Bis[(benzo[b]thiophene-2-carbonyl)amino-8-(ethoxyhydroxyphosphoryl)-5,5-dioxo-5H-5$\lambda^6$-dibenzothiophen-2-yl]-phosphonic acid monoethyl ester. disodium salt:

mp=Decomposed at 315° C. MS(ES)m/z: 780.0(M–H)$^-$, 390.1(M–2H)$^-$/2. $^1$H NMR (DMSO-d$_6$):δ 8.95(t, J=4.5 Hz, J=2.4 Hz, 2H); 8.28(d, J=1.8 Hz, 2H); 8.15(d, J=9.3 Hz, 2H); 8.04(m, 4H); 7.49(m, 4H); 3.69(q, J=5.4 Hz, J=15.60 Hz, 4H); 1.02(t, J=5.4 Hz, J=10.8 Hz, 6H).

and

EXAMPLE 23b

[3,7-Bis[(benzo[b]thiophene-2-carbonyl)amino-8-(diethoxyphosphoryl)-5,5-dioxo-5H-5$\lambda^6$-dibenzothiophen-2-yl]phosphonic acid monoethyl ester, monosodium salt:

mp=Decomposed at 340° C. MS(ES)m/z: 808.9(M–H)$^-$. $^1$H NMR(DMSO-d$_6$):δ 12.12(s, 2H); 9.12(d, J=5.07 Hz, 1H) 9.04(d, J=2.76 Hz, 1H); 8.49(d, J=12.15 Hz, 1H); 8.46(d, J=14.28 Hz, 1H); 8.32(s, 1H); 8.17(s, 1H); 8.13 (m, 4H); 7.54(m, 4H); 4.27(q, J=7.08 Hz, J=22.32 Hz, 4H); 3.75(q, J=14.10 Hz, J=28.03 Hz, 2H); 1.32(t, J=7.08 Hz, J=14.10 Hz, 6H); 1.05(t, J=7.08 Hz, J=14.10 Hz, 3H).

Following the method described for Examples 23a and 23b the following salts can be prepared using the appropriate starting metal base.

| Starting carboxylic acid | starting base | salt product |
| --- | --- | --- |
| [3,7-Bis[(benzo [b]-thiophene-2-carbonyl)-amino-8-(ethoxyhydroxy-phosphoryl)-5,5-dioxo-5H-5$\lambda^6$-dibenzothiophen-2-yl]phosphonic acid monoethyl ester | potassium hydroxide | potassium |
| [3,7-Bis[(benzo[b]-thiophene-2-carbonyl)-amino-8-(ethoxyhydroxy-phosphoryl)-5,5-dioxo-5H-5$\lambda^6$-dibenzothiophen-2-yl]phosphonic acid monoethyl ester | calcium hydroxide | calcium |
| [3,7-Bis[(benzo[b]-thiophene-2-carbonyl)-amino-8-(diethoxy-phosphoryl)-5,5-dioxo-5H-5$\lambda^6$-dibenzothiophen-2-yl]phosphonic acid monoethyl ester | magnesium hydroxide | magnesium |
| [3,7-Bis[(benzo[b]-thiophene-2-carbonyl)-amino-8-(diethoxy-phosphoryl)-5,5-dioxo-5H-5$\lambda^6$-dibenzothiophen-2-yl]phosphonic acid monoethyl ester | ammonium hydroxide | ammonium |

EXAMPLE 24

3,7-Bis-[3-(4-phenylphenyl) acryloylamino]-5,5-dioxo-5H-5$\lambda^6$-dibenzothiophene-2,8-disulfonic acid, disodium salt To 10 ml of thionyl chloride was added 2 g of 4-phenylcinnamic acid. The reaction mixture was heated at 80° C. for 1½ hours, cooled to room temperature, and concentrated in vacuo, at 70° C. to give 3-(4-phenyl)acryloyl chloride as a yellow solid which was not purified but taken on directly.

To a solution of 5 ml of DMAC and 537 μl of N,N-diisopropylethylamine, was added 315 mg of product from Reference Example 10. The mixture was heated in a 90° C. oil bath to afford solution. To the hot solution 750 mg of 3-(4-phenyl)acryloyl chloride prepared above was quickly added. The reaction was maintained at 90° C. until TLC indicated the disappearance of the starting diamine to form 3,7-Bis-[3-(4-phenylphenyl)acryloylamino]-5,5-dioxo-5H-5$\lambda^6$-dibenzothiophene-2,8-disulfonic acid. To the warm solution was added excess cold saturated sodium bicarbonate. The resulting solid was isolated and washed with excess water and dried in vacuo. The precipitate was taken up in 100 ml of methyl alcohol (boiling) followed by the addition of 100 ml of saturated sodium bicarbonate and the mixture was digested for 30 minutes. The solution was cooled and the resulting solid was isolated by filtration and washed with excess water. The solid was dissolved in 300 ml of methanol and digested for 50 minutes with addition of 100 ml of methanol during the boiling time. The solution was filtered warm to remove the precipitate and the solid was washed with methanol and acetone and dried in vacuo to give 487 mg of the desired compound (yellow solid) as the disodium salt. The above filtrate lip was allowed to cool and an additional 55 mg of the product was isolated and treated as described.

$^1$H NMR(300 MHz, DMSO-d$_6$):δ 11.04(s, 2H), 8.93(s, 2H), 8.20(s, 2H), 7.84(d, J 8.37 Hz, 4H), 7.71(m, 10H), 7.48(m, 4H), 7.35(m, 2H), 7.80(d, J=15.66 Hz, 2H). MS(ES): m/z 885.0 (M–H)$^-$, 442.1 (M–2H)$^-$/2. m.p.= Decomposed at 356° C.

Representative compounds of Formula (IV) made by the method of Example 24 are shown in Tables 5 and 6 as the disodium salts.

TABLE 5

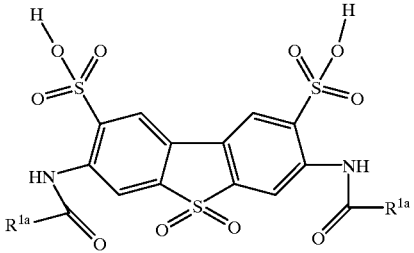

Formula IV

| Example No. | Name | R$^{1a}$ = | MP° C. | MS(ES)m/z: | $^1$H NMR (DMSO-d$_6$): δ |
|---|---|---|---|---|---|
| 25 | 3,7-Bis-[3-(4-nitrophenyl)-acryloylamino]-5,5-dioxo-5H-5λ$^6$-dibenzothiophene-2,8-disulfonic acid, disodium salt | 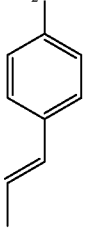 | >350 | 754.6 (M-H)$^-$, 377.0 (M-2H)$^-$/2 | 11.23(s, 2H), 8.95(s, 2H), 8.26(m, 6H), 8.10(d, J=9.00Hz, 4H), 7.76(d, J=10.50Hz, 2H), 7.06(d, J=10.50Hz, 2H). |
| 26 | 3,7-Bis-(3-naphthalen-1-yl-acryloylamino)-5,5-dioxo-5H-5λ$^6$-dibenzothiophene-2,8-disulfonic acid, disodium salt | 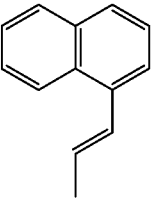 | >300 | 764.8 (M-H)$^-$, 382.0 (M-2H)$^-$/2 | 11.47(s, 2H), 9.03(s, 2H), 8.50(d, J=15.60Hz, 2H), 8.31(m, 4H), 8.05(m, 6H), 7.68(m, 6H), 6.87(d, J=15.60Hz, 2H). |
| 27 | 3,7-Bis[3-(2-chloro-3,4-di-methoxyphenyl)-acryloylamino]-5,5-dioxo-5H-5λ$^6$-dibenzothiophene-2,8-disulfonic acid, disodium salt | 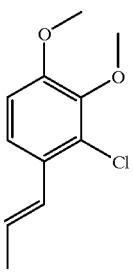 | >300 | 854.6 (M-H)$^-$, 426.0 (M-2H)$^-$/2 | 10.95(s, 2H), 8.97(s, 2H), 8.25(s, 2H), 7.95(d, J=11.70Hz, 2H), 7.85(d,J=6.60Hz, 2H), 7.15(d, J=6.60Hz, 2H), 6.75(d, J=11.70Hz, 2H), 3.94(s, 6H), 3.84(s, 6H). |
| 28 | 5,5-Dioxo-3,7-bis-(3-pyridin-4-ylacryloylamino)-5H-5λ$^6$-dibenzothiophene-2,8-disulfonic acid, disodium salt | 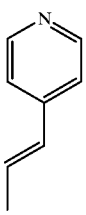 | >355 | 666.8 (M-H)$^-$, 333.0 (M-2H)$^-$/2 | 11.12(s, 2H), 9.00(s, 2H), 8.71(d, J=3.90Hz, 4H), 8.32(s, 2H), 7.83(d, J=4.20Hz, 4H), 7.73(d, J=11.70Hz, 2H), 7.16(d, J=12.00Hz, 2H). |

TABLE 5-continued

Formula IV

| Example No. | Name | R$^{1a}$ = | MP° C. | MS(ES)m/z: | $^1$H NMR (DMSO-d$_6$): δ |
|---|---|---|---|---|---|
| 29 | 3,7-Bis-[3-(4-formylphenyl)-acryloylamino]-5,5-dioxo-5H-5λ$^6$-dibenzothiophene-2,8-disulfonic acid, disodium salt | 4-formylphenyl propenyl | >355 | 720.7 (M-H)$^-$, 360.0 (M-2H)$^-$/2 | 11.08(s, 2H), 10.05(s, 2H), 8.27(s, 2H), 8.04(d, J=9.00Hz, 4H), 7.97(d, J=9.00Hz, 4H), 7.76(d, J=12.00Hz, 2H), 7.01(d, J=12.00Hz, 2H). |
| 30 | 3,7-Bis-[3-(4-methoxyphenyl)-acryloylamino]-5,5-dioxo-5H-5λ$^6$-dibenzothiophene-2,8-disulfonic acid, disodium salt | 4-methoxyphenyl propenyl | >350 | 725.1 (M-H)$^-$, 362.0 (M-2H)$^-$/2 | 11.91(s, 2H), 8.96(s, 2H), 8.22(s, 2H), 7.75(d, J=8.79Hz, 4H), 7.65(d, J=15.60Hz, 2H), 7.01(d, J=8.79Hz, 4H), 6.60(d, J=15.60Hz, 2H), 3.82(s, 6H). |
| 31 | 3,7-Bis-[(E)-3-(3-hydroxy-phenyl)acryloyl amino]-5,5-dioxo-5H-5λ$^6$-dibenzothiophene-2,8-disulfonic acid, disodium salt | 3-hydroxyphenyl propenyl | >400 | 697.0 (M-H)$^-$ | 10.98(s, 2H), 8.95(s, 2H), 8.24(s, 2H), 7.58(d, J=15.60Hz, 2H), 7.24(m, 2H), 7.15(d, J=7.80Hz, 2H), 7.08(s, 2H), 6.83(dd, J=1.20Hz, J=7.80Hz, 2H), 6.63(d, J=15.60Hz, 2H). |
| 32 | 3,7-Bis-[3-(4-cyanophenyl)-acryloylamino]-5,5-dioxo-5H-5λ$^6$-dibenzothiophene-2,8-disulfonic acid, disodium salt | 4-cyanophenyl propenyl | >300 | 357.3 (M-2H)$^-$/2 | 11.05(s, 2H), 8.94(s, 2H), 8.25(s, 2H), 8.01(d, J=6.30Hz, 4H), 7.89(d, J=6.30Hz, 4H), 7.53(d, J=12.00Hz, 2H), 7.01(d, J=12.00Hz, 2H). |

TABLE 5-continued

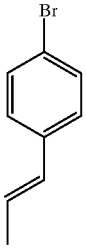

Formula IV

| Example No. | Name | R$^{1a}$ = | MP° C. | MS(ES)m/z: | $^1$H NMR (DMSO-d$_6$): δ |
|---|---|---|---|---|---|
| 33 | 3,7-Bis-[3-(4-bromophenyl)-acryloylamino]-5,5-dioxo-5H-5λ$^6$-dibenzothiophene-2,8-disulfonic acid, disodium salt | 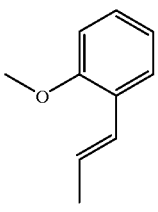 | >300 | 823.0 (M-H)$^-$, 411.2 (M-2H)$^-$/2 | 10.97(s, 2H), 8.95(s, 2H), 8.25(s, 2H), 7.76(d, J=6.30Hz, 4H), 7.62(m, 6H), 6.84(d, J=11.70Hz, 2H). |
| 34 | 3,7-Bis-[3-(2-methoxyphenyl)-acryloylamino]-5,5-dioxo-5H-5λ$^6$-dibenzothiophene-2,8-disulfonic acid, disodium salt | 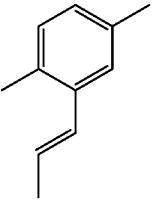 | De-comp. at 355 | 725.0 (M-H)$^-$ | 10.91(s, 2H), 8.97(s, 2H), 8.23(s,2H), 7.96(d, J=15.60Hz, 2H), 7.78(d, J=7.41Hz, 2H), 7.43(m, 4H), 7.13(d, J=8.37Hz, 2H), 7.02(m, 2H), 6.75(d, J=15.60Hz, 2H), 3.91(s, 6H). |
| 35 | 3,7-Bis-[3-(2,5-dimethylphenyl)-acryloylamino]-5,5-dioxo-5H-5λ$^6$-dibenzothiophene-2,8-disulfonic acid, disodium salt |  | De-comp. at 385 | 721.1 (M-H)$^-$, 360.1 (M-2H)$^-$/2 | 11.02(s, 2H), 8.97(s, 2H), 8.23(s, 2H), 7.90(d, J=15.60Hz, 2H), 7.65(s, 2H), 7.17(m, 2H), 6.65(d, J=15.60Hz, 2H), 2.40(s, 6H), 2.33(s, 6H). |
| 36 | 3,7-Bis-[3-(4-isopropylphenyl)-acryloylamino]-5,5-dioxo-5H-5λ$^6$-dibenzothiophene-2,8-disulfonic acid, disodium salt | 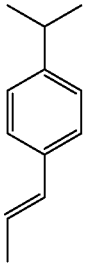 | >350 | 748.9 (M-H)$^-$, 374.2 (M-2H)$^-$/2 | 10.97(s, 2H), 8.97(s, 2H), 8.24(s, 2H), 7.70(d, J=7.80Hz, 4H), 7.65(d, J=15.60Hz, 2H), 7.32(d, J=7.80Hz, 4H), 6.70(d, J=15.60Hz, 2H), 2.93(m, 2H), 1.24(s, 6H), 1.21(s, 6H). |
| 37 | 3,7-Bis-[3-(2-methoxyphenyl)-acryloylamino]-5,5-dioxo-5H-5λ$^6$-dibenzothiophene-2,8-disulfonic acid, disodium salt | 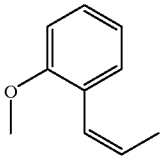 | De-comp. at 390 | 725.0 (M-H)$^-$ | 10.91(s, 2H), 8.97(s, 2H), 8.24(s, 2H), 7.95(d, J=15.60Hz, 2H), 7.78(d, J=7.20Hz, 2H), 7.43(m, 2H), 7.13(d, J=7.20Hz, 2H), 7.03(m, 2H), 6.75(d, J=15.60Hz, 2H), 3.91(s, 6H). |

TABLE 5-continued

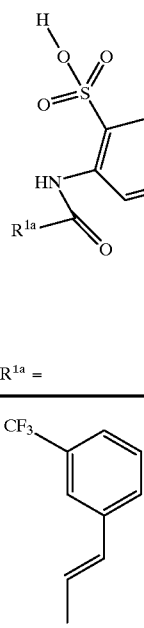

Formula IV

| Example No. | Name | $R^{1a}$ = | MP° C. | MS(ES)m/z: | $^1$H NMR (DMSO-$d_6$): δ |
|---|---|---|---|---|---|
| 38 | 3,7-Bis-[3-(3-trifluoromethyl-phenyl)acryloyl-amino]-5,5-dioxo-5H-5λ$^6$-dibenzothiophene-2,8-disulfonic acid, disodium salt | (3-CF$_3$-phenyl-CH=CH-) | >355 | 800.6 (M-H)$^-$, 400.0 (M-2H)$^-$/2 | 11.00(s, 2H), 8.96(s, 2H), 8.25(s, 2H), 8.23(s, 2H), 8.12(d, J=5.70Hz, 2H), 7.78(m, 4H), 7.67(t, J=5.70Hz, J=11.70Hz, 2H), 7.07(d, J=11.70Hz, 2H). |

TABLE 6

Formula IV

| Example No. | Name | $R^{1a}$ = | MP° C. | MS(ES)m/z: | $^1$H NMR (DMSO-$d_6$): δ |
|---|---|---|---|---|---|
| 40 | 3,7-Bis-[(benzo[b]thiophene-2-carbonyl)amino]-5,5-dioxo-5H-5λ$^6$-dibenzothiophene-2,8-disulfonic acid, disodium salt | (benzo[b]thiophen-2-yl) | >300° | 724.7 (M-H)$^-$, 361.9 (M-2H)$^-$/2 | 11.92(s, 2H), 8.93(s, 2H), 8.35(s, 2H), 8.12(m, 4H), 8.05(s, 2H), 7.53(m, 4H). |
| 41 | 3,7-Bis-[(benzo)[b]thiophene-2-carbonyl-3-chloro)amino]-5,5-dioxo-5H-5λ$^6$-dibenzothiophene-2,8-disulfonic acid, disodium salt | (3-chloro-benzo[b]thiophen-2-yl) | >300 | 794.0 (M-H)$^-$, 396.0 (M-2H)$^-$/2 | 11.17(s, 2H), 8.85(s, 2H), 8.35(s, 2H), 8.22(m, 2H), 8.01(m, 2H), 7.68(m, 4H). |

TABLE 6-continued

Formula IV

| Example No. | Name | R$^{1a}$ = | MP° C. | MS(ES)m/z: | $^1$H NMR (DMSO-d$_6$): δ |
|---|---|---|---|---|---|
| 42 | 3,7-Bis[(benzo[b]furan-2-carbonyl)amino]-5,5-dioxo-5H-5λ$^6$-dibenzothiophene-2,8-disulfonic acid, disodium salt | (2-methylbenzofuran) | >355 | 792.7 (M-H)$^-$, 346.0 (M-2H)$^-$/2 | 11.95(s, 2H), 8.98(s, 2H), 8.31(s, 2H), 7.88(d, J=6.00Hz, 2H), 7.77(s, 2H), 7.76(d, J=6.00Hz, 2H), 7.58(t, J=6.00Hz, J=11.70Hz, 2H), 7.42(t, J=6.00Hz, J=11.40Hz, 2H). |
| 43 | 5,5-Dioxo-3,7-bis-[(thieno[3,2-b]thiophene-2-carbonyl)-amino]-5H-5λ$^6$-dibenzothiophene-2,8-disulfonic acid, disodium salt | (2-methylthieno[3,2-b]thiophene) | Decomp. at 420 | 736.7 (M-H)$^-$, 368.1 (M-2H)$^-$/2 | 11.85(s, 2H), 8.90(s, 2H), 8.30(s, 2H), 8.05(s, 2H), 7.97(d, J=5.22Hz, 2H), 7.58(d, J=5.22Hz, 2H). |
| 44 | 3,7-Bis-[(1,3-di-methyl-1H-thieno[2,3-c]pyrazole-5-carbonyl)amino]-5,5-dioxo-5H-5λ$^6$-dibenzothiophene-2,8-disulfonic acid, disodium salt | (1,3-dimethylthieno[2,3-c]pyrazole) | >420 | 761.1 (M-H)$^-$, 380.1 (M-2H)$^-$/2 | 11.75(s, 2H), 8.87(s, 2H), 8.27(s, 2H), 7.63(s, 2H), 3.92(s, 6H), 2.43(s, 6H). |
| 45 | 3,7-Bis-{[1-(4-chlorophenyl)-5-propyl-1H-pyrazole-4-carbonyl]amino}5,5-dioxo-5H-5λ$^6$-dibenzothiophene-2,8-disulfonic acid, disodium salt | (1-(4-chlorophenyl)-5-propyl-4-methylpyrazole) | Decomp. at 359 | 816.8 (M-H)$^-$, 408.1 (M-2H)$^-$/2 | 11.35(s, 2H), 8.97(s, 2H), 8.25(s, 2H), 8.02(s, 2H), 7.66(m, 8H), 3.00(m, 4H), 1.51(m, 4H), 0.80(t, J=7.29Hz, J=14.67Hz, 6H). |
| 46 | 5,5-Dioxo-3,7-bis-[(2-phenyl-2H-[1,2,3]triazole-4-carbonyl)amino]-5H-5λ$^6$-dibenzothiophene-2,8-disulfonic acid, disodium salt | (5-methyl-2-phenyl-2H-1,2,3-triazole) | >350 | 747.0 (M-H)$^-$, 372.9 (M-2H)$^-$/2 | 12.14(s, 2H), 9.01(s, 2H), 8.69(s, 2H), 8.33(s, 2H), 8.15(d, J=6.00Hz, 4H), 7.69(m, 4H), 7.56(m, 2H). |

TABLE 6-continued

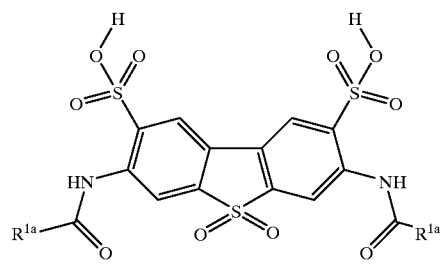

Formula IV

| Example No. | Name | $R^{1a}$ = | MP° C. | MS(ES)m/z: | $^1$H NMR (DMSO-d$_6$): δ |
|---|---|---|---|---|---|
| 47 | 3,7-Bis-[(7-methoxy-2-oxo-benzopyran-3-yl)-carbonylamino]-5,5-dioxo-5H-5λ$^6$-dibenzothiophene-2,8-disulfonic acid, disodium salt | | >360 | 809.2 (M-H)$^-$, 404.1 (M-2H)$^-$/2 | 11.75(s, 2H), 8,98(s, 2H), 8.79(s, 2H), 8.25(s, 2H), 7,9(d, J=8.82Hz, 2H), 7.17(d, J=2.25Hz, 2H), 7.08(dd, J=2.37Hz, J=11.10Hz, 2H). |

Following the method described for Example 24 the following salts can be prepared using the appropriate starting metal base.

| Starting carboxylic acid | starting base | salt product |
|---|---|---|
| 3,7-Bis-[3-(4-phenylphenyl)-acryloylamino]-5,5-dioxo-5H-5λ$^6$-dibenzothiophene-2,8-disulfonic acid | potassium hydroxide | potassium |
| 3,7-Bis-[3-(2-chloro-3,4-di-methoxyphenyl)-acryloylamino]-5,5-dioxo-5H-5λ$^6$-dibenzothiophene-2,8-disulfonic acid | calcium hydroxide | calcium |
| 3,7-Bis-[3-(4-methoxyphenyl)-acryloylamino]-5,5-dioxo-5H-5λ$^6$-dibenzothiophene-2,8-disulfonic acid | magnesium hydroxide | magnesium |
| 3,7-Bis-[3-(2-methoxyphenyl)-acryloylamino]-5,5-dioxo-5H-5λ$^6$-dibenzothiophene-2,8-disulfonic acid | ammonium hydroxide | ammonium |

EXAMPLE 48

3,7-Bis[(4-nitrophenyl-2-carbonyl)amino]-5,5-dioxo-5H-5λ$^6$-dibenzothiophenedioxide-2,8-disulfonic acid, disodium salt A mixture of 25.7 g of 3,7-diaminobenzothiophenedioxide-2,8-disulfonic acid and 176 ml of pyridine was heated to 50° C. and 33 g of 4-nitrobenzoyl chloride was added gradually over a 2 hour period. One hundred and forty ml of 20% sodium bicarbonate (by volume) was added and the pyridine removed by steam distillation. The mixture was cooled to room temperature and the resulting solid, 3,7-bis[(4-nitrophenyl-2-carbonyl)amino]-5,5-dioxo-5H-5λ$^6$-dibenzothiophenedioxide-2,8-disulfonic acid disodium salt, was collected and dried in a vacuum oven at 65° C. (U.S. Pat. No. 2,911,415).

EXAMPLE 49

3,7-Bis[(4-biphenyl-2-carbonyl)amino]-5,5-dioxo-5H-5λ$^6$-dibenzothiophene-2,8-disulfonic acid, di-pyridine salt To a mixture of 23.2 g of benzidinesulfone disulfonic acid pyridine salt, 23.7 g of 4-biphenyl-carboxylic acid and 110 g of pyridine, was added dropwise, 11 g of phosphorous oxychloride. The mixture was heated at the reflux temperature with stirring until tlc showed the absence of any starting material (about 2 hours). After cooling, the precipitated product was collected and recrystallized from the monomethyl ether of ethylene glycol (U.S. Pat. No. 3,226,247).

Representative compounds of Formula (V) made by the method of Example 49 are shown in Table 7 as the disodium salts.

TABLE 7

Formula V

R$^{24}$ = −SO$_2$−O−H (sulfonic acid group)

R$^{23}$ = −NH−C(O)−R$^1$ n = 2

| Example No. | Name | R$^1$ = | MP °C. | MS(ES)m/z: | $^1$H NMR (DMSO-d$_6$): δ |
|---|---|---|---|---|---|
| 50 | 3,7-Bis-(4-methoxybenzoyl-amino)-5,5-dioxo-5H-5λ$^6$-dibenzothiophene-2,8-disulfonic acid, disodium salt | 4-methoxyphenyl | Decomp. at 360 | 673.1 (M—H)$^-$, 336.0 (M-2H)$^-$/2 | 11.55(s, 2H), 9.03(s, 2H), 8.25(s, 2H), 7.95(d, J=8.67Hz, 4H), 7.16(d, J=8.70Hz, 4H), 3.87(s, 6H). |
| 51 | 3,7-Bis-(2,4-dimethoxybenzoyl-amino)-5,5-dioxo-5H-5λ$^6$-dibenzothiophene-2,8-disulfonic acid disodium salt | 2,4-dimethoxyphenyl | >360 | 733.1 (M—H)$^-$, 366.1 (M-2H)$^-$/2 | 11.63(s, 2H), 9.08(s, 2H), 8.22(s, 2H), 8.01(d, J=10.80Hz, 2H), 6.68(m, 4H), 4.00(s, 6H), 3.87(s, 6H). |
| 52 | 5,5-Dioxo-3,7-bis-(4-phenyl-sulfonylbenzoyl-amino)-5H-5λ$^6$-dibenzothiophene-2,8-disulfonic acid, disodium salt | 4-(phenylsulfonyl)phenyl | Decomp. at 365 | 893.0 (M—H)$^-$, 446.0 (M—2H)$^-$/2 | 11.76(s, 2H), 8.95(s, 2H), 8.29(s, 2H), 8.20(d, J=8.43Hz, 4H), 8.13(d, J=8.43Hz, 4H), 8.03(d, J=7.23Hz, 4H), 7.68(m, 6H. |
| 53 | 3,7-Bis-(3-ethoxy-naphthalen-2-ylcarbonylamino)-5,5-dioxo-5H-5λ$^6$-dibenzothiophene-2,8-disulfonic acid, disodium salt | 3-ethoxynaphthalen-2-yl | >360 | 801.2 (M—H)$^-$, 400.1 (M-2H)$^-$/2 | 11.51(s, 2H), 9.05(s, 2H), 8.49(s, 2H), 8.27(s, 2H), 8.01(d, J=8.04Hz, 2H), 7.91(d, J=8.10 Hz, 2H), 7.56(m, 4H), 7.43(m, 2H), 4.40(q, J=6.90Hz, J=13.92Hz, 4H), 1.47(t, J=6.90Hz, J=13.92Hz, 6H). |

TABLE 7-continued

| | | | | | |
|---|---|---|---|---|---|
| 54 | 3,7-Bis-(anthracen-2-ylcarbonylamino)-5,5-dioxo-5H-5λ$^6$-dibenzothiophene-2,8-disulfonic acid, disodium salt | | Decomp. at 360 | 436.0 (M—2H)hu −/2 | 11.93(s, 2H), 9.12(s, 2H), 8.85(s, 2H), 8.80(s, 2H), 8.76(s, 2H), 8.34(s, 2H), 8.31(s, 2H), 8.1(s, 4H), 8.01(dd, J=7.41Hz, J=10.50Hz, 2H), 7.63(m, 4H). |
| 55 | 3,7-Bis-[9,10-dihydro-9,10-dioxoanthracen-2-yl)carbonyl-amino]-5,5-dioxo-5H-5λ$^6$-dibenzothiophene-2,8-disulfonic acid, disodium salt | | >360 | 809.2 (M—H)$^-$, 404.1 (M-2H)$^-$/2 | 12.01(s, 2H), 9.04(s, 2H), 8.78(s, 2H), 8.43(s, 4H), 7.27(m, 6H), 7.98(m, 4H). |
| 56 | 3,7-Bis-(4-ethyl-thiobenzoylamino)-5,5-dioxo-5H-5λ$^6$-dibenzothiophene-2,8-disulfonic acid, disodium salt | | >360 | 713.1 (M—H)$^-$, 356.0 (M-2H)$^-$/2 | 11.63(s, 2H), 9.02(s, 2H), 8.60(s, 2H), 8.31(s, 2H), 8.15(s, 4H), 8.05(s, 4H), 7.68(s, 4H), 3.33(s, 3H), 3.31(s, 3H). |
| 57 | 3,7-Bis-[(naphthalen-2-yl)carbonylamino]-5,5-dioxo-5H-5λ$^6$-dibenzothiophene-2,8-disulfonic acid, disodium salt | | Decomp. at 365 | 673.1 (M—H)$^-$, 336.0 (M-2H)$^-$/2 | 11.85(s, 2H), 9.09(s, 2H), 8.61(s, 2H), 8.31(s, 2H), 8.15(m, 4H), 8.05(m, 4H), 7.69(m, 4H). |
| 58 | 3,7-Bis-({4-[(2,4-dimethoxy-phenyl)carbonyl-amino]-2-methoxy-phenyl}carbonyl-amino)-5,5-dioxo-5H-5λ$^6$-dibenzothiophene-2,8-disulfonic acid, disodium salt | | >360 | 1032.0 (M—H)$^-$, 515.5 (M-2H)/2 | 11.65(s, 2H), 10.24(s, 2H), 9.10(s, 2H), 8.24(s, 2H), 8.02(d, J=8.40Hz, 2H), 7.78(s, 2H), 7.75(s, 2H), 7.43(d, J=7.20Hz, 2H), 6.72(m, 4H), 4.00(s, 6H), 3.97(s, 6H), 3.86(s, 6H). |

TABLE 7-continued

| # | Name | Structure | | MW | NMR |
|---|------|-----------|---|----|-----|
| 59 | 3,7-Bis-[(4-acetylamino-2-methoxy-phenyl)carbonylamino]-5,5-dioxo-5H-5$\lambda^6$-dibenzothiophene-2,8-disulfonic acid, disodium salt | 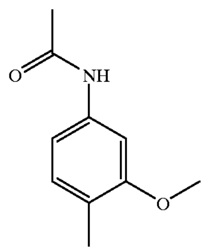 | >350 | 787.1 (M—H)$^-$, 393.1 (M-2H)$^-$/2 | 11.65(s, 2H0, 10.32(s, 2H), 9.08(s, 2H), 8.23(s, 2H), 7.93(d, J=8.70Hz, 2H), 7.58(s, 2H), 7.26(d, J=8.70Hz, 2H), 3.96(s, 6H), 2.10(s, 6H). |
| 60 | 3,7-Bis-(4-benzoylaminobenzoylamino)-5,5-dioxo-5H-5$\lambda^6$-dibenzothiophene-2,8-disulfonic acid, disodium salt | 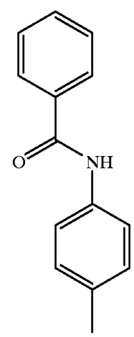 | >360 | 851.1 (M—H)$^-$, 425.0 (M-2H)$^-$/2 | 11.63(s, 2H), 10.62(s, 2H), 9.06(s, 2H), 8.29(s, 2H), 7.99(m, 6H), 7.63(m, 3H). |

BIOLOGICAL ACTIVITY

The following are abbreviations used in this section.
VEGF 165—Vascular Endothelial Growth Factor, 165 amino acid isoform
KDR—Kinase domain receptor, cell surface tyrosine kinase receptor for VEGF
Flt-1—fms-like tyrosine kinase, cell surface tyrosine kinase receptor for VEGF
HEPES—(N-[2-Hydroxyethyl]piperazine-N'-[2-ethanesulfonic acid])
DMEM—Dulbecco's Modified Eagle Medium
KDR-Fc—Fusion protein of the extracellular ligand binding domain of KDR fused to the Fc portion of a human IgGl domain
SPA—Scintillation Proximity Assay
BAE—Bovine Aortic Endothelial Cells
HUVECS—Human Umbilical Vein Endothelial Cells
ELVAX—Ethylene-vinyl Acetate Copolymer
FGF—Fibroblast Growth Factor
BSA—Bovine Serum Albumin
N.T.—Not Tested
PBS—Phosphate Buffered Saline
PVT—Poly Vinyl Toluene
NaPi—Sodium Phosphate The compounds of this invention are tested in the following Standard Pharmacological Test Procedures Inhibition of Binding of VEGF 165 to KDR & Flt-1 Receptors as Measured by SPA Assay 1. Preparation of conditioned media containing the KDR-Fc soluble VEGF receptor.:

Human 293KDR2 cells, which secrete a soluble KDR-Fc fusion protein, were grown in Dulbecco's Modified Eagle Medium supplemented with 10% fetal calf serum, 2 mM glutamine, 10 units/ml penicillin G sulfate, 10 μg/ml streptomycin sulfate and 175 μg/ml geneticin (G418) sulfate. Cells were plated at a density of 106 cells/100 mm dish and incubated at 37° C. in a humidified atmosphere containing 95% air and 5% $CO_2$. After 10 days, conditioned medium was collected and centrifuged at 15,000 rpm for 15 min to remove dead cells. A total of 0.1 volume of 1.15% gelatin and 0.02 volume of 1M HEPES buffer (pH 8) was added. Leupeptin and pepstatin A were added to 1 μg/ml each.

2. Preparation of soluble Flt-1 receptor:

Recombinant human Flt-1-Fc soluble receptor was purchased from R&D Systems, Minneapolis Minn. The soluble receptor was diluted to a concentration of 10 ng/25 μl in DMEM supplemented with gelatin (0.15%) and HEPES buffer (20 mM).

3. Preparation of $^{125}$I-labelled VEGF ligand:

Recombinant human $^{125}$T-labelled VEGF 165 was purchased from Amersham (3,800 cpm/fmol). $^{125}$,-labelled VEGF was diluted in DMEM supplemented with gelatin (0.15%) and HEPES buffer (20 mM) to a final concentration of 40,000 cpm/25 μl.

4. Preparation of SPA beads:

SPA PVT antibody-binding beads were purchased from Amersham. Each bottle of SPA beads (500 mg) was reconstituted in 25 ml of DMEM supplemented with gelatin (0.15%) and HEPES buffer (20 mM). The bottle contents were well mixed (15 min with a stir bar at room temperature).

5. Setting up SPA assay:

SPA assays were performed in flat-bottom polystyrene 96 well microtitre plates.
Representative assay:
  (a) Pipette 50 μl of SPA beads to well.
  (b) Pipette 25 μl of conditioned medium to well.
  (c) Pipette 10 μl of test compound to well (stock 100 μg/ml solution in DMSO) to give a final drug concentration of 10 μg/ml.
  (d) Pipette 25 μl of $^{125}$J-VEGF 165 to well.

The appropriate control wells were set up to measure non-specific binding, solvent effect, etc. The assays were run in duplicate or triplicate wells. Plates were sealed and incubate at room temperature without shaking for 5 to 20 hours. Plates were then counted in a Packard TopCount microtitre plate liquid scintillation counter. The affinity constant for VEGF binding to the soluble KDR-Fc receptor is approximately 100 pM.

Analysis of Results:

A typical assay gave 3,000 to 6,000 cpm bound. Background binding (measured in the presence of 100-fold molar excess of unlabelled VEGF 165) was typically 200 to 300 cpm bound. Compounds were tested at 30, 10, 3, 1, 0.3 and 0.1 µg/ml in DMSO. The $IC_{50}$ values of test compounds were defined as the compound concentration that gave the half maximal binding. Half maximal binding was determined by the following equation:

$$x=b+[(s-b)/2]$$

where
x=half maximal binding,
b=background binding and
s=maximal cpm bound in the absence of compound.

The $IC_{50}$ values were determined graphically by the following procedure:
1. A graph was drawn plotting compound concentration (x-axis) versus cpm bound (y-axis).
2. The half maximal binding was calculated using the equation above.
3. A horizontal line (LINE A) was drawn which intersects the y-axis at the half maximal binding value.
4. A vertical line (LINE B) was drawn through the point where LINE A intersects the inhibition curve.
5. The point where LINE B intersects the x-axis was extrapolated from the graph to give the $IC_{50}$ value.

An active compound is designated as an agent which can inhibit the binding of VEGF 165 to the KDR or Flt-1 receptor with an $IC_{50}$ of <10 µg/ml.

Protocol for measuring binding of $^{125}$I-VEGF 165 to BAE cells

BAE cells were grown to confluence in a cm dish in DMEM supplemented with 10% calf serum, 2 mM glutamine, 10 units/ml penicillin G sulfate and 10 µg/ml streptomycin sulfate. The media was aspirated and the cells were washed once with 10 ml of PBS. The PBS was aspirated and 1 ml of 0.05% trypsin, 0.53 mM EDTA•4Na in Hanks' balanced salt solution was added. The dish was incubated at room temperature for 5 min or until cell were completely detached. 20 ml of DMEM supplemented as described was added and the cells were aliquoted into the wells of four 24-well microtiter plates (200 µl/well). After 2–4 days or when cells were approximately 70–80% confluent, the medium was aspirated and 200 µl of DMEM supplemented with 25 mM HEPES, 0.15% gelatin, and 5 µg/ml heparin was added to each well. Twenty-five µl of cold VEGF 165 was added to appropriate wells. The final cold VEGF concentration was 10 nM. Twenty-five µl of a stock solution of the test compound in DMSO was added to the appropriate wells to yield final concentrations of 30, 10, 3 and 1 µg/ml or 10, 3, 1 and 0.3 µg/ml. Twenty-five µl of DMEM was added to wells not receiving cold VEGF or compound. Twenty-five µl (40,000 cpm, 3,800 cpm/fmol) of $^{125}$I-VEGF 165 was added to all wells and the plates were incubated for 1–1.5 hours at room temperature. The medium was aspirated and the cells were washed twice with 0.5 ml of ice cold PBS supplemented with 0.1% BSA. One-half ml of 20 mM NaPi, 1% Triton was added to each well and the plates were incubated for 30–60 min at room temperature. Samples were transferred to tubes and bound radioactivity was counted with a Packard 5005 Auto-Gamma counter. The amount of cpm bound was estimated by subtracting the background binding (in the presence of 100-fold molar excess of unlabelled VEGF) from the total cpm bound for each sample. The $IC_{50}$ values of test compounds were defined as the compound concentration that gave the half maximal binding. Half maximal binding was determined by the following equation:

$$x=b+[(s-b)/2]$$

where
x=half maximal binding,
b=background binding and
s=maximal cpm bound in the absence of compound.

The ICY, values were determined graphically by the following procedure:
1. A graph was drawn plotting compound concentration (x-axis) versus cpm bound (y-axis).
2. The half maximal binding was calculated using the equation above.
3. A horizontal line (LINE A) was drawn which intersects the y-axis at the half maximal binding value.
4. A vertical line (LINE B) was drawn through the point where LINE A intersects the inhibition curve.
5. The point where LINE B intersects the x-axis was extrapolated from the graph to give the $IC_{50}$ value.

An active compound is designated as an agent which can inhibit the binding of VEGF 165 to BAE cells with an $IC_{50}$ of <10 µg/ml.

Protocol for measuring binding of $^{125}$I-VEGF 165 to HUVEC cells

HUVEC cells were grown to confluence in Endothelial Cell Basal Medium plus supplements as described in the literature provided by Clonetics Corp. (San Diego, Calif.). Cells were detached from the flask in an enzyme-free cell dissociation buffer (GIBCO-BRL, Gaithersburg Md.), washed once with PBS and aliquoted at 100,000 cells/well into a 24-well microtiter plate. Cells were allowed to attach overnight. The medium was aspirated and 155 µl of DMEM supplemented with 25 mM HEPES, 0.15% gelatin, 5 µg/ml heparin was added to each well. Twenty-five µl of cold VEGF 165 was added to the appropriate wells, to give a final cold VEGF concentration of 10 nM. Twenty-five µl of a stock solution of the test compound in DMSO was added to the appropriate wells to yield final concentrations of 30, 10, 3 and 1 µg/ml or 10, 3, 1 and 0.3 µg/ml. Twenty-five µl of DMEM was added to wells not receiving cold VEGF or compound and 25 µl (40,000 cpm, 3,800 cpm/fmol) of $^{125}$I-VEGF165 was added to to all wells. The plates were incubated for 1–1.5 hours at room temperature. The medium was aspirated and the cells were washed twice with 0.5 ml of ice cold PBS supplemented with 0.1% BSA. One-half ml of 20 mM NaPi, 1% Triton was added to each well and the plates were incubated for 30–60 min at room temperature. The samples were transferred to tubes and the bound radioactivity was counted with a Packard 5005 Auto-Gamma counter. The estimated cpm bound was determined by subtracting the background binding (in the presence of 100-fold molar excess of unlabelled VEGF) from total cpm bound for each sample. The $IC_{50}$ values of test compounds were defined as the compound concentration that gave the half maximal binding. Half maximal binding was determined by the following equation:

$$x=b+[(s-b)/2]$$

where x=half maximal binding,
b=background binding and
s=maximal cpm bound in the absence of compound.

The IC$_{50}$ values were determined graphically by the following procedure:
1. A graph was drawn plotting compound concentration (x-axis) versus cpm bound (y-axis).
2. The half maximal binding was calculated using the equation above.
3. A horizontal line (LINE A) was drawn which intersects the y-axis at the half maximal binding value.
4. A vertical line (LINE B) was drawn through the point where LINE A intersects the inhibition curve.
5. The point where LINE B intersects the x-axis was extrapolated from the graph to give the IC$_{50}$ value.

An active compound is designated as an agent which can inhibit the binding of VEGF 165 to HUVEC cells with an IC$_{50}$ of <10 µg/ml.

TABLE 1-A

Inhibition of Binding of VEGF 165 to KDR Receptor as Measured by SPA Assay & BAE Cell Binding Assay by Representatives of Formula I & II

| Compounds of Example # | SPA Assay KDR IC$_{50}$ µg/ml VEGF 165 | Cell Assay VEGF 165 IC$_{50}$ µg/ml BAE |
|---|---|---|
| 9 | 3.4 | 10.0 |
| 10 | 0.9 | 10.0 |
| 8 | 3.0 | 7.0 |
| 11 | 1.7 | 6.6 |
| 12 | 4.9 | 10.0 |
| 3 | 3.4 | |
| 4 | 0.2 | 0.90 |
| 2 | 1.5 | 2.5 |
| 5 | 0.7 | 2.2 |
| 6 | 0.5 | 3.7 |
| 14 | 3.0 | 2.6 |
| 15 | 1.6 | 4.1 |

TABLE 1-B

Inhibition of Binding of VEGF 165 to Flt-1 Receptor as Measured by SPA Assay by Representatives of Formula I

| Compounds of Example # | SPA Assay Flt-1 IC$_{50}$ µg/ml VEGF 165 |
|---|---|
| 2 | 0.4 |
| 8 | 5.0 |

TABLE 2-A

Inhibition of Binding of VEGF 165 to KDR Receptor as Measured by SPA Assay & BAE Cell Binding Assay by Representatives of Formula III

| Compounds of Example # | SPA Assay KDR IC$_{50}$ µg/ml VEGF 165 | Cell Assay VEGF 165 IC$_{50}$ µg/ml BAE |
|---|---|---|
| 23A | 1.65 | 0.67 |
| 21 | 0.2 | 0.80 |
| 22 | 0.06 | 0.068 |

TABLE 2-A-continued

Inhibition of Binding of VEGF 165 to KDR Receptor as Measured by SPA Assay & BAE Cell Binding Assay by Representatives of Formula III

| Compounds of Example # | SPA Assay KDR IC$_{50}$ µg/ml VEGF 165 | Cell Assay VEGF 165 IC$_{50}$ µg/ml BAE |
|---|---|---|
| 19 | 0.55 | 0.59 |
| 20 | 3.9 | 2.3 |
| 23B | 0.58 | 2.8 |

TABLE 2-B

Inhibition of Binding of VEGF 165 to Flt-1 Receptor as Measured by SPA Assay by a Representative of Formula III

| Compound of Example # | SPA Assay Flt-1 IC$_{50}$ µg/ml VEGF 165 |
|---|---|
| 23A | 2.03 |

TABLE 3-A

Inhibition of Binding of VEGF 165 to KDR Receptor as Measured by SPA Assay & BAE Cell Binding Assay by Representatives of Formula IV

| Compounds of Example # | SPA Assay KDR IC$_{50}$ µg/ml VEGF 165 | Cell Assay VEGF 165 IC$_{50}$ µg/ml BAE |
|---|---|---|
| 25 | 1.0 | 0.36 |
| 26 | 1.5 | 0.28 |
| 24 | 0.8 | 0.32 |
| 27 | 2.33 | 0.37 |
| 28 | 2.5 | 0.95 |
| 29 | 0.5 | 0.30 |
| 30 | 0.5 | 0.60 |
| 31 | 5.0 | 0.37 |
| 32 | 0.8 | 0.42 |
| 33 | 0.5 | 0.36 |
| 34 | 2.5 | 0.37 |
| 35 | 2.5 | 0.088 |
| 36 | 6.0 | 1.90 |
| 37 | 2.0 | 0.32 |
| 38 | 5.0 | 2.60 |
| 39 | 1.7 | 0.45 |
| 40 | 4.0 | 2.70 |
| 42 | 0.6 | 0.50 |
| 43 | 0.6 | 0.35 |
| 44 | 1.5 | 0.68 |
| 45 | 2.0 | 1.60 |
| 46 | 5.0 | |
| 47 | 0.5 | 0.6 |

TABLE 3-B

Inhibition of Binding of VEGF 165 to Flt-1 Receptor as Measured by SPA Assay & Inhibition of Binding of VEGF 165 to KDR Receptor as Measured by HUVEC Cell Binding Assay by Representatives of Formula IV

| Compounds of Example # | SPA Assay Flt-1 $IC_{50}$ μg/ml VEGF 165 | Cell Assay VEGF 165 $IC_{50}$ μg/ml HUVEC |
|---|---|---|
| 30 | 1.25 | 1.2 |
| 39 | N.T. | 2.8 |
| 27 | 1.5 | |
| 35 | 1.0 | |
| 43 | 1.0 | |
| 44 | 3.0 | |

TABLE 4-A

Inhibition of Binding of VEGF 165 to KDR Receptor as Measured by SPA Assay & BAE Cell Binding Assay by Representatives of Formula V

| Compounds of Example # | SPA Assay KDR $IC_{50}$ μg/ml VEGF 165 | Cell Assay VEGF 165 $IC_{50}$ μg/ml BAE |
|---|---|---|
| 50 | 5.0 | 0.74 |
| 51 | 5.0 | 1.40 |
| 52 | 7.0 | 2.0 |
| 53 | 7.0 | 10.0 |
| 54 | 0.15 | 0.10 |
| 55 | 1.0 | 0.8 |
| 56 | 0.7 | 0.9 |
| 57 | 5.0 | 0.33 |
| 58 | 1.5 | 1.0 |
| 59 | 6.0 | 0.88 |
| 60 | 0.50 | 0.20 |

TABLE 4-B

Inhibition of Binding of VEGF 165 to Flt-1 Receptor as Measured by SPA Assay & Inhibition of Binding of VEGF 165 to KDR Receptor as Measured by HUVEC Cell Binding Assay by a Representative of Formula V

| Compound of Example # | SPA Assay Flt-1 $IC_{50}$ μg/ml VEGF 165 | Cell Assay VEGF 165 $IC_{50}$ μg/ml HUVEC |
|---|---|---|
| 54 | 0.15 | 0.18 |

In Vivo Inhibition of Growth of Human Epidermoid Tumors (A431)

In vivo testing was performed using BALB/c nu/nu female mice (Charles River, Wilmington, Mass.). The human epidermoid carcinoma cells A-431 (American Type Culture Collection, Rockville, Md. # CRL-155) were grown in vitro and $5 \times 10^6$ cells were injected subcutaneously (SC) into mice. When tumors attained a mass of between 100 and 150 mg, the mice were randomized into treatment groups (Day Zero). Mice were treated either intraperitoneally (IP) or orally (PO) once a day on days 1 through 20 post staging with doses of either 100 or 50 mg/kg/dose in 0.2% Klucel. Tumor mass was determined every 7 days [(length×width$^2$)/2] for up to 42 days post staging. Relative tumor growth (mean tumor mass on day 7, 14, 21, 28, 35 and 42 divided by the mean tumor mass on day zero) was determined for each treatment group. The %T/C (Tumor/Control) was determined by dividing the relative tumor growth of the treated group by the relative tumor growth of the placebo group and multiplying by 100. Data was statistically analyzed via Student-t-test of Log Relative Tumor Growth. A p-value (p≦0.05) indicates a statistically significant reduction in Relative Tumor Growth of Treated Group, compared to Placebo Control. A compound is considered to be active if the %T/C is found to be <60% and a p-value of less than or equal to 0.05 is achieved.

TABLE 5

In Vivo Inhibition of Growth of Human Epidermoid Tumors (A431) in Mice by a Representative of Formula I

| Compound of Example # | Tumor Type | Dose mg/kg | a Route | b % T/C (Day) | c p-value | d S/T |
|---|---|---|---|---|---|---|
| 6 | A431 | 100 | PO | 52(15) | 0.03 | 5/5 | a) Drugs administered (in Klucel) on days 1, 3, 5 . . . 25 with exception of the placebo control (Klucel) which was administered on days 1 through 10 PO.

b) $\% T/C = \dfrac{\text{Relative Tumor Growth of Treated Group}}{\text{Relative Tumor Growth of Placebo Group}} \times 100$ Relative Tumor Growth $= \dfrac{\text{Mean Tumor Mass on Day 7, 14, 21, 28}}{\text{Mean Tumor Mass on Day 0}}$ c) Statistically (p < 0.05) significant; Student-t-test. Significant reduction in Relative Tumor Growth of Treated Group, compared to Placebo Control.
d) S/T = No. Survivors/No. Treated on Day +28 post tumor staging.

TABLE 6

In Vivo Inhibition of Growth of Human Epidermoid Tumors (A431) in Mice by a Representative of Formula III

| Compound of Example # | Tumor Type | Dose mg/kg | a Route | b % T/C (Day) | c p-value | d S/T |
|---|---|---|---|---|---|---|
| 20 | A431 | 100 | PO | 39(29) | 0.02 | 5/5 | a) Drugs administered (in Klucel) on days 1, 3, 5 . . . 25 with exception of the placebo control (Klucel) which was administered on days 1 through 10 PO.

b) $\% T/C = \dfrac{\text{Relative Tumor Growth of Treated Group}}{\text{Relative Tumor Growth of Placebo Group}} \times 100$ Relative Tumor Growth $= \dfrac{\text{Mean Tumor Mass on Day 7, 14, 21, 28}}{\text{Mean Tumor Mass on Day 0}}$ c) Statistically (p < 0.05) significant; Student-t-test. Significant reduction in Relative Tumor Growth of Treated Group, compared to Placebo Control.
d) S/T = No. Survivors/No. Treated on Day +28 post tumor staging.

TABLE 7

In Vivo Inhibition of Growth of Human Epidermoid Tumors (A431) in Mice by Representatives of Formula IV

| Compounds of Example # | Tumor Type | Dose mg/kg | a Route | b % T/C (Day) | c p-value | d S/T |
|---|---|---|---|---|---|---|
| 30 | A431 | 100 | PO | 56(42) | 0.01 | 20/20 |
| 30 | A431 | 50 | PO | 58(28) | 0.03 | 5/5 |
| 27 | A431 | 100 | PO | 30(28) | 0.01 | 5/5 |

TABLE 7-continued

In Vivo Inhibition of Growth of Human Epidermoid Tumors (A431) in Mice by Representatives of Formula IV

| Compounds of Example # | Tumor Type | Dose mg/kg | a Route | b % T/C (Day) | c p-value | d S/T |
|---|---|---|---|---|---|---|
| 27 | A431 | 50 | PO | 51(28) | 0.01 | 5/5 |
| 45 | A431 | 50 | IP | 50(28) | 0.01 | 5/5 | a) Drugs administered (in Klucel) on days 1, 3, 5 . . . 25 with exception of the placebo control (Klucel) which was administered on days 1 through 10 PO.

b) $\% \text{T/C} = \dfrac{\text{Relative Tumor Growth of Treated Group}}{\text{Relative Tumor Growth of Placebo Group}} \times 100$ $\text{Relative Tumor Growth} = \dfrac{\text{Mean Tumor Mass on Day 7, 14, 21, 28}}{\text{Mean Tumor Mass on Day 0}}$ c) Statistically ($p < 0.05$) significant; Student-t-test. Significant reduction in Relative Tumor Growth of Treated Group, compared to Placebo Control.
d) S/T = No. Survivors/No. Treated on Day +28 post tumor staging.

TABLE 8

In Vivo Inhibition of Growth of Human Epidermoid Tumors (A431) in Mice by Representatives of Formula V

| Compounds of Example # | Tumor Type | Dose mg/kg | a Route | b % T/C (Day) | c p-value | d S/T |
|---|---|---|---|---|---|---|
| 54 | A431 | 50 | PO | 38(28) | 0.02 | 5/5 |
| 54 | A431 | 50 | IP | 46(28) | 0.05 | 5/5 |
| 55 | A431 | 50 | PO | 44(28) | 0.01 | 5/5 | a) Drugs administered (in Klucel) on days 1, 3, 5 . . . 25 with exception of the placebo control (Klucel) which was administered on days 1 through 10 PO.

b) $\% \text{T/C} = \dfrac{\text{Relative Tumor Growth of Treated Group}}{\text{Relative Tumor Growth of Placebo Group}} \times 100$ $\text{Relative Tumor Growth} = \dfrac{\text{Mean Tumor Mass on Day 7, 14, 21, 28}}{\text{Mean Tumor Mass on Day 0}}$ c) Statistically ($p < 0.05$) significant; Student-t-test. Significant reduction in Relative Tumor Growth of Treated Group, compared to Placebo Control.
d) S/T = No. Survivors/No. Treated on Day +28 post tumor staging.

Corneal Neovascularization Model

The sustained release preparations of angiogenic agents (ELVAX pellet) were prepared by solvent casting. Growth factors were incorporated into the polymeric mixture by modifications of the procedure described by Tamargo, R. J. et al, Cancer Res.53: 329–333, 1993, the teachings of which are incorporated herein by reference, where the polymer (ethylene-vinyl acetate copolymer) was dissolved in solvent (methylene chloride). The solvent was then evaporated, leaving the angiogenic agent in the polymeric matrix Mice were anesthetized using a 1–1.5 ml/kg solution containing a mixture of 70% ketamine hydrochloride (100 mg/ml) and 30% xylazine (20 mg/ml). Using sterile surgical technique, an ELVAX pellet containing either basic FGF (100 ng) or VEGF (400 ng) was implanted into a previously dissected intrastromal corneal pocket 0.5 mm from the corneoscleral limbus. Following implantation the implantation site margins were reapposed and the eyes were treated with topical antibiotic ointment (bacitracin/neomycin/polymixin). On various days (between postoperative days 4 and 18) the extent of neovascularization was measured.

Neovascularization was monitored by measurements of new vessel growth within the previously avascular cornea. This parameter was obtained by measuring with calipers under microscopic magnification the length of the base of the neovascular bed at the limbus. The area of neovascularization, which is typically triangular, was calculated by dividing the product of the length of the vessel and the base length by two. Data was statistically analyzed via Student-t-test of Log Relative Reduction of Neovascularization. A p-value ($p \leq 0.05$) indicates a statistically significant reduction in neovascularization of Treated Group, compared to Placebo Control. A compound is considered to be active if the %Inhibition is found to be $\leq 80\%$ and a p-value of less than or equal to 0.05 is achieved.

TABLE 9

Inhibition of Corneal Neovascularization by Representatives of the Formula I

| Comp. of Examp. # | a,b Day 4 | c p value | b Day 8 | c p value | b Day1 11 | c p value | b Day 13 | c p value |
|---|---|---|---|---|---|---|---|---|
| 8 | 11% | 0.638 | 24% | 0.201 | 29% | 0.123 | 37% | 0.032 |
| 4 | 55% | 0.016 | 38% | 0.122 | 40% | 0.098 | 23% | 0.453 |
| 12 | 41% | 0.054 | 41% | 0.048 | 34% | 0.110 | 8% | 0.814 | a) Examples (in Klucel) and placebo control (Klucel) were administered at 100 mg/kg, PO, days 1–10.

b) $\% \text{Inhibition} = \dfrac{\text{Vascular Density of Treated Group}}{\text{Vascular Density of Placebo Group}} \times 100$ c) Statistically ($p < 0.05$) significant; Student-t-test. Significant reduction in vascular density of Treated Group compared to Placebo Control.

TABLE 10

Inhibition of Corneal Neovascularization by Representatives of the Formula III

| Comp. of Examp. # | a,b Day 4 | c p value | b Day 8 | c p value | b Day1 11 | c p value | b Day 13 | c p value |
|---|---|---|---|---|---|---|---|---|
| 23A | 70% | 0.001 | 55% | 0.019 | 46% | 0.051 | 50% | 0.051 |
| 20 | 29% | 0.135 | 25% | 0.230 | 30% | 0.112 | 26% | 0.337 | a) Examples (in Klucel) and placebo control (Klucel) were administered at 100 mg/kg, PO, days 1–10.

b) $\% \text{Inhibition} = \dfrac{\text{Vascular Density of Treated Group}}{\text{Vascular Density of Placebo Group}} \times 100$ c) Statistically ($p < 0.05$) significant; Student-t-test. Significant reduction in vascular density of Treated Group, compared to Placebo Control.

Inhibition of Vascular Permeability Assay (Miles Assay)

This assay was performed using BALB/c female mice (Charles River, Wilmington, Mass.). Both sides of the animals were shaved between 24 and 48 hours before the start of the assay. There were 10 animals per experimental group. Compound (in Klucel) or vehicle control (Klucel) was delivered orally either 1 hour, 2 hours or 4 hours prior to the injection of VEGF. At the time of VEGF administration, 25 ng of VEGF 165 (Preprotech, Rocky Hill, N.J.), prepared in 0.1% BSA in normal saline, was injected intradermally (ID) on one side of each animal. Immediately following the ID injection, 200$\mu$l of 0.5% Evans Blue Dye was administered to the animals intravenously (IV). One half hour later the animals were sacrificed by $CO_2$ inhalation. The skin of the animals were peeled back and the area of vascular permeability (as indicated by the area of Evans Blue Dye leakage) was measured in 2 dimensions. Data was statistically analyzed via Student-t-test. A p-value (p≦0.05) indicates a statistically significant difference between the area of vascular permeability of the vehicle control verses the experimental group. Data was statistically analyzed via Student-t-test of Log Relative Area of Permiability. A p-value (p≦0.05) indicates a statistically significant reduction in permeability of Treated Group, compared to Placebo Control. A compound is considered to be active if the %Control is found to be ≦85% and a p-value of less than or equal to 0.05 is achieved.

TABLE 11

Inhibition of Vascular Permeability by a Representative of Formula I

| Compound of Example # | a, b Time (hr) | c Lesion Area | d % Control | e p value |
|---|---|---|---|---|
| 2 | 4 | 34.0 | 57 | 0.01 | a Examples and placebo control were administered at 100 mg/kg, PO at time O.
b Time of administration of agent prior to treatment with VEGF.
c Measured area of vascular permeability in $mm^2$.
d % Control = $\frac{\text{Area of Permeability of Treated Group}}{\text{Area of Permeability of Placebo Group}} \times 100$
e Statistically (p < 0.05) significant; Student-t-test.
Significant reduction in vascular density of Treated Group, compared to Placebo Control.

TABLE 12

Inhibition of Vascular Permeability by Representatives of Formula IV

| Compounds of Example # | a, b Time (hr) | c Lesion Area | d % Control | e p value |
|---|---|---|---|---|
| 27 | 4 | 58.5 | 73 | 0.004 |
| 30 | 4 | 52.9 | 56 | 0.0006 |
| 29 | 4 | 76.5 | 81 | 0.047 |
| 47 | 4 | 32.8 | 71 | 0.03 |
| 24 | 1 | 25.8 | 55 | 0.01 |
| 24 | 2 | 37.8 | 80 | 0.02 |
| 24 | 4 | 23.1 | 49 | 0.01 |
| 39 | 1 | 35.5 | 75 | 0.01 |
| 39 | 2 | 20.6 | 44 | 0.01 |
| 39 | 4 | 28.9 | 61 | 0.01 |
| 42 | 2 | 40.0 | 74 | 0.02 |
| 42 | 2 | 33.5 | 74 | 0.05 |
| 42 | 4 | 31.1 | 69 | 0.03 | a Examples and placebo control were administered at 100 mg/kg, PO at time O.
b Time of administration of agent prior to treatment with VEGF.
c Measured area of vascular permeability in $mm^2$.
d % Control = $\frac{\text{Area of Permeability of Treated Group}}{\text{Area of Permeability of Placebo Group}} \times 100$
e Statistically (p < 0.05) significant; Student-t-test.
Significant reduction in vascular density of Treated Group, compared to Placebo Control.

TABLE 13

Inhibition of Vascular Permeability by a Representative of Formula V

| Compound of Example # | a,b Time (hr) | c Lesion Area | d % Control | e p value |
|---|---|---|---|---|
| 55 | 1 | 71.6 | 77 | 0.021 |
| 55 | 4 | 70.5 | 74 | 0.014 | a) Examples and placebo control were administered at 100 mg/kg, PO at time O.
b) Time of administration of agent prior to treatment with VEGF.
c) Measured area of vascular permeability in $mm^2$.
d) % Control = $\frac{\text{Area of Permeabiltiy of treated Group}}{\text{Area of Permeability of Placebo Group}}$
e) Statistically (p < 0.05) significant; Student-t-test. Significant reduction in vascular density of Treated Group, compared to Placebo Control.

We claim:

1. A compound of general Formulae (I), (II), (III) and (IV),

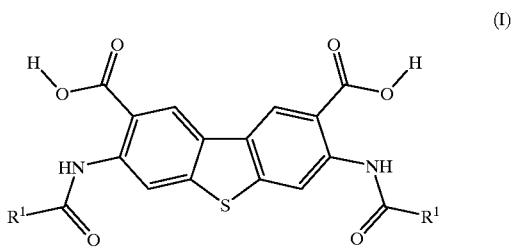

(I)

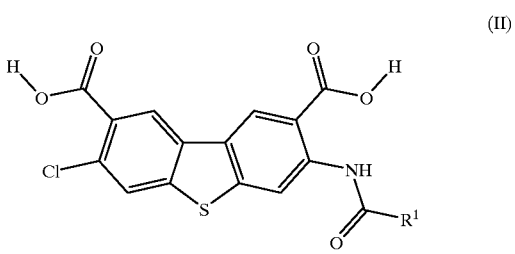

(II)

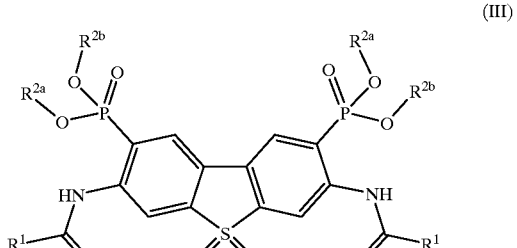

(III)

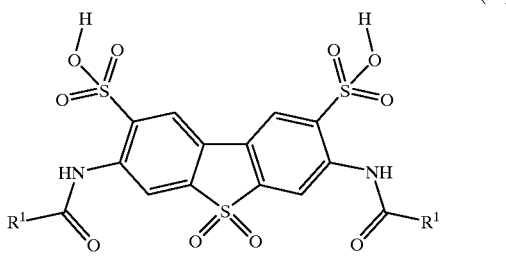

(IV)

wherein:

in general Formulae (I), and (II);

$R^1$ is a moiety selected from the group:

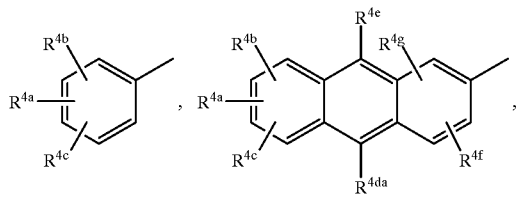

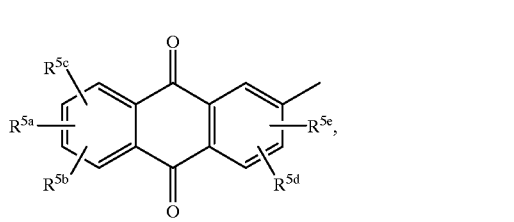

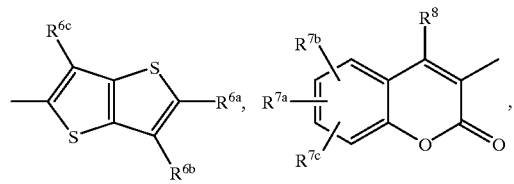

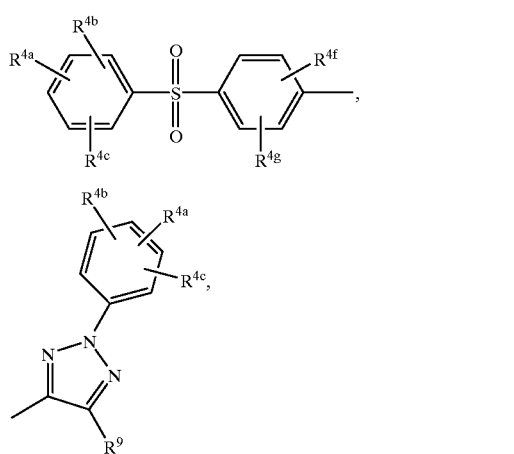

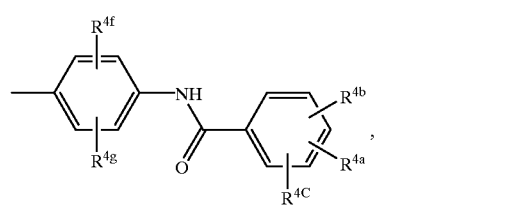

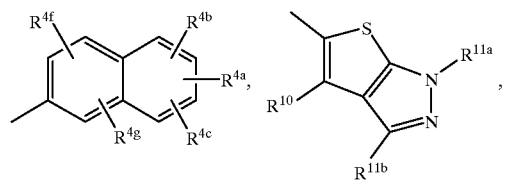

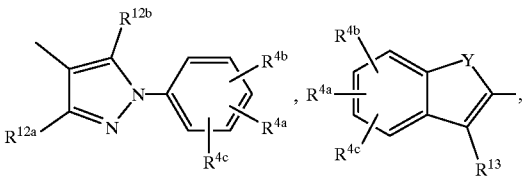

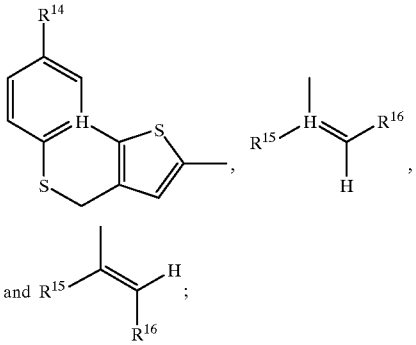

Y is sulfur, oxygen, nitrogen or carbon;

$R^{4a}$, $R^{4b}$, $R^{4c}$, $R^{4d}$, $R^{4e}$, $R^{4f}$ and $R^{4e}$ are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, trifluoromethyl, cyano, nitro, carboxy, alkoxycarbonyl of 1 to 6 carbon atoms, alkoxy of 1 to 6 carbon atoms, alkylcarbonyl of 1 to 6 carbon atoms, alkylcarbonylamino of 1 to 6 carbon atoms, thiol, alkylthio of 1 to 6 carbon atoms, alkylamino of 1 to 6 carbon atoms, —$N(R^{4h})(R^{4i})$, phenyl, phenylamino, and carboxaldehyde;

$R^{4h}$ and $R^{4i}$, independent from each other, are straight chain alkyl of 1 to 6 carbon atoms;

$R^{5a}$, $R^{5b}$, $R^{5c}$, $R^{5d}$, and $R^{5e}$ are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, cyano, nitro, alkylamino of 1 to 6 carbon atoms, and —$N(R^{4h})(R^{4i})$;

$R^{6a}$ and $R^{6b}$ are independently selected from hydrogen, halogen, straight chain alkyl of 1 to 6 carbon atoms, branched chain alkyl of 3 to 7 carbon atoms, alkenyl of 2 to 6 carbon atoms, and alkynyl of 2 to 6 carbon atoms;

$R^{6c}$ is hydrogen, methyl, cyano, halogen;

$R^{7a}$, $R^{7b}$ and $R^{7c}$ are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, alkoxy of 1 to 6 carbon atoms, cyano, nitro, alkoxycarbonyl of 1 to 6 carbon atoms, alkylcarbonyl of 1 to 6 carbon atoms, alkylamino of 1 to 6 carbon atoms, and —$N(R^{4h})(R^{4i})$;

$R^8$ is hydrogen, hydroxy, amino, straight chain alkyl of 1 to 6 carbon atoms or branched chain alkyl of 3 to 7 carbon atoms;

$R^9$, $R^{10}$, $R^{11a}$ and $R^{11b}$ are independently hydrogen or alkyl of 1 or 2 carbon atoms;

$R^{12a}$ and $R^{12b}$ are independently hydrogen, straight chain alkyl of 1 to 6 carbon atoms, alkenyl of 2 to 6 carbon atoms, alkynyl of 2 to 4 carbon atoms, hydroxyalkyl of 2 to 4 carbons, carboxy, alkoxycarbonyl of 1 to 6 carbon atoms, alkoxy of 1 to 6 carbon atoms, thiol, alkylthio of 1 to 4 carbon atoms, alkylamino of 1 to 4 carbon atoms, —N($R^{12c}$)($R^{12d}$); or trifluoromethyl;

$R^{12c}$ and $R^{12d}$, independent from each other, are straight chain alkyl of 1 to 4 carbon atoms;

$R^{13}$ is independently hydrogen, alkyl of 1 or 2 carbon atoms, hydroxy, amino, halogen, hydroxymethyl, or aminomethyl;

$R^{14}$ is hydrogen, alkyl of 1 or 2 carbon atoms, or halogen;

$R^{15}$ is hydrogen or cyano;

$R^{16}$ is a moiety selected from the group:

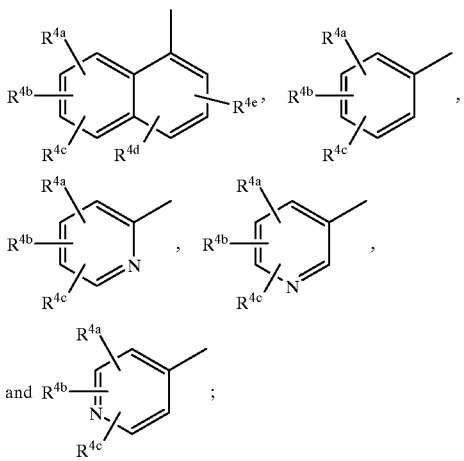

in general formula (III):

$R^{2a}$ and $R^{2b}$ are independently hydrogen, straight chain alkyl of 1 to 6 carbon atoms optionally substituted with trifluoromethyl, branched chain alkyl of 3 to 8 carbon atoms or benzyl with the proviso that each independent $R^{2a}$ and $R^{2b}$ may not simultaneously be hydrogen or a pharmaceutically acceptable salt;

$R^1$, $R^{4a}$, $R^{4b}$, $R^{4c}$, $R^{4d}$, $R^{4e}$, $R^{4f}$, $R^{4g}$, $R^{4h}$, $R^{4i}$, $R^{5a}$, $R^{5b}$, $R^{5c}$, $R^{5d}$, $R^{5e}$, $R^{6a}$, $R^{6b}$, $R^{6c}$, $R^{7a}$, $R^{7b}$, $R^{7c}$, $R^8$, $R^9$, $R^{10}$, $R^{11a}$, $R^{11b}$, $R^{12a}$, $R^{12b}$, $R^{12c}$, $R^{12d}$, $R^{13}$, $R^{14}$, $R^{15}$, $R^{16}$ and Y are as defined for general Formulae (I), and (II);

in general formula (IV):

$R^{1a}$ is a moiety selected from the group:

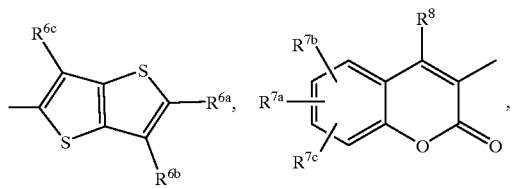

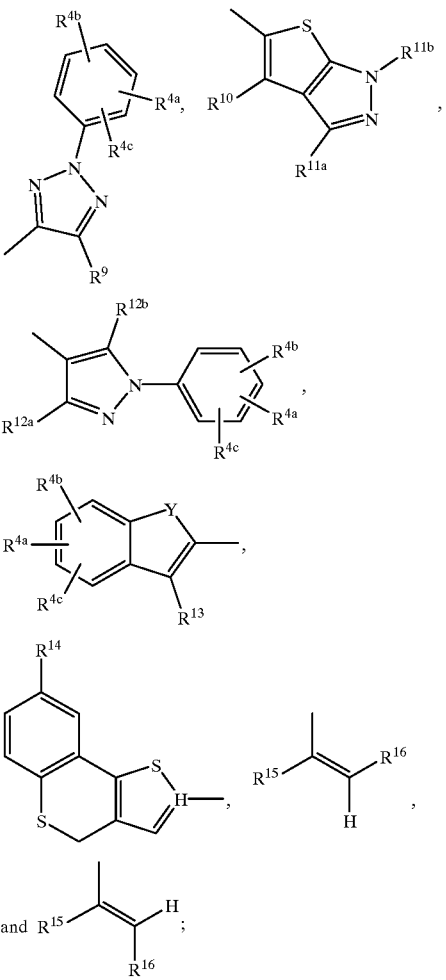

$R^{4a}$, $R^{4b}$, $R^{4c}$, $R^{4h}$, $R^{4i}$, $R^{6a}$, $R^{6b}$, $R^{6c}$, $R^{7a}$, $R^{7b}$, $R^{7c}$, $R^8$, $R^9$, $R^{10}$, $R^{11a}$, $R^{11b}$, $R^{12a}$, $R^{12b}$, $R^{12c}$, $R^{12d}$, $R^{13}$, $R^{14}$, $R^{15}$, $R^{16}$ and Y are as defined for general Formulae (I), (II) and (III); with the proviso that $R^{15}$ is not H when $R^6$ is phenyl;

alkoxycarbonyl of 1 to 6 carbon atoms, alkylcarbonyl of 1 to 6 carbon atoms, alkylcarbonylamino of 1 to 6 carbon atoms, are defined where 1 to 6 carbon atoms describes the length of the alkyl or alkoxy as bonded to the carbonyl carbon;

or a pharmaceutically acceptable salt of Formulae (I), (II), (III) and (IV) thereof.

2. The compound according to claim 1, wherein said salts of Formulae (I), (II), (III), and (IV) are selected from sodium, potassium, calcium, magnesium and ammonium.

3. The compound according to claim 1 and having the general Formula (I) wherein $R^1$ is a moiety selected from the group:

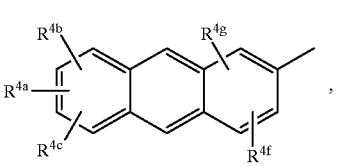

-continued

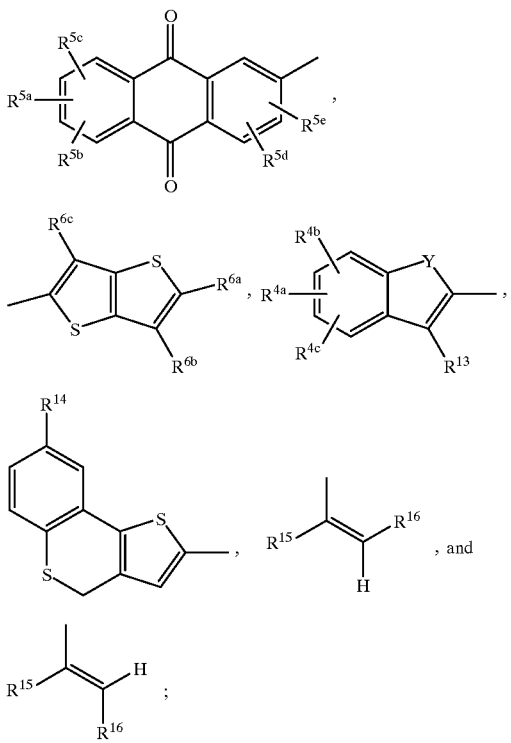

or a pharmaceutically acceptable salt thereof.

4. The compound according to claim 1 and having the general Formula (I) wherein

R¹ is a moiety selected from the group:

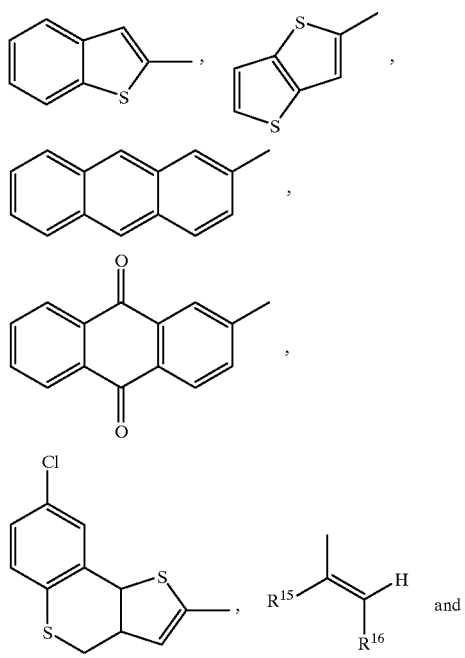

-continued

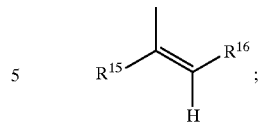

or a pharmaceutically acceptable salt thereof.

5. The compound according to claim 1 and having the general Formula (I) wherein

R¹ is a moiety selected from the group:

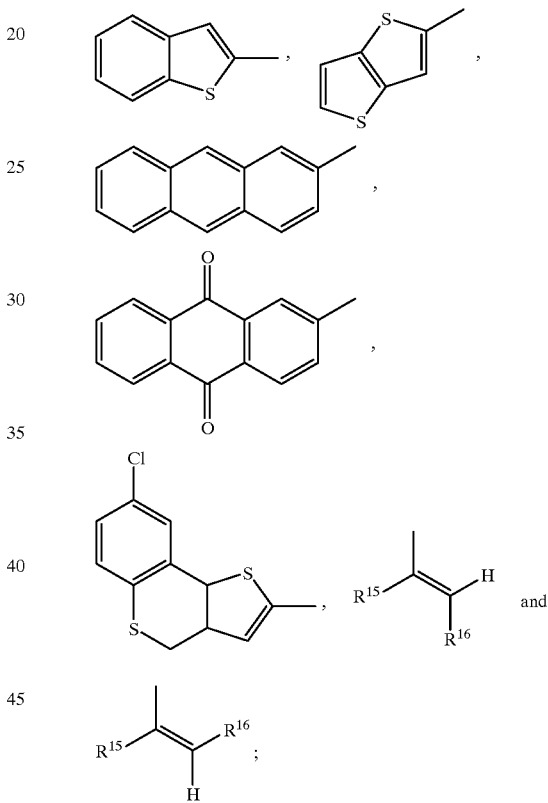

$R^{15}$ is hydrogen;

$R^{16}$ is a moiety selected from the group:

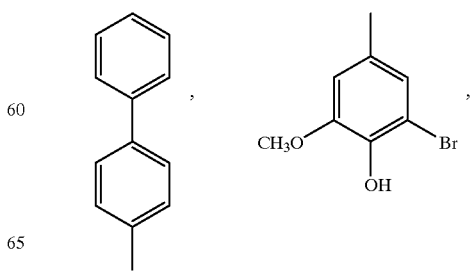

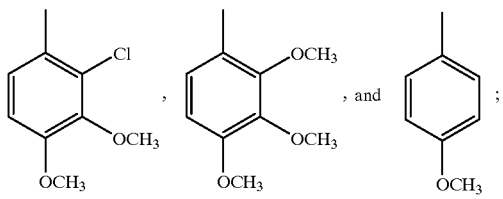

or a pharmaceutically acceptable salt thereof.

6. The compound according to claim 1 and having the general Formula (I) wherein

R¹ is a moiety selected from the group:

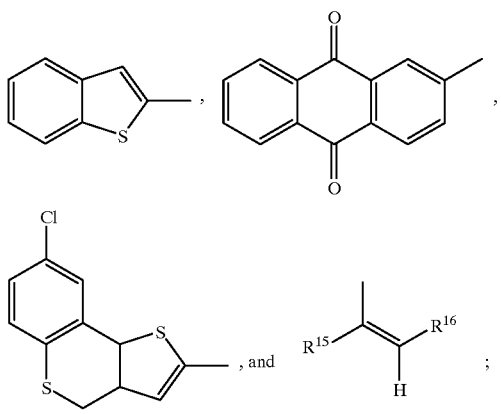

R¹⁵ is hydrogen;
R¹⁶ is a moiety selected from the group:

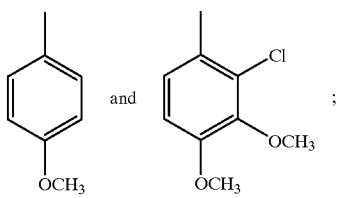

or a pharmaceutically acceptable salt thereof.

7. The compound according to claim 1, 3,7-bis-[(benzo[b]thiophene-2-carbonyl)amino]dibenzothiophene-2,8-dicarboxylic acid or a pharmaceutically acceptable salt and particularly including the disodium salt thereof.

8. The compound according to claim 1, 3,7-bis[(2-anthracenylcarbonyl)amino]-2,8-dibenzothiophene-2,8-dicarboxylic acid or a pharmaceutically acceptable salt and particularly including the disodium salt thereof.

9. The compound according to claim 1, 3,7-bis{[(9,10-dihydro-9,10-dioxo-2-anthracenyl)carbonyl]amino}-dibenzothiophene-2,8-dicarboxylic acid or a pharmaceutically acceptable salt and particularly including the disodium salt thereof.

10. The compound according to claim 1, 3,7-bis[(thieno[3,2-b]thien-2-ylcarbonyl)amino]dibenzothiophen-2,8-dicarboxylic acid or a pharmaceutically acceptable salt and particularly including the disodium salt thereof.

11. The compound according to claim 1, 3,7-bis-[(8-chloro-4H-thieno[3,2-c][1]benzothiopyran-2-carbonyl)amino]-dibenzothiophene-2,8-dicarboxylic acid or a pharmaceutically acceptable salt and particularly including the disodium salt thereof.

12. The compound according to claim 1, 3,7-bis-[3-(2-chloro-3,4-dimethoxyphenyl)acryloylamino]dibenzothiophen-2,8-dicarboxylic acid or a pharmaceutically acceptable salt and particularly including the disodium salt thereof.

13. The compound according to claim 1, 3,7-bis-(3-biphenyl-4-ylacryloylamino)dibenzothiophene-2,8-dicarboxylic acid or a pharmaceutically acceptable salt and particularly including the disodium salt thereof.

14. The compound according to claim 1, 3,7-bis-[3-(3-bromo-4-hydroxy-5-methoxyphenyl)acryloylamino]dibenzothiophen-2,8-dicarboxylic acid or a pharmaceutically acceptable salt and particularly including the disodium salt thereof.

15. The compound according to claim 1, 3,7-bis-[3-(2,3,4-trimethoxyphenyl)acryloylamino]dibenzothiophene-2,8-dicarboxylic acid or a pharmaceutically acceptable salt and particularly including the disodium salt thereof.

16. The compound according to claim 1, 3,7-bis([3-(4-methoxyphenyl)acryloylamino]dibenzothiophene-2,8-dicarboxylic acid or a pharmaceutically acceptable salt and particularly including the disodium salt thereof.

17. The compound according to claim 1 and having the general Formula (II) wherein R¹ is a moiety selected from the group:

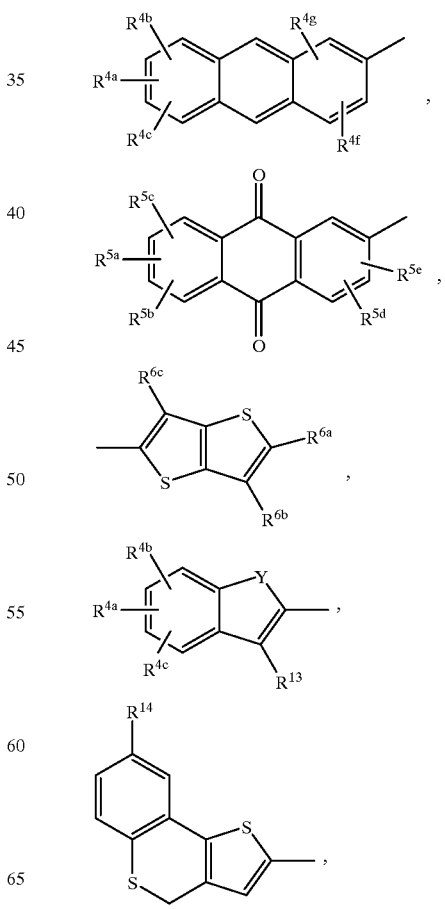

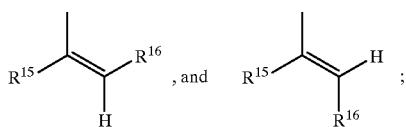, and or a pharmaceutically acceptable salt thereof.

18. The compound according to claim 1 and having the general Formula (II) wherein $R^1$ is a moiety selected from the group:

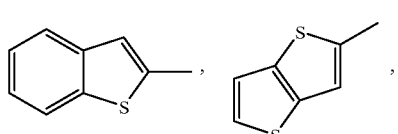,

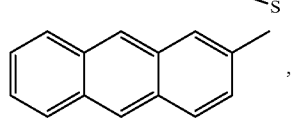,

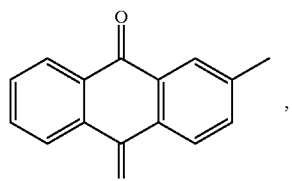,

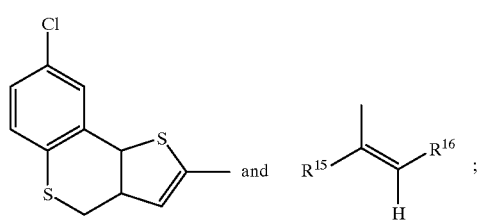

or a pharmaceutically acceptable salt thereof.

19. The compound according to claim 1 and having the general Formula (II) wherein $R^1$ is a moiety selected from the group:

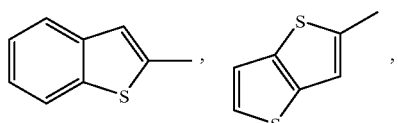,

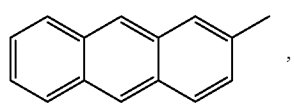,

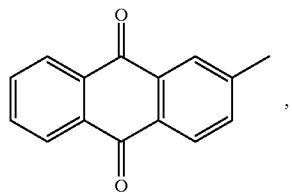,

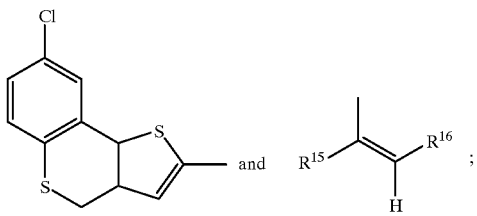

$R^{15}$ is hydrogen;

$R^{16}$ a moiety selected from the group:

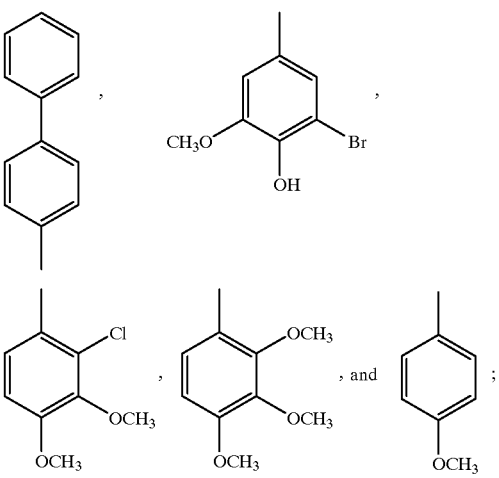

or a pharmaceutically acceptable salt thereof.

20. The compound according to claim 1 and having the general Formula (II) wherein $R^1$ is a moiety selected from the group:

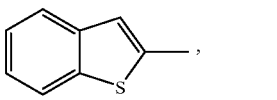,

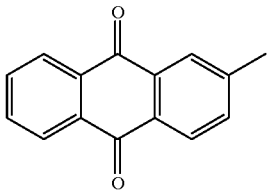,

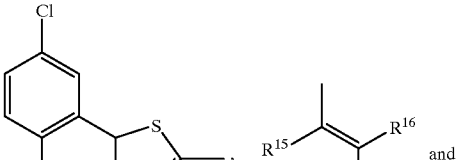

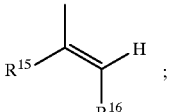;

$R^{15}$ is hydrogen;

$R^{16}$ a moiety selected from the group:

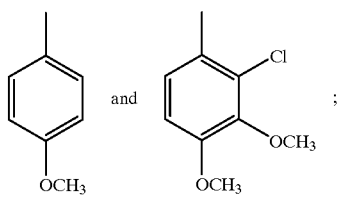

or a pharmaceutically acceptable salt thereof.

21. The compound according to claim 1 and having the general Formula (II) wherein $R^1$ is selected from

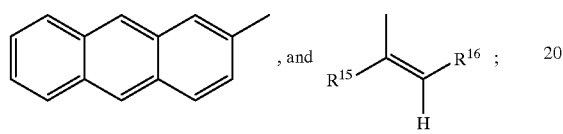

$R^{15}$ is hydrogen;

$R^{16}$ a moiety selected from the group:

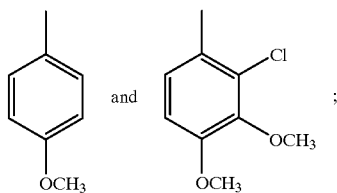

or a pharmaceutically acceptable salt thereof.

22. The compound according to claim 1, 3-[(2-anthracenylcarbonyl)amino]-7-chloro-dibenzo-thiophene-2,8-dicarboxylic acid or a pharmaceutically acceptable salt and in particular the disodium salt thereof.

23. The compound according to claim 1, 3-chloro-7-[2-(2-chloro-3,4-dimethoxyphenyl)acryloylamino]dibenzothiophen-2,8-dicarboxylic acid or a pharmaceutically acceptable salt and in particular the disodium salt thereof.

24. The compound according to claim 1 and having the general Formula (III) wherein $R^1$ is a moiety selected from the group:

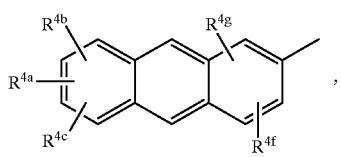

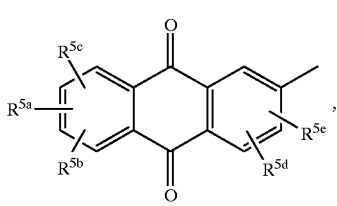

-continued

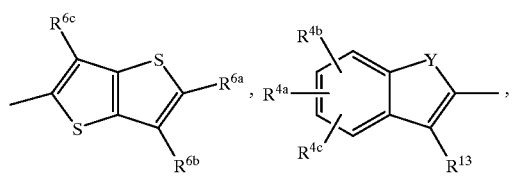

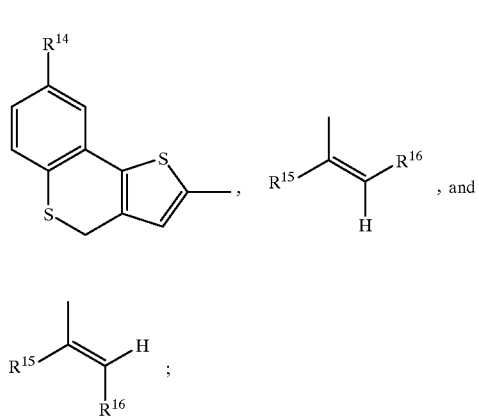

or a pharmaceutically acceptable salt thereof.

25. The compound according to claim 1 and having the general Formula (III) wherein $R^1$ is a moiety selected from the group:

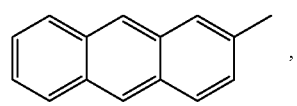

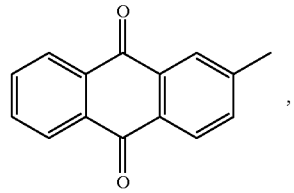

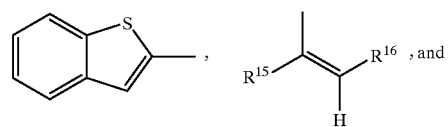

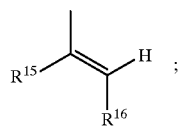

$R^{2a}$ and $R^{2b}$ are independently hydrogen or ethyl with the proviso that each independent $R^{2a}$ and $R^{2b}$ may not simultaneously be hydrogen or a pharmaceutically acceptable salt;

R$^{15}$ is hydrogen;
R$^{16}$ is a moiety selected from the group:

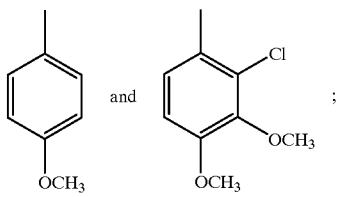

or a pharmaceutically acceptable salt thereof.

26. The compound according to claim 1 and having the general Formula (III) wherein
R$^1$ is a moiety selected from the group:

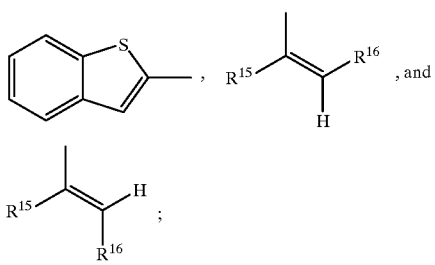

R$^{2a}$ and R$^{2b}$ are independently hydrogen or ethyl with the proviso that each independent R$^{2a}$ and R$^{2b}$ may not simultaneously be hydrogen or a pharmaceutically acceptable salt;
R$^{15}$ is hydrogen;
R$^{16}$ is

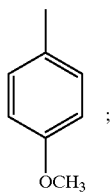

or a pharmaceutically acceptable salt thereof.

27. The compound according to claim 1, [3,7-bis-[(benzo[b]thiophene-2-carbonyl)amino]-8-(ethoxyhydroxyphosphoryl)-5,5-dioxo-5H-5λ6-dibenzothiophen-2-yl]phosphonic acid monoethyl ester or a pharmaceutically acceptable salt and in particular the disodium salt thereof.

28. The compound according to claim 1, [3,7-bis-[(9,10-dioxo-9,10-dihydroanthracene-2-carbonyl)amino]-8-(ethoxyhydroxyphosphoryl)-5,5-dioxo-5H-5λ6-dibenzothiophen-2-yl]phosphonic acid monoethyl ester or a pharmaceutically acceptable salt and in particular the disodium salt thereof.

29. The compound according to claim 1, [3,7-bis-[(anthracene-2-carbonyl)amino]-8-(ethoxyhydroxyphosphoryl)-5,5-dioxo-5H-5λ6-dibenzothiophen-2-yl]phosphonic acid monoethyl ester or a pharmaceutically acceptable salt and in particular the disodium salt thereof.

30. The compound according to claim 1, [3,7-bis-[3-(2-chloro-3,4-dimethoxyphenyl)acryloylamino]-8-(ethoxyhydroxyphosphoryl)-5,5-dioxo-5H-5/%-dibenzothiophen-2-yl]phosphonic acid monoethyl ester or a pharmaceutically acceptable salt and in particular the disodium salt thereof.

31. The compound according to claim 1, [3,7-bis-[4-methoxyphenyl]acryloylamino]-8-(ethoxyhydroxyphosphoryl)-5,5-dioxo-5H-5λ6-dibenzothiophen-2-yl]phosphonic acid monoethyl ester or a pharmaceutically acceptable salt and in particular the disodium salt thereof.

32. The compound according to claim 1, [3,7-bis-[(benzo[b]thiophene-2-carbonyl)amino]-8-(ethoxyhydroxyphosphoryl)-5,5-dioxo-5H-5λ6-dibenzothiophen-2-yl]phosphonic acid monoethyl ester or a pharmaceutically acceptable salt and in particular the monosodium salt thereof.

33. The compound according to claim 1 and having the general Formula (IV) wherein
R$^{1a}$ is a moiety selected from the group:

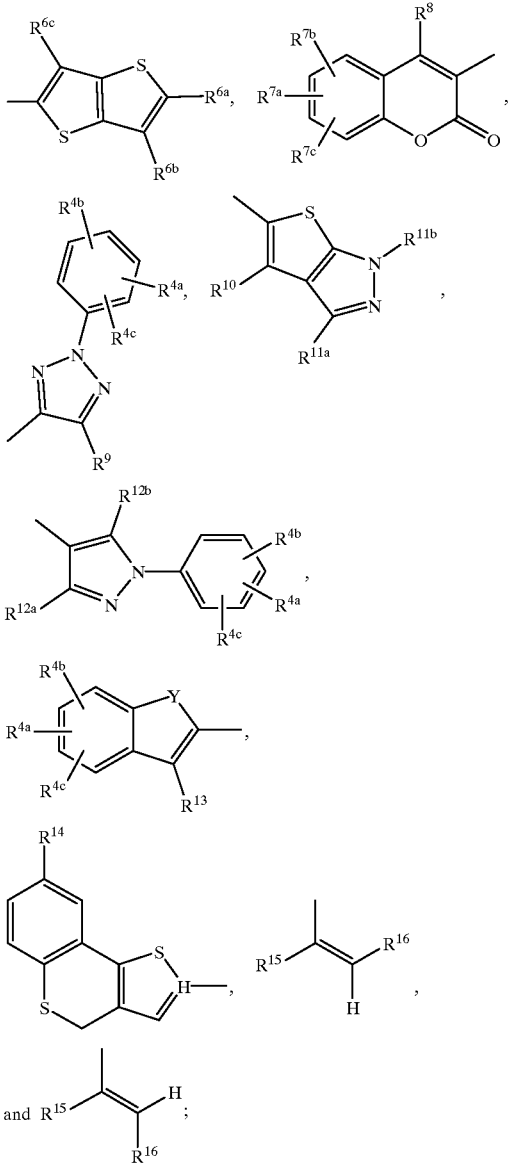

or a pharmaceutically acceptable salt thereof.

34. The compound according to claim 1 and having the general Formula (IV) wherein $R^{1a}$ is a moiety selected from the group:

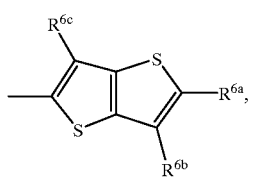

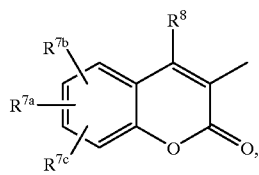

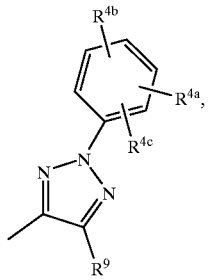

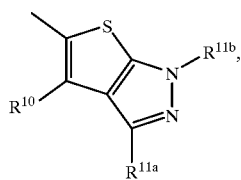

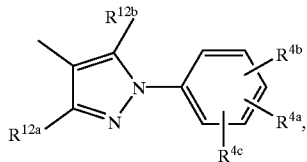

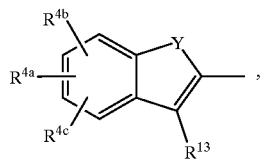

and

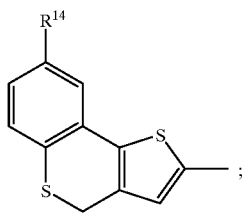

or a pharmaceutically acceptable salt thereof.

35. The compound according to claim 1 and having the general Formula (IV) wherein $R^{1a}$ is a moiety selected from the group:

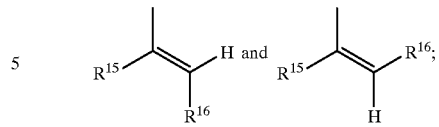

or a pharmaceutically acceptable salt thereof.

36. The compound according to claim 1 and having the general Formula (IV) wherein $R^{1a}$ is a moiety selected from the group:

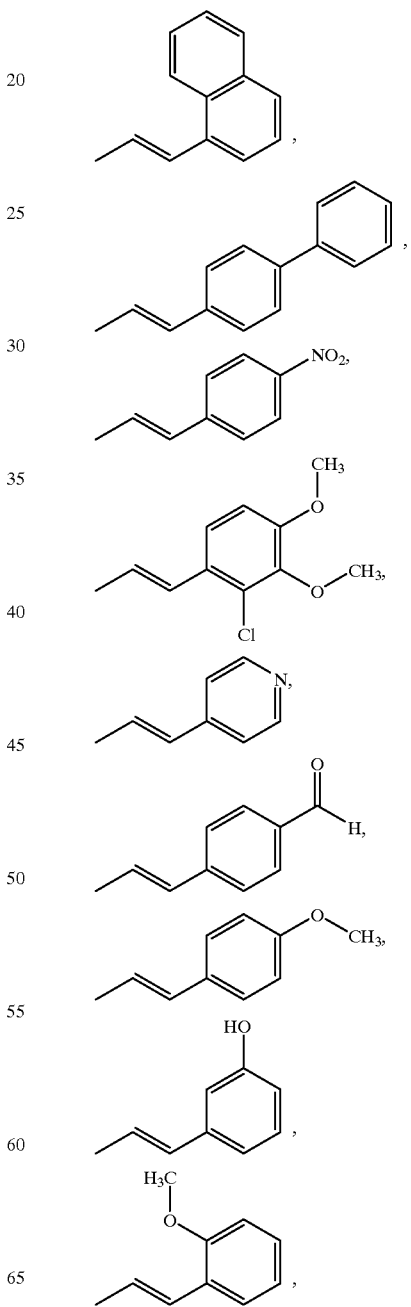

-continued
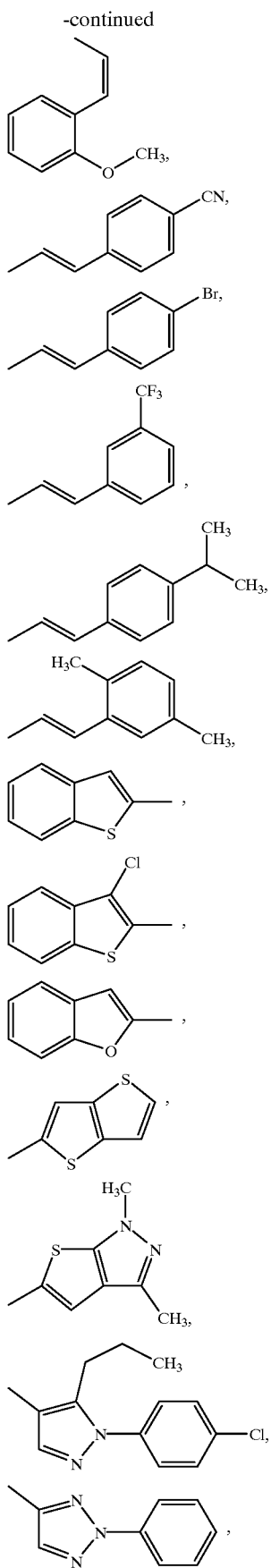
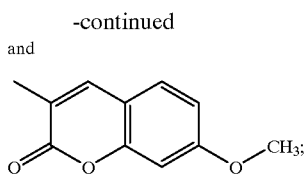
or a pharmaceutically acceptable salt thereof.
37. The compound according to claim 1 and having the general Formula (IV) wherein
$R^{1a}$ is a moiety selected from the group:
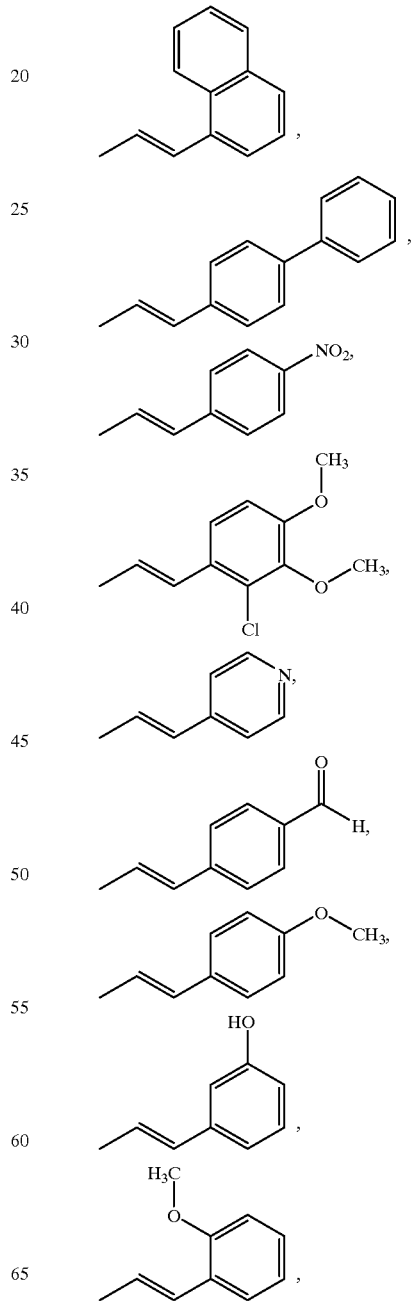

-continued

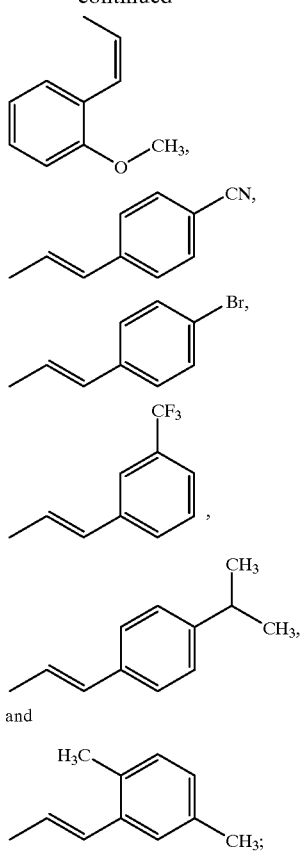

or a pharmaceutically acceptable salt thereof.

38. The compound according to claim 1 and having the general Formula (IV) wherein $R^{1a}$ is a moiety selected from the group:

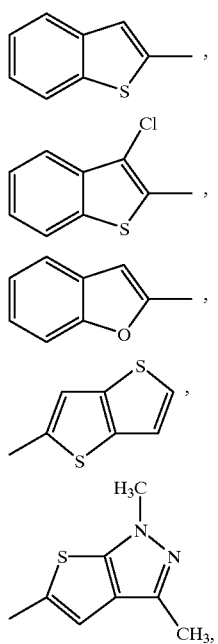

-continued

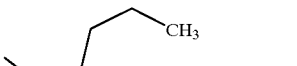

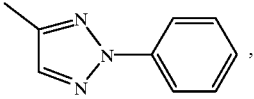

and

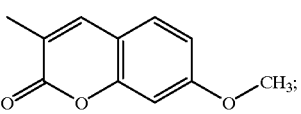

or a pharmaceutically acceptable salt thereof.

39. The compound according to claim 1 and having the general Formula (IV) wherein $R^{1a}$ is a moiety selected from the group:

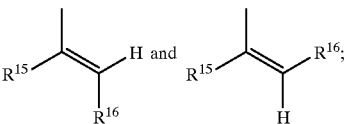

$R^{16}$ is a moiety selected from the group:

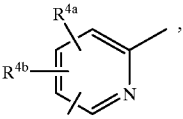

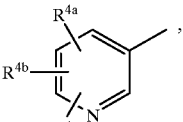

and

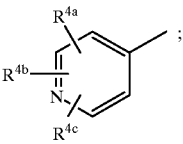

or a pharmaceutically acceptable salt thereof.

40. The compound according to claim 1 and having the general Formula (IV) wherein $R^{1a}$ is a moiety selected from the group:

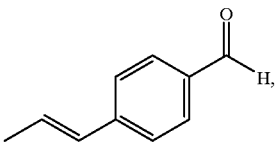

127

-continued

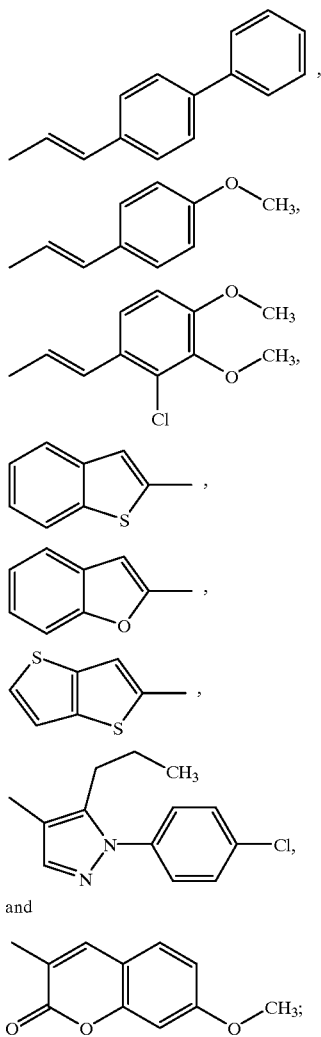

or a pharmaceutically acceptable salt thereof.

41. The compound according to claim 1 and having the general Formula (TV) wherein $R^{1a}$ is a moiety selected from the group:

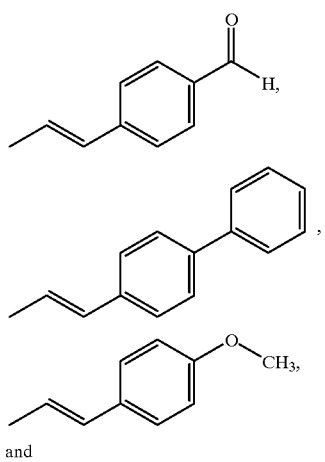

and

128

-continued

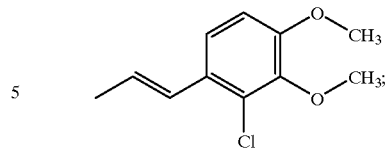

or a pharmaceutically acceptable salt thereof.

42. The compound according to claim 1 and having the general Formula (IV) wherein $R^{1a}$ is a moiety selected from the group:

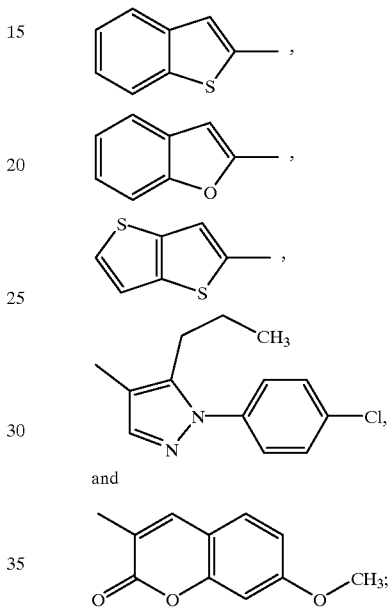

and

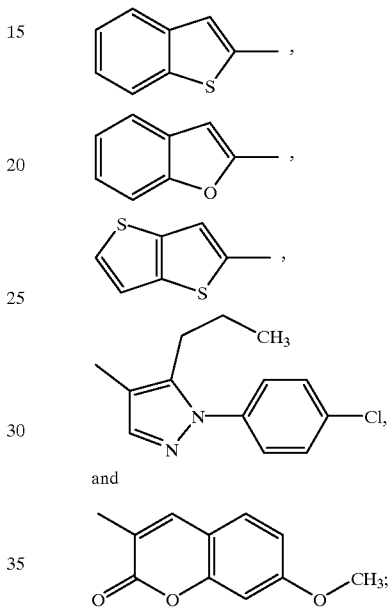

or a pharmaceutically acceptable salt thereof.

43. The compound according to claim 1, 3,7-bis-[3-(4-nitrophenyl)acryloylamino]-5,5-dioxo-5H-5$\lambda^6$-dibenzothiophen-2,8-disulfonic acid or a pharmaceutically acceptable salt and in particular the disodium salt thereof.

44. The compound according to claim 1, 3,7-bis-(3-naphthalen-1-ylacryloylamino)-5,5-dioxo-5H-5%6-dibenzothiophene-2,8-disulfonic acid or a pharmaceutically acceptable salt and in particular the disodium salt thereof.

45. The compound according to claim 1, 3,7-bis-[3-(4-phenylphenyl)acryloylamino]-5,5-dioxo-5H-5$\lambda^6$-dibenzothiophene-2,8-disulfonic acid or a pharmaceutically acceptable salt and in particular the disodium salt thereof.

46. The compound according to claim 1, 3,7-bis-[3-(2-chloro-3,4-di-methoxyphenyl)acryloylamino]-5,5-dioxo-5H-5$\lambda^6$-dibenzothiophene-2,8-disulfonic acid or a pharmaceutically acceptable salt and in particular the disodium salt thereof.

47. The compound according to claim 1, 5,5-dioxo-3,7-bis-(3-pyridin-4-ylacryloylamino)-5H-5$\lambda^6$-dibenzothiophene-2,8-disulfonic acid or a pharmaceutically acceptable salt and in particular the disodium salt thereof.

48. The compound according to claim 1, 3,7-bis-[3-(4-formylphenyl)acryloylamino]-5,5-dioxo-5H-5$\lambda^6$-dibenzothiophen-2,8-disulfonic acid or a pharmaceutically acceptable salt and in particular the disodium salt thereof.

49. The compound according to claim 1, 3,7-bis-[3-(4-methoxyphenyl)acryloylamino]-5,5-dioxo-5H-5$\lambda^6$-dibenzothiophen-2,8-disulfonic acid or a pharmaceutically acceptable salt and in particular the disodium salt thereof.

50. The compound according to claim 1, 3,7-bis-[(E)-3-(3-hydroxyphenyl)acryloylamino]-5,5-dioxo-5H-5λ⁶-dibenzothiophene-2,8-disulfonic acid or a pharmaceutically acceptable salt and in particular the disodium salt thereof.

51. The compound according to claim 1, 3,7-bis-[3-(4-cyanophenyl)acryloylamino]-5,5-dioxo-5H-5?,-dibenzothiophen-2,8-disulfonic acid or a pharmaceutically acceptable salt and in particular the disodium salt thereof.

52. The compound according to claim 1, 3,7-bis-[3-(4-bromophenyl) acryloylamino]-5,5-dioxo-5H-5λ⁶-dibenzothiophen-2,8-disulfonic acid or a pharmaceutically acceptable salt and in particular the disodium salt thereof.

53. The compound according to claim 1, 3,7-bis-[3-(2-methoxyphenyl)acryloylamino]-5,5-dioxo-5H-5λ⁶-dibenzothiophen-2,8-disulfonic acid or a pharmaceutically acceptable salt and in particular the disodium salt thereof.

54. The compound according to claim 1, 3,7-bis-[3-(2,5-dimethylphenyl)acryloylamino]-5,5-dioxo-5H-5λ⁶-dibenzothiophene-2,8-disulfonic acid or a pharmaceutically acceptable salt and in particular the disodium salt thereof.

55. The compound according to claim 1, 3,7-bis-[3-(4-isopropylphenyl)acryloylamino]-5,5-dioxo-5H-5λ⁶-dibenzothiophene-2,8-disulfonic acid or a pharmaceutically acceptable salt and in particular the disodium salt thereof.

56. The compound according to claim 1, 3,7-bis-[3-(2-methoxyphenyl)acryloylamino]-5,5-dioxo-5H-5λ⁶-dibenzothiophene-2,8-disulfonic acid or a pharmaceutically acceptable salt and in particular the disodium salt thereof.

57. The compound according to claim 1, 3,7-bis-[3-(3-trifluoromethylphenyl)acryloylamino]-5,5-dioxo-5H-5λ⁶-dibenzothiophene-2,8-disulfonic acid or a pharmaceutically acceptable salt and in particular the disodium salt thereof.

58. The compound according to claim 1, 3,7-bis-[(benzo[b]thiophene-2-carbonyl)amino]-5,5-dioxo-5H-5λ⁶-dibenzothiophene-2,8-disulfonic acid or a pharmaceutically acceptable salt and in particular the disodium salt thereof.

59. The compound according to claim 1, 3,7-bis-[(benzo[b]thiophene-2-carbonyl-3-chloro)amino]-5,5-dioxo-5H-5λ⁶-dibenzothiophene-2,8-disulfonic acid or a pharmaceutically acceptable salt and in particular the disodium salt thereof.

60. The compound according to claim 1, 3,7-bis-[(benzo[b]furan-2-carbonyl)amino]-5,5-dioxo-5H-5λ⁶-dibenzothiophene-2,8-disulfonic acid or a pharmaceutically acceptable salt and in particular the disodium salt thereof.

61. The compound according to claim 1, 5,5-dioxo-3,7-bis-[(thieno[3,2-b]thiophene-2-carbonyl)amino]-5H-5λ⁶-dibenzothiophene-2,8-disulfonic acid or a pharmaceutically acceptable salt and in particular the disodium salt thereof.

62. The compound according to claim 1, 3,7-bis-[(1,3-dimethyl-1H-thieno[2,3-c]pyrazole-5-carbonyl)amino]-5,5-dioxo-5H-5λ⁶-dibenzothiophene-2,8-disulfonic acid or a pharmaceutically acceptable salt and in particular the disodium salt thereof.

63. The compound according to claim 1, 3,7-bis-{[1-(4-chlorophenyl)-5-propyl-1H-pyrazole-4-carbonyl]amino}-5,5-dioxo-5H-5λ⁶-dibenzothiophene-2,8-disulfonic acid or a pharmaceutically acceptable salt and in particular the disodium salt thereof.

64. The compound according to claim 1, 5,5-dioxo-3,7-bis-[(2-phenyl-2H-[1,2,3]triazole-4-carbonyl)amino]-5H-5λ⁶-dibenzothiophene-2,8-disulfonic acid or a pharmaceutically acceptable salt and in particular the disodium salt thereof.

65. The compound according to claim 1, 3,7-bis-[(7-methoxy-2-oxo-benzopyran-3-yl)carbonylamino]-5,5-dioxo-5H-5λ⁶-dibenzothiophene-2,8-disulfonic acid or a pharmaceutically acceptable salt and in particular the disodium salt thereof.

66. A method for treating or inhibiting disease in a mammal characterized by abnormal angiogenesis, the method comprising administering to a mammal in need thereof an effective amount of a compound of Formula (V)

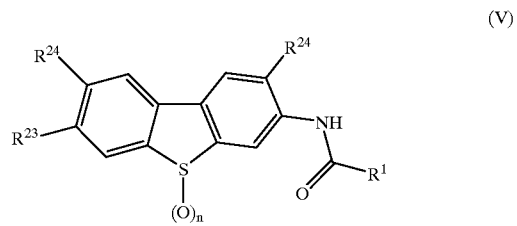

wherein:

In the general Formula (V);

n is an integer of 0 or 2;

R¹ is a moiety selected from the group:

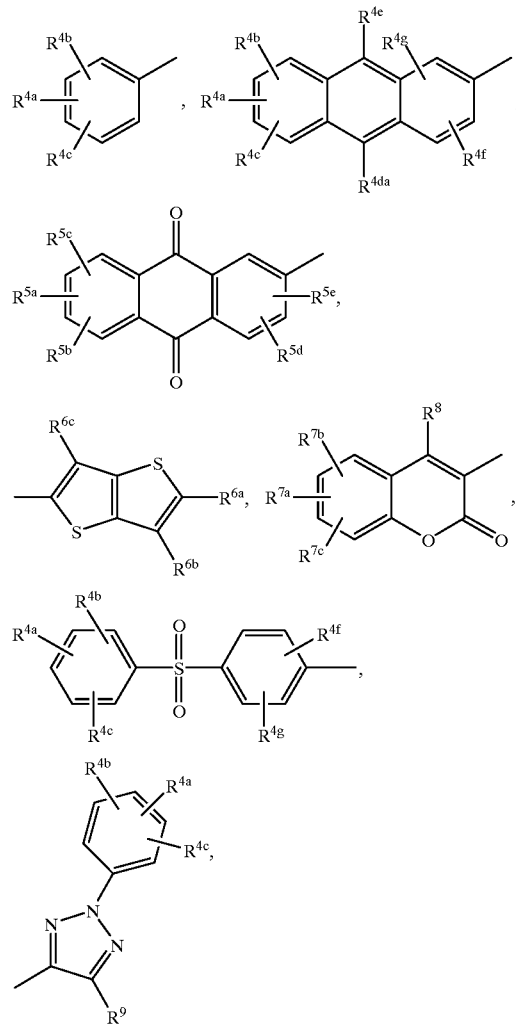

-continued

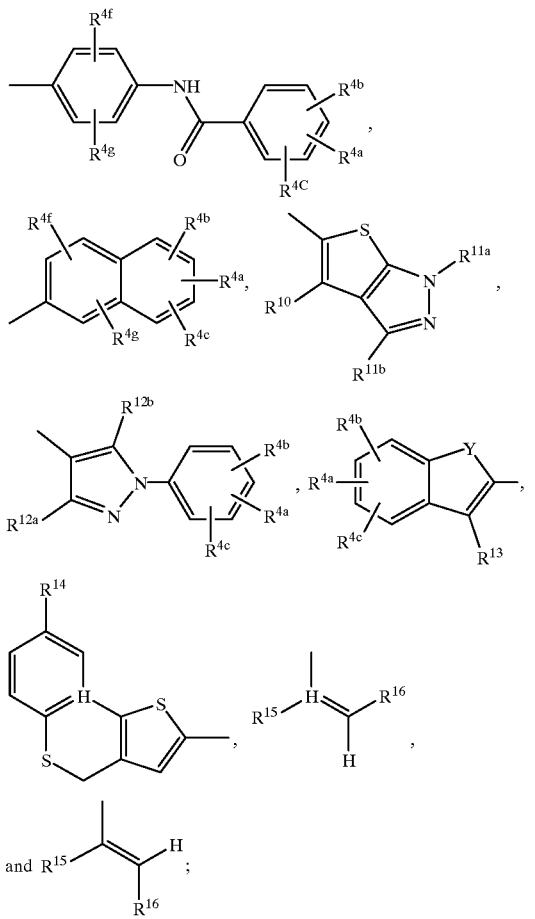

Y is sulfur, oxygen, nitrogen or carbon;

$R^{4a}$, $R^{4b}$, $R^{4c}$, $R^{4d}$, $R^{4e}$, $R^{4f}$ and $R^{4g}$ are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, trifluoromethyl, cyano, nitro, carboxy, alkoxycarbonyl of 1 to 6 carbon atoms, alkoxy of 1 to 6 carbon atoms, alkylcarbonyl of 1 to 6 carbon atoms, alkylcarbonylamino of 1 to 6 carbon atoms, thiol, alkylthio of 1 to 6 carbon atoms, alkylamino of 1 to 6 carbon atoms, —N($R^{4h}$)($R^{4i}$), phenyl, phenylamino, and carboxaldehyde;

$R^{4h}$ and $R^{4i}$, independent from each other, are straight chain alkyl of 1 to 6 carbon atoms;

$R^{5a}$, $R^{5b}$, $R^{5c}$, $R^{5d}$, and $R^{5e}$ are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, cyano, nitro, alkylamino of 1 to 6 carbon atoms, and —N($R^{4h}$)($R^{4i}$);

$R^{6a}$ and $R^{6b}$ are independently selected from hydrogen, halogen, straight chain alkyl of 1 to 6 carbon atoms, branched chain alkyl of 3 to 7 carbon atoms, alkenyl of 2 to 6 carbon atoms, or alkynyl of 2 to 6 carbon atoms;

$R^{6c}$ is hydrogen, methyl, cyano or halogen;

$R^{7a}$, $R^{7b}$ and $R^{7c}$ are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, alkoxy of 1 to 6 carbon atoms, cyano, nitro, alkoxycarbonyl of 1 to 6 carbon atoms, alkylcarbonyl of 1 to 6 carbon atoms, alkylamino of 1 to 6 carbon atoms, and —N($R^{4h}$)($R^{4i}$);

$R^8$ is hydrogen, hydroxy, amino, straight chain alkyl of 1 to 6 carbon atoms or branched chain alkyl of 3 to 7 carbon atoms;

$R^9$, $R^{10}$, $R^{11a}$ and $R^{11b}$ are independently hydrogen or alkyl of 1 or 2 carbon atoms;

$R^{12a}$ and $R^{12b}$ are independently hydrogen, straight chain alkyl of 1 to 6 carbon atoms, alkenyl of 2 to 6 carbon atoms, alkynyl of 2 to 4 carbon atoms, hydroxyalkyl of 2 to 4 carbon atoms, carboxy, alkoxycarbonyl of 1 to 6 carbon atoms, alkoxy of 1 to 6 carbon atoms, thiol, alkylthio of 1 to 4 carbon atoms, alkylamino of 1 to 4 carbon atoms, or —N($R^{12c}$)($R^{12d}$), or trifluoromethyl;

$R^{12c}$ and $R^{12d}$, independent from each other, are straight chain alkyl of 1 to 4 carbon atoms;

$R^{13}$ is independently hydrogen, alkyl of 1 or 2 carbon atoms, hydroxy, amino, halogen, hydroxymethyl, or aminomethyl;

$R^{14}$ is hydrogen, alkyl of 1 or 2 carbon atoms or halogen;

$R^{15}$ is hydrogen or cyano;

$R^{16}$ is a moiety selected from the group:

[Structure: −NH−C(=O)−R¹ or Cl;]

[Structure: CH₃−C(=O)−O−H,]

[Structure: CH₃−P(=O)(−O−R²ᵃ)(−O−R²ᵇ) and]

[Structure: CH₃−S(=O)(=O)−O−H;]

$R^{2a}$ and $R^{2b}$ are independently hydrogen, straight chain alkyl of 1 to 6 carbon atoms optionally substituted with trifluoromethyl, branched chain alkyl of 3 to 8 carbon atoms or benzyl with the proviso that each independent $R^{2a}$ and $R^{2b}$ may not simultaneously be hydrogen or a pharmaceutically acceptable salt;

alkoxycarbonyl of 1 to 6 carbon atoms, alkylcarbonyl of 1 to 6 carbon atoms, alkylcarbonylamino of 1 to 6 carbon atoms, are defined where 1 to 6 carbon atoms describes the length of the alkyl or alkoxy as bonded to the carbonyl carbons;

or a pharmaceutically acceptable salt thereof.

67. The method according to claim 66 wherein $R^{23}$ is [−N(CH₃)H−C(=O)−R¹]; $R^{24}$ is [−C(=O)−O−H];

or a pharmaceutically acceptable salt thereof.

68. The method according to claim 66 wherein $R^{23}$ is Cl;

$R^{23}$ is Cl; $R^{24}$ is [−C(=O)−O−H];

or a pharmaceutically acceptable salt thereof.

69. The method according to claim 66 wherein $R^{23}$ is [−N(CH₃)H−C(=O)−R¹]; $R^{24}$ is [−P(=O)(−O−R²ᵃ)(−O−R²ᵇ)];

or a pharmaceutically acceptable salt thereof.

70. The method according to claim 66 wherein $R^{23}$ is [−N(CH₃)H−C(=O)−R¹]; $R^{24}$ is [−S(=O)(=O)−O−H];

or a pharmaceutically acceptable salt thereof.

71. The method according to claim 66 wherein $R^1$ is a moiety selected from the group:

[Structure: phenyl with $R^{4a}$,]

[Structure: phenyl with $R^{4a}$ and $R^{4b}$,]

[Structure: phenyl($R^{4a}$)−NH−C(=O)−phenyl($R^{4b}$, $R^{4c}$),]

[Structure: anthracene with $R^{4a}$, $R^{4b}$, $R^{4c}$, $R^{4d}$, $R^{4e}$, $R^{4f}$, $R^{4g}$,]

[Structure: anthraquinone with $R^{5a}$, $R^{5b}$, $R^{5c}$, $R^{5d}$, $R^{5e}$,]

[Structure: diphenyl sulfone with $R^{4a}$, $R^{4b}$, $R^{4c}$, $R^{4f}$, $R^{4g}$,]

and

[Structure: naphthyl with $R^{4a}$;]

or a pharmaceutically acceptable salt thereof.

72. The method according to claim 66 wherein

R¹ is a moiety selected from the group:

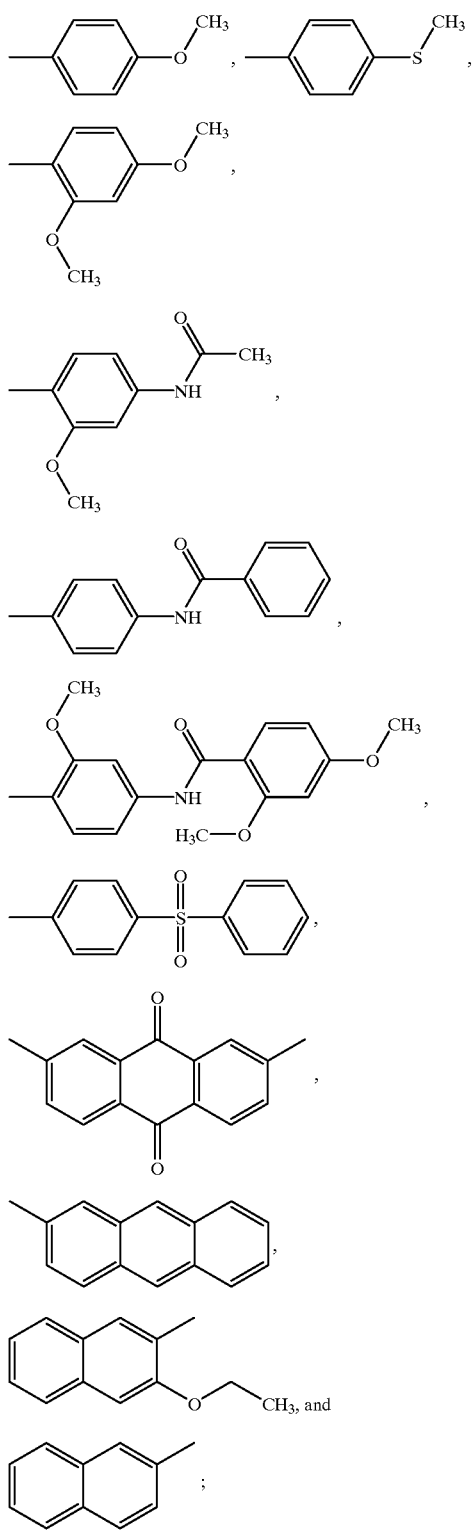

or a pharmaceutically acceptable salt thereof.

73. The method according to claim 66 wherein R¹ is a moiety selected from the group:

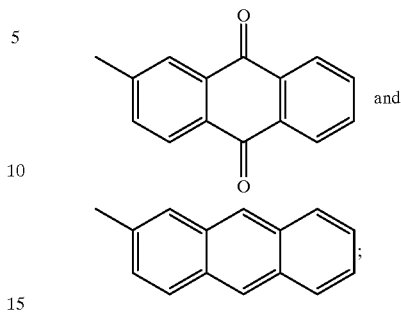

or a pharmaceutically acceptable salt thereof.

74. The method according to claim 66, in which 3,7-bis-[(benzo[b]thiophene-2-carbonyl)amino]dibenzothiophene-2,8-dicarboxylic acid or a pharmaceutically acceptable salt and most particularly the disodium salt thereof is administered.

75. The method according to claim 66, in which 3,7-bis [(2-anthracenylcarbonyl)amino]-2,8-dibenzothiophene-2,8-dicarboxylic acid or a pharmaceutically acceptable salt and most particularly the disodium salt thereof is administered.

76. The method according to claim 66, in which 3,7-bis ([(9,10-dihydro-9,10-dioxo-2-anthracenyl)carbonyl]-amino}dibenzothiophene-2,8-dicarboxylic acid or a pharmaceutically acceptable salt and most particularly the disodium salt thereof is administered.

77. The method according to claim 66, in which 3,7-bis [(thieno[3,2-b]thien-2-ylcarbonyl)amino]dibenzothiophene-2,8-dicarboxylic acid or a pharmaceutically acceptable salt and most particularly the disodium salt thereof is administered.

78. The method according to claim 66, in which 3,7-bis-[(8-chloro-4H-thieno[3,2-c][1]benzothiopyran-2-carbonyl)-amino]-dibenzothiophene-2,8-dicarboxylic acid or a pharmaceutically acceptable salt and most particularly the disodium salt thereof is administered.

79. The method according to claim 66, in which 3,7-bis-[3-(2-chloro-3,4-dimethoxyphenyl)acryloylamino] dibenzothiophen-2,8-dicarboxylic acid or a pharmaceutically acceptable salt and most particularly the disodium salt thereof is administered.

80. The method according to claim 66, in which 3,7-bis-(3-biphenyl-4-ylacryloylamino)dibenzothiophene-2,8-dicarboxylic acid or a pharmaceutically acceptable salt and most particularly the disodium salt thereof is administered.

81. The method according to claim 66, in which 3,7-bis-[3-(3-bromo-4-hydroxy-5-methoxyphenyl)acryloylamino] dibenzothiophen-2,8-dicarboxylic acid or a pharmaceutically acceptable salt and most particularly the disodium salt thereof is administered.

82. The method according to claim 66, in which 3,7-bis-[3-(2,3,4-trimethoxyphenyl)acryloylamino] dibenzothiophen-2,8-dicarboxylic acid or a pharmaceutically acceptable salt and most particularly the disodium salt thereof is administered.

83. The method according to claim 66, in which 3,7-bis{ [3-(4-methoxyphenyl)acryloylamino]dibenzothiophene-2, 8-dicarboxylic acid or a pharmaceutically acceptable salt and most particularly the disodium salt thereof is administered.

84. The method according to claim 66 in which 3-[(2-anthracenylcarbonyl)amino]-7-chlorodibenzothiophene-2, 8-dicarboxylic acid or a pharmaceutically acceptable salt and most particularly the disodium salt thereof is administered.

85. The method according to claim 66 in which 3-chloro-7-[2-(2-chloro-3,4-dimethoxyphenyl)acryloylamino] dibenzothiophen-2,8-dicarboxylic acid or a pharmaceutically acceptable salt and most particularly the disodium salt thereof is administered.

86. The method according to claim 66, in which [3,7-bis-[(benzo[b]thiophene-2-carbonyl)amino]-8-(ethoxyhydroxyphosphoryl)-5,5-dioxo-5H-5$\lambda^6$-dibenzothiophen-2-yl]phosphonic acid monoethyl ester or a pharmaceutically acceptable salt and in particular the disodium salt thereof is administered.

87. The method according to claim 66, in which [3,7-bis-[(9,10-dioxo-9,10-dihydroanthracene-2-carbonyl)amino]-8-(ethoxyhydroxyphosphoryl)-5,5-dioxo-5H-5$\lambda^6$-dibenzothiophen-2-yl]phosphonic acid monoethyl ester or a pharmaceutically acceptable salt and in particular the disodium salt thereof is administered.

88. The method according to claim 66, in which [3,7-bis-[(anthracene-2-carbonyl)amino]-8-(ethoxyhydroxyphosphoryl)-5,5-dioxo-5H-5$\lambda^6$-dibenzothiophen-2-yl]phosphonic acid monoethyl ester or a pharmaceutically acceptable salt and in particular the disodium salt thereof is administered.

89. The method according to claim 66, in which [3,7-bis-[3-(2-chloro-3,4-dimethoxyphenyl)acryloylamino]-8-(ethoxy-hydroxyphosphoryl)-5,5-dioxo-5H-5$\lambda^6$-dibenzothiophen-2-yl]phosphonic acid monoethyl ester or a pharmaceutically acceptable salt and in particular the disodium salt thereof is administered.

90. The method according to claim 66, in which [3,7-bis-[4-methoxyphenyl]acryloylamino]-8-(ethoxyhydroxyphosphoryl)-5,5-dioxo-5H-5$\lambda^6$-dibenzothiophen-2-yl]phosphonic acid monoethyl ester or a pharmaceutically acceptable salt and in particular the disodium salt thereof is administered.

91. The method according to claim 66, in which [3,7-bis-[(benzo[b]thiophene-2-carbonyl)amino]-8-(ethoxyhydroxyphosphoryl)-5,5-dioxo-5H-5$\lambda^6$-dibenzothiophen-2-yl]phosphonic acid monoethyl ester or a pharmaceutically acceptable salt and in particular the monosodium salt thereof is administered.

92. The method according to claim 66, in which 3,7-bis-[3-(4-nitrophenyl)acryloylamino]-5,5-dioxo-5H-5$\lambda^6$-dibenzo-thiophene-2,8-disulfonic acid or a pharmaceutically acceptable salt and in particular the disodium salt thereof is administered.

93. The method according to claim 66, in which 3,7-bis-(3-naphthalen-1-ylacryloylamino)-5,5-dioxo-5H-5$\lambda^6$-dibenzothiophene-2,8-disulfonic acid or a pharmaceutically acceptable salt and in particular the disodium salt thereof is administered.

94. The method according to claim 66, in which 3,7-bis-[3-(4-phenylphenyl)acryloylamino]-5,5-dioxo-5H-5$\lambda^6$-dibenzothiophene-2,8-disulfonic acid or a pharmaceutically acceptable salt and in particular the disodium salt thereof is administered.

95. The method according to claim 66, in which 3,7-bis-[3-(2-chloro-3,4-di-methoxyphenyl)acryloylamino]-5,5-dioxo-5H-5-dibenzothiophene-2,8-disulfonic acid or a pharmaceutically acceptable salt and in particular the disodium salt thereof is administered.

96. The method according to claim 66, in which 5,5-dioxo-3,7-bis-(3-pyridin-4-ylacryloylamino)-5H-5$\lambda^6$-dibenzothiophene-2,8-disulfonic acid or a pharmaceutically acceptable salt and in particular the disodium salt thereof is administered.

97. The method according to claim 66, in which 3,7-bis-[3-(4-formylphenyl)acryloylamino]-5,5-dioxo-5H-5$\lambda^6$-dibenzothiophene-2,8-disulfonic acid or a pharmaceutically acceptable salt and in particular the disodium salt thereof is administered.

98. The method according to claim 66, in which 3,7-bis-[3-(4-methoxyphenyl)acryloylamino]-5,5-dioxo-5H-5$\lambda^6$-dibenzothiophene-2,8-disulfonic acid or a pharmaceutically acceptable salt and in particular the disodium salt thereof is administered.

99. The method according to claim 66, in which 3,7-bis-[(E)-3-(3-hydroxyphenyl)acryloylamino]-5,5-dioxo-5H-5$\lambda^6$-dibenzothiophene-2,8-disulfonic acid or a pharmaceutically acceptable salt and in particular the disodium salt thereof is administered.

100. The method according to claim 66, in which 3,7-bis-[3-(4-cyanophenyl)acryloylamino]-5,5-dioxo-5H-5$\lambda^6$-dibenzothiophene-2,8-disulfonic acid or a pharmaceutically acceptable salt and in particular the disodium salt thereof is administered.

101. The method according to claim 66, in which 3,7-bis-[3-(4-bromophenyl)acryloylamino]-5,5-dioxo-5H-5$\lambda^6$-dibenzothiophene-2,8-disulfonic acid or a pharmaceutically acceptable salt and in particular the disodium salt thereof is administered.

102. The method according to claim 66, in which 3,7-bis-[3-(2-methoxyphenyl)acryloylamino]-5,5-dioxo-5H-5$\lambda^6$-dibenzothiophene-2,8-disulfonic acid or a pharmaceutically acceptable salt and in particular the disodium salt thereof is administered.

103. The method according to claim 66, in which 3,7-bis-[3-(2,5-dimethylphenyl)acryloylamino]-5,5-dioxo-5H-5$\lambda^6$-dibenzothiophene-2,8-disulfonic acid or a pharmaceutically acceptable salt and in particular the disodium salt thereof is administered.

104. The method according to claim 66, in which 3,7-bis-[3-(4-isopropylphenyl)acryloylamino]-5,5-dioxo-5H-5$\lambda^6$-dibenzothiophene-2,8-disulfonic acid or a pharmaceutically acceptable salt and in particular the disodium salt thereof is administered.

105. The method according to claim 66, in which 3,7-bis-[3-(2-methoxyphenyl)acryloylamino]-5,5-dioxo-5H-5$\lambda^6$-dibenzothiophene-2,8-disulfonic acid or a pharmaceutically acceptable salt and in particular the disodium salt thereof is administered.

106. The method according to claim 66, in which 3,7-bis-[3-(3-trifluoromethylphenyl)acryloylamino]-5,5-dioxo-5H-5 •$^6$-dibenzothiophene-2,8-disulfonic acid or a pharmaceutically acceptable salt and in particular the disodium salt thereof is administered.

107. The method according to claim 66, in which 3,7-bis-[(benzo[b]thiophene-2-carbonyl)amino]-5,5-dioxo-5H-5$\lambda^6$-dibenzothiophene-2,8-disulfonic acid or a pharmaceutically acceptable salt and in particular the disodium salt thereof is administered.

108. The method according to claim 66, in which 3,7-bis-[(benzo[b]thiophene-2-carbonyl-3-chloro)amino]-5,5-dioxo-5H-5$\lambda^6$-dibenzothiophene-2,8-disulfonic acid or a pharmaceutically acceptable salt and in particular the disodium salt thereof is administered.

109. The method according to claim 66, in which 3,7-bis-[(benzo[b]furan-2-carbonyl)amino]-5,5-dioxo-5H-5$\lambda^6$-dibenzothiophene-2,8-disulfonic acid or a pharmaceutically acceptable salt and in particular the disodium salt thereof is administered.

110. The method according to claim 66, in which 5,5-dioxo-3,7-bis-[(thieno[3,2-b]thiophene-2-carbonyl)amino]-

5H-5λ⁶-dibenzothiophene-2,8-disulfonic acid or a pharmaceutically acceptable salt and in particular the disodium salt thereof is administered.

111. The method according to claim 66, in which 3,7-bis-[(1,3-dimethyl-1H-thieno[2,3-c]pyrazole-5-carbonyl)amino]-5,5-dioxo-5H-5λ⁶-dibenzothiophene-2,8-disulfonic acid or a pharmaceutically acceptable salt and in particular the disodium salt thereof is administered.

112. The method according to claim 66, in which 3,7-bis-{[1-(4-chlorophenyl)-5-propyl-1H-pyrazole-4-carbonyl]amino}-5,5-dioxo-5H-5λ⁶-dibenzothiophene-2,8-disulfonic acid or a pharmaceutically acceptable salt and in particular the disodium salt thereof is administered.

113. The method according to claim 66, in which 5,5-dioxo-3,7-bis-[(2-phenyl-2H-[1,2,3]triazole-4-carbonyl)amino]-5H-5λ⁶-dibenzothiophene-2,8-disulfonic acid or a pharmaceutically acceptable salt and in particular the disodium salt thereof is administered.

114. The method according to claim 66, in which 3,7-bis-[(7-methoxy-2-oxo-benzopyran-3-yl)carbonylamino]-5,5-dioxo-5H-5λ⁶-dibenzothiophene-2,8-disulfonic acid or a pharmaceutically acceptable salt and in particular the disodium salt thereof is administered.

115. The method of claim 66 wherein the disease in a mammal characterized by abnormal angiogenesis is ocular neovascular disease, neovascular glaucoma, diabetic retinopathy, fibroplasia, hemangiomas, angiofibromas, psoriasis, rheumatoid arthritis or solid tumor growth.

116. A pharmaceutical composition for treating or inhibiting disease in a mammal characterized by abnormal angiogenesis, which comprises administering to a mammal in need thereof an effective amount of a compound of Formula (V)

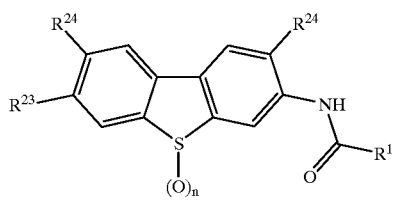

(V)

wherein:
In the general Formula (V);
    n is an integer of 0 or 2;
    R¹ is a moiety selected from the group:

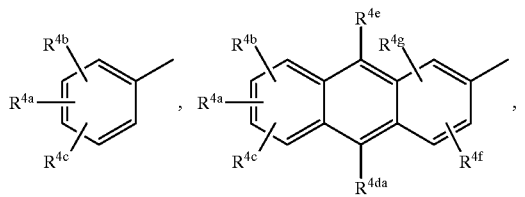

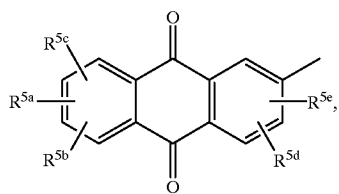

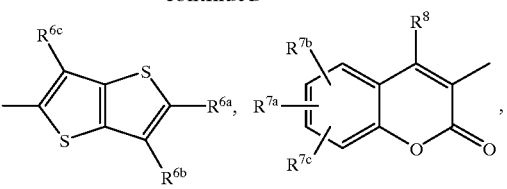

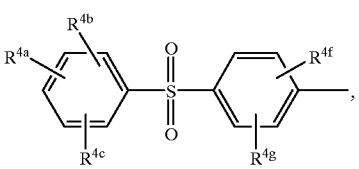

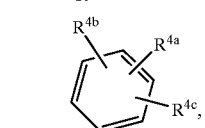

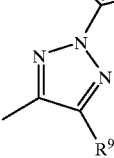

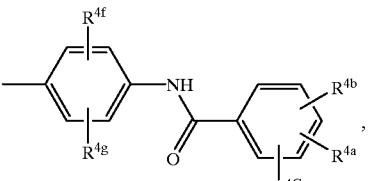

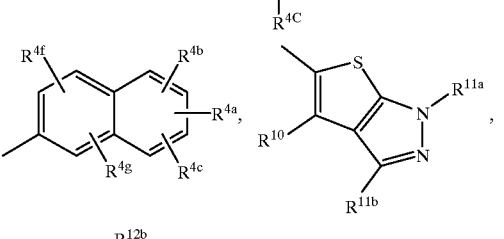

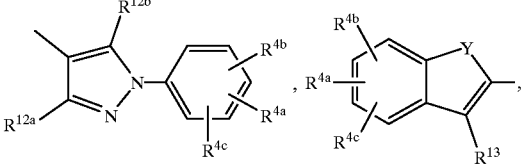

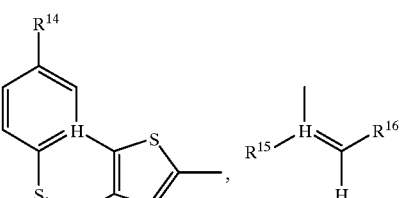

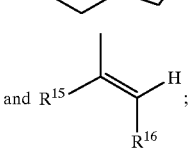

Y is sulfur, oxygen, nitrogen or carbon;
R$^{2a}$ and R$^{2b}$ are independently hydrogen, straight chain alkyl of 1 to 6 carbon atoms optionally substituted with trifluoromethyl, branched chain alkyl of 3 to 8 carbon atoms or benzyl with the proviso that each independent $R^2$ may not simultaneously be hydrogen or a pharmaceutically acceptable salt;

$R^{4a}$, $R^{4b}$, $R^{4c}$, $R^{4d}$, $R^{4e}$, $R^{4f}$ and $R^{4g}$ are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, trifluoromethyl, cyano, nitro, carboxy, alkoxycarbonyl of 1 to 6 carbon atoms, alkoxy of 1 to 6 carbon atoms, alkylcarbonyl of 1 to 6 carbon atoms, alkylcarbonylamino of 1 to 6 carbon atoms, thiol, alkylthio of 1 to 6 carbon atoms, alkylamino of 1 to 6 carbon atoms, $-N(R^{4h})(R^{4i})$, phenyl, phenylamino, and carboxaldehyde;

$R^{4h}$ and $R^{4i}$, independent from each other, are straight chain alkyl of 1 to 6 carbon atoms;

$R^{5a}$, $R^{5b}$, $R^{5c}$, $R^{5d}$, and $R^{5e}$ are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, cyano, nitro, alkylamino of 1 to 6 carbon atoms, and $-N(R^{4h})(R^{4i})$;

$R^{6a}$ and $R^{6b}$ are independently selected from hydrogen, halogen, straight chain alkyl of 1 to 6 carbon atoms, branched chain alkyl of 3 to 7 carbon atoms, alkenyl of 2 to 6 carbon atoms, and alkynyl of 2 to 6 carbon atoms;

$R^{6c}$ is hydrogen, methyl, cyano or halogen;

$R^{7a}$, $R^{7b}$ and $R^{7c}$ are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, alkoxy of 1 to 6 carbon atoms, cyano, nitro, alkoxycarbonyl of 1 to 6 carbon atoms, alkylcarbonyl of 1 to 6 carbon atoms, alkylamino of 1 to 6 carbon atoms, and $-N(R^{4h})(R^{4i})$;

$R^8$ is hydrogen, hydroxy, amino, straight chain alkyl of 1 to 6 carbon atoms or branched chain alkyl of 3 to 7 carbon atoms;

$R^9$, $R^{10}$, $R^{11a}$ and $R^{11b}$ are independently, hydrogen or alkyl of 1 to 2 carbon atoms;

$R^{12a}$ and $R^{12b}$ are independently hydrogen, straight chain alkyl of 1 to 6 carbon atoms, alkenyl of 2 to 6 carbon atoms, alkynyl of 2 to 4 carbon atoms, hydroxyalkyl of 2 to 4 carbons, carboxy, alkoxycarbonyl of 1 to 6 carbon atoms, alkoxy of 1 to 6 carbon atoms, thiol, alkylthio of 1 to 4 carbon atoms, alkylamino of 1 to 4 carbon atoms, $-N(R^{12c})(R^{12d})$, or trifluoromethyl;

$R^{12c}$ and $R^{12d}$, independent from each other, are straight chain alkyl of 1 to 4 carbon atoms;

$R^{13}$ is independently hydrogen, alkyl of 1 or 2 carbon atoms, hydroxy, amino, halogen, hydroxymethyl, or aminomethyl;

$R^{14}$ is hydrogen, alkyl of 1 or 2 carbon atoms, or halogen;

$R^{15}$ is hydrogen or cyano;

$R^{16}$ is a moiety selected from the group:

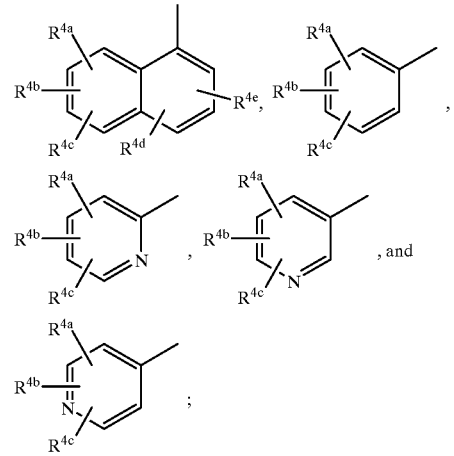

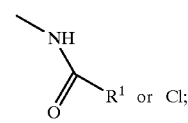

$R^1$ or Cl;

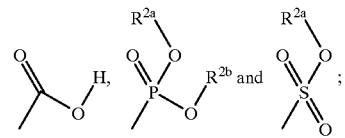

alkoxycarbonyl of 1 to 6 carbon atoms, alkylcarbonyl of 1 to 6 carbon atoms, alkylcarbonylamino of 1 to 6 carbon atoms, are defined where 1 to 6 carbon atoms describes the length of the alkyl or alkoxy as bonded to the carbonyl carbon;

$R^{2a}$ and $R^{2b}$ are independently hydrogen, straight chain alkyl of 1 to 6 carbon atoms optionally substituted with trifluoromethyl, branched chain alkyl of 3 to 8 carbon atoms or benzyl with the proviso that each independent $R^{2a}$ and $R^{2b}$ may not simultaneously be hydrogen or a pharmaceutically acceptable salt, together with a pharmaceutically acceptable carrier.

117. The pharmaceutical composition according to claim 116, containing 3,7-bis-[(benzo[b]thiophene-2-carbonyl)amino]dibenzothiophene-2,8-dicarboxylic acid or a pharmaceutically acceptable salt and particularly including the disodium salt thereof together with a pharmaceutically acceptable carrier.

118. The pharmaceutical composition according to claim 116, containing 3,7-bis[(2-anthracenylcarbonyl)amino]-2,8-dibenzothiophene-2,8-dicarboxylic acid or a pharmaceutically acceptable salt and particularly including the disodium salt thereof together with a pharmaceutically acceptable carrier.

119. The pharmaceutical composition according to claim 116, containing 3,7-bis{[(9,10-dihydro-9,10-dioxo-2-anthracenyl)carbonyl]amino}dibenzothiophene-2,8-dicarboxylic acid or a pharmaceutically acceptable salt and particularly including the disodium salt thereof together with a pharmaceutically acceptable carrier.

120. The pharmaceutical composition according to claim 116, containing 3,7-bis[(thieno[3,2-b]thien-2-ylcarbonyl) amino]dibenzothiophene-2,8-dicarboxylic acid or a pharmaceutically acceptable salt and particularly including the disodium salt thereof together with a pharmaceutically acceptable carrier.

121. The pharmaceutical composition according to claim 116, containing 3,7-bis-[(8-chloro-4H-thieno[3,2-c]-[1] benzothiopyran-2-carbonyl)amino]dibenzothiophene-2,8-dicarboxylic acid or a pharmaceutically acceptable salt and particularly including the disodium salt thereof together with a pharmaceutically acceptable carrier.

122. The pharmaceutical composition according to claim 116, containing 3,7-bis-[3-(2-chloro-3,4-dimethoxyphenyl) acryloylamino]dibenzothiophene-2,8-dicarboxylic acid or a pharmaceutically acceptable salt and particularly including the disodium salt thereof together with a pharmaceutically acceptable carrier.

123. The pharmaceutical composition according to claim 116, containing 3,7-bis-(3-biphenyl-4-ylacryloylamino) dibenzothiophene-2,8-dicarboxylic acid or a pharmaceutically acceptable salt and particularly including the disodium salt thereof together with a pharmaceutically acceptable carrier.

124. The pharmaceutical composition according to claim 116, containing 3,7-bis-[3-(3-bromo-4-hydroxy-5-methoxyphenyl)acryloylamino]dibenzothiophene-2,8-dicarboxylic acid or a pharmaceutically acceptable salt and particularly including the disodium salt thereof together with a pharmaceutically acceptable carrier.

125. The pharmaceutical composition according to claim 116, containing 3,7-bis-[3-(2,3,4-trimethoxyphenyl) acryloylamino]dibenzothiophene-2,8-dicarboxylic acid or a pharmaceutically acceptable salt and particularly including the disodium salt thereof together with a pharmaceutically acceptable carrier.

126. The pharmaceutical composition according to claim 116, containing 3,7-bis([3-(4-methoxyphenyl) acryloylamino]dibenzothiophene-2,8-dicarboxylic acid or a pharmaceutically acceptable salt and particularly including the disodium salt thereof together with a pharmaceutically acceptable carrier.

127. The pharmaceutical composition according to claim 116 containing 3-[(2-anthracenylcarbonyl)amino]-7-chloro-dibenzothiophene-2,8-dicarboxylic acid or a pharmaceutically acceptable salt and most particularly the disodium salt thereof, together with a pharmaceutically acceptable carrier.

128. The pharmaceutical composition according to claim 116 containing 3-chloro-7-[2-(2-chloro-3,4-dimethoxyphenyl)acryloylamino]dibenzothiophene-2,8-dicarboxylic acid or a pharmaceutically acceptable salt and most particularly the disodium salt thereof together with a pharmaceutically acceptable carrier.

129. The pharmaceutical composition according to claim 116, containing [3,7-bis-[(benzo[b]thiophene-2-carbonyl) amino]-8-(ethoxyhydroxyphosphoryl)-5,5-dioxo-5H-5$\lambda^6$-dibenzothiophen-2-yl]phosphonic acid monoethyl ester or a pharmaceutically acceptable salt and in particular the disodium salt thereof together with a pharmaceutically acceptable carrier.

130. The pharmaceutical composition according to claim 116, containing [3,7-bis-[(9,10-dioxo-9,10-dihydroanthracene-2-carbonyl)amino]-8-(ethoxyhydroxyphosphoryl)-5,5-dioxo-5H-5$\lambda^6$-dibenzothiophen-2-yl]phosphonic acid monoethyl ester or a pharmaceutically acceptable salt and in particular the disodium salt thereof together with a pharmaceutically acceptable carrier.

131. The pharmaceutical composition according to claim 116, containing [3,7-bis-[(anthracene-2-carbonyl)amino]-8-(ethoxyhydroxy-phosphoryl)-5,5-dioxo-5H-5$\lambda^6$-dibenzothiophen-2-yl]phosphonic acid monoethyl ester or a pharmaceutically acceptable salt and in particular the disodium salt thereof together with a pharmaceutically acceptable carrier.

132. The pharmaceutical composition according to claim 116, containing [3,7-bis-[3-(2-chloro-3,4-dimethoxyphenyl) acryloylamino]-8-(ethoxyhydroxyphosphoryl)-5,5-dioxo-5H-5$\lambda^6$-dibenzothiophen-2-yl]phosphonic acid monoethyl ester or a pharmaceutically acceptable salt and in particular the disodium salt thereof together with a pharmaceutically acceptable carrier.

133. The pharmaceutical composition according to claim 116, containing [3,7-bis-[4-methoxyphenyl]acryloylamino]-8-(ethoxyhydroxyphosphoryl)-5,5-dioxo-5H-5$\lambda^6$-dibenzothiophen-2-yl]phosphonic acid monoethyl ester or a pharmaceutically acceptable salt and in particular the disodium salt thereof together with a pharmaceutically acceptable carrier.

134. The pharmaceutical composition according to claim 116, containing [3,7-bis-[(benzo[b]thiophene-2-carbonyl) amino]-8-(ethoxyhydroxyphosphoryl)-5,5-dioxo-5H-5$\lambda^6$-dibenzothiophen-2-yl]phosphonic acid monoethyl ester or a pharmaceutically acceptable salt and in particular the monosodium salt thereof together with a pharmaceutically acceptable carrier.

135. The pharmaceutical composition according to claim 116, containing 3,7-bis-[3-(4-nitrophenyl)acryloylamino]-5,5-dioxo-5H-5$\lambda^6$-dibenzothiophene-2,8-disulfonic acid or a pharmaceutically acceptable salt and in particular the disodium salt thereof together with a pharmaceutically acceptable carrier.

136. The pharmaceutical composition according to claim 116, containing 3,7-bis-(3-naphthalen-1-ylacryloylamino)-5,5-dioxo-5H-5$\lambda^6$-dibenzothiophene-2,8-disulfonic acid or a pharmaceutically acceptable salt and in particular the disodium salt thereof together with a pharmaceutically acceptable carrier.

137. The pharmaceutical composition according to claim 116, containing 3,7-bis-[3-(4-phenylphenyl)acryloylamino]-5,5-dioxo-5H-5$\lambda^6$-dibenzothiophene-2,8-disulfonic acid or a pharmaceutically acceptable salt and in particular the disodium salt thereof together with a pharmaceutically acceptable carrier.

138. The pharmaceutical composition according to claim 116, containing 3,7-bis-[3-(2-chloro-3,4-dimethoxyphenyl) acryloylamino]-5,5-dioxo-5H-5$\lambda^6$-dibenzothiophene- 2,8-disulfonic acid or a pharmaceutically acceptable salt and in particular the disodium salt thereof together with a pharmaceutically acceptable carrier.

139. The pharmaceutical composition according to claim 116, containing 5,5-dioxo-3,7-bis-(3-pyridin-4-ylacryloylamino)-5H-5$\lambda^6$-dibenzothiophene-2,8-disulfonic acid or a pharmaceutically acceptable salt and in particular the disodium salt thereof together with a pharmaceutically acceptable carrier.

140. The pharmaceutical composition according to claim 116, containing 3,7-bis-[3-(4-formylphenyl)acryloylamino]-5,5-dioxo-5H-5$\lambda^6$-dibenzothiophene-2,8-disulfonic acid or a pharmaceutically acceptable salt and in particular the disodium salt thereof together with a pharmaceutically acceptable carrier.

141. The pharmaceutical composition according to claim 116, containing 3,7-bis-[3-(4-methoxyphenyl) acryloylamino]-5,5-dioxo-5H-5$\lambda^6$-dibenzothiophene-2,8- disulfonic acid or a pharmaceutically acceptable salt and in particular the disodium salt thereof together with a pharmaceutically acceptable carrier.

142. The pharmaceutical composition according to claim 116, containing 3,7-bis-[(E)-3-(3-hydroxyphenyl) acryloylamino]-5,5-dioxo-5H-5λ$^6$-dibenzothiophene-2,8-disulfonic acid or a pharmaceutically acceptable salt and in particular the disodium salt thereof together with a pharmaceutically acceptable carrier.

143. The pharmaceutical composition according to claim 116, containing 3,7-bis-[3-(4-cyanophenyl)acryloylamino]-5,5-dioxo-5H-5λ$^6$-dibenzothiophene-2,8-disulfonic acid or a pharmaceutically acceptable salt and in particular the disodium salt thereof together with a pharmaceutically acceptable carrier.

144. The pharmaceutical composition according to claim 116, containing 3,7-bis-[3-(4-bromophenyl)acryloylamino]-5,5-dioxo-5H-5λ$^6$-dibenzothiophene-2,8-disulfonic acid or a pharmaceutically acceptable salt and in particular the disodium salt thereof together with a pharmaceutically acceptable carrier.

145. The pharmaceutical composition according to claim 116, containing 3,7-bis-[3-(2-methoxyphenyl) acryloylamino]-5,5-dioxo-5H-5λ$^6$-dibenzothiophene-2,8-disulfonic acid or a pharmaceutically acceptable salt and in particular the disodium salt thereof together with a pharmaceutically acceptable carrier.

146. The pharmaceutical composition according to claim 116, containing 3,7-bis-[3-(2,5-dimethylphenyl) acryloylamino]-5,5-dioxo-5H-5λ$^6$-dibenzothiophene-2,8-disulfonic acid or a pharmaceutically acceptable salt and in particular the disodium salt thereof together with a pharmaceutically acceptable carrier.

147. The pharmaceutical composition according to claim 116, containing 3,7-bis-[3-(4-isopropylphenyl) acryloylamino]-5,5-dioxo-5H-5λ$^6$-dibenzothiophene-2,8-disulfonic acid or a pharmaceutically acceptable salt and in particular the disodium salt thereof together with a pharmaceutically acceptable carrier.

148. The pharmaceutical composition according to claim 116, containing 3,7-bis-[3-(2-methoxyphenyl) acryloylamino]-5,5-dioxo-5H-5λ$^6$-dibenzothiophene-2,8-disulfonic acid or a pharmaceutically acceptable salt and in particular the disodium salt thereof together with a pharmaceutically acceptable carrier.

149. The pharmaceutical composition according to claim 116, containing 3,7-bis-[3-(3-trifluoromethylphenyl) acryloylamino]-5,5-dioxo-5H-5λ$^6$-dibenzothiophene-2,8-disulfonic acid or a pharmaceutically acceptable salt and in particular the disodium salt thereof together with a pharmaceutically acceptable carrier.

150. The pharmaceutical composition according to claim 116, containing 3,7-bis-[(benzo[b]thiophene-2-carbonyl) amino]-5,5-dioxo-5H-5λ$^6$-dibenzothiophene-2,8-disulfonic acid or a pharmaceutically acceptable salt and in particular the disodium salt thereof together with a pharmaceutically acceptable carrier.

151. The pharmaceutical composition according to claim 116, containing 3,7-bis-[(benzo[b]thiophene-2-carbonyl-3-chloro)amino]-5,5-dioxo-5H-5λ$^6$-dibenzothiophene-2,8-disulfonic acid or a pharmaceutically acceptable salt and in particular the disodium salt thereof together with a pharmaceutically acceptable carrier.

152. The pharmaceutical composition according to claim 116, containing 3,7-bis-[(benzo[b]furan-2-carbonyl)amino]-5,5-dioxo-5H-5λ$^6$-dibenzothiophene-2,8-disulfonic acid or a pharmaceutically acceptable salt and in particular the disodium salt thereof together with a pharmaceutically acceptable carrier.

153. The pharmaceutical composition according to claim 116, containing 5,5-dioxo-3,7-bis-[(thieno[3,2-b]-thiophene-2-carbonyl)amino]-5H-5λ$^6$-dibenzothiophene-2,8-disulfonic acid or a pharmaceutically acceptable salt and in particular the disodium salt thereof together with a pharmaceutically acceptable carrier.

154. The pharmaceutical composition according to claim 116, containing 3,7-bis-[(1,3-dimethyl-1H-thieno[2,3-c]-pyrazole-5-carbonyl) amino]-5,5-dioxo-5H-5λ$^6$-dibenzothiophen-2,8-disulfonic acid or a pharmaceutically acceptable salt and in particular the disodium salt thereof together with a pharmaceutically acceptable carrier.

155. The pharmaceutical composition according to claim 116, containing 3,7-bis-{[1-(4-chlorophenyl)-5-propyl-1H-pyrazole-4-carbonyl]amino}-5,5-dioxo-5H-5λ$^6$-dibenzothiophene-2,8-disulfonic acid or a pharmaceutically acceptable salt and in particular the disodium salt thereof together with a pharmaceutically acceptable carrier.

156. The pharmaceutical composition according to claim 116, containing 5,5-dioxo-3,7-bis-[(2-phenyl-2H-[1,2,3] triazole-4-carbonyl) amino]-5H-5λ$^6$-dibenzothiophen-2,8-disulfonic acid or a pharmaceutically acceptable salt and in particular the disodium salt thereof together with a pharmaceutically acceptable carrier.

157. The pharmaceutical composition according to claim 116, containing 3,7-bis-[(7-methoxy-2-oxo-benzopyran-3-yl) carbonylamino]-5,5-dioxo-5H-5λ$^6$-dibenzothiophene-2,8-disulfonic acid or a pharmaceutically acceptable salt and in particular the disodium salt thereof together with a pharmaceutically acceptable carrier.

158. A compound of general Formulae (VI) and (VII)

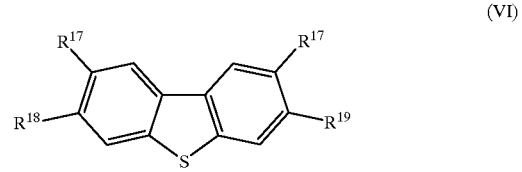

(VI)

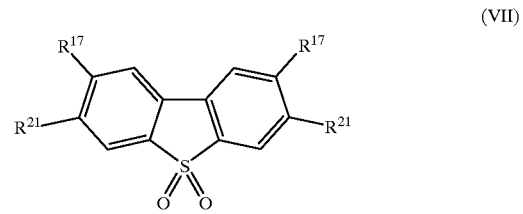

(VII)

wherein:

R$^1$ is a moiety selected from the group:

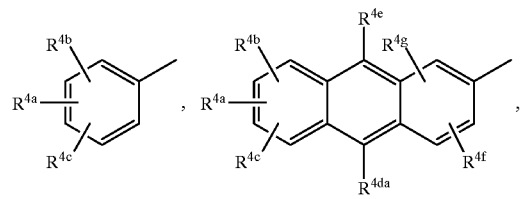

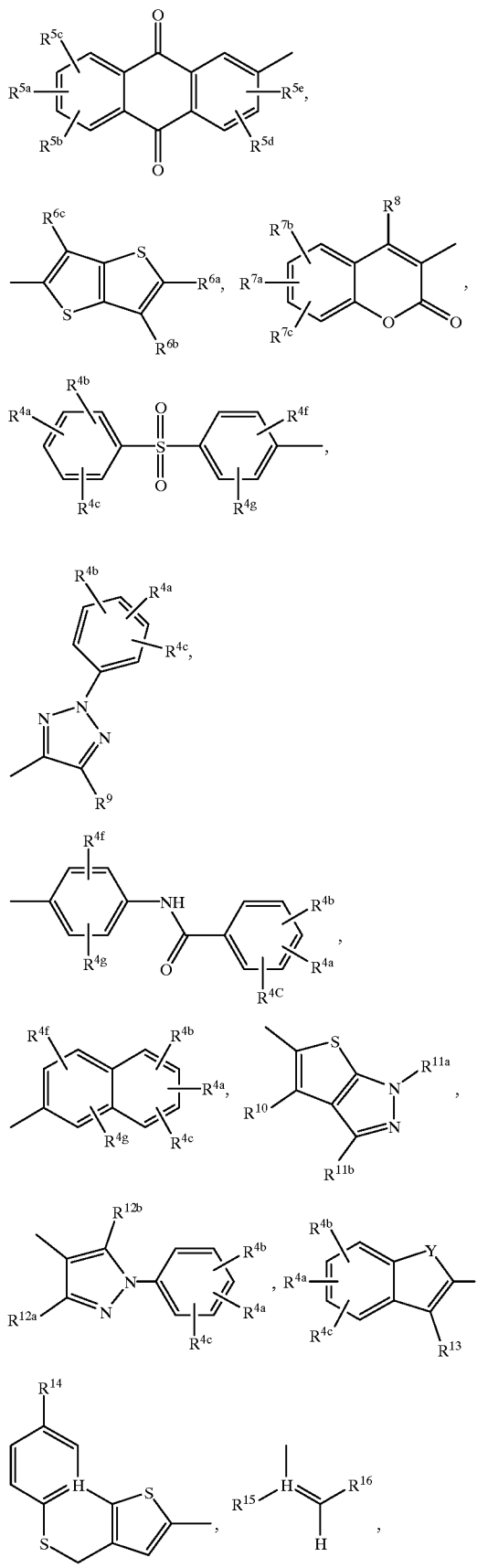
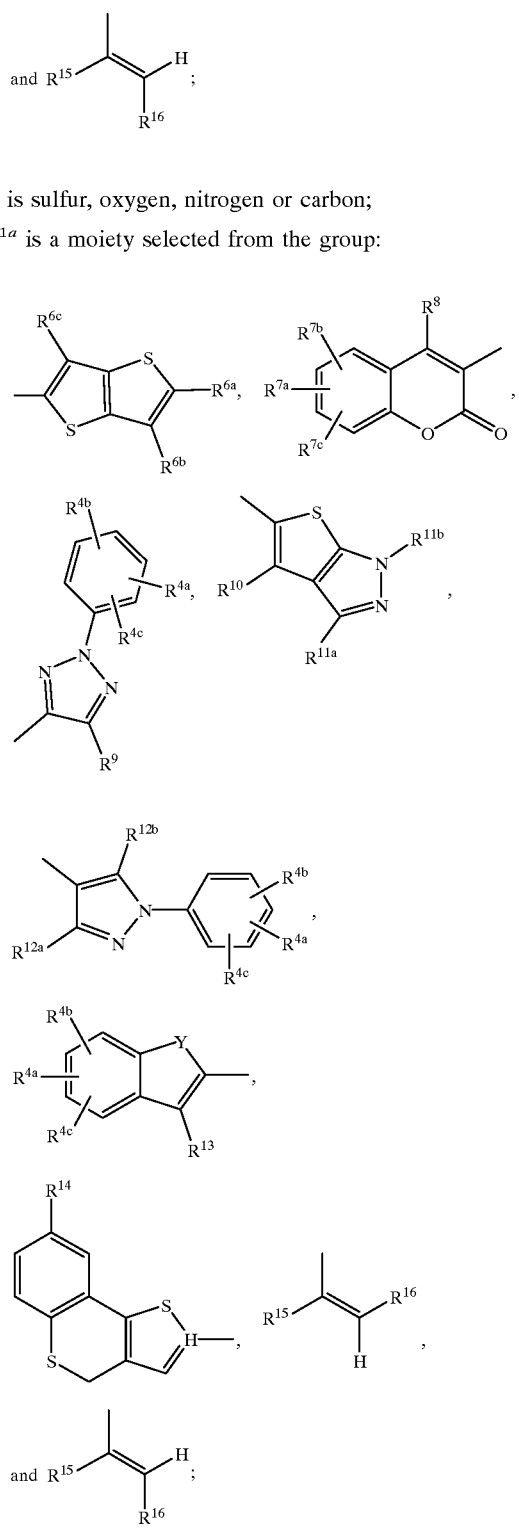
Y is sulfur, oxygen, nitrogen or carbon;
$R^{1a}$ is a moiety selected from the group:
$R^{17}$ is —CN or a moiety —COOR$^3$;
$R^3$ is hydrogen, straight chain alkyl of 1 to 5 carbon atoms, branched chain alkyl of 3 to 5 carbon atoms or benzyl;
$R^{18}$ is nitro, chloro or amino;

$R^{19}$ is nitro or amino;

$R^{21}$ is nitro, amino or a moiety selected from the group:

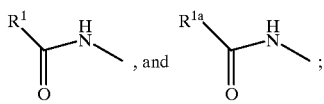

$R^{4a}$, $R^{4b}$, $R^{4c}$, $R^{4d}$, $R^{4e}$, $R^{4f}$ and $R^{4g}$ are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, trifluoromethyl, cyano, nitro, carboxy, alkoxycarbonyl of 1 to 6 carbon atoms, alkoxy of 1 to 6 carbon atoms, alkylcarbonyl of 1 to 6 carbon atoms, alkylcarbonylamino of 1 to 6 carbon atoms, thiol, alkylthio of 1 to 6 carbon atoms, alkylamino of 1 to 6 carbon atoms, —$N(R^{4h})(R^{4i})$, phenyl, phenylamino, and carboxaldehyde;

$R^{4h}$ and $R^{4i}$, independent from each other, are straight chain alkyl of 1 to 6 carbon atoms;

$R^{5a}$, $R^{5b}$, $R^{5c}$, $R^{5d}$, and $R^{5e}$ are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, cyano, nitro, alkylamino of 1 to 6 carbon atoms, or —$N(R^{4h})(R^{4i})$;

$R^{6a}$ and $R^{6b}$ are independently selected from hydrogen, halogen, straight chain alkyl of 1 to 6 carbon atoms, branched chain alkyl of 3 to 7 carbon atoms, alkenyl of 2 to 6 carbon atoms, or alkynyl of 2 to 6 carbon atoms;

$R^{6c}$ is hydrogen, methyl, cyano, or halogen;

$R^{7a}$, $R^{7b}$ and $R^{7c}$ are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, alkoxy of 1 to 6 carbon atoms, cyano, nitro, alkoxycarbonyl of 1 to 6 carbon atoms, alkylcarbonyl of 1 to 6 carbon atoms, alkylamino of 1 to 6 carbon atoms, and —$N(R^{4h})(R^{4i})$;

$R^8$ is hydrogen, hydroxy, amino, straight chain alkyl of 1 to 6 carbon atoms or branched chain alkyl of 3 to 7 carbon atoms;

$R^9$, $R_{10}$, $R^{11a}$ and $R^{11b}$ are independently hydrogen or alkyl of 1 or 2 carbon atoms;

$R^{12a}$ and $R^{12b}$ are independently hydrogen, straight chain alkyl of 1 to 6 carbon atoms, alkenyl of 2 to 6 carbon atoms, alkynyl of 2 to 4 carbon atoms, hydroxyalkyl of 2 to 4 carbon atoms, carboxy, alkoxycarbonyl of 1 to 6 carbon atoms, alkoxy of 1 to 6 carbon atoms, thiol, alkylthio of 1 to 4 carbon atoms, alkylamino of 1 to 4 carbon atoms, —$N(R^{12c})(R^{12d})$, or trifluoromethyl;

$R^{12c}$ and $R^{12d}$, independent from each other, are straight chain alkyl of 1 to 4 carbon atoms;

$R^{13}$ is independently hydrogen, alkyl of 1 or 2 carbon atoms, hydroxy, amino, bromine, chlorine, fluorine, iodine, hydroxymethyl, or aminomethyl;

$R^{14}$ is hydrogen, alkyl of 1 or 2 carbon atoms, or halogen;

$R^{15}$ is hydrogen or cyano;

$R^{16}$ is a moiety selected from the group:

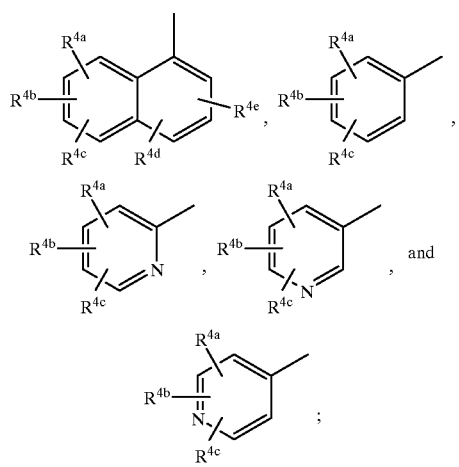

alkoxycarbonyl of 1 to 6 carbon atoms, alkylcarbonyl of 1 to 6 carbon atoms, alkylcarbonylamino of 1 to 6 carbon atoms, are defined where 1 to 6 carbon atoms describes the length of the alkyl or alkoxy as bonded to the carbonyl carbon;

or a pharmaceutically acceptable salt thereof.

159. The compound according to claim 158, 3,7-dinitrodibenzothiophene-2,8-dicarbonitrile.

160. The compound according to claim 158, 3-nitro-7-chlorodibenzothiophene-2,8-dicarbonitrile.

161. The compound according to claim 158, 3,7-dinitrodibenzothiophene-2,8-dicarboxylic acid.

162. The compound according to claim 158, 3-nitrodibenzothiophene-2,8-dicarboxylic acid.

163. The compound according to claim 158, 3,7-dinitrodibenzothiophene-2,8-dicarboxylic acid dimethyl ester.

164. The compound according to claim 158, 3-nitro-7-chlorodibenzothiophene-2,8-dicarboxylic acid dimethyl ester.

165. The compound according to claim 158, 3,7-diaminodibenzothiophene-2,8-dicarboxylic acid dimethyl ester.

166. The compound according to claim 158, 3-amino-7-chlorodibenzothiophene-2,8-dicarboxylic acid dimethyl ester.

167. The compound according to claim 80, 3-chloro-7-[2-(2-chloro-3,4-dimethoxyphenyl)acryloylamino]dibenzothiophene-2,8-dicarboxylic acid dimethyl ester.

168. The compound according to claim 80, 3-[(2-anthracenylcarbonyl)amino]-7-chloro-dibenzothiophene-2,8-dicarboxylic acid dimethyl ester.

169. A process for preparing a compound of Formula (I) or a pharmaceutically acceptable salt thereof

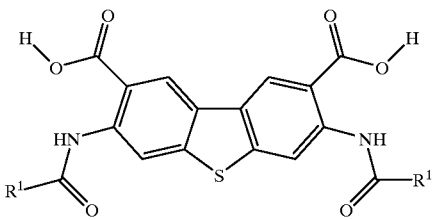

(I)

wherein:

R¹ is a moiety selected from the group:

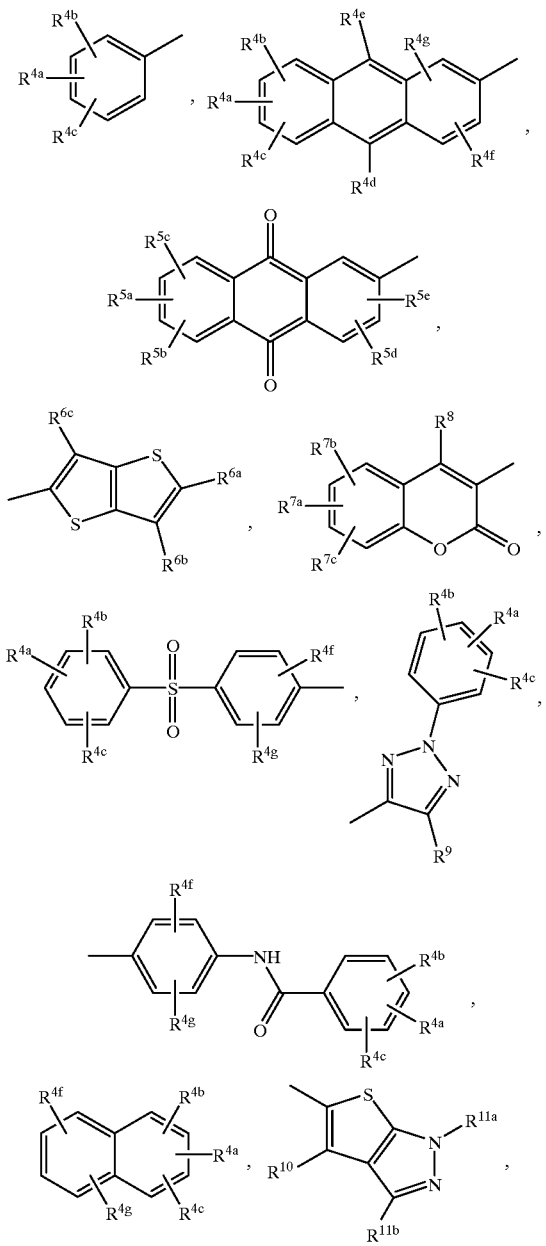

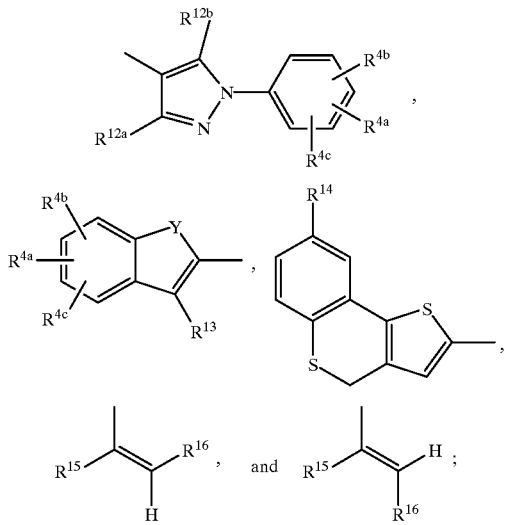

Y is sulfur, oxygen, nitrogen or carbon;

$R^{4a}$, $R^{4b}$, $R^{4c}$, $R^{4d}$, $R^{4e}$, $R^{4f}$ and $R^{4g}$ are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, trifluoromethyl, cyano, nitro, carboxy, alkoxycarbonyl of 1 to 6 carbon atoms, alkoxy of 1 to 6 carbon atoms, alkylcarbonyl of 1 to 6 carbon atoms, alkylcarbonylamino of 1 to 6 carbon atoms, thiol, alkylthio of 1 to 6 carbon atoms, alkylamino of 1 to 6 carbon atoms, —N($R^{4h}$)($R^{4i}$), phenyl, phenylamino, and carboxaldehyde;

$R^{4h}$ and $R^{4i}$, independent from each other, are straight chain alkyl of 1 to 6 carbon atoms;

$R^{5a}$, $R^{5b}$, $R^{5c}$, $R^{5d}$, and $R^{5e}$ are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, cyano, nitro, alkylamino of 1 to 6 carbon atoms, and —N($R^{4h}$)($R^{4i}$);

$R^{6a}$, and $R^{6b}$ are independently selected from hydrogen, halogen, straight chain alkyl of 1 to 6 carbon atoms, branched chain alkyl of 3 to 7 carbon atoms, alkenyl of 2 to 6 carbon atoms, or alkynyl of 2 to 6 carbon atoms;

$R^{6c}$ is hydrogen, methyl, cyano or halogen;

$R^{7a}$, $R^{7b}$ and $R^{7c}$ are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, alkoxy of 1 to 6 carbon atoms, cyano, nitro, alkoxycarbonyl of 1 to 6 carbon atoms, alkylcarbonyl of 1 to 6 carbon atoms, alkylamino of 1 to 6 carbon atoms, and —N($R^{4h}$)($R^{4i}$);

$R^8$ is hydrogen, hydroxy, amino, straight chain alkyl of 1 to 6 carbon atoms or branched chain alkyl of 3 to 7 carbon atoms;

$R^9$, $R^{10}$, $R^{11a}$ and $R^{11b}$ are independently, hydrogen or alkyl of 1 or 2 carbon atoms;

$R^{12a}$ and $R^{12b}$ are independently hydrogen, straight chain alkyl of 1 to 6 carbon atoms, alkenyl of 2 to 6 carbon atoms, alkynyl of 2 to 4 carbon atoms, hydroxyalkyl of 2 to 4 carbons, carboxy, alkoxycarbonyl of 1 to 6 carbon atoms, alkoxy of 1 to 6 carbon atoms, thiol, alkylthio of 1 to 4 carbon atoms, alkylamino of 1 to 4 carbon atoms, —N($R^{12c}$)($R^{12d}$); or trifluoromethyl;

$R^{12c}$ and $R^{12d}$, independent from each other, are straight chain alkyl of 1 to 4 carbon atoms;

$R^{13}$ is independently hydrogen, alkyl of 1 or 2 carbon atoms, hydroxy, amino, halogen, hydroxymethyl, or aminomethyl;

$R^4$ is hydrogen, alkyl of 1 or 2 carbon atoms, or halogen;

$R^{15}$ is hydrogen or cyano;

$R^{16}$ is a moiety selected from the group:

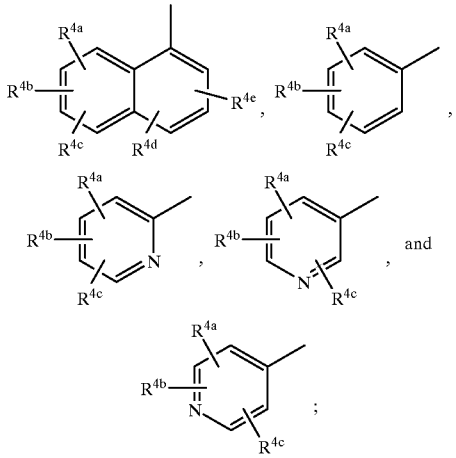

alkoxycarbonyl of 1 to 6 carbon atoms, alkylcarbonyl of 1 to 6 carbon atoms, alkylcarbonylamino of 1 to 6 carbon atoms, are defined where 1 to 6 carbon atoms describes the length of the alkyl or alkoxy as bonded to the carbonyl carbon;

a) reacting 2,8-dibromodibenzothiophene with >90% nitric acid at 50–60° C. and recovering a mixture of 2,8-dibromo-3,7-dinitrodibenzothiophene-5-oxide and 2,8-dibromo-3-nitrodibenzothiophene-5-oxide;

b) reacting said mixture of 2,8-dibromo-3,7-dinitrodibenzothiophene-5-oxide and 2,8-dibromo-3-nitrodibenzothiophene-5-oxide with copper (I) cyanide at 50–150° C. for about 10 hours; heating with ferric chloride/hydrochloric acid and recovering a mixture of 3,7-dinitrodibenzothiophene-2,8-dicarbonitrile and 3-chloro-7-nitrodibenzothiophene-2,8-dicarbonitrile;

c) reacting said mixture of 3,7-dinitrodibenzothiophen-2,8-dicarbonitrile and 3-chloro-7-nitrodibenzothiophene-2,8-dicarbonitrile with aqueous acetic acid/hydrobromic acid at 50–100° C.; treating with aqueous sodium hydroxide at 50–100° C.; adjusting the pH to between 1 and 5 and recovering a mixture of 3,7-dinitrodibenzothiophene-2,8-dicarboxylic acid and 3-chloro-7-nitro-dibenzothiophene-2,8-dicarboxylic acid;

d) reacting said mixture of 3,7-dinitrodibenzothiophen-2, 8-dicarboxylic acid and 3-chloro-7-nitrodibenzothiophene- 2,8-dicarboxylic acid with a halogenating agent; treating with an alkylamine base and an alcohol, $R^3$OH, where $R^3$ is straight chain alkyl of 1 to 6 carbon atoms, branched chain alkyl of 3 to 7 carbon atoms or benzyl at about 0 to 75° C. for 1 to 100 hours and recovering a mixture of 3,7-dinitrodibenzothiophene-2,8-dicarboxylic acid diester and 3-chloro-7-nitrodibenzothiophene-2,8-dicarboxylic acid diester;

e) treating said mixture of 3,7-dinitrodibenzothiophen-2, 8-dicarboxylic acid diester and 3-chloro-7-nitrodibenzothiophene-2,8-dicarboxylic acid diester with a reducing agent in the presence of an alcoholic solvent and an organic acid at 50 to 120° C.; recovering a mixture of 3,7-diaminodibenzothiophene-2,8-dicarboxylic acid diester and 3-amino-7-chloro-dibenzothiophene-2,8-dicarboxylic acid diester and f) separating said mixture of 3,7-diaminodibenzothiophen-2,8-dicarboxylic acid diester and 3-amino-7-chlorodibenzothiophene-2,8-dicarboxylic acid diester by chromatography and recovering the pure 3,7-diaminodibenzothiophene-2,8-dicarboxylic acid diester and 3-amino-7-chlorodibenzothiophene-2,8-dicarboxylic acid diester;

g) reacting said separated 3,7-diaminodibenzothiophene-2,8-dicarboxylic acid diester with an acid chloride of the formula:

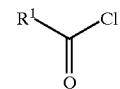

wherein $R^1$ is as defined hereinabove, in a polar-aprotic solvent for 0.25 to 24 hours in the presence of an alkylamine base and recovering the 3,7-bis-($R^1$-carbonylamino) dibenzothiophene-2,8-dicarboxylic acid ester;

h) cleaving the ester of said 3,7-bis-($R^1$-carbonylamino) dibenzothiophene-2,8-dicarboxylic acid ester with an ester cleaving reagent; treating with acid to form 3,7-bis-($R^1$-carbonylamino) dibenzothiophene-2,8-dicarboxylic acid of Formula (I) where $R^1$ is hereinbefore defined; and I) reacting said 3,7-bis-($R^1$-carbonylamino) dibenzothiophen-2,8-dicarboxylic acid with an alkali metal or alkaline earth metal base to yield the bimetal base of Formula (I) where $R^1$ is hereinbefore defined.

170. A process for preparing a compound of Formula (II) or a pharmaceutically acceptable salt thereof

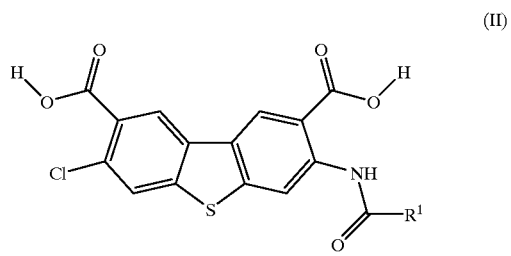

wherein:

R¹ is a moiety selected from the group:

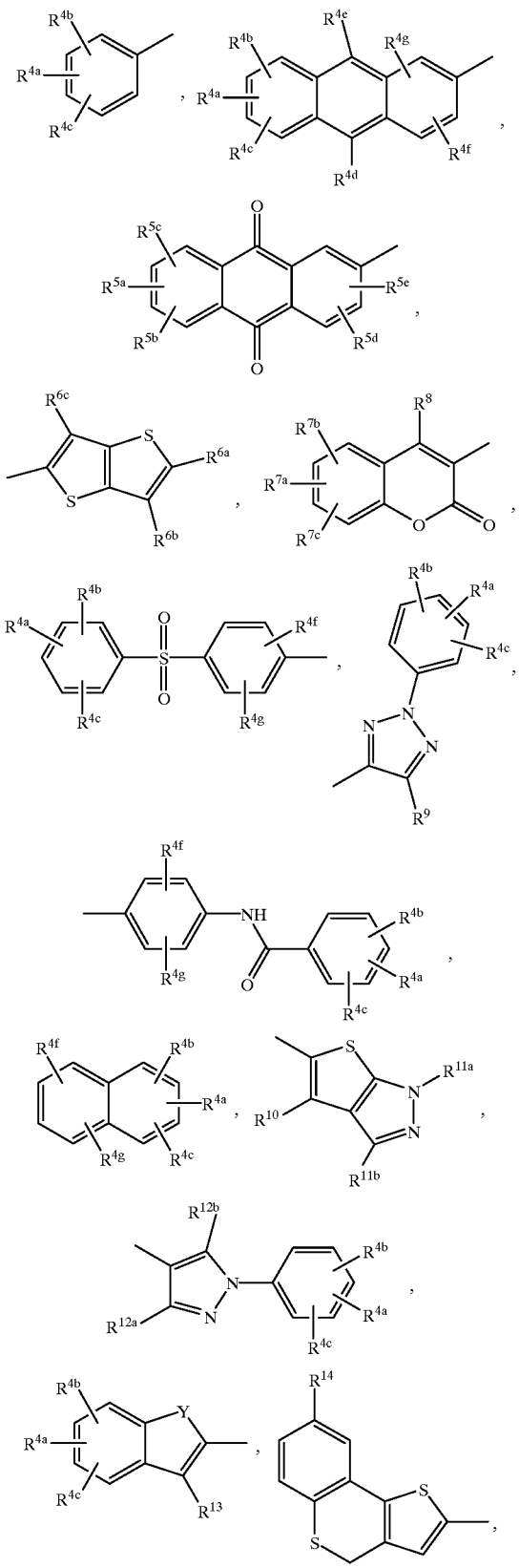

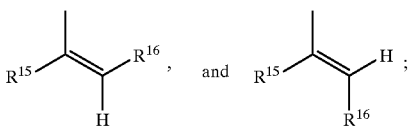

Y is sulfur, oxygen, nitrogen or carbon;

$R^{4a}$, $R^{4b}$, $R^{4c}$, $R^{4d}$, $R^{4e}$, $R^{4f}$ and $R^{4g}$ are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, trifluoromethyl, cyano, nitro, carboxy, alkoxycarbonyl of 1 to 6 carbon atoms, alkoxy of 1 to 6 carbon atoms, alkylcarbonyl of 1 to 6 carbon atoms, alkylcarbonylamino of 1 to 6 carbon atoms, thiol, alkylthio of 1 to 6 carbon atoms, alkylamino of 1 to 6 carbon atoms, —N($R^{4h}$)($R^{4i}$), phenyl, phenylamino, and carboxaldehyde;

$R^{4h}$ and $R^{4i}$, independent from each other, are straight chain alkyl of 1 to 6 carbon atoms;

$R^{5a}$, $R^{5b}$, $R^{5c}$, $R^{5d}$, and $R^{5e}$ are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, cyano, nitro, alkylamino of 1 to 6 carbon atoms, and —N($R^{4h}$)($R^{4i}$);

$R^{6a}$, and $R^{6b}$ are independently selected from hydrogen, halogen, straight chain alkyl of 1 to 6 carbon atoms, branched chain alkyl of 3 to 7 carbon atoms, alkenyl of 2 to 6 carbon atoms, and alkynyl of 2 to 6 carbon atoms;

$R^{6c}$ is hydrogen, methyl, cyano or halogen;

$R^{7a}$, $R^{7b}$ and $R^{7c}$ are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, alkoxy of 1 to 6 carbon atoms, cyano, nitro, alkoxycarbonyl of 1 to 6 carbon atoms, alkylcarbonyl of 1 to 6 carbon atoms, alkylamino of 1 to 6 carbon atoms, and —N($R^{4h}$)($R^{4i}$);

$R^8$ is hydrogen, hydroxy, amino, straight chain alkyl of 1 to 6 carbon atoms or branched chain alkyl of 3 to 7 carbon atoms;

$R^9$, $R^{10}$, $R^{11a}$ and $R^{11b}$ are independently, hydrogen or alkyl of 1 or 2 carbon atoms;

$R^{12a}$ and $R^{12b}$ are independently hydrogen, straight chain alkyl of 1 to 6 carbon atoms, alkenyl of 2 to 6 carbon atoms, alkynyl of 2 to 4 carbon atoms, hydroxyalkyl of 2 to 4 carbons, carboxy, alkoxycarbonyl of 1 to 6 carbon atoms, alkoxy of 1 to 6 carbon atoms, thiol, alkylthio of 1 to 4 carbon atoms, alkylamino of 1 to 4 carbon atoms, —N($R^{12c}$)($R^{12d}$); or trifluoromethyl;

$R^{12c}$ and $R^{12d}$, independent from each other, are straight chain alkyl of 1 to 4 carbon atoms;

$R^{13}$ is independently hydrogen, alkyl of 1 or 2 carbon atoms, hydroxy, amino, halogen, hydroxymethyl, or aminomethyl;

$R^{14}$ is hydrogen, alkyl of 1 or 2 carbon atoms, or halogen;

$R^{15}$ is hydrogen or cyano;
$R^{16}$ is a moiety selected from the group:

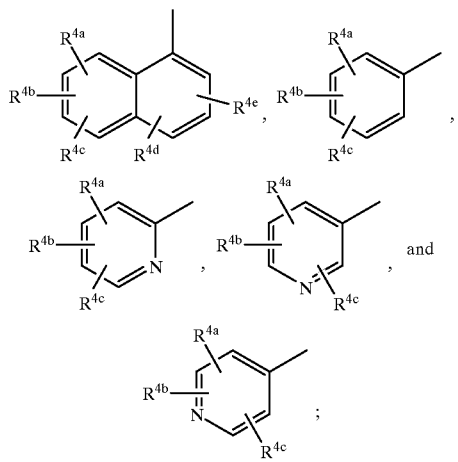

alkoxycarbonyl of 1 to 6 carbon atoms, alkylcarbonyl of 1 to 6 carbon atoms, alkylcarbonylamino of 1 to 6 carbon atoms, are defined where 1 to 6 carbon atoms describes the length of the alkyl or alkoxy as bonded to the carbonyl carbon;
which comprises the steps of:
 a) reacting 2,8-dibromodibenzothiophene with >90% nitric acid at 50–60° C. and recovering a mixture of 2,8-dibromo-3,7-dinitrodibenzothiophene-5-oxide and 2,8-dibromo-3-nitrodibenzothiophene-5-oxide;
 b) reacting said mixture of 2,8-dibromo-3,7-dinitrodibenzothiophene-5-oxide and 2,8-dibromo-3-nitrodibenzothiophene-5-oxide with copper (I) cyanide at 50–150° C. for about 10 hours; heating with ferric chloride/hydrochloric acid and recovering a mixture of 3,7-dinitrodibenzothiophene-2,8-dicarbonitrile and 3-chloro-7-nitrodibenzothiophene-2,8-dicarbonitrile;
 c) reacting said mixture of 3,7-dinitrodibenzothiophene-2,8-dicarbonitrile and 3-chloro-7-nitrodibenzothiophen-2,8-dicarbonitrile with aqueous acetic acid/hydrobromic acid at 50–100° C.; treating with aqueous sodium hydroxide at 50–100° C.; adjusting the pH to between 1 and 5 and recovering a mixture of 3,7-dinitrodibenzothiophene-2,8-dicarboxylic acid and 3-chloro-7-nitrodibenzothiophene-2,8-dicarboxylic acid;
 d) reacting said mixture of 3,7-dinitrodibenzothiophene-2,8-dicarboxylic acid and 3-chloro-7-nitrodibenzothiophene-2,8-dicarboxylic acid with a halogenating agent; treating with an alkylamine base and an alcohol, $R^3OH$, where $R^3$ is straight chain alkyl of 1 to 6 carbon atoms, branched chain alkyl of 3 to 7 carbon atoms or benzyl at about 0 to 75° C. for 1 to 100 hours; and recovering a mixture of 3,7-dinitrodibenzothiophene-2,8-dicarboxylic acid diester and 3-chloro-7-nitrodibenzothiophene-2,8-dicarboxylic acid diester;
 e) treating said mixture of 3,7-dinitrodibenzothiophene-2,8-dicarboxylic acid diester; and 3-chloro-7-nitrodibenzothiophene-2,8-dicarboxylic acid diester with a reducing agent in the presence of an alcoholic solvent and an organic acid at 50 to 120° C.; recovering a mixture of 3,7-diaminodibenzothiophene-2,8-dicarboxylic acid diester and 3-amino-7-chlorodibenzothiophene-2,8-dicarboxylic acid diester and
 f) separating said mixture of 3,7-diaminodibenzothiophene-2,8-dicarboxylic acid diester and 3-amino-7-chlorodibenzothiophene-2,8-dicarboxylic acid diester by chromatography and recovering separated 3,7-diaminodibenzothiophene-2,8-dicarboxylic acid diester from 3-amino-7-chlorodibenzothiophene-2,8-dicarboxylic acid diester;
 g) reacting said separated 3-amino-7-chlorodibenzothiophen-2,8-dicarboxylic acid diester with an acid chloride of the formula:

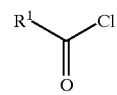

wherein $R^1$ is as defined hereinabove, in a polar-aprotic solvent for 0.25 to 24 hours in the presence of an alkylamine base and recovering 3-($R^1$-carbonylamino)-7-chlorodibenzothiophene-2,8-dicarboxylic acid ester;

h) cleaving the ester of said 3-($R^1$-carbonylamino)-7-chlorodibenzothiophene-2,8-dicarboxylic acid ester with an ester cleaving reagent at from room temperature to 155° C. for 0.10 to 24 hours; treating with acid to form the 3-($R^1$-carbonylamino)-7-chlorodibenzothiophene-2,8-dicarboxylic acid of Formula (II) where $R^1$ is hereinbefore defined; and
 I) reacting said 3-($R^1$-carbonylamino)-7-chlorodibenzothiophene-2,8-dicarboxylic acid with an alkali metal or alkaline earth metal base to yield the bimetal base of Formula (II) where $R^1$ is hereinbefore defined.

171. A process for preparing a compound of Formula IV or a pharmaceutically acceptable salt thereof

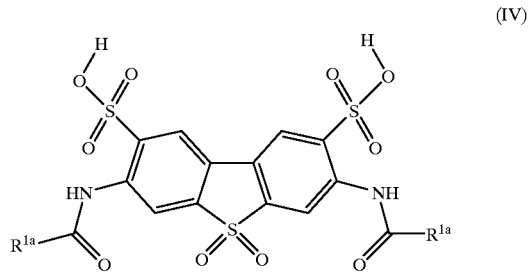

wherein:

$R^{1a}$ is a moiety selected from the group:

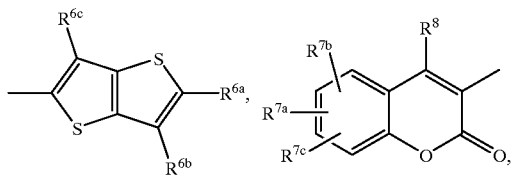

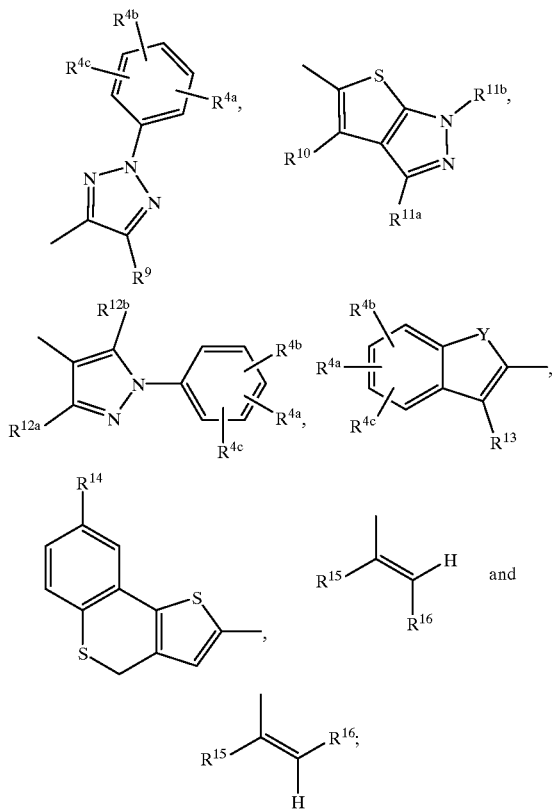

with the proviso that $R^{15}$ is not H when $R^{16}$ is phenyl;

Y is sulfur, oxygen, nitrogen or carbon;

$R^{4a}$, $R^{4b}$, $R^{4c}$, $R^{4d}$, $R^{4e}$, $R^{4f}$ and $R^{4g}$ are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, trifluoromethyl, cyano, nitro, carboxy, alkoxycarbonyl of 1 to 6 carbon atoms, alkoxy of 1 to 6 carbon atoms, alkylcarbonyl of I to 6 carbon atoms, alkylcarbonylamino of 1 to 6 carbon atoms, thiol, alkylthio of 1 to 6 carbon atoms, alkylamino of 1 to 6 carbon atoms, —N($R^{4h}$)($R^{4i}$), phenyl, phenylamino, and carboxaldehyde;

$R^{4h}$ and $R^{4i}$, independent from each other, are straight chain alkyl of 1 to 6 carbon atoms;

$R^{5a}$, $R^{5b}$, $R^{5c}$, $R^{5d}$, and $R^{5e}$ are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, cyano, nitro, alkylamino of 1 to 6 carbon atoms, and —N($R^{4h}$)($R^{4i}$);

$R^{6a}$ and $R^{6b}$ are independently selected from hydrogen, halogen, straight chain alkyl of 1 to 6 carbon atoms, branched chain alkyl of 3 to 7 carbon atoms, alkenyl of 2 to 6 carbon atoms, and alkynyl of 2 to 6 carbon atoms;

$R^{6c}$ is hydrogen, methyl, cyano, or halogen;

$R^{7a}$, $R^{7b}$ and $R^{7c}$ are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, alkoxy of 1 to 6 carbon atoms, cyano, nitro, alkoxycarbonyl of 1 to 6 carbon atoms, alkylcarbonyl of 1 to 6 carbon atoms, alkylamino of 1 to 6 carbon atoms, and —N($R^{4h}$)($R^{4i}$);

$R^8$ is hydrogen, hydroxy, amino, straight chain alkyl of 1 to 6 carbon atoms or branched chain alkyl of 3 to 7 carbon atoms;

$R^9$, $R^{10}$, $R^{11a}$ and $R^{11b}$ are independently, hydrogen or alkyl of 1 or 2 carbon atoms;

$R^{12a}$ and $R^{12b}$ are independently hydrogen, straight chain alkyl of 1 to 6 carbon atoms, alkenyl of 2 to 6 carbon atoms, alkynyl of 2 to 4 carbon atoms, hydroxyalkyl of 2 to 4 carbons, carboxy, alkoxycarbonyl of 1 to 6 carbon atoms, alkoxy of 1 to 6 carbon atoms, thiol, alkylthio of 1 to 4 carbon atoms, alkylamino of 1 to 4 carbon atoms, —N($R^{12c}$)($R^{12d}$); or trifluoromethyl;

$R^{12c}$ and $R^{12d}$, independent from each other, are straight chain alkyl of 1 to 4 carbon atoms;

$R^{13}$ is independently hydrogen, alkyl of 1 or 2 carbon atoms, hydroxy, amino, halogen, hydroxymethyl, or aminomethyl;

$R^{14}$ is hydrogen, alkyl of 1 or 2 carbon atoms, or halogen;

$R^{15}$ is hydrogen or cyano;

$R^{16}$ is a moiety selected from the group:

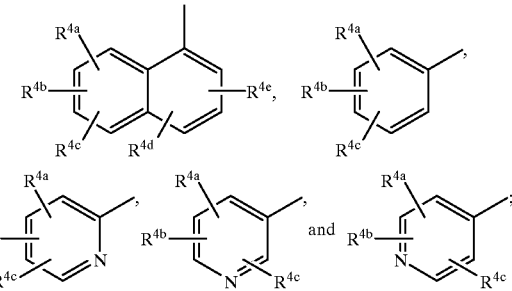

alkoxycarbonyl of 1 to 6 carbon atoms, alkylcarbonyl of 1 to 6 carbon atoms, alkylcarbonylamino of 1 to 6 carbon atoms, are defined where 1 to 6 carbon atoms describes the length of the alkyl or alkoxy as bonded to the carbonyl carbon;

which comprises the steps of:
a) reacting 3,7-diaminodibenzothiophene-5,5-dioxide with oleum; heating at about 25 to 200° C. for 0.5 to 3 hours; pouring in ice; adjusting the pH to from 8 to 12 with alkylamine and recovering 3,7-diamino-5,5-dioxo-5λ$^6$-dibenzothiophene-2,8-disulfonic acid dialkylamine salt;
b) reacting said 3,7-diamino-5,5-dioxo-5λ$^6$-dibenzothiophene-2,8-disulfonic acid dialkylamine salt with an acid chloride of the formula:

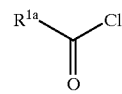

where $R^{1a}$ is hereinbefore defined and an alkylamine in a polar aprotic solvent with heating to about 90° C.; adding excess aqueous base and recovering the 3,7-bis-($R^{1a}$-carbonylamino)-5,5-dioxo-5H,5λ$^6$-dibenzothiophene-2,8-disulfonic acid dimetal salt.

172. A process for preparing a compound of Formula (III) or a pharmaceutically acceptable salt thereof

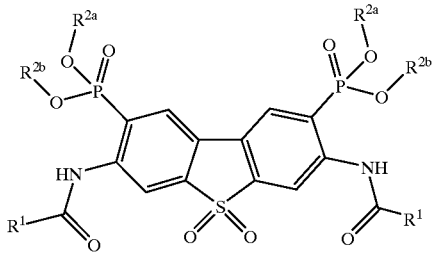

(III)

wherein:

$R^{2a}$ and $R^{2b}$ are independently hydrogen, straight chain alkyl of 1 to 6 carbon atoms (optionally substituted with trifluoromethyl), branched chain alkyl of 3 to 8 carbon atoms or benzyl with the proviso that each independent $R^{2a}$ and $R^{2b}$ may not simultaneously be hydrogen or a pharmaceutically acceptable salt;

$R^1$ is a moiety selected from the group:

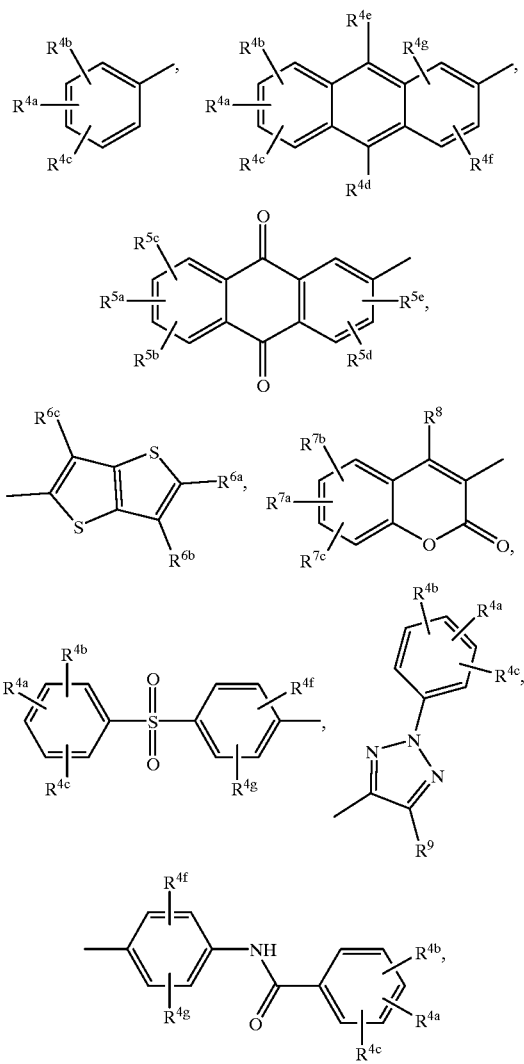

-continued

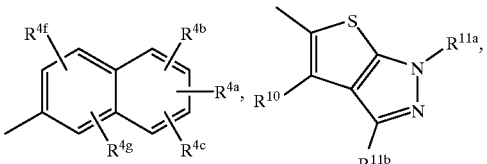

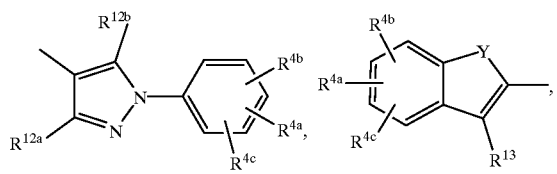

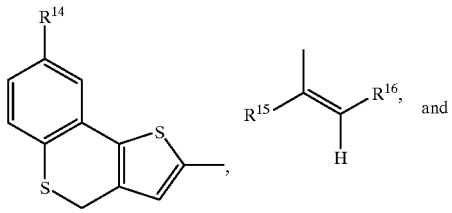

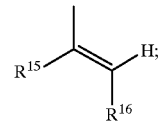 and

Y is sulfur, oxygen, nitrogen or carbon;

$R^{4a}$, $R^{4b}$, $R^{4c}$, $R^{4d}$, $R^{4e}$, $R^{4f}$ and $R^{4g}$ are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, trifluoromethyl, cyano, nitro, carboxy, alkoxycarbonyl of 1 to 6 carbon atoms, alkoxy of 1 to 6 carbon atoms, alkylcarbonyl of 1 to 6 carbon atoms, alkylcarbonylamino of 1 to 6 carbon atoms, thiol, alkylthio of 1 to 6 carbon atoms, alkylamino of 1 to 6 carbon atoms, —N($R^{4h}$)($R^{4i}$), phenyl, phenylamino, and carboxaldehyde;

$R^{4h}$ and $R^{4i}$, independent from each other, are straight chain alkyl of 1 to 6 carbon atoms;

$R^{5a}$, $R^{5b}$, $R^{5c}$, $R^{5d}$, and $R^{5e}$ are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, cyano, nitro, alkylamino of 1 to 6 carbon atoms, and —N($R^{4h}$)($R^{4i}$);

$R^{6a}$ and $R^{6b}$ are independently selected from hydrogen, halogen, straight chain alkyl of 1 to 6 carbon atoms, branched chain alkyl of 3 to 7 carbon atoms, alkenyl of 2 to 6 carbon atoms, or alkynyl of 2 to 6 carbon atoms;

$R^{6c}$ is hydrogen, methyl, cyano, or halogen;

$R^{7a}$, $R^{7b}$ and $R^{7c}$ are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, alkoxy of 1 to 6 carbon atoms, cyano, nitro, alkoxycarbonyl of 1 to 6 carbon atoms, alkylcarbonyl of 1 to 6 carbon atoms, alkylamino of 1 to 6 carbon atoms, and —N($R^{4h}$)($R^{4i}$);

$R^8$ is hydrogen, hydroxy, amino, straight chain alkyl of 1 to 6 carbon atoms or branched chain alkyl of 3 to 7 carbon atoms;

$R^9$, $R^{10}$, $R^{11a}$ and $R^{11b}$ are independently, hydrogen or alkyl of 1 or 2 carbon atoms;

$R^{12a}$ and $R^{12b}$ are independently hydrogen, straight chain alkyl of 1 to 6 carbon atoms, alkenyl of 2 to 6 carbon atoms, alkynyl of 2 to 4 carbon atoms, hydroxyalkyl of 2 to 4 carbons, carboxy, alkoxycarbonyl of 1 to 6 carbon atoms, alkoxy of 1 to 6 carbon atoms, thiol, alkylthio of 1 to 4 carbon atoms, alkylamino of 1 to 4 carbon atoms, —$N(R^{12c})(R^{12d})$; or trifluoromethyl;

$R^{12c}$ and $R^{12d}$, independent from each other, are straight chain alkyl of 1 to 4 carbon atoms;

$R^{13}$ is independently hydrogen, alkyl of 1 or 2 carbon atoms, hydroxy, amino, halogen, hydroxymethyl, or aminomethyl;

$R^{14}$ is hydrogen, alkyl of 1 or 2 carbon atoms, or halogen;

$R^{15}$ is hydrogen or cyano;

$R^{16}$ is a moiety selected from the group:

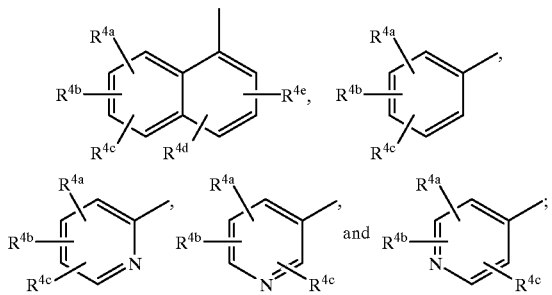

alkoxycarbonyl of 1 to 6 carbon atoms, alkylcarbonyl of 1 to 6 carbon atoms, alkylcarbonylamino of 1 to 6 carbon atoms, are defined where 1 to 6 carbon atoms describes the length of the alkyl or alkoxy as bonded to the carbonyl carbon;

which comprises the steps of:
a) reacting 2,8-dibromodibenzothiophene with >90% nitric acid at 50–60° C. and recovering a mixture of 2,8-dibromo-3,7-dinitrodibenzothiophene-5-oxide and 2,8-dibromo-3-nitro-dibenzothiophene-5-oxide;
b) reacting said mixture of 2,8-dibromo-3,7-dinitrodibenzothiophene-5-oxide and 2,8-dibromo-3-nitrodibenzothiophene-5-oxide with sodium periodate and ruthenium (III) chloride and recovering 2,8-dibromo-3,7-dinitrodibenzothiophene-5,5-dioxide;
c) treating said 2,8-dibromo-3,7-dinitrodibenzothiophene-5,5-dioxide with a reducing agent in the presence of an alcoholic solvent and an organic acid at 50 to 120° C.; recovering the 2,8-dibromo-5,5-dioxo-5H-5$\lambda^6$-dibenzothiophene-3,7-diamine;
d) reacting said 2,8-dibromo-5,5-dioxo-5H-5$\lambda^6$-dibenzothiophene-3,7-diamine with an acid chloride of the formula:

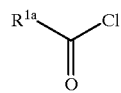

where $R^1$ is hereinbefore defined, in a polar-aprotic solvent in the presence of an alkylamine base at room temperature to about 120° C. for 0.25 to about 24 hours to give 2,8-dibromo-3,7-($R^1$-carbonylamino)-5,5-dioxo-5H-5$\lambda^6$-dibenzothiophene;

e) reacting said 2,8-dibromo-3,7-($R^1$-carbonylamino)-5,5-dioxo-5H-5$\lambda^6$-dibenzothiophene with a disubstituted phosphite of the formula HPO($R^2$)$_2$ where $R^1$ is independently $R^{2a}$ or $R^{2b}$, with the proviso that $R^2$ is not H, in a polar aprotic solvent in the presence of an alkylamine, palladium (O) and heating for 1.5 to 100 hours at room temperature to 150° C.; treating with acid and recovering a mixture of [3,7-bis-($R^1$-carbonylamino)-8-[($R^2$-oxy)hydroxyphosphoryl]-5,5-dioxo-5H-5$\lambda^6$-dibenzothiophene-2-yl]phosphonic acid mono-$R^2$ ester di(trisubstituted alkylamine) salt and 3,7-bis-($R^1$-carbonylamino)-8-[(di-$R^2$-oxy)phosphoryl]-5,5-dioxo-5H-5$\lambda^6$-dibenzothiophene-2-yl] phosphonic acid mono-$R^2$ ester mono (trisubstituted alkylamine) salt; separating said mixture by column chromatography and isolating [3,7-bis-($R^1$-carbonylamino)-8-[($R^2$-oxy)hydroxyphosphoryl]-5,5-dioxo-5H-5$\lambda^6$-dibenzothiophene-2-yl]phosphonic acid mono-$R^2$ ester di(trisubstituted alkylamine) salt from 3,7-bis-($R^1$-carbonylamino)-8-[(di-$R^1$-oxy)phosphoryl]-5,5-dioxo-5H-5$\lambda^6$-dibenzothiophene-2-yl]phosphonic acid mono-$R^2$ ester mono (trisubstituted alkylamine) salt;

f) treating [3,7-bis-($R^1$-carbonylamino)-8-[($R^2$-oxy)hydroxyphosphoryl]-5,5-dioxo-5H-5$\lambda^6$-dibenzothiophene-2-yl]phosphonic acid mono-$R^1$ ester di(trisubstituted alkylamine) salt with aqueous acid giving the free acid;

g) reacting said free acid with an alkaline metal or alkaline earth metal base in a heated polar solvent mixture and isolating the 3,7-bis-($R^1$-carbonylamino)-8-[($R^2$-oxy)hydroxyphosphoryl]-5,5-dioxo-5H-5$\lambda^6$-dibenzothiophen-2-yl]phosphonic acid mono-$R^2$ ester dimetal salt.

173. A process for preparing a compound of Formula (III) or a pharmaceutically acceptable salt thereof

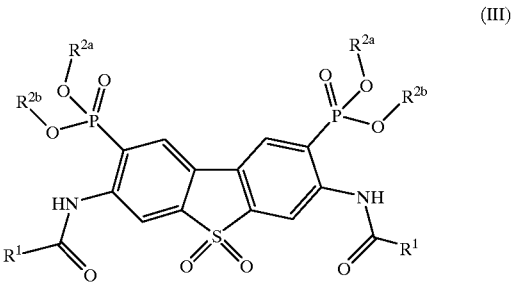

(III)

wherein:

$R^{2a}$ and $R^{2b}$ are independently hydrogen, straight chain alkyl of 1 to 6 carbon atoms (optionally substituted with trifluoromethyl), branched chain alkyl of 3 to 8 carbon atoms or benzyl with the proviso that each independent $R^{2a}$ and $R^{2b}$ may not simultaneously be hydrogen or a pharmaceutically acceptable salt;

$R^1$ is a moiety selected from the group:

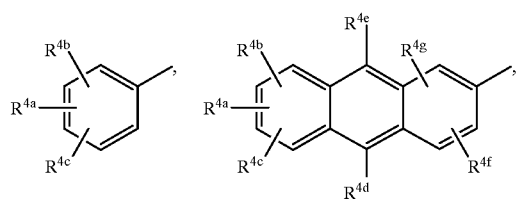

-continued

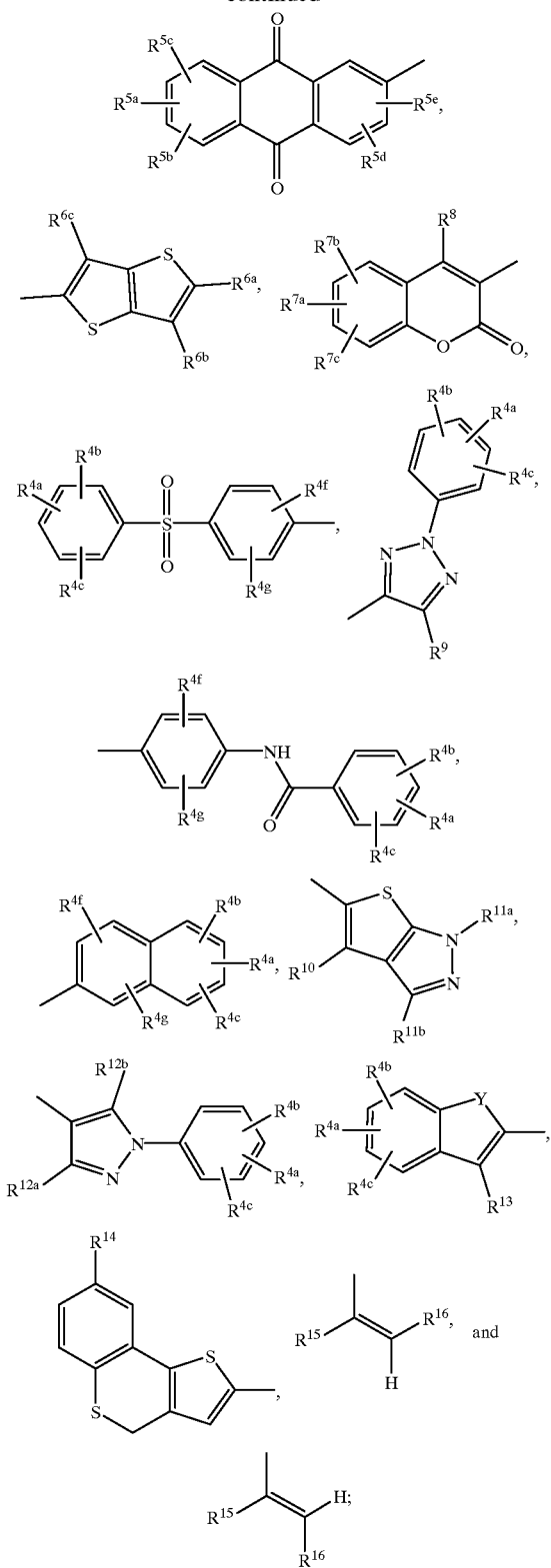

Y is sulfur, oxygen, nitrogen or carbon;
R$^{4a}$, R$^{4b}$, R$^{4c}$, R$^{4d}$, R$^{4e}$, R$^{4f}$ and R$^{4g}$ are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, trifluoromethyl, cyano, nitro, carboxy, alkoxycarbonyl of 1 to 6 carbon atoms, alkoxy of 1 to 6 carbon atoms, alkylcarbonyl of 1 to 6 carbon atoms, alkylcarbonylamino of 1 to 6 carbon atoms, thiol, alkylthio of 1 to 6 carbon atoms, alkylamino of 1 to 6 carbon atoms, —N(R$^{4h}$)(R$^{4i}$), phenyl, phenylamino, and carboxaldehyde;

R$^{4h}$ and R$^{4i}$, independent from each other, are straight chain alkyl of 1 to 6 carbon atoms;

R$^{5a}$, R$^{5b}$, R$^{5c}$, R$^{5d}$, and R$^{5e}$ are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, cyano, nitro, alkylamino of 1 to 6 carbon atoms, and —N(R$^{4h}$)(R$^{4i}$);

R$^{6a}$ and R$^{6b}$ are independently selected from hydrogen, halogen, straight chain alkyl of 1 to 6 carbon atoms, branched chain alkyl of 3 to 7 carbon atoms, alkenyl of 2 to 6 carbon atoms, or alkynyl of 2 to 6 carbon atoms;

R$^{6c}$ is hydrogen, methyl, cyano or halogen;

R$^{7a}$, R$^{7b}$ and R$^{7c}$ are independently selected from hydrogen, hydroxy, amino, halogen, straight chain alkyl of 1 to 6 carbon atoms, branched chain alkyl of 3 to 7 carbon atoms, alkenyl of 2 to 6 carbon atoms, alkynyl of 2 to 6 carbon atoms, hydroxyalkyl of 2 to 6 carbon atoms, alkoxy of 1 to 6 carbon atoms, cyano, nitro, alkoxycarbonyl of 1 to 6 carbon atoms, alkylcarbonyl of 1 to 6 carbon atoms, alkylamino of 1 to 6 carbon atoms, and —N(R$^{4h}$)(R$^{4i}$);

R$^8$ is hydrogen, hydroxy, amino, straight chain alkyl of 1 to 6 carbon atoms or branched chain alkyl of 3 to 7 carbon atoms;

R$^9$, R$^{10}$, R$^{11a}$ and R$^{11b}$ are independently, hydrogen or alkyl of 1 or 2 carbon atoms;

R$^{12a}$ and R$^{12b}$ are independently hydrogen, straight chain alkyl of 1 to 6 carbon atoms, alkenyl of 2 to 6 carbon atoms, alkynyl of 2 to 4 carbon atoms, hydroxyalkyl of 2 to 4 carbons, carboxy, alkoxycarbonyl of 1 to 6 carbon atoms, alkoxy of 1 to 6 carbon atoms, thiol, alkylthio of 1 to 4 carbon atoms, alkylamino of 1 to 4 carbon atoms, —N(R$^{12c}$)(R$^{12d}$) or trifluoromethyl;

R$^{12c}$ and R$^{12d}$, independent from each other, are straight chain alkyl of 1 to 4 carbon atoms;

R$^{13}$ is independently hydrogen, alkyl of 1 or 2 carbon atoms, hydroxy, amino, halogen, hydroxymethyl, or aminomethyl;

R$^{14}$ is hydrogen, alkyl of 1 or 2 carbon atoms, or halogen;

R$^{15}$ is hydrogen or cyano;

R$^{16}$ is a moiety selected from the group:

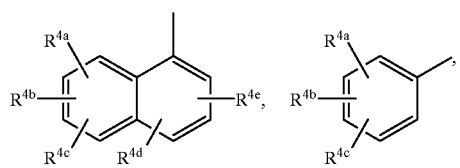

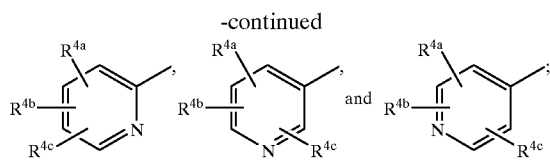

alkoxycarbonyl of 1 to 6 carbon atoms, alkylcarbonyl of 1 to 6 carbon atoms, alkylcarbonylamino of 1 to 6 carbon atoms, are defined where 1 to 6 carbon atoms decribes the length of the alkyl or alkoxy as bonded to the carbonyl carbon;

which comprises the steps of:

a) reacting 2,8-dibromodibenzothiophene with >90% nitric acid at 50–60° C. and recovering a mixture of 2,8-dibromo-3,7-dinitrodibenzothiophene-5-oxide and 2,8-dibromo-3-nitrodibenzothiophene-5-oxide;

b) reacting said mixture of 2,8-dibromodibenzothiophene, 2,8-dibromo-3,7-dinitrodibenzothiophene-5-oxide and 2,8-dibromo-3-nitrodibenzothiophene-5-oxide with sodium periodate and ruthenium (III) chloride and recovering 2,8-dibromo-3,7-dinitrodibenzothiophene-5,5-dioxide;

c) treating said 2,8-dibromo-3,7-dinitrodibenzothiophen-5,5-dioxide with a reducing agent in the presence of an alcoholic solvent and an organic acid at 50 to 120° C.; recovering the 2,8-dibromo-5,5-dioxo-5H-5$\lambda^6$-dibenzothiophene-3,7-diamine;

d) reacting said 2,8-dibromo-5,5-dioxo-5H-5$\lambda^6$-dibenzothiophene-3,7-diamine with an acid chloride of the formula:

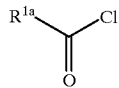

where $R^1$ is hereinbefore defined, in a polar-aprotic solvent in the presence of an alkylamine base at room temperature to about 120° C. for 0.25 to about 24 hours to give 2,8-dibromo-3,7-($R^1$-carbonylamino)-5,5-dioxo-5H-5$\lambda^6$-dibenzothiophene;

e) reacting said 2,8-dibromo-3,7-($R^1$-carbonylamino)-5,5-dioxo-5H-5$\lambda^6$-dibenzothiophene with a disubstituted phosphite of the formula HPO($OR^2$)$_2$ where $R^2$ is independently $R^{2a}$ or $R^{2b}$, with the proviso that $R^2$ is not H, in a polar aprotic solvent in the presence of an alkylamine, palladium(O) and heating for 1.5 to 100 hours at room temperature to 150° C.; treating with acid and recovering a mixture of [3,7-bis-($R^1$-carbonylamino)-8-[($R^2$-oxy)hydroxyphosphoryl]-5,5-dioxo-5H-5$\lambda^6$-dibenzothiophene-2-yl]phosphonic acid mono-$R^2$ ester di(trisubstituted alkylamine) salt and 3,7-bis-($R^1$-carbonylamino)-8-[(di-$R^2$-oxy)phosphoryl]-5,5-dioxo-5H-5$\lambda^6$-dibenzothiophene-2-yl]phosphonic acid mono-$R^2$ ester mono (trisubstituted alkylamine) salt; separating said mixture by column chromatography and isolating [3,7-bis-($R^1$-carbonylamino)-8-[($R^2$-oxy)hydroxyphosphoryl]-5,5-dioxo-5H-5$\lambda^6$-dibenzothiophene-2-yl]phosphonic acid mono -$R^2$ ester di(trisubstituted alkylamine) salt from 3,7-bis-($R^1$-carbonylamino)-8-[(di-$R^2$-oxy)phosphoryl]-5,5-dioxo-5H-5$\lambda^6$-dibenzothiophene-2-yl]phosphonic acid mono-$R^2$ ester mono (trisubstituted alkylamine) salt;

f) treating 3,7-bis-($R^1$-carbonylamino)-8-[(di-$R^2$-oxy)phosphoryl]-5,5-dioxo-5H-5$\lambda^6$-dibenzothiophene-2-yl]phosphonic acid mono-$R^2$ ester mono (trisubstituted alkylamine) salt with aqueous acid giving the free acid;

g) reacting said free acid with an alkaline metal or alkaline earth metal base in a heated polar solvent mixture and isolating the 3,7-bis-($R^1$-carbonylamino)-8-[(di-$R^2$-oxy)phosphoryl]-5,5-dioxo-5H-5$\lambda^6$-dibenzothiophene-2-yl]phosphonic acid mono-$R^2$ ester monometal salt.

* * * * *